US012653885B2

(12) United States Patent
Abend et al.

(10) Patent No.: US 12,653,885 B2
(45) Date of Patent: Jun. 16, 2026

(54) POLYOMAVIRUS NEUTRALIZING ANTIBODIES

(71) Applicant: Novartis AG, Basel (CH)

(72) Inventors: Johanna Abend, Emeryville, CA (US);
Vanessa Cornacchione, Basel (CH);
John Michael Lindner, Basel (CH);
Elisabetta Traggiai, Basel (CH)

(73) Assignee: Novartis AG, Basel (CH)

( * ) Notice: Subject to any disclaimer, the term of this patent is extended or adjusted under 35 U.S.C. 154(b) by 835 days.

(21) Appl. No.: 17/821,558

(22) Filed: Aug. 23, 2022

(65) Prior Publication Data

US 2023/0079587 A1 Mar. 16, 2023

Related U.S. Application Data

(63) Continuation of application No. 16/768,429, filed as application No. PCT/IB2018/059429 on Nov. 28, 2018, now Pat. No. 11,433,132.

(60) Provisional application No. 62/727,168, filed on Sep. 5, 2018, provisional application No. 62/593,566, filed on Dec. 1, 2017.

(51) Int. Cl.
| | |
|---|---|
| C07K 16/00 | (2006.01) |
| A61K 31/343 | (2006.01) |
| A61K 31/436 | (2006.01) |
| A61K 31/52 | (2006.01) |
| A61K 38/13 | (2006.01) |
| A61K 39/42 | (2006.01) |
| A61P 31/20 | (2006.01) |
| C07K 16/084 | (2026.01) |

(52) U.S. Cl.
CPC ............ *A61K 39/42* (2013.01); *A61K 31/343* (2013.01); *A61K 31/436* (2013.01); *A61K 31/52* (2013.01); *A61K 38/13* (2013.01); *A61P 31/20* (2018.01); *C07K 16/084* (2013.01); *C07K 2317/33* (2013.01); *C07K 2317/51* (2013.01); *C07K 2317/515* (2013.01); *C07K 2317/565* (2013.01); *C07K 2317/622* (2013.01); *C07K 2317/70* (2013.01); *C07K 2317/76* (2013.01)

(58) Field of Classification Search
CPC .......... C07K 2317/51; C07K 2317/515; C07K 2317/565; C07K 2317/622; C07K 2317/70
See application file for complete search history.

(56) References Cited

U.S. PATENT DOCUMENTS

| | | | |
|---|---|---|---|
| 8,470,979 B2 | 6/2013 | Bondensgaard et al. | |
| 9,862,760 B2 | 1/2018 | Abend et al. | |
| 10,011,648 B2 | 7/2018 | Burioni et al. | |
| 10,435,460 B2 | 10/2019 | Abend et al. | |
| 10,450,366 B2 | 10/2019 | Abend et al. | |
| 10,654,914 B2 | 5/2020 | Abend et al. | |
| 11,161,894 B2 | 11/2021 | Abend et al. | |
| 11,433,132 B2 | 9/2022 | Abend et al. | |
| 11,639,378 B2 | 5/2023 | Abend et al. | |
| 12,077,571 B2 | 9/2024 | Abend et al. | |
| 2008/0107658 A1 | 5/2008 | Franks et al. | |
| 2010/0215662 A1 | 8/2010 | Bradbury | |
| 2013/0337438 A1 | 12/2013 | Mori et al. | |
| 2014/0294841 A1 | 10/2014 | Scheinberg et al. | |
| 2015/0056188 A1 | 2/2015 | Simon et al. | |
| 2016/0052996 A1* | 2/2016 | Grimm ..................... A61P 1/04 |
| | | | 435/69.6 |
| 2022/0363735 A1 | 11/2022 | Abend et al. | |
| 2023/0220051 A1 | 7/2023 | Abend et al. | |
| 2023/0399382 A1 | 12/2023 | Abend et al. | |
| 2025/0051423 A1 | 2/2025 | Abend et al. | |

FOREIGN PATENT DOCUMENTS

| | | |
|---|---|---|
| CN | 104520318 A | 4/2015 |
| CN | 104936980 A | 9/2015 |
| JP | 2015524389 A | 8/2015 |
| JP | 2016513072 A | 5/2016 |
| WO | WO-03105894 A1 | 12/2003 |
| WO | WO-2013142299 A1 | 9/2013 |
| WO | WO-2013142300 A2 | 9/2013 |
| WO | WO-2014002035 A2 | 1/2014 |
| WO | WO-2014102399 A1 | 7/2014 |
| WO | WO-2015095770 A1 | 6/2015 |
| WO | WO-2015114150 A1 | 8/2015 |
| WO | WO-2017046676 A1 | 3/2017 |
| WO | WO-2019106578 A2 | 6/2019 |

OTHER PUBLICATIONS

Ambalathingal, George R. et al., "BK Polyomavirus: Clinical Aspects, Immune Regulation, and Emerging Therapies," Clin Microbiol Rev, Feb. 22, 2017, vol. 30(2), pp. 503-528.

Caldas, Cristina et al., "Humanization of the anti-CD18 antibody 6.7: an unexpected effect of a framework residue in binding to antigen," Molecular Immunology, vol. 39, No. 15, May 1, 2003, pp. 941-952.

Casadevall, A. et al., "Immunoglobulin isotype influences affinity and specificity," Proceedings of the National Academy of Sciences, vol. 109, No. 31, Jul. 31, 2012, pp. 12272-12273.

Du, J. et al., "Molecular basis of recognition of human osteopontin by 23C3, a potential therapeutic antibody for treatment of rheumatoid arthritis," Journal of Molecular Biology, Academic Press, United Kingdom, by vol. 382, No. 4, Oct. 17, 2008, pp. 835-842.

Geoghegan, Eileen M. E et al., "Infectious Entry and Neutralization of Pathogenic JC Polyomaviruses," Cell Rep, Oct. 31, 2017, vol. 21,pp. 1169-1179.

Jelcic, Ivan et al., "Broadly neutralizing human monoclonal JC polyomavirus VP1-specific antibodies as candidate therapeutics for progressive multifocal leukoencephalopathy," Sci Transl Med, 2015, vol. 7(306), 28 pages.

(Continued)

*Primary Examiner* — Lei Yao
(74) *Attorney, Agent, or Firm* — COOLEY LLP

(57) ABSTRACT
The present invention relates to anti-polyomavirus antibodies, antibody fragments, and their uses for the prevention and treatment of BK or JC virus infection and associated diseases.

8 Claims, 10 Drawing Sheets

Specification includes a Sequence Listing.

(56)                    References Cited

OTHER PUBLICATIONS

Kunik, Vared et al., "Structural Consensus among Antibodies Defines the Antigen Binding Site," PLoS Computational Biology, vol. 8, No. 2, Feb. 23, 2012, pp. 1168-1179.

Chang, D., et al., "Production of the antigen and the antibody of the JC virus major capsid protein VP1", Journal of Virological Methods, 1996, vol. 59, No. 1-2, pp. 177-187.

Henmi, C., et al., "Establishment of an immunoscreening system using recombinant VP1 protein for the isolation of a monoclonal antibody that blocks JC virus infection", Biochemical and Biophysical Research Communications, 2005, 327, No. 1, pp. 242-251.

Wang, Dianli, JC Virus VP2 Egg White antigen antibody preparation and nuclear localization signal and nuclear import and translocation body identification, Excellent Master's Degree Thesis in China Text database (Medical and health science and technology Series), Feb. 15, 2009, vol. 2009, No. 2, 118 pages [with machine translation].

Wang, Xinxin, "Early Kidney Transplantation," Studies on BK virus activation in post-recipients Study, Excellent Master's Degree Thesis in China Text database (Medical and health science and technology Series), Jan. 15, 2014, vol. 2014, Issue 1, 181 pages [with machine translation].

U.S. Appl. No. 18/186,064, filed Mar. 17, 2023, 156 pages.

Abend et al. (2007). "Inhibitory Effect of Gamma Interferon on BK Virus Gene Expression and Replication" J. Virology 81 :272-279.

Altschul et al., "Gapped BLAST and PSI-BLAST: a new generation of protein database search programs," Nucleic Acids Research (1997) 25(17):3389-3402.

Antinori et al. (2003). "Clinical epidemiology and survival of progressive multifocal leukoencephalopathy in the era of highly active antiretroviral therapy: Data from the Italian Registry Investigative Neuro AIDS (IRINA)" Journal of Neuro Virology 9(supplemental 1): 47-53.

Astrom et al. (1958). "Progressive Multifocal Leuko-Encephalopathy a Hitherto Unrecognized Complication of Chronic Lymphatic Leukemia and Hodgkin's Disease" Brain 81(1): 93-111.

Bennett et al. (2012). "BK polyomavirus: emerging pathogen" Microbes and Infection 14(9):672-683.

Binet et al. (1999). "Polyomavirus Disease Under New Immunosuppressive Drugs: A Cause of Renal Graft Dysfunction and Graft Loss" Transplantation 67(6):918-922.

Brennan et al. (2005). "Incidence of BK with tacrolimus versus cyclosporine and impact of preemptive immunosuppression reduction" Am. J. Transplant 5(3):582-594.

Bressollette-Bodin et al. (2005). "A Prospective Longitudinal Study of BK Virus Infection in 104 Renal Transplant Recipients" American Journal of Transplantation 5(8): 1926-1933.

Broekema et al. (2010). "A system for the analysis of BKV non-coding control regions: Application to clinical isolates from an HIV/AIDS patient" Virology 407:368-373.

Carter et al. (2003). "Lack of Serologic Evidence for Prevalent Simian Virus 40 Infection in Humans" J. Natl. Cancer Inst. 95:1522-1530.

Chatterjee et al. (2000). "Identification of Archetype and Rearranged Forms of BK Virus in Leukocytes From Healthy Individuals" Journal of Medical Virology 60:353-362.

Chen et al. (2015). "Synthetic antibodies and peptides recognizing progressive multifocal leukoencephalopathyspecific point mutations in polyomavirus JC capsid viral protein 1" mABS 7(4):681-692.

Chothia C., et al., "Canonical Structures for the Hypervariable Regions of Immunoglobulins," Journal of Molecular Biology, Aug. 20, 1987, vol. 196, No. 4, pp. 901-917.

Chothia C., et al., "Conformations Of Immunoglobulin Hypervariable Regions," Nature, Dec. 1989, vol. 342, pp. 877-883.

Chothia, et al., Structural repertoire of the human VH segments, Journal of Molecular Biology, Oct. 5, 1992, pp. 799-817, vol. 227, No. 3.

Derienzo et al. (2000). "Evaluation of the Half-Life of Intravenous Human Cytomegalovirus Immune Globulin in Patients Receiving Partially Mismatched Related Donor Bone Marrow Transplantation" Pharmacotherapy 20: 1175-1178.

European Patent Office, International Search Report and Written Opinion for PCT/IB2016/055339, Feb. 1, 2017, 15 pages.

European Patent Office, International Search Report and Written Opinion for PCT/IB2018/059429, Jun. 4, 2019, 19 pages.

Garcia-Suarez et al. (2005). "Changes in the Natural History of Progressive Multifocal Leukoencephalopathy in HIV-negative Lymphoproliferative Disorders: Impact of Novel Therapies" Am. J Hematol 80(4):271-281.

Gardner. (1971). "New human papovavirus (B.K.) isolated from urine after renal transplantation" Lancet 297(7712):1253-1257.

Gorelik et al. (2011). "Progressive Multifocal Leukoencephalopathy (PML) Development is Associated with Mutations in JC Virus Capsid Protein VP1 that Change its Receptor Specificity" Journal of Infectious Diseases 204:237-244.

Goudsmit et al. (1982). "The role of BK virus in acute respiratory tract disease and the presence of BKV DNA in tonsils" Journal of Medical Virology 10:91-99.

Henikoff, et al., Trans-inactivation of the Drosophila brown gene: evidence for transcriptional repression and somatic pairing dependence, Proc. Natl. Acad. Sci., Sep. 1, 1989, pp. 6704-6708, vol. 86, Issue 17.

Heritage et al. (1981). "The persistence of papovavirus BK DNA sequences in normal human renal tissue" Journal of Medical Virology 8:143-150.

Hirsch. (2002). "Polyomavirus BK nephropathy: a (re-)emerging complication in renal transplantation" Am. J. Transplant 2 (1):25-30.

Hirsch et al. (2002). "Prospective Study of Polyomavirus Type BK Replication and Nephropathy in Renal-Transplant Recipients" New England J. Medicine 347(7):488-496.

Hirsch et al. (2005). "Polyomavirus-Associated Nephropathy in Renal Transplantation: Interdisciplinary Analyses and Recommendations" Transplantation 79(1):1277-1286.

Jiang et al. (2009). "The Role of Polyomaviruses in Human Disease" Virology 384(2):266-273.

Johne et al. (2004). "Nuclear Localization of Avian Polyomavirus Structural Protein VP1 Is a Prerequisite for the Formation of Virus-Like Particles." Journal of Virology, 78(2): 930-937.

Johne et al. (2011). "Taxonomical Developments in the Family Polyomaviridae" Arch. Virol. 156(9):1627-1634.

Johnson, et al., Kabat Database and its applications: future directions, Nucleic Acids Research, Jan. 1, 2001, pp. 205-206, vol. 29, No. 1.

Knowles et al. (2006). "Discovery and Epidemiology of the Human Polyomaviruses BK Virus (BKV) and JC Virus (JCV)" Adv. Exp. Med. Biol. 577: 19-45.

Lipshutz et al. (2004). "BK Nephropathy in Kidney Transplant Recipients Treated with a Calcineurin Inhibitor-Free Immunosuppression Regimen" American Journal of Transplantation 2004; 4: 2132-2134.

Liu. (2015). "Antibody Glycosylation and its Impact on the Pharmacokinetics and Pharmacodynamics of Monoclonal Antibodies and Fe-fusion Proteins" J. Pharm. Sci. 104(6): 1866-1884.

Mengelle et al. (2011). "JC Virus DNA in the Peripheral Blood of Renal Transplant Patients: a 1-Year Prospective Follow-up in France" J. Med. Viral. 83(1):132-136.

Neu et al. (2013). Plos Pathogens 9(10):e1003714 and e1003688.

Nickeleit et al. (1999). "Polymavirus Infection of Renal Allograft Recipients: From Latent Infection to Manifest Disease" J. Am. Seo. Neprol. 10(5):1080-1089.

O'Hara et al. (2014). "Gallic acid-based small-molecule inhibitors of JC and BK polyomaviral infection" Virus Research 189:280-285.

Padgett et al. (1971). "Cultivation of Papova-Like Virus from Human Brain with Progressive Multifocal Leucoencephalopathy" Lancet 297(7712):1257-1260.

Padgett et al. (1973). "Prevalence of Antibodies in Human Sera against JC Virus, an Isolate from a Case of Progressive Multifocal Leukoencephalopathy" Journal of Infectious Diseases 127(4):467-470.

(56) References Cited

OTHER PUBLICATIONS

Pastrana et al. (2012). "Neutralization Serotyping of BK Polyomavirus Infection in Kidney Transplant Recipients" PLoS Pathogens vol. 8(4)e1002650.

Purighalla et al. (1995). "BK Virus Infection in a Kidney Allograft Diagnosed by Needle Biopsy" American Journal of Kidney Diseases 26(4):671-673.

Qian et al. (2010). "Lipids and Proteins Act in Opposing Manners To Regulate Polyomavirus Infection" Journal of Virology 84(19):9840-9852.

Randhawa et al. (1999). "Human Polyoma Virus-Associated Interstital Nephritis in the Allograft Kidney" Transplantation 67:103-109.

Randhawa et al. (2006). "BK Virus Infection in Transplant Recipients: An Overview and Update" American Journal of Transplantation 6(9):2000-2005.

Randhawa et al. (2009). "Identification of Species-Specific and Cross-Reactive Epitopes in Human Polyomavirus Capsids Using Monoclonal Antibodies" Journal of General Virology 90:634-639.

Randhawa et al. (2015). "Commercially Available Immunoglobulins Contain Virus Neutralizing Antibodies Against all Major Genotypes of Polyomavirus" BK. Am J Transplant. 15(4):1014-20.

Reid et al. (2011). "Sequencing and Analysis of JC Virus DNA From Natalizumab-Treated PML Patients" J Infect Dis. 204:237-244.

Reploeg et al. (2001). "BK Virus: A Clinical Review" Clin Infect. Dis. 33(2):191-202.

Richardson. (1961). "Progressive Multifocal Leukoencephalopathy." New England Journal of Medicine 265(17):815-823.

Rudikoff et al., "Single amino acid substitution altering antigen-binding specificity", PNAS USA, Mar. 1982, 79(6):1979-1983.

Sabath et al. (2002). "Traffic of JC Virus from Sites of Initial Infection to the Brain: The Path to Progressive Multifocal Leukoencephalopathy" Journal Infectious Diseases 186:S180-S186.

Shinohara et al. (1993). "BK Virus Infection of the Human Urinary Tract" Journal of Medical Virology 41(4):301-305.

Wiseman et al. (2009). "Polyomavirus Nephropathy: A Current Perspective and Clinical Considerations" Am.J. Kidney Dis 54 (1):131-142.

Extended European Search Report for European Application No. 24158407.7, mailed Sep. 26, 2024, 11 pages.

Lindner J., et al., "Human Memory B Cells Harbor Diverse Cross-Neutralizing Antibodies against BK and JC Polyomaviruses," Immunity, Mar. 1, 2019, vol. 50, No. 3, pp. 668-676.

National Institute of Health, "Immunoglobulin lambda light chain VLJ region, partial [*Homo sapiens*]," GenBank: BAC01663.1, Jul. 26, 2016, 2 pages.

* cited by examiner

FIGURE 2A/2B

| Antibody | $K_d$ (pM) | | | |
|---|---|---|---|---|
| | BKV VLP ST1 | BKV VLP ST2 | BKV VLP ST3 | BKV VLP ST4 |
| NOV581 | 44 ± 10 | 69 ± 2 | 92 ± 23 | > 6600 |
| NOV796 | 3 ± 1 | 6 ± 2 | 7 ± 3 | 0.9 ± 0.6 |
| NOV530 | 15 ± 3 | 54 ± 13 | 44 ± 20 | 19 ± 5 |

FIGURE 3D

PENTAMER B$_2$

|  |  | 316---------330 |  |
|---|---|---|---|
| | ST1 | RVDGQPMYGMESQVE | (SEQ ID NO:386) |
| BKV | ST2 | KVDGQPMYGMESQVE | (SEQ ID NO:387) |
| | ST3 | KVDGQPMYGMESQVE | (SEQ ID NO:388) |
| | ST4 | RVDGQPMYGMESQVE | (SEQ ID NO:389) |
| | JCV | RVDGQPMYGMDAQVE | (SEQ ID NO:390) |
| | MCV | KVSGQPMEGKDNQVE | (SEQ ID NO:391) |

FIGURE 3E

PENTAMER A₄

|  |  | 169 | 182------193 |  |
|---|---|---|---|---|
| | ST1 | Y/ | NPTAQSQVMNTD | (SEQ ID NO:392) |
| BKV | ST2 | Y/ | NPTAQSQVMNTD | (SEQ ID NO:393) |
| | ST3 | Y/ | NPTAQSQVMNTD | (SEQ ID NO:394) |
| | ST4 | Y/ | NPTAQSQVMNTD | (SEQ ID NO:395) |
| | JCV | Y/ | NATVQSQVMNTE | (SEQ ID NO:396) |
| | MCV | Y/ | KMTPKNQGLDPQ | (SEQ ID NO:397) |

FIGURE 3F

PENTAMER A₃

| BKV | 59---64 | | 81---87 | |
|---|---|---|---|---|
| ST1 | PDENLR | (SEQ ID NO:398) | PDRKMLP | (SEQ ID NO:404) |
| ST2 | PDDNLR | (SEQ ID NO:399) | PDKKMLP | (SEQ ID NO:405) |
| ST3 | PDDNLR | (SEQ ID NO:400) | PDRKMLP | (SEQ ID NO:406) |
| ST4 | PDNNLR | (SEQ ID NO:401) | PDRKMLP | (SEQ ID NO:407) |
| JCV | PDEHLR | (SEQ ID NO:402) | PSKDMLP | (SEQ ID NO:408) |
| MCV | NSPDLP | (SEQ ID NO:403) | PIKENLP | (SEQ ID NO:409) |

| BKV | 172-176 | | 198-201 | |
|---|---|---|---|---|
| ST1 | KYPDG | (SEQ ID NO:410) | LDKN | (SEQ ID NO:416) |
| ST2 | KYPQG | (SEQ ID NO:411) | LDKN | (SEQ ID NO:417) |
| ST3 | KYPQG | (SEQ ID NO:412) | LDKN | (SEQ ID NO:418) |
| ST4 | KYPEG | (SEQ ID NO:413) | LDKN | (SEQ ID NO:419) |
| JCV | KYPDG | (SEQ ID NO:414) | LDKN | (SEQ ID NO:420) |
| MCV | EYPKT | (SEQ ID NO:415) | LDKD | (SEQ ID NO:421) |

FIGURE 3G

NOV530 VH4-31

CDR1  GGSISGGGYYWS  (SEQ ID NO:422)

CDR2  SGS  (SEQ ID NO:423)
      YIYYNRGT

CDR3  ARCVLGGYGSDAFDR  (SEQ ID NO:424)

FIGURE 3H

```
                                            Y
NOV530 VK3-11      CDR1 RASQSVSSHLA (SEQ ID NO:425)

N   T
                   CDR2 (Y)DASSRAN      (SEQ ID NO:426)

N
                   CDR3 QQRSSWPPSLT (SEQ ID NO:427)
```

POLYOMAVIRUS NEUTRALIZING ANTIBODIES

CROSS REFERENCE TO RELATED APPLICATIONS

This application is a continuation of U.S. application Ser. No. 16/768,429, filed May 29, 2020, which is the national stage of PCT Application No. PCT/IB2018/059429, filed Nov. 28, 2018, which claims priority to U.S. Provisional Application No. 62/727,168 filed Sep. 5, 2018, and U.S. Provisional Application No. 62/593,566 filed Dec. 1, 2017. The entire content of these applications is hereby incorporated by reference.

SEQUENCE LISTING

The instant application contains a Sequence Listing which has been submitted in XML format via EFS-Web and is hereby incorporated by reference in its entirety. Said XML copy, created on Jun. 29, 2022 is named "VETH_013_03US_SeqList_ST26.xml" and is 434,201 bytes in size.

FIELD OF THE INVENTION

The present disclosure is directed to anti-polyomavirus antibodies, antibody fragments, and their uses for the reducing the likelihood or treatment of polyomaviral infection.

BACKGROUND OF THE INVENTION

Of the human polyomaviruses, BK virus (BKV) and JC virus (JCV) were the first two identified. These two polyomaviruses were isolated from immunosuppressed patients and published in the same issue of Lancet in 1971 (Gardner et al., Lancet 1971 1:1253-1527, and Padgett et al., Lancet 1971 1:1257-1260). Polyomaviruses are icosahedral, non-enveloped, double-stranded DNA viruses. They measure 40-45 nm in diameter and are comprised of 88% protein and 12% DNA.

The BKV genome is a circular double-stranded DNA of approximately 5000 base pairs in length and contains three major divisions: the early coding region, the late coding region, and a non-coding control region. The early coding region encodes for the three regulatory proteins (large tumor antigen [TAg], small tumor antigen [tAg], and truncated tumor antigen [truncTAg]), which are the first viral proteins expressed in a newly infected cell and are responsible for facilitating viral DNA replication and establishing a favorable cellular environment. The late coding region encodes the three structural proteins (VP1, VP2, and VP3) that make up the viral capsid, as well as the agnoprotein, the role of which during viral replication is less well-defined. The non-coding control region contains the genomic origin of replication as well as the early and late promoters that drive expression of the viral gene products.

BKV has been detected in many different cell types, including epithelial cells of the kidney, bladder, and ureter (typical sites of persistence), tonsillar tissue, and lymphocytes (proposed sites of primary infection and dissemination) (Chatterjee et al., J. Med. Virol. 2000; 60:353-362, Goudsmit et al., J. Med. Virol. 1982; 10:91-99, Heritage et al., J. Med. Virol. 1981; 8:143-150, Shinohara et al., J. Med. Virol. 1993; 41(4):301-305). The primary cell surface receptors for BKV are the gangliosides GT1b, GD1b, and GD3, all of which have a terminal α2,8-linked sialic acid and are fairly ubiquitous, allowing infection of various cell types (Neu et al., PLos Patholog. 2013; 9(10):e1003714 and e1003688, see also, O'Hara et al., Virus Res. 2014; 189: 208-285). The non-enveloped icosahedral virion of BKV is composed of three distinct viral proteins: 360 copies of the major viral capsid protein VP1 arranged in 72 pentamers and 72 copies combined of the minor viral capsid proteins VP2 and VP3, with one VP2 or VP3 molecule associated with each VP1 pentamer. Only VP1 is exposed on the virion surface at entry and each pentamer has five low-affinity binding sites for the ganglioside receptor. Binding of VP1 pentamers to ganglioside receptors on the cell surface initiates internalization through a caveolae-mediated endocytic pathway, followed by trafficking of the virus to the endoplasmic reticulum and finally, to the nucleus (Tsai and Qian, J. Virol 2010; 84(19):9840-9852).

Infection with BKV is essentially ubiquitous, with estimates ranging between 80% and 90% of the population globally infected (Knowles W. A., Adv. Exp. Med. Biol. 2006; 577:19-45). Primary infection most often occurs during childhood (i.e., before age 10) and results in either a mild, non-specific, self-limited illness or no symptoms at all. Persistent infection is established in the epithelial cells of the renal tubules, ureters, and bladder, and is effectively controlled by the immune system. Transient asymptomatic viral shedding in the urine of immunocompetent adults occurs sporadically but results in no disease or sequelae. However, compromised immune function, particularly upon immunosuppression following renal or hematopoietic stem cell transplantation, can lead to uncontrolled BKV replication and ultimately to BKV-associated nephropathy (BKVAN) or hemorrhagic cystitis (HC), a painful disease of the bladder. There are no effective antiviral therapies against BKV and the current standard of care is reduction of immunosuppression, which increases the risk of acute rejection. Even with the current, more aggressive approaches to monitoring and prevention, up to 10% of renal transplant recipients will develop BKVAN and 15-30% of those patients will suffer graft loss due to BKVAN. Among those undergoing reduction in immunosuppressive regimen upon detection of BK viremia, up to 30% will experience an acute rejection episode as a result.

Although BKV was first described in 1971 (supra), it was not until the 1990s that BKVAN was reported in the literature as a cause of kidney transplant injury (Purighalla et al., Am. J. Kidney Dis. 1995; 26:671-673 and Randhawa et al., Transplantation 1999; 67:103-109). In early management of BKVAN, testing positive for BK had severe consequences, with more than 50% of the patients having graft dysfunction and graft loss (Hirsch et al., New Engl. J. Med. 2002; 347:488-496). BKV reactivation and replication follows a well-established clinical course in kidney transplant patients, evidenced first by detection of virus and viral DNA in the urine (viruria), followed by detection of virus in the bloodstream (viremia), and finally signs of nephropathy and diminished kidney function as a result of viral replication. Approximately 30-40% of all kidney transplant recipients will have viruria and 10-20% of recipients will have BK viremia, typically within the first 3 months post-transplantation (Sawinski and Goral, Nephrol Dial Transplant. 2015; 30:209-217; Hirsch et al., Am J Transplant. 2013; 13:136-145; Dharnidharka et al., Pediatr Nephrol. 2011; 26:1763-1774; Babel et al., Transplantation. 2009; 88:89-95). Approximately 1-10% of all kidney transplant recipients will progress to BKVAN, typically within the first year post-transplant (Bohl and Brennan, Clin J Am Soc Nephrol. 2007; 2(Suppl 1): S36-46; Sawinski and Goral, Nephrol Dial Transplant. 2015; 30:209-217). BKV replication in the renal tubular epithelial cells causes necrosis and lytic destruction, leading to denudation of the basement membrane, accumulation of tubular fluid in the interstitum, and ultimately results in interstitial fibrosis and tubular atrophy (Nickeleit et al., J. Am. Soc. Neprol. 1999; 10(5):1080-1089). Patients may present with deterioration of renal function, tubule-interstitial nephritis and ureteric stenosis (Garner et al., Lancet 1971; 1(7712):1253-1257 and Hirsch Am. J. Transplant 2002; 2(1)25-30).

BKV can also cause pneumonitis, retinitis, and meningo-encephalitis in immunocompromised hosts (Reploeg et al., Clin. Infect. Dis. 2001; 33(2):191-202). BKV disease in hematopoietic stem cell transplant (HSCT) recipients typically manifests as hemorrhagic cystitis (HC), which can vary in severity. Viruria (but not always viremia) and painful hematuria are associated with the clinical presentation of HC. The current standard of care is supportive in nature, involving primarily forced hydration/diuresis and pain management measures. The most severe cases require blood transfusions, clot evacuation, and can lead to death in some instances. HC of any cause (e.g. drug, radiation, viral) is relatively common among HSCT recipients but BKV-associated HC occurs in approximately 10-12% of patients usually within 6 months post-transplantation. There are other viral etiologies of HC, with adenovirus being a more common cause of HC among pediatric HSCT recipients compared with adult HSCT recipients. BK virus has also been observed in other immunocompromised conditions such as solid organ transplants and in HIV/AIDS patients (Jiang et al., Virol. 2009; 384:266-273).

At this point, the standard of care treatment of BKVAN is the reduction of immunosuppression in an attempt to prevent graft dysfunction and graft loss (Wiseman et al., Am. J. Kidney Dis. 2009; 54(1): 131-142 and Hirsch et al., Transplantation 2005; 79(1): 1277-1286). There are no fixed clinical regimes for the reduction, as reduction of the immunosuppression may help to prevent progression from viremia to the extensive damage associated with clinical nephropathy, but this also increases the risk of acute organ rejection (Brennan et al., Am. J. Transplant 2005; 5(3):582-594). Clinicians have reported the use of therapeutics such as cidofovir, leflunomide, or quinolones in combination with the reduction of immunosuppressants; however, the reports find this approach ineffective, with the added burden of managing additional side effects (Randhawa and Brennan Am. J. Transplant 2006; 6(9):2000-2005). As such, there is an unmet and useful need in the field for therapies that neutralize polyoma viruses such as BKV and that can be used in an immunocompromised host.

JC virus (JCV) is another human polyomavirus which is highly prevalent in the population (80%), although JCV is generally acquired later than BKV (Padgett et al., J. Infect. Dis. 1973; 127(4):467-470 and Sabath et al., J. Infect. Dis. 2002; 186 Suppl. 2:5180-5186). After initial infection, JCV establishes latency in the lymphoid organs and kidneys and when reactivated, invades the central nervous system (CNS) via infected B lymphocytes. Once in the CNS, the JCV causes progressive multifocal leukoencephalopathy (PML), which is a progressive demyelinating CNS disorder. Most cases of PML are associated with immunomodulatory therapies used for the treatment of multiple sclerosis (e.g., natalizumab, fingolimod) or rheumatoid arthritis (e.g., rituximab) and disease progression is usually halted by cessation of treatment. Given the progressive nature of PML, it may be possible to document significant improvement in patients receiving JCV neutralizing antibodies over several months, either by clinical criteria or by MRI, which is already routinely used to monitor multiple sclerosis, in patients receiving JCV neutralizing antibodies over several months. PML may also manifest in HIV/AIDS patients and has also been reported in immunosuppressed patients (Angstrom et al., Brain 1958; 81(1):93-111 and Garcia-Suarez et al., Am. J. Hematol. 2005; 80(4):271-281). PML patients present with confusion, mental status changes, gait ataxia, focal neurological defects such as hemi paresis, limb paresis, and visual changes (Richardson E. P., N. Eng. J. Med. 1961; 265:815-823). The prognosis of patients with PML is poor and is especially poor in patients with HIV/AIDS (Antinori et al., J. Neurovirol. 2003; 9 suppl. 1:47-53). This further highlights the unmet and useful need in the field for therapies that neutralize polyomaviruses such as JCV.

SUMMARY OF THE INVENTION

The present disclosure is directed to neutralizing antibodies to human polyomaviruses and/or fragments thereof, antibodies that recognize BK virus and/or JC virus.

An antibody, wherein said antibody or antigen binding fragment thereof specifically binds BK virus and/or JC virus.

The antibody wherein said antibody or antigen binding fragment thereof specifically binds BK virus and/or JC virus. In one embodiment, the antibody or antigen binding fragment thereof binds to BKV serotype I, BKV serotype II, BKV serotype III or BKV serotype IV or a combination of serotypes I-IV. In another embodiment, the antibody or antigen binding fragment thereof further binds to JC virus.

The antibody wherein said antibody or antigen binding fragment specifically binds to and neutralizes BK and/or JC virus. In one embodiment, the antibody or antigen binding fragment thereof binds to and neutralizes BK serotype I. In one embodiment, the antibody or antigen binding fragment thereof binds to and neutralizes BKV serotype I and BKV serotype II. In another embodiment, the antibody or antigen binding fragment thereof binds to and neutralizes BKV serotype I and BKV serotype III. In another embodiment, the antibody or antigen binding fragment thereof binds to and neutralizes BKV serotype I and BKV serotype IV. In another embodiment, the antibody or antigen binding fragment thereof binds to and neutralizes BKV serotype II and BKV serotype III. In another embodiment, the antibody or antigen binding fragment thereof binds to and neutralizes BKV serotype II and BKV serotype IV. In another embodiment, the antibody or antigen binding fragment thereof binds to an neutralizes BKV serotype I and JCV. In a preferred embodiment, the antibody or antigen binding fragment thereof binds to and neutralizes BKV serotypes I, II, III and IV. Furthermore, the antibody or antigen binding fragment thereof binds to and neutralizes BKV serotypes I, II, III and IV and JCV.

An isolated antibody or antigen binding fragment thereof, wherein said antibody or antigen binding fragment thereof comprises: (i) a heavy chain region and (ii) a light chain region set forth in Table 2.

An isolated antibody, wherein said antibody or antigen binding fragment thereof comprises:

(i) a heavy chain variable region that comprises (a) a HCDR1 (CDR-Complementarity Determining Region) of SEQ ID NO: 9, (b) a HCDR2 of SEQ ID NO:10, (c) a HCDR3 of SEQ ID NO:11 and a light chain variable region that comprises: (d) a LCDR1 of SEQ ID NO:25, (e) a LCDR2 of SEQ ID NO:26, and (f) a LCDR3 of SEQ ID NO:27;

(ii) a heavy chain variable region that comprises (a) a HCDR1 of SEQ ID NO:41, (b) a HCDR2 of SEQ ID NO:42, (c) a HCDR3 of SEQ ID NO:43; and a light chain variable region that comprises: (d) a LCDR1 of SEQ ID NO:57, (e) a LCDR2 of SEQ ID NO:58, and (f) a LCDR3 of SEQ ID NO:59;

(iii) a heavy chain variable region that comprises (a) a HCDR1 of SEQ ID NO:73, (b) a HCDR2 of SEQ ID NO:74, (c) a HCDR3 of SEQ ID NO:75; and a light chain variable region that comprises: (d) a LCDR1 of SEQ ID NO:89, (e) a LCDR2 of SEQ ID NO:90, and (f) a LCDR3 of SEQ ID NO:91;

(iv) a heavy chain variable region that comprises: (a) a HCDR1 of SEQ ID NO:105, (b) a HCDR2 of SEQ ID NO:106, (c) a HCDR3 of SEQ ID NO:107; and a light chain variable region that comprises: (d) a LCDR1 of SEQ ID NO:121, (e) a LCDR2 of SEQ ID NO:122, and (f) a LCDR3 of SEQ ID NO:123;

(v) a heavy chain variable region that comprises: (a) a HCDR1 of SEQ ID NO:137, (b) a HCDR2 of SEQ ID NO:138, (c) a HCDR3 of SEQ ID NO:139; and a light chain variable region that comprises: (d) a LCDR1 of SEQ ID NO:153, (e) a LCDR2 of SEQ ID NO:154, and (f) a LCDR3 of SEQ ID NO:155;

(vi) a heavy chain variable region that comprises: (a) a HCDR1 of SEQ ID NO:169, (b) a HCDR2 of SEQ ID NO:170, (c) a HCDR3 of SEQ ID NO:171; and a light chain variable region that comprises: (d) a LCDR1 of SEQ ID NO:185, (e) a LCDR2 of SEQ ID NO:186, and (f) a LCDR3 of SEQ ID NO:187;

(vii) a heavy chain variable region that comprises: (a) a HCDR1 of SEQ ID NO:201, (b) a HCDR2 of SEQ ID NO: 202, (c) a HCDR3 of SEQ ID NO:203; and a light chain variable region that comprises: (d) a LCDR1 of SEQ ID NO:217, (e) a LCDR2 of SEQ ID NO:218, and (f) a LCDR3 of SEQ ID NO:219;

(viii) a heavy chain variable region that comprises: (a) a HCDR1 of SEQ ID NO:233, (b) a HCDR2 of SEQ ID NO:234, (c) a HCDR3 of SEQ ID NO:235; and a light chain variable region that comprises: (d) a LCDR1 of SEQ ID NO:249, (e) a LCDR2 of SEQ ID NO:250, and (f) a LCDR3 of SEQ ID NO:251; and (ix) a heavy chain variable region that comprises: (a) a HCDR1 of SEQ ID NO:265, (b) a HCDR2 of SEQ ID NO: 266, (c) a HCDR3 of SEQ ID NO:267; and a light chain variable region that comprises: (d) a LCDR1 of SEQ ID NO:281, (e) a LCDR2 of SEQ ID NO:282, and (f) a LCDR3 of SEQ ID NO: 283.

The antibody wherein one or two amino acids within a CDR have been modified, deleted, or substituted.

The antibody that retains at least 90, 91, 92, 93, 94, 95, 96, 97, 98 or 99% identity over either the variable heavy chain region or the variable light chain region.

The antibody wherein the antibody is a monoclonal antibody, a chimeric antibody, a humanized antibody, a human engineered antibody, a human antibody, a single chain antibody (scFv), or an antibody fragment.

An isolated antibody or antigen binding fragment thereof, wherein said antibody or antigen binding fragment thereof comprises:

(i) a heavy chain variable region (vH) that comprises SEQ ID NO:18, and a light chain variable region (vL) that comprises SEQ ID NO: 34;

(ii) a heavy chain variable region (vH) that comprises SEQ ID NO: 50, and a light chain variable region (vL) that comprises SEQ ID NO: 66;

(iii) a heavy chain variable region (vH) that comprises SEQ ID NO: 82, and a light chain variable region (vL) that comprises SEQ ID NO:98;

(iv) a heavy chain variable region (vH) that comprises SEQ ID NO:114, and a light chain variable region (vL) that comprises SEQ ID NO:130;

(v) a heavy chain variable region (vH) that comprises SEQ ID NO:146, and a light chain variable region (vL) that comprises SEQ ID NO:162;

(vi) a heavy chain variable region (vH) that comprises SEQ ID NO:178, and a light chain variable region (vL) that comprises SEQ ID NO:194;

(vii) a heavy chain variable region (vH) that comprises SEQ ID NO:210, and a light chain variable region (vL) that comprises SEQ ID NO:226;

(viii) a heavy chain variable region (vH) that comprises SEQ ID NO: 242, and a light chain variable region (vL) that comprises SEQ ID NO:258; and (ix) a heavy chain variable region (vH) that comprises SEQ ID NO:274, and a light chain variable region (vL) that comprises SEQ ID NO:290.

The antibody or fragment thereof, that retains at least 90, 91, 92, 93, 94, 95, 96, 97, 98 or 99% identity over either the variable light or variable heavy region.

The antibody wherein one, two, three, four or five, but less than 10 amino acids within the variable light or variable heavy region have been modified, deleted or substituted.

The antibody wherein the antibody is a monoclonal antibody, a chimeric antibody, a humanized antibody, a human engineered antibody, a human antibody, a single chain antibody (scFv) or an antibody fragment.

The method of isolating and producing the antibody, in which the natural signal/leader peptide sequence matching the appropriate VH and/or VL gene segments is used.

The method of isolating and producing the antibody, in which a synthetic and/or optimized signal/leader peptide sequence is used to improve expression and yield.

The antibody wherein the antibody or fragment thereof has reduced glycosylation or no glycosylation or is hypofucosylated.

A pharmaceutical composition comprising the antibody or fragment thereof, further comprising a pharmaceutically acceptable carrier.

The pharmaceutical composition, wherein the pharmaceutically acceptable carrier contains histadine or a sugar.

The pharmaceutical composition, wherein the sugar is sucrose.

A pharmaceutical composition comprising a plurality of an antibody or antigen binding fragment, wherein at least 0.05%, 0.1%, 0.5%, 1%, 2%, 3%, 5% or more or more of the antibodies in the composition have an α2,3-linked sialic acid residue.

A pharmaceutical composition comprising a plurality of an antibody or antigen binding fragment, wherein none of the antibodies comprise a bisecting GlcNAc.

The pharmaceutical composition comprising the antibody or fragment thereof, wherein the composition is prepared as a lyophilisate.

A method of neutralizing a BK virus or JC virus infection comprising administering via injection or infusion to a patient in need an effective amount of the antibody.

The method wherein the patient in need is diagnosed with BK viruria or BK viremia.

The method wherein the patient in need is diagnosed with JC viruria or JC viremia.

A method of treating or reducing the likelihood of a BK virus or JC virus associated disorder, comprising administering via injection or infusion to a patient in need an effective amount of the antibody, and wherein the disorder is: nephropathy, BKVAN, hemorrhagic cystitis (HC), Progressive Multifocal Leukoencephalopathy (PML), granule cell neuronopathy (GCN), interstitial kidney disease, ureteral stenosis, vasculitis, colitis, retinitis, meningitis, and immune reconstitution inflammatory syndrome (IRIS).

The method wherein the antibody or composition is reconstituted prior to injection or infusion.

The method wherein the antibody or the pharmaceutical composition is administered in combination with another therapeutic agent.

The method wherein the therapeutic agent is an immunosuppressive agent.

The method wherein the immune suppressive agent is: a monophosphate dehydrogenase inhibitor, a purine synthesis inhibitor, a calcineurin inhibitor or an mTOR inhibitor.

The method wherein the immunosuppressive agent is mycophenolate mofetil (MMF), mycophenolate sodium, azathioprine, tacrolimus, sirolimus or cyclosporine.

The method wherein the therapeutic agent is an additional anti-VP1 antibody.

The method wherein the PML is associated with the treatment of multiple sclerosis or rheumatoid arthritis, or psoriasis.

The method wherein the multiple sclerosis treatment is natalizumab, fingolimod, or dimethyl fumarate, fumaric acid esters, or alemtuzumab.

The method wherein the rheumatoid arthritis treatment is rituximab.

The method wherein the psoriasis treatment is efalizumab.

The antibody or fragment thereof for use as a medicament.

The antibody or fragment thereof for use in the neutralization of a BK virus or JC virus infection.

The antibody or fragment thereof, for use in the treatment or reducing the likelihood of: nephropathy, BKVAN hemorrhagic cystitis (HC), Progressive Multifocal Leukoencephalopathy (PML), granule cell neuronopathy (GCN), interstitial kidney disease, ureteral stenosis, vasculitis, colitis, retinitis, meningitis, and immune reconstitution inflammatory syndrome (IRIS).

The use of the antibody or fragment thereof, administered in combination with another therapeutic agent.

The use of the antibody or fragment thereof wherein the therapeutic agent is an immunosuppressive agent.

The use of the antibody or fragment thereof wherein the immunosuppressive agent is a monophosphate dehydrogenase inhibitor, a purine synthesis inhibitor, a calcineurin inhibitor or an mTOR inhibitor.

The use of the antibody or fragment thereof wherein the immunosuppressive agent is: mycophenolate mofetil (MMF), mycophenolate sodium, azathioprine, tacrolimus, sirolimus or cyclosporine.

The use of the antibody or fragment thereof, wherein the therapeutic agent is an additional anti-BK antibody.

The use of the antibody or fragment thereof, the PML is associated with the treatment of multiple sclerosis, rheumatoid arthritis or psoriasis.

The use wherein the multiple sclerosis treatment is natalizumab, fingolimod, or dimethyl fumarate, fumaric acid esters, or alemtuzumab.

The use wherein the rheumatoid arthritis treatment is rituximab.

The use wherein the psoriasis treatment is efalizumab.

A nucleic acid that encodes the antibody or antigen binding fragment.

A vector comprising the nucleic acid.

A host cell comprising the vector.

A diagnostic reagent comprising the antibody or antigen binding fragment thereof, which is labeled.

The diagnostic reagent, wherein the label is selected from the group consisting of a radiolabel, a fluorophore, a chromophore, an imaging agent, and a metal ion.

Definitions

Unless stated otherwise, the following terms and phrases as used herein are intended to have the following meanings:

The term "antibody" as used herein refers to a polypeptide of the immunoglobulin family that is capable of binding a corresponding antigen non-covalently, reversibly, and in a specific manner. For example, a naturally occurring IgG antibody is a tetramer comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antibody" includes, but is not limited to, monoclonal antibodies, human antibodies, humanized antibodies, camelid antibodies, chimeric antibodies, and anti-idiotypic (anti-Id) antibodies (including, e.g., anti-Id antibodies to antibodies of the present disclosure). The antibodies can be of any isotype/class (e.g., IgG, IgE, IgM, IgD, IgA and IgY), or subclass (e.g., IgG1, IgG2, IgG3, IgG4, IgA1 and IgA2).

"Complementarity-determining domains" or "complementarity-determining regions" ("CDRs") interchangeably refer to the hypervariable regions of VL and VH. The CDRs are the target protein-binding site of the antibody chains that harbors specificity for such target protein. There are three CDRs (CDR1-3, numbered sequentially from the N-terminus) in each human VL or VH, constituting in total about 15-20% of the variable domains. CDRs can be referred to by their region and order. For example, "VHCDR1" or "HCDR1" both refer to the first CDR of the heavy chain variable region. The CDRs are structurally complementary to the epitope of the target protein and are thus directly responsible for the binding specificity. The remaining stretches of the VL or VH, the so-called framework regions, exhibit less variation in amino acid sequence (Kuby, Immunology, 4th ed., Chapter 4. W.H. Freeman & Co., New York, 2000).

The positions of the CDRs and framework regions can be determined using various well known definitions in the art, e.g., Kabat, Chothia, IMGT, and AbM (see, e.g., Johnson et al., Nucleic Acids Res., 29:205-206 (2001); Chothia and Lesk, J. Mol. Biol., 196:901-917 (1987); Chothia et al., Nature, 342:877-883 (1989); Chothia et al., J. Mol. Biol., 227:799-817 (1992); Lefranc, M. P., Nucleic Acids Res., 29:207-209 (2001); Al-Lazikani et al., J. Mol. Biol., 273: 927-748 (1997)). Definitions of antigen combining sites are also described in the following: Ruiz et al., Nucleic Acids Res., 28:219-221 (2000); MacCallum et al., J. Mol. Biol., 262:732-745 (1996); and Martin et al., Proc. Natl. Acad. Sci. USA, 86:9268-9272 (1989); Martin et al., Methods Enzymol., 203:121-153 (1991); and Rees et al., In Sternberg M. J. E. (ed.), Protein Structure Prediction, Oxford University Press, Oxford, 141-172 (1996). In a combined Kabat and Chothia numbering scheme, in some embodiments, the CDRs correspond to the amino acid residues that are part of a Kabat CDR, a Chothia CDR, or both. For instance, in some embodiments, the CDRs correspond to amino acid residues 26-35 (HC CDR1), 50-65 (HC CDR2), and 95-102 (HC CDR3) in a VH, e.g., a mammalian VH, e.g., a human VH; and amino acid residues 24-34 (LC CDR1), 50-56 (LC CDR2), and 89-97 (LC CDR3) in a VL, e.g., a mammalian VL, e.g., a human VL. Under IMGT the CDR amino acid residues in the VH are numbered approximately 26-35 (CDR1), 51-57 (CDR2) and 93-102 (CDR3), and the CDR amino acid residues in the VL are numbered approximately 27-32 (CDR1), 50-52 (CDR2), and 89-97 (CDR3) (numbering according to "Kabat"). Under IMGT, the CDR regions of an antibody can be determined using the program IMGT/DomainGap Align.

Both the light and heavy chains are divided into regions of structural and functional homology. The terms "constant" and "variable" are used functionally. In this regard, it will be appreciated that the variable domains of both the light (VL) and heavy (VH) chain portions determine antigen recognition and specificity. Conversely, the constant domains of the light chain (CL) and the heavy chain (CH1, CH2, or CH3) confer important biological properties such as secretion, transplacental mobility, Fc receptor binding, complement binding, and the like. By convention, the numbering of the constant region domains increases as they become more distal from the antigen binding site or amino-terminus of the antibody. The N-terminus is a variable region and at the C-terminus is a constant region; the CH3 and CL domains actually comprise the carboxy-terminal domains of the heavy and light chain, respectively.

The term "antigen binding fragment," as used herein, refers to one or more portions of an antibody that retain the ability to specifically interact with (e.g., by binding, steric hindrance, stabilizing/destabilizing, spatial distribution) an epitope of an antigen. Examples of binding fragments include, but are not limited to, single-chain Fvs (scFv), disulfide-linked Fvs (sdFv), Fab fragments, F(ab') fragments, a monovalent fragment consisting of the VL, VH, CL and CH1 domains; a F(ab)2 fragment, a bivalent fragment comprising two Fab fragments linked by a disulfide bridge at the hinge region; an Fd fragment consisting of the VH and CH1 domains; an Fv fragment consisting of the VL and VH domains of a single arm of an antibody; a dAb fragment (Ward et al., Nature 341:544-546, 1989), which consists of a VH domain; and an isolated complementarity determining region (CDR), or other epitope-binding fragments of an antibody.

Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv ("scFv"); see, e.g., Bird et al., Science 242:423-426, 1988; and Huston et al., Proc. Natl. Acad. Sci. 85:5879-5883, 1988). Such single chain antibodies are also intended to be encompassed within the term "antigen binding fragment." These antigen binding fragments are obtained using conventional techniques known to those of skill in the art, and the fragments are screened for utility in the same manner as are intact antibodies.

Antigen binding fragments can also be incorporated into single domain antibodies, maxibodies, minibodies, nanobodies, intrabodies, diabodies, triabodies, tetrabodies, v-NAR, and bis-scFv (see, e.g., Hollinger and Hudson, Nature Biotechnology 23:1126-1136, 2005). Antigen binding fragments can be grafted into scaffolds based on polypeptides such as fibronectin type III (Fn3) (see U.S. Pat. No. 6,703,199, which describes fibronectin polypeptide monobodies).

Antigen binding fragments can be incorporated into single chain molecules comprising a pair of tandem Fv segments (VH-CH1-VH-CH1) which, together with complementary light chain polypeptides, form a pair of antigen binding regions (Zapata et al., Protein Eng. 8:1057-1062, 1995; and U.S. Pat. No. 5,641,870).

The term "monoclonal antibody" or "monoclonal antibody composition" as used herein refers to polypeptides, including antibodies and antigen binding fragments that have substantially identical amino acid sequence or are derived from the same genetic source. This term also includes preparations of antibody molecules of single molecular composition. A monoclonal antibody composition displays a single binding specificity and affinity for a particular epitope.

The term "human antibody," as used herein, includes antibodies having variable regions in which both the framework and CDR regions are derived from sequences of human origin. Furthermore, if the antibody contains a constant region, the constant region also is derived from such human sequences, e.g., human germline sequences, or mutated versions of human germline sequences or antibody containing consensus framework sequences derived from human framework sequences analysis, for example, as described in Knappik et al., J. Mol. Biol. 296:57-86, 2000).

The human antibodies of the present disclosure can include amino acid residues not encoded by human sequences (e.g., mutations introduced by random or site-specific mutagenesis in vitro or by somatic mutation in vivo, or a conservative substitution to promote stability or manufacturing).

The term "recognize" as used herein refers to an antibody or antigen binding fragment thereof that finds and interacts (e.g., binds) with its epitope, whether that epitope is linear or conformational. The term "epitope" refers to a site on an antigen to which an antibody or antigen binding fragment of the disclosure specifically binds. Epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods of determining spatial conformation of epitopes include techniques in the art, for example, x-ray crystallography and 2-dimensional nuclear magnetic resonance (see, e.g., Epitope Mapping Protocols in Methods in Molecular Biology, Vol. 66, G. E. Morris, Ed. (1996)), or electron microscopy. A "paratope" is the part of the antibody which recognizes the epitope of the antigen.

The phrase "specifically binds" or "selectively binds," when used in the context of describing the interaction between an antigen (e.g., a protein) and an antibody, antibody fragment, or antibody-derived binding agent, refers to a binding reaction that is determinative of the presence of the antigen in a heterogeneous population of proteins and other biologics, e.g., in a biological sample, e.g., a blood, serum, plasma or tissue sample. Thus, under certain designated immunoassay conditions, the antibodies or binding agents with a particular binding specificity bind to a particular antigen at least two times the background and do not substantially bind in a significant amount to other antigens present in the sample. In one aspect, under designated immunoassay conditions, the antibody or binding agent with a particular binding specificity binds to a particular antigen at least ten (10) times the background and does not substantially bind in a significant amount to other antigens present in the sample. Specific binding to an antibody or binding agent under such conditions may require the antibody or agent to have been selected for its specificity for a particular protein. As desired or appropriate, this selection may be achieved by subtracting out antibodies that cross-react with molecules from other species (e.g., mouse or rat) or other subtypes. Alternatively, in some aspects, antibodies or antibody fragments are selected that cross-react with certain desired molecules.

The term "affinity" as used herein refers to the strength of interaction between antibody and antigen at single antigenic sites. Within each antigenic site, the variable region of the antibody "arm" interacts through weak non-covalent forces with antigen at numerous sites; the more interactions, the stronger the affinity.

The term "isolated antibody" refers to an antibody that is substantially free of other antibodies having different antigenic specificities. An isolated antibody that specifically binds to one antigen may, however, have cross-reactivity to other antigens. Moreover, an isolated antibody may be substantially free of other cellular material and/or chemicals.

The term "corresponding human germline sequence" refers to the nucleic acid sequence encoding a human variable region amino acid sequence or subsequence that shares the highest determined amino acid sequence identity with a reference variable region amino acid sequence or subsequence in comparison to all other all other known or inferred variable region amino acid sequences encoded by human germline immunoglobulin variable region sequences. The corresponding human germline sequence can also refer to the human variable region amino acid sequence or subsequence with the highest amino acid sequence identity with a reference variable region amino acid sequence or subsequence in comparison to all other evaluated variable region amino acid sequences. The corresponding human germline sequence can be framework regions only, complementarity determining regions only, framework and complementarity determining regions, a variable segment (as defined above), or other combinations of sequences or subsequences that comprise a variable region. Sequence identity can be determined using the methods described herein, for example, aligning two sequences using BLAST, ALIGN, or another alignment algorithm known in the art. The corresponding human germline nucleic acid or amino acid sequence can have at least about 90%, 91% 92%, 93%, 94%, 95%, 96%, 97%, 98%, 99%, or 100% sequence identity with the reference variable region nucleic acid or amino acid sequence.

A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998), for a description of immunoassay formats and conditions that can be used to determine specific immunoreactivity). Typically, a specific or selective binding reaction will produce a signal at least twice over the background signal and, more typically, at least 10 to 100 times over the background.

The term "equilibrium dissociation constant (KD, M)" refers to the dissociation rate constant (kd, time−1) divided by the association rate constant (ka, time−1, M−1). Equilibrium dissociation constants can be measured using any known method in the art. The antibodies of the present disclosure generally will have an equilibrium dissociation constant of less than about $10^{-7}$ or $10^{-8}$ M, for example, less than about $10^{-9}$ M or $10^{-10}$ M, in some aspects, less than about $10^{-11}$ M, $10^{-12}$ M or $10^{-13}$ M.

The term "bioavailability" refers to the systemic availability (i.e., blood/plasma levels) of a given amount of drug administered to a patient. Bioavailability is an absolute term that indicates measurement of both the time (rate) and total amount (extent) of drug that reaches the general circulation from an administered dosage form.

As used herein, the phrase "consisting essentially of" refers to the genera or species of active pharmaceutical agents included in a method or composition, as well as any excipients inactive for the intended purpose of the methods or compositions. In some aspects, the phrase "consisting essentially of" expressly excludes the inclusion of one or more additional active agents other than an anti-BK or JC antibody of the present disclosure. In some aspects, the phrase "consisting essentially of" expressly excludes the inclusion of one or more additional active agents other than an anti-BK or JC antibody of the present disclosure and a second co-administered agent.

The term "amino acid" refers to naturally occurring, synthetic, and unnatural amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refer to compounds that have the same basic chemical structure as a naturally occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The term "conservatively modified variant" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG, and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

For polypeptide sequences, "conservatively modified variants" include individual substitutions, deletions or additions to a polypeptide sequence which result in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles. The following eight groups contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). In some aspects, the term "conservative sequence modifications" are used to refer to amino acid modifications that do not significantly affect or alter the binding characteristics of the antibody containing the amino acid sequence.

The term "optimized" as used herein refers to a nucleotide sequence that has been altered to encode an amino acid sequence using codons that are preferred in the production cell or organism, generally a eukaryotic cell, for example, a yeast cell, a *Pichia* cell, a fungal cell, a *Trichoderma* cell, a Chinese Hamster Ovary cell (CHO) or a human cell. The optimized nucleotide sequence is engineered to retain completely or as much as possible the amino acid sequence originally encoded by the starting nucleotide sequence, which is also known as the "parental" sequence.

The terms "percent identical" or "percent identity," in the context of two or more nucleic acids or polypeptide sequences, refers to the extent to which two or more sequences or subsequences that are the same. Two sequences are "identical" if they have the same sequence of amino acids or nucleotides over the region being compared. Two sequences are "substantially identical" if two sequences have a specified percentage of amino acid residues or nucleotides that are the same (i.e., 60% identity, optionally 65%, 70%, 75%, 80%, 85%, 90%, 95%, or 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 30 nucleotides (or 10 amino acids) in length, or more preferably over a region that is 100 to 500 or 1000 or more nucleotides (or 20, 50, 200 or more amino acids) in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman, Adv. Appl. Math. 2:482c (1970), by the homology alignment algorithm of Needleman and Wunsch, J. Mol. Biol. 48:443 (1970), by the search for similarity method of Pearson and Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., Brent et al., Current Protocols in Molecular Biology, 2003).

Two examples of algorithms that are suitable for determining percent sequence identity and sequence similarity are the BLAST and BLAST 2.0 algorithms, which are described in Altschul et al., Nuc. Acids Res. 25:3389-3402, 1977; and Altschul et al., J. Mol. Biol. 215:403-410, 1990, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) or 10, M=5, N=−4 and a comparison of both strands. For amino acid sequences, the BLASTP program uses as defaults a word length of 3, and expectation (E) of 10, and the BLOSUM62 scoring matrix (see Henikoff and Henikoff, (1989) Proc. Natl. Acad. Sci. USA 89:10915)

alignments (B) of 50, expectation (E) of 10, M=5, N=−4, and a comparison of both strands.

The BLAST algorithm also performs a statistical analysis of the similarity between two sequences (see, e.g., Karlin and Altschul, Proc. Natl. Acad. Sci. USA 90:5873-5787, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The percent identity between two amino acid sequences can also be determined using the algorithm of E. Meyers and W. Miller, (Comput. Appl. Biosci. 4:11-17, 1988) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch, (J. Mol. Biol. 48:444-453, 1970), algorithm which has been incorporated into the GAP program in the GCG software package (available from University of South Florida), using either a BLOSUM 62 matrix or a PAM250 matrix, and a gap weight of 16, 14, 12, 10, 8, 6, or 4 and a length weight of 1, 2, 3, 4, 5, or 6.

Other than percentage of sequence identity noted above, another indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The term "nucleic acid" is used herein interchangeably with the term "polynucleotide" and refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, as detailed below, degenerate codon substitutions may be achieved by generating sequences in which the third position of one or more selected (or all) codons is substituted with mixed-base and/or deoxyinosine residues (Batzer et al., (1991) Nucleic Acid Res. 19:5081; Ohtsuka et al., (1985) J. Biol. Chem. 260: 2605-2608; and Rossolini et al., (1994) Mol. Cell. Probes 8:91-98).

The term "operably linked" in the context of nucleic acids refers to a functional relationship between two or more polynucleotide (e.g., DNA) segments. Typically, it refers to the functional relationship of a transcriptional regulatory sequence to a transcribed sequence. For example, a promoter or enhancer sequence is operably linked to a coding sequence if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

The terms "polypeptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Unless otherwise indicated, a particular polypeptide sequence also implicitly encompasses conservatively modified variants thereof.

The term "subject" includes human and non-human animals. Non-human animals include all vertebrates, e.g., mammals and non-mammals, such as non-human primates, sheep, dog, cow, chickens, amphibians, and reptiles. Except when noted, the terms "patient" or "subject" are used herein interchangeably.

The terms "BKV" or "BK virus" refer to a member of the family Polyomaviridae, genus Orthopolyomavirus. Polyomaviruses are icosahedral, non-enveloped, double-stranded DNA viruses with a genome of approximately 5,000 base pairs. They measure approximately 40-45 nM in diameter (Bennett et al., Microbes and Infection. 2012:14(9):672-683).

"JCV" or "JC virus" refers to a member of the family Polyomaviridae, genus Orthopolyomavirus. JCV is related to BKV, and is also an icosahedral, non-enveloped, double-stranded DNA virus with a genome of approximately 5,000 base pairs. They measure approximately 40-45 nM in diameter (Johne et al., Arch. Virol. 2011; 156(9):1627-1634).

The terms "BKV nephropathy" or "BKV-associated nephropathy" or "BKVAN" refer to the inflammatory interstitial nephropathy resulting from the lytic infection with BKV, characterized by viral cytopathogenic changes and viral gene expression, primarily in the renal tubular epithelium.

The term "VP1" refers to the major polyoma virus capsid subunit protein. "VP1 pentamers" are composed of five monomers of VP1.

TABLE 1

VP1 sequences

| Name | Sequence | SEQ ID NO |
|---|---|---|
| VP1 BKV serotype I | MAPTKRKGECPGAAPKKPKEPVQVPKLLIKGGVEVLEV KTGVDAITEVECFLNPEMGDPDENLRGFSLKLSAENDFS SDSPERKMLPCYSTARIPLPNLNEDLTCGNLLMWEAVTV QTEVIGITSMLNLHAGSQKVHEHGGGKPIQGSNFHFFAV GGDPLEMQGVLMNYRTKYPEGTITPKNPTAQSQVMNTD | (SEQ ID NO: 1) |

TABLE 1-continued

VP1 sequences

| Name | Sequence | SEQ ID NO |
|---|---|---|
| | HKAYLDKNNAYPVECWIPDPSRNENTRYFGTFTGGENV<br>PPVLHVTNTATTVLLDEQGVGPLCKADSLYVSAADICGL<br>FTNSSGTQQWRGLARYFKIRLRKRSVKNPYPISFLLSDLI<br>NRRTQRVDGQPMYGMESQVEEVRVFDGTERLPGDPDMI<br>RYIDKQGQLQTKML | |
| VP1 BKV<br>serotype II | MAPTKRKGECPGAAPKKPKEPVQVPKLLIKGGVEVLEV<br>KTGVDAITEVECFLNPEMGDPDDNLRGYSLKLTAENAFD<br>SDSPDKKMLPCYSTARIPLPNLNEDLTCGNLLMWEAVTV<br>KTEVIGITSMLNLHAGSQKVHENGGGKPVQGSNFHFFAV<br>GGDPLEMQGVLMNYRTKYPQGTITPKNPTAQSQVMNTD<br>HKAYLDKNNAYPVECWIPDPSRNENTRYFGTYTGGENV<br>PPVLHVTNTATTVLLDEQGVGPLCKADSLYVSAADICGL<br>FTNSSGTQQWRGLARYFKIRLRKRSVKNPYPISFLLSDLI<br>NRRTQKVDGQPMYGMESQVEEVRVFDGTEQLPGDPDMI<br>RYIDRQGQLQTKMV | (SEQ ID<br>NO: 2) |
| VP1 BKV<br>serotype III | MAPTKRKGECPGAAPKKPKEPVQVPKLLIKGGVEVLEV<br>KTGVDAITEVECFLNPEMGDPDDHLRGYSQHLSAENAF<br>DSDSPDKKMLPCYSTARIPLPNLNEDLTCGNLLMWEAVT<br>VKTEVIGITSMLNLHAGSQKVHENGGGKPVQGSNFHFFA<br>VGGDPLEMQGVLMNYRTKYPQGTITPKNPTAQSQVMNT<br>DHKAYLDKNNAYPVECWIPDPSKNENTRYFGTYTGGEN<br>VPPVLHVTNTATTVLLDEQGVGPLCKADSLYVSAADICG<br>LFTNSSGTQQWRGLARYFKIRLRKRSVKNPYPISFLLSDL<br>INRRTQKVDGQPMYGMESQVEEVRVFDGTEQLPGDPDM<br>IRYIDRQGQLQTKMV | (SEQ ID<br>NO: 3) |
| VP1 BKV<br>serotype IV | MAPTKRKGECPGAAPKKPKEPVQVPKLLIKGGVEVLEV<br>KTGVDAITEVECFLNPEMGDPDNDLRGYSLRLTAETAFD<br>SDSPDRKMLPCYSTARIPLPNLNEDLTCGNLLMWEAVTV<br>KTEVIGITSMLNLHAGSQKVHENGGGKPIQGSNFHFFAV<br>GGDPLEMQGVLMNYRTKYPEGTVTPKNPTAQSQVMNT<br>DHKAYLDKNNAYPVECWIPDPSRNENTRYFGTYTGGEN<br>VPPVLHVTNTATTVLLDEQGVGPLCKADSLYVSAADICG<br>LFTNSSGTQQWRGLPRYFKIRLRKRSVKNPYPISFLLSDLI<br>NRRTQRVDGQPMYGMESQVEEVRVFDGTEQLPGDPDMI<br>RYIDRQGQLQTKMV | (SEQ ID<br>NO: 4) |
| JCV VP1 | MAPTKRKGERKDPVQVPKLLIRGGVEVLEVKTGVDSITE<br>VECFLTPEMGDPDEHLRGFSKSISISDTFESDSPNKDMLP<br>CYSVARIPLPNLNEDLTCGNILMWEAVTLKTEVIGVTTL<br>MNVHSNGQATHDNGAGKPVQGTSFHFFSVGGEALELQG<br>VVFNYRTKYPDGTIFPKNATVQSQVMNTEHKAYLDKNK<br>AYPVECWVPDPTRNENTRYFGTLTGGENVPPVLHITNTA<br>TTVLLDEFGVGPLCKGDNLYLSAVDVCGMFTNRSGSQQ<br>WRGLSRYFKVQLRKRRVKNPYPISFLLTDLINRRTPRVD<br>GQPMYGMDAQVEEVRVFEGTEELPGDPDMMRYVDRYG<br>QLQTKML | (SEQ ID<br>NO: 5) |

"Virus-like particles" or "VLP" are an assembly of VP1 pentamers into viral capsids. VLPs are composed of 72 VP1 pentamers. VLPs are structurally very similar to actual virus but lack the minor capsid proteins (VP2 and VP3) as well as the viral DNA genome, and therefore are non-infectious. VLPs are useful as viral epitopes are presented in a similar conformation to the actual virus.

"IC50" (half-maximal inhibitory concentration) refers to the concentration of a particular antibody which induces a signal halfway (50%) between the baseline control and the maximum possible signal. For example, the IC50 is the concentration of antibody at which 50% of the available binding sites on the VP1 antigen are occupied.

"EC50" (half-maximal effective concentration) refers to the concentration of a particular antibody which induces a response halfway (50%) between the baseline control and the maximum possible effect after a specific exposure or treatment time. For example, the EC50 is the concentration of antibody at which virus infection is neutralized by 50%.

"EC90" refers to the concentration of a particular antibody which induces a response corresponding to 90% of the maximum possible effect after a specific exposure or treatment time. For example, the EC90 is the concentration of antibody at which virus infection is neutralized by 90%.

"Neutralization" refers to the inhibition of viral infection of a host cell, as demonstrated by the absence of viral gene expression. Without being held to any one theory, mechanisms of neutralization by a particular antibody could include blocking the interaction of viral capsid proteins with cell surface receptors or disruption of any stage of the entry and trafficking process prior to delivery of the viral genome to the nucleus of the host cell.

As used herein, the terms "treat," "treating," or "treatment" of any disease or disorder refer in one aspect, to ameliorating the disease or disorder (i.e., slowing or arresting or reducing the development of the disease or at least one of the clinical symptoms thereof). In another aspect, "treat," "treating," or "treatment" refers to alleviating or ameliorating at least one physical parameter including those which may not be discernible by the patient. In yet another aspect, "treat," "treating," or "treatment" refers to modulating the disease or disorder, either physically, (e.g., stabilization of a discernible symptom), physiologically, (e.g., stabilization of a physical parameter), or both.

The phrase "reducing the likelihood" refers to delaying the onset or development or progression of the disease, infection or disorder.

The term "therapeutically acceptable amount" or "therapeutically effective dose" interchangeably refers to an amount sufficient to effect the desired result (i.e., a reduction in tumor size, inhibition of tumor growth, prevention of metastasis, inhibition or prevention of viral, bacterial, fungal or parasitic infection). In some aspects, a therapeutically acceptable amount does not induce or cause undesirable side effects. A therapeutically acceptable amount can be determined by first administering a low dose, and then incrementally increasing that dose until the desired effect is achieved. A "prophylactically effective dosage," and a "therapeutically effective dosage," of the molecules of the present disclosure can prevent the onset of, or result in a decrease in severity of, respectively, disease symptoms, including symptoms associated polyoma viral infection.

The term "co-administer" refers to the simultaneous presence of two active agents in the blood of an individual. Active agents that are co-administered can be concurrently or sequentially delivered.

BRIEF DESCRIPTION OF THE DRAWINGS

FIGS. 3D-F are amino acid alignments of the BKV subtypes 1-4, JCV, and Merkel cell virus (MCV) VP1 protein at positions contributing to the NOV530 epitope on BKV ST1 (numbering). Highlighted residues represent conserved positions predicted to be located within a 5 Å radius of the scFv. The highlighted residues from 316-330 in FIG. 3D correspond match the VP1 chain Pentamer $B_2$ depicted in FIG. 3B. The highlighted residues 169, 182-193 in FIG. 3E correspond with Pentamer $A_4$ from FIG. 3B. The highlighted residues 59-64, 81-87, 172-176 and 198-201 in FIG. 3F correspond to Pentamer $A_3$ from FIG. 3B. FIG. 3G and FIG. 3H depict the NOV530 heavy and light chain complementarity-determining variable regions, except tyrosine-49 (in parentheses), which belongs to VK-FR2. Residues in bold text are predicted to be located within a 5 Å radius from viral amino acids. Somatically hypermutated residues are indicated by the germline amino acid above the mutated position. Underlined residues indicate CDR3 sequences generated by junctional diversity during V(D)J recombination processes.

DETAILED DESCRIPTION

Figure 1:
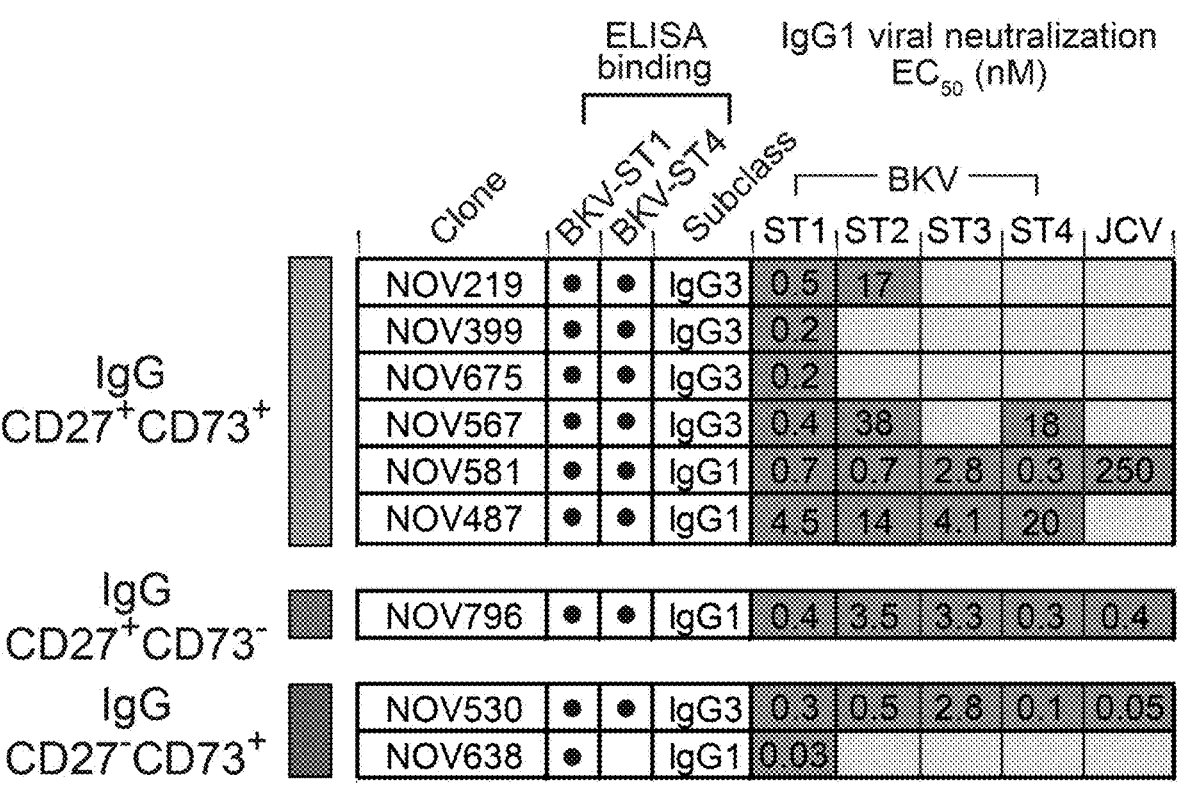
FIG. 1 graphically represents ELISA binding properties and viral neutralization capacity of a panel of antibodies, with the IC50 in nM given for each serotype neutralized.

The present disclosure provides for antibodies, antibody fragments (e.g., antigen binding fragments), that bind and neutralize BKV. Furthermore, the present disclosure provides antibodies that have desirable pharmacokinetic characteristics and other desirable attributes, and thus can be used for reducing the likelihood of or treating BK virus-associated nephropathy (e.g. BKVAN) and/or JC virus-associated progressive multifocal leukoencephalopathy (PML). The present disclosure further provides pharmaceutical compositions comprising the antibodies and methods of making and using such pharmaceutical compositions for the prevention and treatment of polyomavirus infection and associated disorders.

Anti-Polyomavirus Antibodies

The present disclosure provides for antibodies or antibody fragments (e.g., antigen binding fragments) that specifically bind to BK virus or JC virus. Antibodies or antibody fragments (e.g., antigen binding fragments) of the present disclosure include, but are not limited to, the human monoclonal antibodies or fragments thereof, isolated as described, in the Examples below.

The present disclosure in certain aspects provides antibodies or antibody fragments (e.g., antigen binding fragments) that specifically bind to BK or JC virus, said antibodies or antibody fragments (e.g., antigen binding fragments) comprise a VH domain having an amino acid sequence of SEQ ID NO: 18, 50, 82, 114, 146, 178, 210, 242 and 274 (Table 2). The present disclosure also provides antibodies or antibody fragments (e.g., antigen binding fragments) that specifically bind to BK or JC virus, said antibodies or antibody fragments (e.g., antigen binding fragments) comprise a VH CDR having an amino acid sequence of any one of the VH CDRs listed in Table 2. In particular aspects, the present disclosure provides antibodies or antibody fragments (e.g., antigen binding fragments) that specifically bind to BK or JC virus, said antibodies comprising (or alternatively, consist of) one, two, three, or more VH CDRs having an amino acid sequence of any of the VH CDRs listed in Table 2.

The present disclosure provides antibodies or antibody fragments (e.g., antigen binding fragments) that specifically bind to BK or JC virus, said antibodies or antibody fragments (e.g., antigen binding fragments) comprise a VL domain having an amino acid sequence of SEQ ID NO: 34, 66, 98, 130, 162, 194, 226, 258 and 290 (Table 2). The present disclosure also provides antibodies or antibody fragments (e.g., antigen binding fragments) that specifically bind to BK or JC virus, said antibodies or antibody fragments (e.g., antigen binding fragments) comprise a VL CDR having an amino acid sequence of any one of the VL CDRs listed in Table 2. In particular, the disclosure provides antibodies or antibody fragments (e.g., antigen binding fragments) that specifically bind to BK or JC virus, said antibodies or antibody fragments (e.g., antigen binding fragments) comprise (or alternatively, consist of) one, two, three or more VL CDRs having an amino acid sequence of any of the VL CDRs listed in Table 2.

Other antibodies or antibody fragments (e.g., antigen binding fragments) of the present disclosure include amino acids that have been mutated, yet have at least 60, 70, 80, 90 or 95 percent identity in the CDR regions with the CDR regions depicted in the sequences described in Table 2. In some aspects, it includes mutant amino acid sequences wherein no more than 1, 2, 3, 4 or 5 amino acids have been mutated in the CDR regions when compared with the CDR regions depicted in the sequence described in Table 2.

The present disclosure also provides nucleic acid sequences that encode VH, VL, the full length heavy chain, and the full length light chain of the antibodies that specifically bind to BK or JC virus. Such nucleic acid sequences can be optimized for expression in mammalian cells.

TABLE 2

| Anti-Polyoma virus Antibodies | | |
|---|---|---|
| NOV530 | | |
| SEQ ID NO: 6 (Combined) | HCDR1 | GGSISGGGYYWS |
| SEQ ID NO: 7 (Combined) | HCDR2 | YIYYNRGTYYNPALKS |
| SEQ ID NO: 8 (Combined) | HCDR3 | CVLGGYGSDAFDR |
| SEQ ID NO: 9 (Kabat) | HCDR1 | GGGYYWS |
| SEQ ID NO: 10 (Kabat) | HCDR2 | YIYYNRGTYYNPALKS |
| SEQ ID NO: 11 (Kabat) | HCDR3 | CVLGGYGSDAFDR |
| SEQ ID NO: 12 (Chothia) | HCDR1 | GGSISGGGY |
| SEQ ID NO: 13 (Chothia) | HCDR2 | YYNRG |
| SEQ ID NO: 14 (Chothia) | HCDR3 | CVLGGYGSDAFDR |
| SEQ ID NO: 15 (IMGT) | HCDR1 | GGSISGGGYY |
| SEQ ID NO: 16 (IMGT) | HCDR2 | IYYNRGT |
| SEQ ID NO: 17 (IMGT) | HCDR3 | ARCVLGGYGSDAFDR |
| SEQ ID NO: 18 | VH | QVQLQESGPGLVKPSQTLSLTCTVSGGSISGGGYYWSWIR QHPGKGLEFIGYIYYNRGTYYNPALKSRLTISVDTSKNDF SLKLSSVSAADTAVYYCARCVLGGYGSDAFDRWGQGTTVT VAS |
| SEQ ID NO: 19 | DNA VH | CAGGTGCAGCTGCAGGAGTCGGGCCCAGGACTGGTGAAGC CTTCACAGACCCTGTCCCTCACCTGCACTGTCTCTGGTGG CTCCATCAGCGGTGGTGGTTACTACTGGAGCTGGATCCGC CAGCACCCAGGGAAGGGCCTGGAGTTCATTGGATACATAT ATTATAATAGGGGCACCTACTACAATCCGGCCCTCAAGAG TCGACTTACCATATCAGTAGACACCTCTAAGAATGACTTC TCCCTGAAGCTGAGCTCTGTGAGTGCCGCGGACACGGCCG TGTATTACTGTGCGAGATGTGTCCTTGGTGGCTACGGTTC TGATGCTTTTGATAGGTGGGGCCAAGGGACAACGGTCACC GTCGCTTCA |
| SEQ ID NO: 20 | Heavy Chain | QVQLQESGPGLVKPSQTLSLTCTVSGGSISGGGYYWSWIR QHPGKGLEFIGYIYYNRGTYYNPALKSRLTISVDTSKNDF SLKLSSVSAADTAVYYCARCVLGGYGSDAFDRWGQGTTVT VASASTKGPSVFPLAPCSRSTSGGTAALGCLVKDYFPEPV TVSWNSGALTSGVHTFPTVLQSSGLYSLSSVVTVPSSSLG TQTYICNVNHKPSNTKVDKRVEPKSCDKTHTCPPCPAPEL LGGPSVFLFPPKPKDTLMISRTPEVTCVVVDVSHEDPEVK FNWYVDGVEVHNAKTKPREEQYNSTYRVVSVLTVLHQDWL NGKEYKCKVSNKALPAPIEKTISKAKGQPREPQVYTLPPS REEMTKNQVSLTCLVKGFYPSDIAVEWESNGQPENNYKTT PPVLDSDGSFFLYSKLTVDKSRWQQGNVFSCSVMHEALHN HYTQKSLSLSPGK |

TABLE 2-continued

| Anti-Polyoma virus Antibodies | | |
|---|---|---|
| SEQ ID NO: 21 | DNA<br>Heavy<br>Chain | CAGGTGCAGCTGCAGGAGTCGGGCCCAGGACTGGTGAAGC<br>CTTCACAGACCCTGTCCCTCACCTGCACTGTCTCTGGTGG<br>CTCCATCAGCGGTGGTGGTTACTACTGGAGCTGGATCCGC<br>CAGCACCCAGGGAAGGGCCTGGAGTTCATTGGATACATAT<br>ATTATAATAGGGGCACCTACTACAATCCGGCCCTCAAGAG<br>TCGACTTACCATATCAGTAGACACCTCTAAGAATGACTTC<br>TCCCTGAAGCTGAGCTCTGTGAGTGCCGCGGACACGGCCG<br>TGTATTACTGTGCGAGATGTGTCCTTGGTGGCTACGGTTC<br>TGATGCTTTTGATAGGTGGGGCCAAGGGACAACGGTCACC<br>GTCGCTTCAGCTTCCACCAAGGGCCCATCGGTCTTCCCCC<br>TGGCGCCCTGCTCCAGGAGCACCTCTGGGGGCACAGCGGC<br>CCTGGGCTGCCTGGTCAAGGACTACTTCCCCGAACCGGTG<br>ACGGTGTCGTGGAACTCAGGCGCCCTGACCAGCGGCGTGC<br>ACACCTTCCCGACTGTCCTACAGTCCTCAGGACTCTACTC<br>CCTCAGCAGCGTGGTGACCGTGCCCTCCAGCAGCTTGGGC<br>ACCCAGACCTACATCTGCAACGTGAACCACAAGCCCAGCA<br>ACACCAAGGTGGACAAGAGAGTGGAGCCCAAGAGCTGCGA<br>CAAGACCCACACCTGCCCCCCCTGCCCAGCCCCAGAGCTG<br>CTGGGCGGACCCTCCGTGTTCCTGTTCCCCCCCAAGCCCA<br>AGGACACCCTGATGATCAGCAGGACCCCCGAGGTGACCTG<br>CGTGGTGGTGGACGTGAGCCACGAGGACCCAGAGGTGAAG<br>TTCAACTGGTACGTGGACGGCGTGGAGGTGCACAACGCCA<br>AGACCAAGCCCAGAGAGGAGCAGTACAACAGCACCTACAG<br>GGTGGTGTCCGTGCTGACCGTGCTGCACCAGGACTGGCTG<br>AACGGCAAGGAATACAAGTGCAAGGTCTCCAACAAGGCCC<br>TGCCAGCCCCCATCGAAAAGACCATCAGCAAGGCCAAGGG<br>CCAGCCACGGGAGCCCCAGGTGTACACCCTGCCCCCCTCC<br>CGGGAGGAGATGACCAAGAACCAGGTGTCCCTGACCTGTC<br>TGGTGAAGGGCTTCTACCCCAGCGACATCGCCGTGGAGTG<br>GGAGAGCAACGGCCAGCCCGAGAACAACTACAAGACCACC<br>CCCCCAGTGCTGGACAGCGACGGCAGCTTCTTCCTGTACA<br>GCAAGCTGACCGTGGACAAGTCCAGGTGGCAGCAGGGCAA<br>CGTGTTCAGCTGCAGCGTGATGCACGAGGCCCTGCACAAC<br>CACTACACCCAGAAGAGCCTGAGCCTGTCCCCCGGCAAG |
| SEQ ID NO: 22<br>(Combined) | LCDR1 | RASQSVSSHLA |
| SEQ ID NO: 23<br>(Combined) | LCDR2 | DASSRAN |
| SEQ ID NO: 24<br>(Combined) | LCDR3 | QQRSSWPPSLT |
| SEQ ID NO: 25<br>(Kabat) | LCDR1 | RASQSVSSHLA |
| SEQ ID NO: 26<br>(Kabat) | LCDR2 | DASSRAN |
| SEQ ID NO: 27<br>(Kabat) | LCDR3 | QQRSSWPPSLT |
| SEQ ID NO: 28<br>(Chothia) | LCDR1 | SQSVSSH |
| SEQ ID NO: 29<br>(Chothia) | LCDR2 | DAS |
| SEQ ID NO: 30<br>(Chothia) | LCDR3 | RSSWPPSL |
| SEQ ID NO: 31<br>(IMGT) | LCDR1 | QSVSSH |
| SEQ ID NO: 32<br>(IMGT) | LCDR2 | DASSRANGIP |
| SEQ ID NO: 33<br>(IMGT) | LCDR3 | QQRSSWPPSLT |
| SEQ ID NO: 34 | VL | EIVLTQSPVTLSLSPGERAILSCRASQSVSSHLAWYQQKP<br>GQAPRLLIYDASSRANGIPARFSGSGSGTDFTLTISSLAP<br>EDFAVYYCQQRSSWPPSLTFGGGTKVEIR |
| SEQ ID NO: 35 | DNA VL | GAAATTGTGTTGACACAGTCCCCAGTCACCCTGTCTTTGT<br>CTCCAGGGGAAAGAGCCATCCTCTCCTGTAGGGCCAGTCA<br>GAGTGTTAGCAGCCACTTAGCCTGGTACCAACAGAAGCCT |

TABLE 2-continued

Anti-Polyoma virus Antibodies

|  |  |  |
|---|---|---|
|  |  | GGCCAGGCTCCCAGGCTCCTCATCTATGATGCATCCAGCA GGGCCAATGGCATCCCAGCCAGGTTCAGTGGCAGTGGGTC TGGGACAGACTTCACTCTCACCATCAGCAGCCTAGCGCCT GAAGATTTTGCAGTTTATTACTGTCAGCAGCGTAGCAGCT GGCCTCCGTCCCTCACTTTCGGCGGAGGGACCAAGGTGGA GATCAGA |
| SEQ ID NO: 36 | Light Chain | EIVLTQSPVTLSLSPGERAILSCRASQSVSSHLAWYQQKP GQAPRLLIYDASSRANGIPARFSGSGSGTDFTLTISSLAP EDFAVYYCQQRSSWPPSLTFGGGTKVEIRRTVAAPSVFIF PPSDEQLKSGTASVVCLLNNFYPREAKVQWKVDNALQSGN SQESVTEQDSKDSTYSLSSTLTLSKADYEKHKVYACEVTH QGLSSPVTKSFNRGEC |
| SEQ ID NO: 37 | DNA Light Chain | GAAATTGTGTTGACACAGTCCCCAGTCACCCTGTCTTTGT CTCCAGGGGAAAGAGCCATCCTCTCCTGTAGGGCCAGTCA GAGTGTTAGCAGCCACTTAGCCTGGTACCAACAGAAGCCT GGCCAGGCTCCCAGGCTCCTCATCTATGATGCATCCAGCA GGGCCAATGGCATCCCAGCCAGGTTCAGTGGCAGTGGGTC TGGGACAGACTTCACTCTCACCATCAGCAGCCTAGCGCCT GAAGATTTTGCAGTTTATTACTGTCAGCAGCGTAGCAGCT GGCCTCCGTCCCTCACTTTCGGCGGAGGGACCAAGGTGGA GATCAGACGAACTGTGGCTGCACCATCTGTCTTCATCTTC CCGCCATCTGATGAGCAGTTGAAATCTGGAACTGCCTCTG TTGTGTGCCTGCTGAATAACTTCTATCCCAGAGAGGCCAA AGTACAGTGGAAGGTGGACAACGCCCTGCAGAGCGGCAAC AGCCAGGAGAGCGTCACCGAGCAGGACAGCAAGGACTCCA CCTACAGCCTGAGCAGCACCCTGACCCTGAGCAAGGCCGA CTACGAGAAGCATAAGGTGTACGCCTGCGAGGTGACCCAC CAGGGCCTGTCCAGCCCCGTGACCAAGAGCTTCAACAGGG GCGAGTGC |
| NOV399 | | |
| SEQ ID NO: 38 (Combined) | HCDR1 | GFTFRSYMMN |
| SEQ ID NO: 39 (Combined) | HCDR2 | YISGSGGTKYYVDSVKG |
| SEQ ID NO: 40 (Combined) | HCDR3 | DLDCSGGTCYDGMDV |
| SEQ ID NO: 41 (Kabat) | HCDR1 | SYMMN |
| SEQ ID NO: 42 (Kabat) | HCDR2 | YISGSGGTKYYVDSVKG |
| SEQ ID NO: 43 (Kabat) | HCDR3 | DLDCSGGTCYDGMDV |
| SEQ ID NO: 44 (Chothia) | HCDR1 | GFTFRSY |
| SEQ ID NO: 45 (Chothia) | HCDR2 | SGSGGT |
| SEQ ID NO: 46 (Chothia) | HCDR3 | DLDCSGGTCYDGMDV |
| SEQ ID NO: 47 (IMGT) | HCDR1 | GFTFRSYM |
| SEQ ID NO: 48 (IMGT) | HCDR2 | ISGSGGTK |
| SEQ ID NO: 49 (IMGT) | HCDR3 | ARDLDCSGGTCYDGMDV |
| SEQ ID NO: 50 | VH | EVQLVESGGGLVQPGGSLRLSCAASGFTFRSYMMNWVRQA PGKGLEWVSYISGSGGTKYYVDSVKGRFTISRDNAKNSLY LQMHSLRAEDTAVYYCARDLDCSGGTCYDGMDVWGQGTTV TVSS |
| SEQ ID NO: 51 | DNA VH | GAGGTGCAGCTGGTGGAGTCGGGGGGAGGCTTGGTACAGC CTGGGGGGTCCCTGAGACTCTCCTGTGCAGCCTCTGGATT CACCTTCAGGAGTTATATGATGAATTGGGTCCGCCAGGCT |

TABLE 2-continued

Anti-Polyoma virus Antibodies

|  |  |  |
|---|---|---|
|  |  | CCAGGGAAGGGGCTGGAGTGGGTTTCATATATTAGTGGTA GTGGTGGAACCAAATACTACGTAGACTCTGTGAAGGGCCG ATTCACCATATCCAGAGACAACGCCAAGAACTCACTGTAT CTGCAAATGCACAGCCTGAGAGCCGAGGACACGGCTGTGT ATTACTGTGCGAGAGATCTCGATTGCAGTGGTGGGACCTG CTACGACGGTATGGACGTCTGGGGCCAAGGGACCACGGTC ACCGTCTCCTCA |
| SEQ ID NO: 52 | Heavy Chain | EVQLVESGGGLVQPGGSLRLSCAASGFTFRSYMMNWVRQA PGKGLEWVSYISGSGGTKYYVDSVKGRFTISRDNAKNSLY LQMHSLRAEDTAVYYCARDLDCSGGTCYDGMDVWGQGTTV TVSSASTKGPSVFPLAPCSRSTSGGTAALGCLVKDYFPEP VTVSWNSGALTSGVHTFPAVLQSSGLYSLSSVVTVPSSSL GTQTYICNVNHKPSNTKVDKRVEPKSCDKTHTCPPCPAPE LLGGPSVFLFPPKPKDTLMISRTPEVTCVVVDVSHEDPEV KFNWYVDGVEVHNAKTKPREEQYNSTYRVVSVLTVLHQDW LNGKEYKCKVSNKALPAPIEKTISKAKGQPREPQVYTLPP SREEMTKNQVSLTCLVKGFYPSDIAVEWESNGQPENNYKT TPPVLDSDGSFFLYSKLTVDKSRWQQGNVFSCSVMHEALH NHYTQKSLSLSPGK |
| SEQ ID NO: 53 | DNA Heavy Chain | GAGGTGCAGCTGGTGGAGTCGGGGGGAGGCTTGGTACAGC CTGGGGGGTCCCTGAGACTCTCCTGTGCAGCCTCTGGATT CACCTTCAGGAGTTATATGATGAATTGGGTCCGCCAGGCT CCAGGGAAGGGGCTGGAGTGGGTTTCATATATTAGTGGTA GTGGTGGAACCAAATACTACGTAGACTCTGTGAAGGGCCG ATTCACCATATCCAGAGACAACGCCAAGAACTCACTGTAT CTGCAAATGCACAGCCTGAGAGCCGAGGACACGGCTGTGT ATTACTGTGCGAGAGATCTCGATTGCAGTGGTGGGACCTG CTACGACGGTATGGACGTCTGGGGCCAAGGGACCACGGTC ACCGTCTCCTCAGCTTCCACCAAGGGCCCATCGGTCTTCC CCCTGGCGCCCTGCTCCAGGAGCACCTCTGGGGGCACAGC GGCCCTGGGCTGCCTGGTCAAGGACTACTTCCCCGAACCG GTGACGGTGTCGTGGAACTCAGGCGCCCTGACCAGCGGCG TGCACACCTTCCCGGCTGTCCTACAGTCCTCAGGACTCTA CTCCCTCAGCAGCGTGGTGACCGTGCCCTCCAGCAGCTTG GGCACCCAGACCTACATCTGCAACGTGAACCACAAGCCCA GCAACACCAAGGTGGACAAGAGAGTGGAGCCCAAGAGCTG CGACAAGACCCACACCTGCCCCCCCTGCCCAGCCCCAGAG CTGCTGGGCGGACCCTCCGTGTTCCTGTTCCCCCCCAAGC CCAAGGACACCCTGATGATCAGCAGGACCCCCGAGGTGAC CTGCGTGGTGGTGGACGTGAGCCACGAGGACCCAGAGGTG AAGTTCAACTGGTACGTGGACGGCGTGGAGGTGCACAACG CCAAGACCAAGCCCAGAGAGGAGCAGTACAACAGCACCTA CAGGGTGGTGTCCGTGCTGACCGTGCTGCACCAGGACTGG CTGAACGGCAAGGAATACAAGTGCAAGGTCTCCAACAAGG CCCTGCCAGCCCCCATCGAAAAGACCATCAGCAAGGCCAA GGGCCAGCCACGGGAGCCCCAGGTGTACACCCTGCCCCCC TCCCGGGAGGAGATGACCAAGAACCAGGTGTCCCTGACCT GTCTGGTGAAGGGCTTCTACCCCAGCGACATCGCCGTGGA GTGGGAGAGCAACGGCCAGCCCGAGAACAACTACAAGACC ACCCCCCCAGTGCTGGACAGCGACGGCAGCTTCTTCCTGT ACAGCAAGCTGACCGTGGACAAGTCCAGGTGGCAGCAGGG CAACGTGTTCAGCTGCAGCGTGATGCACGAGGCCCTGCAC AACCACTACACCCAGAAGAGCCTGAGCCTGTCCCCCGGCA AG |
| SEQ ID NO: 54 (Combined) | LCDR1 | SGDKLGNKYVY |
| SEQ ID NO: 55 (Combined) | LCDR2 | QHTKRPS |
| SEQ ID NO: 56 (Combined) | LCDR3 | QAWDSSIVI |
| SEQ ID NO: 57 (Kabat) | LCDR1 | SGDKLGNKYVY |
| SEQ ID NO: 58 (Kabat) | LCDR2 | QHTKRPS |
| SEQ ID NO: 59 (Kabat) | LCDR3 | QAWDSSIVI |
| SEQ ID NO: 60 (Chothia) | LCDR1 | DKLGNKY |

TABLE 2-continued

Anti-Polyoma virus Antibodies

| SEQ ID NO: 61 (Chothia) | LCDR2 | QHT |
| --- | --- | --- |
| SEQ ID NO: 62 (Chothia) | LCDR3 | WDSSIV |
| SEQ ID NO: 63 (IMGT) | LCDR1 | KLGNKY |
| SEQ ID NO: 64 (IMGT) | LCDR2 | QHT |
| SEQ ID NO: 65 (IMGT) | LCDR3 | QAWDSSIVI |
| SEQ ID NO: 66 | VL | SYELTQPPSVSVSPGQTATITCSGDKLGNKYVYWFQHRPG QSPVLVIYQHTKRPSGIPERFSGSNSGNTATLTISGTQAM DEADYYCQAWDSSIVIFGGGTKLTVL |
| SEQ ID NO: 67 | DNA VL | TCCTATGAGCTGACTCAGCCACCCTCAGTGTCCGTGTCCC CTGGACAGACAGCCACCATCACCTGCTCTGGAGATAAATT GGGTAATAAATATGTTTACTGGTTTCAGCACAGGCCAGGC CAGTCCCCTGTGCTGGTCATCTATCAACATACCAAGCGGC CCTCAGGGATCCCTGAGCGATTCTCTGGCTCCAACTCTGG GAACACAGCCACTCTGACCATCAGCGGGACCCAGGCTATG GATGAGGCTGACTATTACTGTCAGGCGTGGGACAGTAGCA TTGTGATATTCGGCGGAGGGACCAAGCTGACCGTCCTA |
| SEQ ID NO: 68 | Light Chain | SYELTQPPSVSVSPGQTATITCSGDKLGNKYVYWFQHRPG QSPVLVIYQHTKRPSGIPERFSGSNSGNTATLTISGTQAM DEADYYCQAWDSSIVIFGGGTKLTVLGQPKAAPSVTLFPP SSEELQANKATLVCLISDFYPGAVTVAWKADSSPVKAGVE TTTPSKQSNNKYAASSYLSLTPEQWKSHRSYSCQVTHEGS TVEKTVAPTECS |
| SEQ ID NO: 69 | DNA Light Chain | TCCTATGAGCTGACTCAGCCACCCTCAGTGTCCGTGTCCC CTGGACAGACAGCCACCATCACCTGCTCTGGAGATAAATT GGGTAATAAATATGTTTACTGGTTTCAGCACAGGCCAGGC CAGTCCCCTGTGCTGGTCATCTATCAACATACCAAGCGGC CCTCAGGGATCCCTGAGCGATTCTCTGGCTCCAACTCTGG GAACACAGCCACTCTGACCATCAGCGGGACCCAGGCTATG GATGAGGCTGACTATTACTGTCAGGCGTGGGACAGTAGCA TTGTGATATTCGGCGGAGGGACCAAGCTGACCGTCCTAGG TCAGCCCAAGGCTGCCCCCTCGGTCACTCTGTTCCCGCCC TCCTCTGAGGAGCTTCAAGCCAACAAGGCCACACTGGTGT GTCTCATAAGTGACTTCTACCCGGGAGCCGTGACAGTGGC CTGGAAGGCAGATAGCAGCCCCGTCAAGGCGGGAGTGGAG ACCACCACACCCTCCAAACAAAGCAACAACAAGTACGCCG CCAGCAGCTACCTGAGCCTGACCCCCGAGCAGTGGAAGAG CCACAGAAGCTACAGCTGCCAGGTCACCCACGAGGGCAGC ACCGTGGAGAAAACCGTGGCCCCCACCGAGTGCAGC |

NOV567

| SEQ ID NO: 70 (Combined) | HCDR1 | GYTFTAYYMH |
| --- | --- | --- |
| SEQ ID NO: 71 (Combined) | HCDR2 | WINPNTGVTNFAQKFQG |
| SEQ ID NO: 72 (Combined) | HCDR3 | DRDASMASYYYGMDV |
| SEQ ID NO: 73 (Kabat) | HCDR1 | AYYMH |
| SEQ ID NO: 74 (Kabat) | HCDR2 | WINPNTGVTNFAQKFQG |
| SEQ ID NO: 75 (Kabat) | HCDR3 | DRDASMASYYYGMDV |
| SEQ ID NO: 76 (Chothia) | HCDR1 | GYTFTAY |
| SEQ ID NO: 77 (Chothia) | HCDR2 | NPNTGV |

TABLE 2-continued

| Anti-Polyoma virus Antibodies | | |
| --- | --- | --- |
| SEQ ID NO: 78 (Chothia) | HCDR3 | DRDASMASYYYYGMDV |
| SEQ ID NO: 79 (IMGT) | HCDR1 | GYTFTAYY |
| SEQ ID NO: 80 (IMGT) | HCDR2 | INPNTGVT |
| SEQ ID NO: 81 (IMGT) | HCDR3 | ARDRDASMASYYYYGMDV |
| SEQ ID NO: 82 | VH | QVQLVQSGAEVKKPGASVKVSCKASGYTFTAYYMHWVRQA<br>PGQGLEWMGWINPNTGVTNFAQKFQGRVTMTRDTSIGTAY<br>IELSWLRSDDTAVYYCARDRDASMASYYYYGMDVWGQGTT<br>VTVSS |
| SEQ ID NO: 83 | DNA VH | CAGGTGCAGCTGGTGCAGTCTGGGGCTGAGGTGAAGAAGC<br>CTGGGGCCTCAGTGAAGGTCTCCTGCAAGGCTTCTGGATA<br>CACCTTCACCGCCTATTATATGCACTGGGTGCGACAGGCC<br>CCTGGACAAGGGCTTGAGTGGATGGGCTGGATCAACCCTA<br>ACACTGGTGTCACAAACTTTGCACAGAAGTTTCAGGGCAG<br>GGTCACCATGACCAGGGACACGTCCATCGGCACAGCCTAC<br>ATTGAATTGAGCTGGCTGAGATCTGACGACACGGCCGTGT<br>ATTACTGTGCGAGGGATAGGGATGCATCTATGGCCTCCTA<br>CTACTACTACGGTATGGACGTCTGGGGCCAAGGGACCACG<br>GTCACCGTCTCCTCA |
| SEQ ID NO: 84 | Heavy Chain | QVQLVQSGAEVKKPGASVKVSCKASGYTFTAYYMHWVRQA<br>PGQGLEWMGWINPNTGVTNFAQKFQGRVTMTRDTSIGTAY<br>IELSWLRSDDTAVYYCARDRDASMASYYYYGMDVWGQGTT<br>VTVSSASTKGPSVFPLAPCSRSTSGGTAALGCLVKDYFPE<br>PVTVSWNSGALTSGVHTFPAVLQSSGLYSLSSVVTVPSSS<br>LGTQTYICNVNHKPSNTKVDKRVEPKSCDKTHTCPPCPAP<br>ELLGGPSVFLFPPKPKDTLMISRTPEVTCVVVDVSHEDPE<br>VKFNWYVDGVEVHNAKTKPREEQYNSTYRVVSVLTVLHQD<br>WLNGKEYKCKVSNKALPAPIEKTISKAKGQPREPQVYTLP<br>PSREEMTKNQVSLTCLVKGFYPSDIAVEWESNGQPENNYK<br>TTPPVLDSDGSFFLYSKLTVDKSRWQQGNVFSCSVMHEAL<br>HNHYTQKSLSLSPGK |
| SEQ ID NO: 85 | DNA Heavy Chain | CAGGTGCAGCTGGTGCAGTCTGGGGCTGAGGTGAAGAAGC<br>CTGGGGCCTCAGTGAAGGTCTCCTGCAAGGCTTCTGGATA<br>CACCTTCACCGCCTATTATATGCACTGGGTGCGACAGGCC<br>CCTGGACAAGGGCTTGAGTGGATGGGCTGGATCAACCCTA<br>ACACTGGTGTCACAAACTTTGCACAGAAGTTTCAGGGCAG<br>GGTCACCATGACCAGGGACACGTCCATCGGCACAGCCTAC<br>ATTGAATTGAGCTGGCTGAGATCTGACGACACGGCCGTGT<br>ATTACTGTGCGAGGGATAGGGATGCATCTATGGCCTCCTA<br>CTACTACTACGGTATGGACGTCTGGGGCCAAGGGACCACG<br>GTCACCGTCTCCTCAGCTTCCACCAAGGGCCCATCGGTCT<br>TCCCCCTGGCGCCCTGCTCCAGGAGCACCTCTGGGGGCAC<br>AGCGGCCCTGGGCTGCCTGGTCAAGGACTACTTCCCCGAA<br>CCGGTGACGGTGTCGTGGAACTCAGGCGCCCTGACCAGCG<br>GCGTGCACACCTTCCCGGCTGTCCTACAGTCCTCAGGACT<br>CTACTCCCTCAGCAGCGTGGTGACCGTGCCCTCCAGCAGC<br>TTGGGCACCCAGACCTACATCTGCAACGTGAACCACAAGC<br>CCAGCAACACCAAGGTGGACAAGAGAGTGGAGCCCAAGAG<br>CTGCGACAAGACCCACACCTGCCCCCCCTGCCCAGCCCCA<br>GAGCTGCTGGGCGGACCCTCCGTGTTCCTGTTCCCCCCCA<br>AGCCCAAGGACACCCTGATGATCAGCAGGACCCCCGAGGT<br>GACCTGCGTGGTGGTGGACGTGAGCCACGAGGACCCAGAG<br>GTGAAGTTCAACTGGTACGTGGACGGCGTGGAGGTGCACA<br>ACGCCAAGACCAAGCCCAGAGAGGAGCAGTACAACAGCAC<br>CTACAGGGTGGTGTCCGTGCTGACCGTGCTGCACCAGGAC<br>TGGCTGAACGGCAAGGAATACAAGTGCAAGGTCTCCAACA<br>AGGCCCTGCCAGCCCCCATCGRAAAGACCATCAGCAAGGC<br>CAAGGGCCAGCCACGGGAGCCCCAGGTGTACACCCTGCCC<br>CCCTCCCGGGAGGAGATGACCAAGAACCAGGTGTCCCTGA<br>CCTGTCTGGTGAAGGGCTTCTACCCCAGCGACATCGCCGT<br>GGAGTGGGAGAGCAACGGCCAGCCCGAGAACAACTACAAG<br>ACCACCCCCCCAGTGCTGGACAGCGACGGCAGCTTCTTCC<br>TGTACAGCAAGCTGACCGTGGACAAGTCCAGGTGGCAGCA<br>GGGCAACGTGTTCAGCTGCAGCGTGATGCACGAGGCCCTG<br>CACAACCACTACACCCAGAAGAGCCTGAGCCTGTCCCCCG<br>GCAAG |

TABLE 2-continued

Anti-Polyoma virus Antibodies

| SEQ ID NO: 86 (Combined) | LCDR1 | SGSSSNIGNNYVS |
|---|---|---|
| SEQ ID NO: 87 (Combined) | LCDR2 | DNYKRPS |
| SEQ ID NO: 88 (Combined) | LCDR3 | GTWDRSLSAW |
| SEQ ID NO: 89 (Kabat) | LCDR1 | SGSSSNIGNNYVS |
| SEQ ID NO: 90 (Kabat) | LCDR2 | DNYKRPS |
| SEQ ID NO: 91 (Kabat) | LCDR3 | GTWDRSLSAW |
| SEQ ID NO: 92 (Chothia) | LCDR1 | SSSNIGNNY |
| SEQ ID NO: 93 (Chothia) | LCDR2 | DNY |
| SEQ ID NO: 94 (Chothia) | LCDR3 | WDRSLSAV |
| SEQ ID NO: 95 (IMGT) | LCDR1 | SSNIGNNY |
| SEQ ID NO: 96 (IMGT) | LCDR2 | DNY |
| SEQ ID NO: 97 (IMGT) | LCDR3 | GTWDRSLSAW |
| SEQ ID NO: 98 | VL | QSVLTQPPSVSAAAGQKVTISCSGSSSNIGNNYVSWYQHL PGTAPKLLIYDNYKRPSGIPDRFSGSKSGTSATLGITGLQ TGDEADYYCGTWDRSLSAWFGGGTKLTVL |
| SEQ ID NO: 99 | DNA VL | CAGTCTGTGCTGACGCAGCCGCCCTCAGTGTCTGCGGCCG CAGGACAGAAGGTCACCATCTCCTGCTCTGGAAGCAGTTC CAACATTGGGAATAATTATGTATCCTGGTACCAGCACCTC CCAGGAACAGCCCCCAAACTCCTCATTTATGACAATTATA AGCGACCCTCAGGGATTCCTGACCGATTCTCTGGCTCCAA GTCTGGCACGTCAGCCACCCTGGGCATCACCGGACTCCAG ACTGGGGACGAGGCCGACTATTATTGCGGAACATGGGATA GGAGCCTGAGTGCTGTGGTATTCGGCGGAGGGACCAAGCT GACCGTCCTA |
| SEQ ID NO: 100 | Light Chain | QSVLTQPPSVSAAAGQKVTISCSGSSSNIGNNYVSWYQHL PGTAPKLLIYDNYKRPSGIPDRFSGSKSGTSATLGITGLQ TGDEADYYCGTWDRSLSAVVFGGGTKLTVLGQPKAAPSVT LFPPSSEELQANKATLVCLISDFYPGAVTVAWKADSSPVK AGVETTTPSKQSNNKYAASSYLSLTPEQWKSHRSYSCQVT HEGSTVEKTVAPTECS |
| SEQ ID NO: 101 | DNA Light Chain | CAGTCTGTGCTGACGCAGCCGCCCTCAGTGTCTGCGGCCG CAGGACAGAAGGTCACCATCTCCTGCTCTGGAAGCAGTTC CAACATTGGGAATAATTATGTATCCTGGTACCAGCACCTC CCAGGAACAGCCCCCAAACTCCTCATTTATGACAATTATA AGCGACCCTCAGGGATTCCTGACCGATTCTCTGGCTCCAA GTCTGGCACGTCAGCCACCCTGGGCATCACCGGACTCCAG ACTGGGGACGAGGCCGACTATTATTGCGGAACATGGGATA GGAGCCTGAGTGCTGTGGTATTCGGCGGAGGGACCAAGCT GACCGTCCTAGGTCAGCCCAAGGCTGCCCCCTCGGTCACT CTGTTCCCGCCCTCCTCTGAGGAGCTTCAAGCCAACAAGG CCACACTGGTGTGTCTCATAAGTGACTTCTACCCGGGAGC CGTGACAGTGGCCTGGAAGGCAGATAGCAGCCCCGTCAAG GCGGGAGTGGAGACCACCACACCCTCCAAACAAAGCAACA ACAAGTACGCCGCCAGCAGCTATCTGAGCCTGACGCCTGA GCAGTGGAAGTCCCACAGAAGCTACAGCTGCCAGGTCACC CACGAGGGCAGCACCGTGGAGAAAACCGTGGCCCCCACCG AGTGCAGC |

TABLE 2-continued

| Anti-Polyoma virus Antibodies | | |
|---|---|---|

NOV675

| SEQ ID NO: 102 (Combined) | HCDR1 | GYRFTSHWIS |
|---|---|---|
| SEQ ID NO: 103 (Combined) | HCDR2 | RIDPSDSYIKYSPSFQG |
| SEQ ID NO: 104 (Combined) | HCDR3 | LGYSSGWYYFDY |
| SEQ ID NO: 105 (Kabat) | HCDR1 | SHWIS |
| SEQ ID NO: 106 (Kabat) | HCDR2 | RIDPSDSYIKYSPSFQG |
| SEQ ID NO: 107 (Kabat) | HCDR3 | LGYSSGWYYFDY |
| SEQ ID NO: 108 (Chothia) | HCDR1 | GYRFTSH |
| SEQ ID NO: 109 (Chothia) | HCDR2 | DPSDSY |
| SEQ ID NO: 110 (Chothia) | HCDR3 | LGYSSGWYYFDY |
| SEQ ID NO: 111 (IMGT) | HCDR1 | GYRFTSHW |
| SEQ ID NO: 112 (IMGT) | HCDR2 | IDPSDSYI |
| SEQ ID NO: 113 (IMGT) | HCDR3 | ARLGYSSGWYYFDY |
| SEQ ID NO: 114 | VH | EVQLVQSGAEVKKPGESLRISCKGSGYRFTSHWISWVRQM PGKGLEWVARIDPSDSYIKYSPSFQGHVTISADKSTSTAF LQWSSLKASDTAMYYCARLGYSSGWYYFDYWGQGTLVTVS S |
| SEQ ID NO: 115 | DNA VH | GAAGTGCAGCTGGTGCAGTCTGGAGCAGAGGTGAAAAAGC CCGGGGAGTCTCTGAGGATCTCTTGTAAGGGTTCTGGATA CAGGTTTACCAGCCACTGGATCAGCTGGGTGCGCCAGATG CCCGGGAAAGGCCTGGAGTGGGTGGCGAGGATTGATCCTA GTGACTCTTATATCAAGTACAGCCCGTCCTTCCAAGGCCA CGTCACCATCTCAGCTGACAAGTCCACCAGCACAGCCTTC CTGCAGTGGAGCAGCCTGAAGGCCTCGGACACCGCCATGT ATTACTGTGCGAGACTAGGGTATAGCAGTGGCTGGTACTA TTTTGACTACTGGGGCCAGGGAACCCTGGTCACCGTCTCC TCA |
| SEQ ID NO: 116 | Heavy Chain | EVQLVQSGAEVKKPGESLRISCKGSGYRFTSHWISWVRQM PGKGLEWVARIDPSDSYIKYSPSFQGHVTISADKSTSTAF LQWSSLKASDTAMYYCARLGYSSGWYYFDYWGQGTLVTVS SASTKGPSVFPLAPCSRSTSGGTAALGCLVKDYFPEPVTV SWNSGALTSGVHTFPAVLQSSGLYSLSSVVTVPSSSLGTQ TYICNVNHKPSNTKVDKRVEPKSCDKTHTCPPCPAPELLG GPSVFLFPPKPKDTLMISRTPEVTCVVVDVSHEDPEVKFN WYVDGVEVHNAKTKPREEQYNSTYRVVSVLTVLHQDWLNG KEYKCKVSNKALPAPIEKTISKAKGQPREPQVYTLPPSRE EMTKNQVSLTCLVKGFYPSDIAVEWESNGQPENNYKTTPP VLDSDGSFFLYSKLTVDKSRWQQGNVFSCSVMHEALHNHY TQKSLSLSPGK |
| SEQ ID NO: 117 | DNA Heavy Chain | GAAGTGCAGCTGGTGCAGTCTGGAGCAGAGGTGAAAAAGC CCGGGGAGTCTCTGAGGATCTCTTGTAAGGGTTCTGGATA CAGGTTTACCAGCCACTGGATCAGCTGGGTGCGCCAGATG CCCGGGAAAGGCCTGGAGTGGGTGGCGAGGATTGATCCTA GTGACTCTTATATCAAGTACAGCCCGTCCTTCCAAGGCCA CGTCACCATCTCAGCTGACAAGTCCACCAGCACAGCCTTC CTGCAGTGGAGCAGCCTGAAGGCCTCGGACACCGCCATGT ATTACTGTGCGAGACTAGGGTATAGCAGTGGCTGGTACTA TTTTGACTACTGGGGCCAGGGAACCCTGGTCACCGTCTCC TCAGCTTCCACCAAGGGCCCATCGGTCTTCCCCCTGGCGC CCTGCTCCAGGAGCACCTCTGGGGGCACAGCGGCCCTGGG |

TABLE 2-continued

Anti-Polyoma virus Antibodies

```
                                    CTGCCTGGTCAAGGACTACTTCCCCGAACCGGTGACGGTG
                                    TCGTGGAACTCAGGCGCCCTGACCAGCGGCGTGCACACCT
                                    TCCCGGCTGTCCTACAGTCCTCAGGACTCTACTCCCTCAG
                                    CAGCGTGGTGACCGTGCCCTCCAGCAGCTTGGGCACCCAG
                                    ACCTACATCTGCAACGTGAACCACAAGCCCAGCAACACCA
                                    AGGTGGACAAGAGAGTGGAGCCCAAGAGCTGCGACAAGAC
                                    CCACACCTGCCCCCCCTGCCCAGCCCCAGAGCTGCTGGGC
                                    GGACCCTCCGTGTTCCTGTTCCCCCCCAAGCCCAAGGACA
                                    CCCTGATGATCAGCAGGACCCCCGAGGTGACCTGCGTGGT
                                    GGTGGACGTGAGCCACGAGGACCCAGAGGTGAAGTTCAAC
                                    TGGTACGTGGACGGCGTGGAGGTGCACAACGCCAAGACCA
                                    AGCCCAGAGAGGAGCAGTACAACAGCACCTACAGGGTGGT
                                    GTCCGTGCTGACCGTGCTGCACCAGGACTGGCTGAACGGC
                                    AAGGAATACAAGTGCAAGGTCTCCAACAAGGCCCTGCCAG
                                    CCCCCATCGAAAAGACCATCAGCAAGGCCAAGGGCCAGCC
                                    ACGGGAGCCCCAGGTGTACACCCTGCCCCCCTCCCGGGAG
                                    GAGATGACCAAGAACCAGGTGTCCCTGACCTGTCTGGTGA
                                    AGGGCTTCTACCCCAGCGACATCGCCGTGGAGTGGGAGAG
                                    CAACGGCCAGCCCGAGAACAACTACAAGACCACCCCCCCA
                                    GTGCTGGACAGCGACGGCAGCTTCTTCCTGTACAGCAAGC
                                    TGACCGTGGACAAGTCCAGGTGGCAGCAGGGCAACGTGTT
                                    CAGCTGCAGCGTGATGCACGAGGCCCTGCACAACCACTAC
                                    ACCCAGAAGAGCCTGAGCCTGTCCCCCGGCAAG

SEQ ID NO: 118        LCDR1        SGSRTNIGSNAVN
(Combined)

SEQ ID                LCDR2        SSDQRPS
NO: 119 (Combined)

SEQ ID                LCDR3        AAWDDSLHGWV
NO: 120 (Combined)

SEQ ID                LCDR1        SGSRTNIGSNAVN
NO: 121 (Kabat)

SEQ ID                LCDR2        SSDQRPS
NO: 122 (Kabat)

SEQ ID                LCDR3        AAWDDSLHGWV
NO: 123 (Kabat)

SEQ ID                LCDR1        SRTNIGSNA
NO: 124 (Chothia)

SEQ ID                LCDR2        SSD
NO: 125 (Chothia)

SEQ ID                LCDR3        WDDSLHGW
NO: 126 (Chothia)

SEQ ID                LCDR1        RTNIGSNA
NO: 127 (IMGT)

SEQ ID                LCDR2        SSD
NO: 128 (IMGT)

SEQ ID                LCDR3        AAWDDSLHGWV
NO: 129 (IMGT)

SEQ ID NO: 130        VL           SPVLTQPPSASGTPGQRVTISCSGSRTNIGSNAVNWYQQV
                                   PGTAPKLLIYSSDQRPSGVSDRFSGSKSGTSGSLAISGLQ
                                   SEDETDYYCAAWDDSLHGWVFGGGTKLTVL

SEQ ID NO: 131        DNA VL       TCGCCTGTGCTGACTCAGCCGCCCTCAGCGTCTGGGACCC
                                   CCGGGCAGAGGGTCACCATCTCTTGTTCTGGAAGCAGGAC
                                   CAACATCGGAAGTAATGCTGTAAACTGGTACCAGCAGGTC
                                   CCAGGAACGGCCCCCAAACTCCTCATCTATAGTAGTGATC
                                   AGCGGCCCTCAGGGGTCTCTGACCGATTCTCTGGCTCCAA
                                   GTCTGGCACCTCAGGCTCCCTGGCCATCAGTGGCCTCCAG
                                   TCTGAGGATGAAACTGATTATTACTGTGCAGCATGGGATG
                                   ACAGCCTGCATGGTTGGGTGTTCGGCGGAGGGACCAAGCT
                                   GACCGTCCTA

SEQ ID NO: 132        Light        SPVLTQPPSASGTPGQRVTISCSGSRTNIGSNAVNWYQQV
                      Chain        PGTAPKLLIYSSDQRPSGVSDRFSGSKSGTSGSLAISGLQ
                                   SEDETDYYCAAWDDSLHGWVFGGGTKLTVLGQPKAAPSVT
                                   LFPPSSEELQANKATLVCLISDFYPGAVTVAWKADSSPVK
```

TABLE 2-continued

Anti-Polyoma virus Antibodies

|  |  | AGVETTTPSKQSNNKYAASSYLSLTPEQWKSHRSYSCQVT<br>HEGSTVEKTVAPTECS |
|---|---|---|
| SEQ ID NO: 133 | DNA<br>Light<br>Chain | TCGCCTGTGCTGACTCAGCCGCCCTCAGCGTCTGGGACCC<br>CCGGGCAGAGGGTCACCATCTCTTGTTCTGGAAGCAGGAC<br>CAACATCGGAAGTAATGCTGTAAACTGGTACCAGCAGGTC<br>CCAGGAACGGCCCCCAAACTCCTCATCTATAGTAGTGATC<br>AGCGGCCCTCAGGGGTCTCTGACCGATTCTCTGGCTCCAA<br>GTCTGGCACCTCAGGCTCCCTGGCCATCAGTGGCCTCCAG<br>TCTGAGGATGAAACTGATTATTACTGTGCAGCATGGGATG<br>ACAGCCTGCATGGTTGGGTGTTCGGCGGAGGGACCAAGCT<br>GACCGTCCTAGGTCAGCCCAAGGCTGCCCCCTCGGTCACT<br>CTGTTCCCGCCCTCCTCTGAGGAGCTTCAAGCCAACAAGG<br>CCACACTGGTGTGTCTCATAAGTGACTTCTACCCGGGAGC<br>CGTGACAGTGGCCTGGAAGGCAGATAGCAGCCCCGTCAAG<br>GCGGGAGTGGAGACCACCACACCCTCCAAACAAAGCAACA<br>ACAAGTACGCCGCCAGCAGCTACCTGAGCCTGACCCCCGA<br>GCAGTGGAAGAGCCACAGAAGCTACAGCTGCCAGGTCACC<br>CACGAGGGCAGCACCGTGGAGAAAACCGTGGCCCCCACCG<br>AGTGCAGC |

NOV219

| SEQ ID NO: 134<br>(Combined) | HCDR1 | GYRFTSHWIS |
|---|---|---|
| SEQ ID<br>NO: 135 (Combined) | HCDR2 | RIDPSDSYTKYSPSFQG |
| SEQ ID<br>NO: 136 (Combined) | HCDR3 | LGYHSGWYYFDY |
| SEQ ID<br>NO: 137 (Kabat) | HCDR1 | SHWIS |
| SEQ ID<br>NO: 138 (Kabat) | HCDR2 | RIDPSDSYTKYSPSFQG |
| SEQ ID<br>NO: 139 (Kabat) | HCDR3 | LGYHSGWYYFDY |
| SEQ ID NO:<br>140 (Chothia) | HCDR1 | GYRFTSH |
| SEQ ID<br>NO: 141 (Chothia) | HCDR2 | DPSDSY |
| SEQ ID<br>NO: 142 (Chothia) | HCDR3 | LGYHSGWYYFDY |
| SEQ ID<br>NO: 143 (IMGT) | HCDR1 | GYRFTSHW |
| SEQ ID<br>NO: 144 (IMGT) | HCDR2 | IDPSDSYT |
| SEQ ID<br>NO: 145 (IMGT) | HCDR3 | ARLGYHSGWYYFDY |
| SEQ ID NO: 146 | VH | QVQLVESGAEVKKPGESLRISCKGSGYRFTSHWISWVRQM<br>PGKGLEWVARIDPSDSYTKYSPSFQGHVTISTDKSTSTAY<br>LHWSSLKASDTAMYYCARLGYHSGWYYFDYWGQGTLVTVS<br>S |
| SEQ ID NO: 147 | DNA VH | CAGGTGCAGCTGGTGGAGTCTGGAGCAGAGGTGAAAAAGC<br>CCGGGGAGTCTCTGAGGATCTCCTGTAAGGGTTCTGGATA<br>CAGGTTTACCAGCCACTGGATCAGCTGGGTGCGCCAGATG<br>CCCGGGAAAGGCCTGGAGTGGGTGGCGAGGATTGATCCTA<br>GTGACTCTTATACCAAGTACAGCCCGTCCTTCCAAGGCCA<br>CGTCACCATCTCAACTGACAAGTCCACCAGCACAGCCTAC<br>CTGCACTGGAGCAGCCTGAAGGCCTCGGACACCGCCATGT<br>ATTACTGTGCGAGACTAGGGTATCACAGTGGCTGGTACTA<br>CTTTGACTACTGGGGCCAGGGAACCCTGGTCACCGTCTCC<br>TCA |
| SEQ ID NO: 148 | Heavy<br>Chain | QVQLVESGAEVKKPGESLRISCKGSGYRFTSHWISWVRQM<br>PGKGLEWVARIDPSDSYTKYSPSFQGHVTISTDKSTSTAY |

TABLE 2-continued

Anti-Polyoma virus Antibodies

|  |  |  |
|---|---|---|
|  |  | LHWSSLKASDTAMYYCARLGYHSGWYYFDYWGQGTLVTVS SASTKGPSVFPLAPCSRSTSGGTAALGCLVKDYFPEPVTV SWNSGALTSGVHTFPAVLQSSGLYSLSSVVTVPSSSLGTQ TYICNVNHKPSNTKVDKRVEPKSCDKTHTCPPCPAPELLG GPSVFLFPPKPKDTLMISRTPEVTCVVVDVSHEDPEVKFN WYVDGVEVHNAKTKPREEQYNSTYRVVSVLTVLHQDWLNG KEYKCKVSNKALPAPIEKTISKAKGQPREPQVYTLPPSRE EMTKNQVSLTCLVKGFYPSDIAVEWESNGQPENNYKTTPP VLDSDGSFFLYSKLTVDKSRWQQGNVFSCSVMHEALHNHY TQKSLSLSPGK |
| SEQ ID NO: 149 | DNA Heavy Chain | CAGGTGCAGCTGGTGGAGTCTGGAGCAGAGGTGAAAAAGC CCGGGGAGTCTCTGAGGATCTCCTGTAAGGGTTCTGGATA CAGGTTTACCAGCCACTGGATCAGCTGGGTGCGCCAGATG CCCGGGAAAGGCCTGGAGTGGGTGGCGAGGATTGATCCTA GTGACTCTTATACCAAGTACAGCCCGTCCTTCCAAGGCCA CGTCACCATCTCAACTGACAAGTCCACCAGCACAGCCTAC CTGCACTGGAGCAGCCTGAAGGCCTCGGACACCGCCATGT ATTACTGTGCGAGACTAGGGTATCACAGTGGCTGGTACTA CTTTGACTACTGGGGCCAGGGAACCCTGGTCACCGTCTCC TCAGCTTCCACCAAGGGCCCATCGGTCTTCCCCCTGGCGC CCTGCTCCAGGAGCACCTCTGGGGGCACAGCGGCCCTGGG CTGCCTGGTCAAGGACTACTTCCCCGAACCGGTGACGGTG TCGTGGAACTCAGGCGCCCTGACCAGCGGCGTGCACACCT TCCCGGCTGTCCTACAGTCCTCAGGACTCTACTCCCTCAG CAGCGTGGTGACCGTGCCCTCCAGCAGCTTGGGCACCCAG ACCTACATCTGCAACGTGAACCACAAGCCCAGCAACACCA AGGTGGACAAGAGAGTGGAGCCCAAGAGCTGCGACAAGAC CCACACCTGCCCCCCCTGCCCAGCCCCAGAGCTGCTGGGC GGACCCTCCGTGTTCCTGTTCCCCCCCAAGCCCAAGGACA CCCTGATGATCAGCAGGACCCCCGAGGTGACCTGCGTGGT GGTGGACGTGAGCCACGAGGACCCAGAGGTGAAGTTCAAC TGGTACGTGGACGGCGTGGAGGTGCACAACGCCAAGACCA AGCCCAGAGAGGAGCAGTACAACAGCACCTACAGGGTGGT GTCCGTGCTGACCGTGCTGCACCAGGACTGGCTGAACGGC AAGGAATACAAGTGCAAGGTCTCCAACAAGGCCCTGCCAG CCCCCATCGRAAAGACCATCAGCAAGGCCAAGGGCCAGCC ACGGGAGCCCCAGGTGTACACCCTGCCCCCCTCCCGGGAG GAGATGACCAAGAACCAGGTGTCCCTGACCTGTCTGGTGA AGGGCTTCTACCCCAGCGACATCGCCGTGGAGTGGGAGAG CAACGGCCAGCCCGAGAACAACTACAAGACCACCCCCCCA GTGCTGGACAGCGACGGCAGCTTCTTCCTGTACAGCAAGC TGACCGTGGACAAGTCCAGGTGGCAGCAGGGCAACGTGTT CAGCTGCAGCGTGATGCACGAGGCCCTGCACAACCACTAC ACCCAGAAGAGCCTGAGCCTGTCCCCCGGCAAG |
| SEQ ID NO: 150 (Combined) | LCDR1 | SGSSSNIGSNAVN |
| SEQ ID NO: 151 (Combined) | LCDR2 | SSDQRPS |
| SEQ ID NO: 152 (Combined) | LCDR3 | AAWDDSLHGWI |
| SEQ ID NO: 153 (Kabat) | LCDR1 | SGSSSNIGSNAVN |
| SEQ ID NO: 154 (Kabat) | LCDR2 | SSDQRPS |
| SEQ ID NO: 155 (Kabat) | LCDR3 | AAWDDSLHGWI |
| SEQ ID NO: 156 (Chothia) | LCDR1 | SSSNIGSNA |
| SEQ ID NO: 157 (Chothia) | LCDR2 | SSD |
| SEQ ID NO: 158 (Chothia) | LCDR3 | WDDSLHGW |
| SEQ ID NO: 159 (IMGT) | LCDR1 | SSNIGSNA |
| SEQ ID NO: 160 (IMGT) | LCDR2 | SSD |

TABLE 2-continued

Anti-Polyoma virus Antibodies

| SEQ ID<br>NO: 161 (IMGT) | LCDR3 | AAWDDSLHGWI |
|---|---|---|
| SEQ ID NO: 162 | VL | QSALTQPPSASGTPGQRVTISCSGSSSNIGSNAVNWYQQL<br>PGTAPKLLIYSSDQRPSGVPDRFSGSKSGTSGSLAISGLH<br>SEDETDYYCAAWDDSLHGWIFGGGTKLTVI |
| SEQ ID NO: 163 | DNA VL | CAGTCTGCCCTGACTCAGCCACCCTCAGCGTCTGGGACCC<br>CCGGGCAGAGGGTCACCATCTCTTGTTCTGGAAGCAGCTC<br>CAACATCGGAAGTAATGCTGTAAACTGGTACCAGCAGCTC<br>CCAGGAACGGCCCCCAAACTCCTCATCTATAGTAGTGATC<br>AGCGGCCCTCAGGGGTCCCTGACCGATTCTCTGGCTCCAA<br>GTCTGGCACCTCAGGCTCCCTGGCCATCAGTGGGCTCCAC<br>TCTGAGGATGAGACTGATTATTACTGTGCAGCATGGGATG<br>ACAGCCTGCATGGTTGGATATTCGGCGGAGGGACCAAGCT<br>GACCGTCATA |
| SEQ ID NO: 164 | Light<br>Chain | QSALTQPPSASGTPGQRVTISCSGSSSNIGSNAVNWYQQL<br>PGTAPKLLIYSSDQRPSGVPDRFSGSKSGTSGSLAISGLH<br>SEDETDYYCAAWDDSLHGWIFGGGTKLTVIGQPKAAPSVT<br>LFPPSSEELQANKATLVCLISDFYPGAVTVAWKADSSPVK<br>AGVETTTPSKQSNNKYAASSYLSLTPEQWKSHRSYSCQVT<br>HEGSTVEKTVAPTECS |
| SEQ ID NO: 165 | DNA<br>Light<br>Chain | CAGTCTGCCCTGACTCAGCCACCCTCAGCGTCTGGGACCC<br>CCGGGCAGAGGGTCACCATCTCTTGTTCTGGAAGCAGCTC<br>CAACATCGGAAGTAATGCTGTAAACTGGTACCAGCAGCTC<br>CCAGGAACGGCCCCCAAACTCCTCATCTATAGTAGTGATC<br>AGCGGCCCTCAGGGGTCCCTGACCGATTCTCTGGCTCCAA<br>GTCTGGCACCTCAGGCTCCCTGGCCATCAGTGGGCTCCAC<br>TCTGAGGATGAGACTGATTATTACTGTGCAGCATGGGATG<br>ACAGCCTGCATGGTTGGATATTCGGCGGAGGGACCAAGCT<br>GACCGTCATAGGTCAGCCCAAGGCTGCCCCCTCGGTCACT<br>CTGTTCCCGCCCTCCTCTGAGGAGCTTCAAGCCAACAAGG<br>CCACACTGGTGTGTCTCATAAGTGACTTCTACCCGGGAGC<br>CGTGACAGTGGCCTGGAAGGCAGATAGCAGCCCCGTCAAG<br>GCGGGAGTGGAGACCACCACACCCTCCAAACAAAGCAACA<br>ACAAGTACGCCGCCAGCAGCTACCTGAGCCTGACGCCTGA<br>GCAGTGGAAGTCCCACAGAAGCTACAGCTGCCAGGTCACC<br>CACGAGGGCAGCACCGTGGAGAAAACCGTGGCCCCCACCG<br>AGTGCAGC |

NOV487

| SEQ ID NO: 166<br>(Combined) | HCDR1 | GASISSGSDYWS |
|---|---|---|
| SEQ ID NO: 167<br>(Combined) | HCDR2 | RIYTSGRNSYNPSLKS |
| SEQ ID NO: 168<br>(Combined) | HCDR3 | NSRRYGGYDLFDV |
| SEQ ID<br>NO: 169 (Kabat) | HCDR1 | SGSDYWS |
| SEQ ID<br>NO: 170 (Kabat) | HCDR2 | RIYTSGRNSYNPSLKS |
| SEQ ID<br>NO: 171 (Kabat) | HCDR3 | NSRRYGGYDLFDV |
| SEQ ID<br>NO: 172 (Chothia) | HCDR1 | GASISSGSD |
| SEQ ID<br>NO: 173 (Chothia) | HCDR2 | YTSGR |
| SEQ ID<br>NO: 174 (Chothia) | HCDR3 | NSRRYGGYDLFDV |
| SEQ ID<br>NO: 175 (IMGT) | HCDR1 | GASISSGSDY |
| SEQ ID<br>NO: 176 (IMGT) | HCDR2 | IYTSGRN |

TABLE 2-continued

Anti-Polyoma virus Antibodies

| SEQ ID NO: 177 (IMGT) | HCDR3 | ARNSRRYGGYDLFDV |
|---|---|---|
| SEQ ID NO: 178 | VH | QVQLQESGPGLVKPSQTLSLTCTVSGASISSGSDYWSWIR<br>QPAGKGLEWIGRIYTSGRNSYNPSLKSRVTIAVDTSKNQF<br>SLKLSSVSATDTAVYYCARNSRRYGGYDLFDVWGQGTMVT<br>VSS |
| SEQ ID NO: 179 | DNA VH | CAGGTGCAGCTGCAGGAGTCGGGCCCAGGACTGGTGAAGC<br>CTTCACAGACCCTGTCCCTCACCTGCACTGTCTCTGGTGC<br>CTCCATCAGCAGTGGTAGTGACTACTGGAGCTGGATCCGG<br>CAGCCCGCCGGGAAGGGACTGGAGTGGATTGGGCGTATCT<br>ATACCAGTGGGAGGAACAGCTACAACCCCTCCCTCAAGAG<br>TCGAGTCACCATAGCAGTAGACACGTCCAAGAACCAGTTC<br>TCCCTGAAGCTGAGTAGTGTGAGTGCCACAGACACGGCCG<br>TGTATTACTGTGCGAGGAATAGCAGAAGATATGGTGGCTA<br>CGATCTGTTTGATGTCTGGGGCCAAGGGACAATGGTCACC<br>GTCTCTTCA |
| SEQ ID NO: 180 | Heavy<br>Chain | QVQLQESGPGLVKPSQTLSLTCTVSGASISSGSDYWSWIR<br>QPAGKGLEWIGRIYTSGRNSYNPSLKSRVTIAVDTSKNQF<br>SLKLSSVSATDTAVYYCARNSRRYGGYDLFDVWGQGTMVT<br>VSSASTKGPSVFPLAPSSKSTSGGTAALGCLVKDYFPEPV<br>TVSWNSGALTSGVHTFPAVLQSSGLYSLSSVVTVPSSSLG<br>TQTYICNVNHKPSNTKVDKRVEPKSCDKTHTCPPCPAPEL<br>LGGPSVFLFPPKPKDTLMISRTPEVTCVVVDVSHEDPEVK<br>FNWYVDGVEVHNAKTKPREEQYNSTYRVVSVLTVLHQDWL<br>NGKEYKCKVSNKALPAPIEKTISKAKGQPREPQVYTLPPS<br>REEMTKNQVSLTCLVKGFYPSDIAVEWESNGQPENNYKTT<br>PPVLDSDGSFFLYSKLTVDKSRWQQGNVFSCSVMHEALHN<br>HYTQKSLSLSPGK |
| SEQ ID NO: 181 | DNA<br>Heavy<br>Chain | CAGGTGCAGCTGCAGGAGTCGGGCCCAGGACTGGTGAAGC<br>CTTCACAGACCCTGTCCCTCACCTGCACTGTCTCTGGTGC<br>CTCCATCAGCAGTGGTAGTGACTACTGGAGCTGGATCCGG<br>CAGCCCGCCGGGAAGGGACTGGAGTGGATTGGGCGTATCT<br>ATACCAGTGGGAGGAACAGCTACAACCCCTCCCTCAAGAG<br>TCGAGTCACCATAGCAGTAGACACGTCCAAGAACCAGTTC<br>TCCCTGAAGCTGAGTAGTGTGAGTGCCACAGACACGGCCG<br>TGTATTACTGTGCGAGGAATAGCAGAAGATATGGTGGCTA<br>CGATCTGTTTGATGTCTGGGGCCAAGGGACAATGGTCACC<br>GTCTCTTCAGCCTCCACCAAGGGCCCATCGGTCTTCCCCC<br>TGGCACCCTCCTCCAAGAGCACCTCTGGGGGCACAGCGGC<br>CCTGGGCTGCCTGGTCAAGGACTACTTCCCCGAACCGGTG<br>ACGGTGTCGTGGAACTCAGGCGCCCTGACCAGCGGCGTGC<br>ACACCTTCCCGGCTGTCCTACAGTCCTCAGGACTCTACTC<br>CCTCAGCAGCGTGGTGACCGTGCCCTCCAGCAGCTTGGGC<br>ACCCAGACCTACATCTGCAACGTGAACCACAAGCCCAGCA<br>ACACCAAGGTGGACAAGAGAGTGGAGCCCAAGAGCTGCGA<br>CAAGACCCACACCTGCCCCCCCCTGCCCAGCCCCAGAGCTG<br>CTGGGCGGACCCTCCGTGTTCCTGTTCCCCCCCAAGCCCA<br>AGGACACCCTGATGATCAGCAGGACCCCCGAGGTGACCTG<br>CGTGGTGGTGGACGTGAGCCACGAGGACCCAGAGGTGAAG<br>TTCAACTGGTACGTGGACGGCGTGGAGGTGCACAACGCCA<br>AGACCAAGCCCAGAGAGGAGCAGTACAACAGCACCTACAG<br>GGTGGTGTCCGTGCTGACCGTGCTGCACCAGGACTGGCTG<br>AACGGCAAGGAATACAAGTGCAAGGTCTCCAACAAGGCCC<br>TGCCAGCCCCCATCGAAAAGACCATCAGCAAGGCCAAGGG<br>CCAGCCACGGGAGCCCCAGGTGTACACCCTGCCCCCCTCC<br>CGGGAGGAGATGACCAAGAACCAGGTGTCCCTGACCTGTC<br>TGGTGAAGGGCTTCTACCCCAGCGACATCGCCGTGGAGTG<br>GGAGAGCAACGGCCAGCCCGAGAACAACTACAAGACCACC<br>CCCCCAGTGCTGGACAGCGACGGCAGCTTCTTCCTGTACA<br>GCAAGCTGACCGTGGACAAGTCCAGGTGGCAGCAGGGCAA<br>CGTGTTCAGCTGCAGCGTGATGCACGAGGCCCTGCACAAC<br>CACTACACCCAGAAGAGCCTGAGCCTGTCCCCCGGCAAG |
| SEQ ID NO: 182 (Combined) | LCDR1 | GGNNIGSKSVH |
| SEQ ID NO: 183 (Combined) | LCDR2 | YDGDRPS |
| SEQ ID NO: 184 (Combined) | LCDR3 | QVWDTSSDHPV |
| SEQ ID NO: 185 (Kabat) | LCDR1 | GGNNIGSKSVH |

TABLE 2-continued

Anti-Polyoma virus Antibodies

| SEQ ID NO: 186 (Kabat) | LCDR2 | YDGDRPS |
|---|---|---|
| SEQ ID NO: 187 (Kabat) | LCDR3 | QVWDTSSDHPV |
| SEQ ID NO: 188 (Chothia) | LCDR1 | NNIGSKS |
| SEQ ID NO: 189 (Chothia) | LCDR2 | YDG |
| SEQ ID NO: 190 (Chothia) | LCDR3 | WDTSSDHP |
| SEQ ID NO: 191 (IMGT) | LCDR1 | NIGSKS |
| SEQ ID NO: 192 (IMGT) | LCDR2 | YDG |
| SEQ ID NO: 193 (IMGT) | LCDR3 | QVWDTSSDHPV |
| SEQ ID NO: 194 | VL | SYVLTQPPSVSEAPGKTARITCGGNNIGSKSVHWYQQKPG QAPVLVIYYDGDRPSGIPERFSGSNSGNTATLTISRVEAG DEADYYCQVWDTSSDHPVFGGGTKLTVL |
| SEQ ID NO: 195 | DNA VL | TCCTATGTGCTGACTCAGCCACCCTCAGTGTCAGAGGCCC CAGGAAAGACGGCCAGGATTACCTGTGGGGGAAACAACAT TGGAAGTAAAAGTGTGCACTGGTACCAGCAGAAGCCAGGC CAGGCCCCTGTGCTGGTCATCTATTATGATGGCGACCGGC CCTCAGGGATCCCTGAGCGATTCTCTGGCTCCAACTCTGG GAACACGGCCACCCTGACCATCAGCAGGGTCGAAGCCGGG GATGAGGCCGACTATTACTGTCAGGTGTGGGATACTAGTA GTGATCACCCGGTGTTCGGCGGAGGGACCAAGCTGACCGT CCTA |
| SEQ ID NO: 196 | Light Chain | SYVLTQPPSVSEAPGKTARITCGGNNIGSKSVHWYQQKPG QAPVLVIYYDGDRPSGIPERFSGSNSGNTATLTISRVEAG DEADYYCQVWDTSSDHPVFGGGTKLTVLGQPKAAPSVTLF PPSSEELQANKATLVCLISDFYPGAVTVAWKADSSPVKAG VETTTPSKQSNNKYAASSYLSLTPEQWKSHRSYSCQVTHE GSTVEKTVAPTECS |
| SEQ ID NO: 197 | DNA Light Chain | TCCTATGTGCTGACTCAGCCACCCTCAGTGTCAGAGGCCC CAGGAAAGACGGCCAGGATTACCTGTGGGGGAAACAACAT TGGAAGTAAAAGTGTGCACTGGTACCAGCAGAAGCCAGGC CAGGCCCCTGTGCTGGTCATCTATTATGATGGCGACCGGC CCTCAGGGATCCCTGAGCGATTCTCTGGCTCCAACTCTGG GAACACGGCCACCCTGACCATCAGCAGGGTCGAAGCCGGG GATGAGGCCGACTATTACTGTCAGGTGTGGGATACTAGTA GTGATCACCCGGTGTTCGGCGGAGGGACCAAGCTGACCGT CCTAGGTCAGCCCAAGGCTGCCCCCTCGGTCACTCTGTTC CCGCCCTCCTCTGAGGAGCTTCAAGCCAACAAGGCCACAC TGGTGTGTCTCATAAGTGACTTCTACCCGGGAGCCGTGAC AGTGGCCTGGAAGGCAGATAGCAGCCCCGTCAAGGCGGGA GTGGAGACCACCACACCCTCCAAACAAAGCAACAACAAGT ACGCCGCCAGCAGCTACCTGAGCCTGACCCCCGAGCAGTG GAAGAGCCACAGAAGCTACAGCTGCCAGGTCACCCACGAG GGCAGCACCGTGGAGAAAACCGTGGCCCCCACCGAGTGCA GC |

NOV581

| SEQ ID NO: 198 (Combined) | HCDR1 | GFTFSGYNMH |
|---|---|---|
| SEQ ID NO: 199 (Combined) | HCDR2 | YISNSGRTIYYADSVKG |
| SEQ ID NO: 200 (Combined) | HCDR3 | DRDPQWLGNDALQI |
| SEQ ID NO: 201 (Kabat) | HCDR1 | GYNMH |

TABLE 2-continued

Anti-Polyoma virus Antibodies

| SEQ ID NO: 202 (Kabat) | HCDR2 | YISNSGRTIYYADSVKG |
|---|---|---|
| SEQ ID NO: 203 (Kabat) | HCDR3 | DRDPQWLGNDALQI |
| SEQ ID NO: 204 (Chothia) | HCDR1 | GFTFSGY |
| SEQ ID NO: 205 (Chothia) | HCDR2 | SNSGRT |
| SEQ ID NO: 206 (Chothia) | HCDR3 | DRDPQWLGNDALQI |
| SEQ ID NO: 207 (IMGT) | HCDR1 | GFTFSGYN |
| SEQ ID NO: 208 (IMGT) | HCDR2 | ISNSGRTI |
| SEQ ID NO: 209 (IMGT) | HCDR3 | ARDRDPQWLGNDALQI |
| SEQ ID NO: 210 | VH | QVQLVESGGGLVQPGGSLRLSCVASGFTFSGYNMHWVRQA PGKGLEWVSYISNSGRTIYYADSVKGRFTLSRDNAKNSLY LQMNSLRAEDTAVYFCARDRDPQWLGNDALQIWGQGTMVT VSS |
| SEQ ID NO: 211 | DNA VH | CAGGTGCAGCTGGTGGAGTCTGGGGGAGGCTTGGTACAGC CTGGGGGGTCCCTGAGGCTCTCCTGTGTAGCCTCTGGATT CACCTTCAGTGGCTATAACATGCACTGGGTCCGCCAGGCT CCAGGGAAGGGGCTGGAGTGGGTCTCATACATTAGTAATA GTGGTAGAACCATATACTACGCAGACTCTGTGAAGGGCCG ATTCACCCTGTCCAGAGACAACGCCAAGAACTCACTGTAT CTGCAGATGAACAGCCTGAGAGCCGAGGACACGGCTGTCT ATTTTTGTGCGAGAGATCGGGATCCCCAGTGGCTGGGAAA TGATGCTCTTCAAATCTGGGGCCAAGGGACAATGGTCACC GTCTCTTCA |
| SEQ ID NO: 212 | Heavy Chain | QVQLVESGGGLVQPGGSLRLSCVASGFTFSGYNMHWVRQA PGKGLEWVSYISNSGRTIYYADSVKGRFTLSRDNAKNSLY LQMNSLRAEDTAVYFCARDRDPQWLGNDALQIWGQGTMVT VSSASTKGPSVFPLAPSSKSTSGGTAALGCLVKDYFPEPV TVSWNSGALTSGVHTFPAVLQSSGLYSLSSVVTVPSSSLG TQTYICNVNHKPSNTKVDKRVEPKSCDKTHTCPPCPAPEL LGGPSVFLFPPKPKDTLMISRTPEVTCVVVDVSHEDPEVK FNWYVDGVEVHNAKTKPREEQYNSTYRVVSVLTVLHQDWL NGKEYKCKVSNKALPAPIEKTISKAKGQPREPQVYTLPPS REEMTKNQVSLTCLVKGFYPSDIAVEWESNGQPENNYKTT PPVLDSDGSFFLYSKLTVDKSRWQQGNVFSCSVMHEALHN HYTQKSLSLSPGK |
| SEQ ID NO: 213 | DNA Heavy Chain | CAGGTGCAGCTGGTGGAGTCTGGGGGAGGCTTGGTACAGC CTGGGGGGTCCCTGAGGCTCTCCTGTGTAGCCTCTGGATT CACCTTCAGTGGCTATAACATGCACTGGGTCCGCCAGGCT CCAGGGAAGGGGCTGGAGTGGGTCTCATACATTAGTAATA GTGGTAGAACCATATACTACGCAGACTCTGTGAAGGGCCG ATTCACCCTGTCCAGAGACAACGCCAAGAACTCACTGTAT CTGCAGATGAACAGCCTGAGAGCCGAGGACACGGCTGTCT ATTTTTGTGCGAGAGATCGGGATCCCCAGTGGCTGGGAAA TGATGCTCTTCAAATCTGGGGCCAAGGGACAATGGTCACC GTCTCTTCAGCCTCCACCAAGGGCCCATCGGTCTTCCCCC TGGCACCCTCCTCCAAGAGCACCTCTGGGGGCACAGCGGC CCTGGGCTGCCTGGTCAAGGACTACTTCCCCGAACCGGTG ACGGTGTCGTGGAACTCAGGCGCCCTGACCAGCGGCGTGC ACACCTTCCCGGCTGTCCTACAGTCCTCAGGACTCTACTC CCTCAGCAGCGTGGTGACCGTGCCCTCCAGCAGCTTGGGC ACCCAGACCTACATCTGCAACGTGAATCACAAGCCCAGCA ACACCAAGGTGGACAAGAGAGTGGAGCCCAAGAGCTGCGA CAAGACCCACACCTGCCCCCCCTGCCCAGCCCCAGAGCTG CTGGGCGGACCCTCCGTGTTCCTGTTCCCCCCCAAGCCCA AGGACACCCTGATGATCAGCAGGACCCCCGAGGTGACCTG CGTGGTGGTGGACGTGAGCCACGAGGACCCAGAGGTGAAG TTCAACTGGTACGTGGACGGCGTGGAGGTGCACAACGCCA AGACCAAGCCCAGAGAGGAGCAGTACAACAGCACCTACAG GGTGGTGTCCGTGCTGACCGTGCTGCACCAGGACTGGCTG AACGGCAAGGAATACAAGTGCAAGGTCTCCAACAAGGCCC |

TABLE 2-continued

Anti-Polyoma virus Antibodies

|  |  |  |
|---|---|---|
|  |  | TGCCAGCCCCCATCGAAAAGACCATCAGCAAGGCCAAGGG<br>CCAGCCACGGGAGCCCCAGGTGTACACCCTGCCCCCCTCC<br>CGGGAGGAGATGACCAAGAACCAGGTGTCCCTGACCTGTC<br>TGGTGAAGGGCTTCTACCCCAGCGACATCGCCGTGGAGTG<br>GGAGAGCAACGGCCAGCCCGAGAACAACTACAAGACCACC<br>CCCCCAGTGCTGGACAGCGACGGCAGCTTCTTCCTGTACA<br>GCAAGCTGACCGTGGACAAGTCCAGGTGGCAGCAGGGCAA<br>CGTGTTCAGCTGCAGCGTGATGCACGAGGCCCTGCACAAC<br>CACTACACCCAGAAGAGCCTGAGCCTGTCCCCCGGCAAG |
| SEQ ID NO: 214<br>(Combined) | LCDR1 | RASQSVSSGYLA |
| SEQ ID<br>NO: 215 (Combined) | LCDR2 | GASSRAT |
| SEQ ID<br>NO: 216 (Combined) | LCDR3 | QQYGTSRKT |
| SEQ ID<br>NO: 217 (Kabat) | LCDR1 | RASQSVSSGYLA |
| SEQ ID<br>NO: 218 (Kabat) | LCDR2 | GASSRAT |
| SEQ ID<br>NO: 219 (Kabat) | LCDR3 | QQYGTSRKT |
| SEQ ID<br>NO: 220 (Chothia) | LCDR1 | SQSVSSGY |
| SEQ ID<br>NO: 221 (Chothia) | LCDR2 | GAS |
| SEQ ID<br>NO: 222 (Chothia) | LCDR3 | YGTSRK |
| SEQ ID<br>NO: 223 (IMGT) | LCDR1 | QSVSSGY |
| SEQ ID<br>NO: 224 (IMGT) | LCDR2 | GAS |
| SEQ ID<br>NO: 225 (IMGT) | LCDR3 | QQYGTSRKT |
| SEQ ID NO: 226 | VL | EIVLTQSPGTLSLSPGERATLSCRASQSVSSGYLAWYQQK<br>PGQAPRLLIYGASSRATGIPDRFSGSGSGTDFTLTISRLE<br>PEDFAVYYCQQYGTSRKTFGQGTKVEIK |
| SEQ ID NO: 227 | DNA VL | GAAATTGTTTTGACGCAGTCTCCAGGCACCCTGTCTTTGT<br>CTCCAGGGGAAAGAGCCACCCTCTCCTGCAGGGCCAGTCA<br>GAGTGTTAGCAGTGGCTACTTAGCCTGGTATCAGCAGAAA<br>CCTGGCCAGGCTCCCAGGCTCCTCATCTATGGTGCATCCA<br>GCAGGGCCACTGGCATCCCAGACAGGTTCAGTGGCAGTGG<br>GTCTGGGACAGACTTCACTCTCACCATCAGCAGACTGGAG<br>CCTGAAGATTTTGCAGTGTATTATTGTCAGCAGTATGGTA<br>CCTCACGTAAGACGTTCGGCCAAGGGACCAAGGTGGAAAT<br>CAAA |
| SEQ ID NO: 228 | Light<br>Chain | EIVLTQSPGTLSLSPGERATLSCRASQSVSSGYLAWYQQK<br>PGQAPRLLIYGASSRATGIPDRFSGSGSGTDFTLTISRLE<br>PEDFAVYYCQQYGTSRKTFGQGTKVEIKRTVAAPSVFIFP<br>PSDEQLKSGTASVVCLLNNFYPREAKVQWKVDNALQSGNS<br>QESVTEQDSKDSTYSLSSTLTLSKADYEKHKVYACEVTHQ<br>GLSSPVTKSFNRGEC |
| SEQ ID NO: 229 | DNA<br>Light<br>Chain | GAAATTGTTTTGACGCAGTCTCCAGGCACCCTGTCTTTGT<br>CTCCAGGGGAAAGAGCCACCCTCTCCTGCAGGGCCAGTCA<br>GAGTGTTAGCAGTGGCTACTTAGCCTGGTATCAGCAGAAA<br>CCTGGCCAGGCTCCCAGGCTCCTCATCTATGGTGCATCCA<br>GCAGGGCCACTGGCATCCCAGACAGGTTCAGTGGCAGTGG<br>GTCTGGGACAGACTTCACTCTCACCATCAGCAGACTGGAG<br>CCTGAAGATTTTGCAGTGTATTATTGTCAGCAGTATGGTA<br>CCTCACGTAAGACGTTCGGCCAAGGGACCAAGGTGGAAAT<br>CAAACGAACTGTGGCTGCACCATCTGTCTTCATCTTCCCG<br>CCATCTGATGAGCAGTTGAAATCTGGAACTGCCTCTGTTG<br>TGTGCCTGCTGAATAACTTCTATCCCAGAGAGGCCAAAGT |

TABLE 2-continued

Anti-Polyoma virus Antibodies

ACAGTGGAAGGTGGACAACGCCCTGCAGAGCGGCAACAGC
CAGGAGAGCGTCACCGAGCAGGACAGCAAGGACTCCACCT
ACAGCCTGAGCAGCACCCTGACCCTGAGCAAGGCCGACTA
CGAGAAGCATAAGGTGTACGCCTGCGAGGTGACCCACCAG
GGCCTGTCCAGCCCCGTGACCAAGAGCTTCAACAGGGGCG
AGTGC

NOV796

| SEQ ID NO: 230 (Combined) | HCDR1 | GGSISGYYWS |
|---|---|---|
| SEQ ID NO: 231 (Combined) | HCDR2 | LIYESGSANYNPSLKS |
| SEQ ID NO: 232 (Combined) | HCDR3 | RVRGWSYGMDV |
| SEQ ID NO: 233 (Kabat) | HCDR1 | GYYWS |
| SEQ ID NO: 234 (Kabat) | HCDR2 | LIYESGSANYNPSLKS |
| SEQ ID NO: 235 (Kabat) | HCDR3 | RVRGWSYGMDV |
| SEQ ID NO: 236 (Chothia) | HCDR1 | GGSISGY |
| SEQ ID NO: 237 (Chothia) | HCDR2 | YESGS |
| SEQ ID NO: 238 (Chothia) | HCDR3 | RVRGWSYGMDV |
| SEQ ID NO: 239 (IMGT) | HCDR1 | GGSISGYY |
| SEQ ID NO: 240 (IMGT) | HCDR2 | IYESGSA |
| SEQ ID NO: 241 (IMGT) | HCDR3 | ARRVRGWSYGMDV |

| SEQ ID NO: 242 | VH | QVQLVQSGPGLVKPSETLSLTCSVSGGSISGYYWSWIRQP<br>PGKGLEWIGLIYESGSANYNPSLKSRVTISLDTSKNQFSL<br>KLKSVTAADTAVYYCARRVRGWSYGMDVWGQGTTVAVSS |
|---|---|---|
| SEQ ID NO: 243 | DNA VH | CAGGTGCAGCTGGTGCAGTCTGGCCCAGGACTGGTGAAGC<br>CTTCGGAGACCCTGTCCCTCACCTGCAGTGTCTCTGGTGG<br>CTCCATCAGTGGTTACTACTGGAGCTGGATCCGGCAGCCC<br>CCAGGGAAGGGACTGGAGTGGATCGGCTTAATTTATGAGA<br>GTGGGAGCGCCAACTACAATCCCTCCCTCAAGAGTCGAGT<br>CACCATATCGCTAGACACGTCCAAGAATCAGTTCTCCCTG<br>AAGCTGAAGTCTGTGACCGCCGCGGACACGGCCGTGTATT<br>ACTGTGCGAGACGAGTCCGTGGCTGGTCTTACGGTATGGA<br>CGTCTGGGGCCAAGGGACCACGGTCGCCGTCTCCTCA |
| SEQ ID NO: 244 | Heavy Chain | QVQLVQSGPGLVKPSETLSLTCSVSGGSISGYYWSWIRQP<br>PGKGLEWIGLIYESGSANYNPSLKSRVTISLDTSKNQFSL<br>KLKSVTAADTAVYYCARRVRGWSYGMDVWGQGTTVAVSSA<br>STKGPSVFPLAPSSKSTSGGTAALGCLVKDYFPEPVTVSW<br>NSGALTSGVHTFPAVLQSSGLYSLSSVVTVPSSSLGTQTY<br>ICNVNHKPSNTKVDKRVEPKSCDKTHTCPPCPAPELLGGP<br>SVFLFPPKPKDTLMISRTPEVTCVVVDVSHEDPEVKFNWY<br>VDGVEVHNAKTKPREEQYNSTYRVVSVLTVLHQDWLNGKE<br>YKCKVSNKALPAPIEKTISKAKGQPREPQVYTLPPSREEM<br>TKNQVSLTCLVKGFYPSDIAVEWESNGQPENNYKTTPPVL<br>DSDGSFFLYSKLTVDKSRWQQGNVFSCSVMHEALHNHYTQ<br>KSLSLSPGK |
| SEQ ID NO: 245 | DNA Heavy Chain | CAGGTGCAGCTGGTGCAGTCTGGCCCAGGACTGGTGAAGC<br>CTTCGGAGACCCTGTCCCTCACCTGCAGTGTCTCTGGTGG<br>CTCCATCAGTGGTTACTACTGGAGCTGGATCCGGCAGCCC<br>CCAGGGAAGGGACTGGAGTGGATCGGCTTAATTTATGAGA<br>GTGGGAGCGCCAACTACAATCCCTCCCTCAAGAGTCGAGT<br>CACCATATCGCTAGACACGTCCAAGAATCAGTTCTCCCTG |

TABLE 2-continued

Anti-Polyoma virus Antibodies

|  |  |  |
|---|---|---|
|  |  | AAGCTGAAGTCTGTGACCGCCGCGGACACGGCCGTGTATT<br>ACTGTGCGAGACGAGTCCGTGGCTGGTCTTACGGTATGGA<br>CGTCTGGGGCCAAGGGACCACGGTCGCCGTCTCCTCAGCC<br>TCCACCAAGGGCCCATCGGTCTTCCCCCTGGCACCCTCCT<br>CCAAGAGCACCTCTGGGGGCACAGCGGCCCTGGGCTGCCT<br>GGTCAAGGACTACTTCCCCGAACCGGTGACGGTGTCGTGG<br>AACTCAGGCGCCCTGACCAGCGGCGTGCACACCTTCCCGG<br>CTGTCCTACAGTCCTCAGGACTCTACTCCCTCAGCAGCGT<br>GGTGACCGTGCCCTCCAGCAGCTTGGGCACCCAGACCTAC<br>ATCTGCAACGTGAACCACAAGCCCAGCAACACCAAGGTGG<br>ACAAGAGAGTTGGAGCCCAAGAGCTGCGACAAGACCCACAC<br>CTGCCCCCCCTGCCCAGCCCCAGAGCTGCTGGGCGGACCC<br>TCCGTGTTCCTGTTCCCCCCCAAGCCCAAGGACACCCTGA<br>TGATCAGCAGGACCCCCGAGGTGACCTGCGTGGTGGTGGA<br>CGTGAGCCACGAGGACCCAGAGGTGAAGTTCAACTGGTAC<br>GTGGACGGCGTGGAGGTGCACAACGCCAAGACCAAGCCCA<br>GAGAGGAGCAGTACAACAGCACCTACAGGGTGGTGTCCGT<br>GCTGACCGTGCTGCACCAGGACTGGCTGAACGGCAAGGAA<br>TACAAGTGCAAGGTCTCCAACAAGGCCCTGCCAGCCCCCA<br>TCGAAAAGACCATCAGCAAGGCCAAGGGCCAGCCACGGGA<br>GCCCCAGGTGTACACCCTGCCCCCCTCCCGGGAGGAGATG<br>ACCAAGAACCAGGTGTCCCTGACCTGTCTGGTGAAGGGCT<br>TCTACCCCAGCGACATCGCCGTGGAGTGGGAGAGCAACGG<br>CCAGCCCGAGAACAACTACAAGACCACCCCCCCCAGTGCTG<br>GACAGCGACGGCAGCTTCTTCCTGTACAGCAAGCTGACCG<br>TGGACAAGTCCAGGTGGCAGCAGGGCAACGTGTTCAGCTG<br>CAGCGTGATGCACGAGGCCCTGCACAACCACTACACCCAG<br>AAGAGCCTGAGCCTGTCCCCCGGCAAG |
| SEQ ID<br>NO: 246 (Combined) | LCDR1 | RASQILSSSFLA |
| SEQ ID<br>NO: 247 (Combined) | LCDR2 | AASSRAT |
| SEQ ID<br>NO: 248 (Combined) | LCDR3 | QHYGSSPPWT |
| SEQ ID<br>NO: 249 (Kabat) | LCDR1 | RASQILSSSFLA |
| SEQ ID<br>NO: 250 (Kabat) | LCDR2 | AASSRAT |
| SEQ ID<br>NO: 251 (Kabat) | LCDR3 | QHYGSSPPWT |
| SEQ ID NO: 252<br>(Chothia) | LCDR1 | SQILSSSF |
| SEQ ID<br>NO: 253 (Chothia) | LCDR2 | AAS |
| SEQ ID NO: 254<br>(Chothia) | LCDR3 | YGSSPPW |
| SEQ ID NO: 255<br>(IMGT) | LCDR1 | QILSSSF |
| SEQ ID NO: 256<br>(IMGT) | LCDR2 | AAS |
| SEQ ID NO: 257<br>(IMGT) | LCDR3 | QHYGSSPPWT |
| SEQ ID NO: 258 | VL | DIVLTQSPGTLSLSPGETATLSCRASQILSSSFLAWFQQI<br>PGQAPRLLIYAASSRATGIPDRFSGSGSGTDFSLTISRLE<br>PEDFAVYYCQHYGSSPPWTFGQGTKVEIK |
| SEQ ID NO: 259 | DNA VL | GATATTGTGTTGACGCAGTCTCCAGGCACCCTGTCTTTGT<br>CTCCAGGGGAGAGCAGCCACCCTCTCCTGCAGGGCCAGTCA<br>GATTCTTAGCAGCAGCTTCTTAGCCTGGTTCCAGCAGATA<br>CCTGGCCAGGCTCCCAGACTCCTCATCTATGCTGCATCCA<br>GCAGGGCCACTGGCATCCCAGACAGGTTCAGTGGCAGTGG<br>GTCTGGGACAGACTTCAGTCTCACCATCAGCAGACTGGAG<br>CCTGAAGATTTTGCAGTGTATTACTGTCAGCACTATGGTA<br>GCTCACCTCCTTGGACGTTCGGCCAAGGGACCAAGGTGGA<br>AATCAAA |

TABLE 2-continued

| | | Anti-Polyoma virus Antibodies |
|---|---|---|
| SEQ ID NO: 260 | Light<br>Chain | DIVLTQSPGTLSLSPGETATLSCRASQILSSSFLAWFQQI<br>PGQAPRLLIYAASSRATGIPDRFSGSGSGTDFSLTISRLE<br>PEDFAVYYCQHYGSSPPWTFGQGTKVEIKRTVAAPSVFIF<br>PPSDEQLKSGTASVVCLLNNFYPREAKVQWKVDNALQSGN<br>SQESVTEQDSKDSTYSLSSTLTLSKADYEKHKVYACEVTH<br>QGLSSPVTKSFNRGEC |
| SEQ ID NO: 261 | DNA<br>Light<br>Chain | GATATTGTGTTGACGCAGTCTCCAGGCACCCTGTCTTTGT<br>CTCCAGGGGAGACAGCCACCCTCTCCTGCAGGGCCAGTCA<br>GATTCTTAGCAGCAGCTTCTTAGCCTGGTTCCAGCAGATA<br>CCTGGCCAGGCTCCCAGACTCCTCATCTATGCTGCATCCA<br>GCAGGGCCACTGGCATCCCAGACAGGTTCAGTGGCAGTGG<br>GTCTGGGACAGACTTCAGTCTCACCATCAGCAGACTGGAG<br>CCTGAAGATTTTGCAGTGTATTACTGTCAGCACTATGGTA<br>GCTCACCTCCTTGGACGTTCGGCCAAGGGACCAAGGTGGA<br>AATCAAACGAACTGTGGCTGCACCATCTGTCTTCATCTTC<br>CCGCCATCTGATGAGCAGTTGAAATCTGGAACTGCCTCTG<br>TTGTGTGCCTGCTGAATAACTTCTATCCCAGAGAGGCCAA<br>AGTACAGTGGAAGGTGGACAACGCCCTGCAGAGCGGCAAC<br>AGCCAGGAGAGCGTCACCGAGCAGGACAGCAAGGACTCCA<br>CCTACAGCCTGAGCAGCACCCTGACCCTGAGCAAGGCCGA<br>CTACGAGAAGCATAAGGTGTACGCCTGCGAGGTGACCCAC<br>CAGGGCCTGTCCAGCCCCGTGACCAAGAGCTTCAACAGGG<br>GCGAGTGC |

NOV638

| | | |
|---|---|---|
| SEQ ID NO: 262<br>(Combined) | HCDR1 | GYTFTSYDII |
| SEQ ID NO: 263<br>(Combined) | HCDR2 | RMNPTGGNTDYVPKFQG |
| SEQ ID NO: 264<br>(Combined) | HCDR3 | GVKSLGVSEIDY |
| SEQ ID NO: 265<br>(Kabat) | HCDR1 | SYDII |
| SEQ ID NO: 266<br>(Kabat) | HCDR2 | RMNPTGGNTDYVPKFQG |
| SEQ ID NO: 267<br>(Kabat) | HCDR3 | GVKSLGVSEIDY |
| SEQ ID NO: 268<br>(Chothia) | HCDR1 | GYTFTSY |
| SEQ ID NO: 269<br>(Chothia) | HCDR2 | NPTGGN |
| SEQ ID NO: 270<br>(Chothia) | HCDR3 | GVKSLGVSEIDY |
| SEQ ID NO: 271<br>(IMGT) | HCDR1 | GYTFTSYD |
| SEQ ID NO: 272<br>(IMGT) | HCDR2 | MNPTGGNT |
| SEQ ID NO: 273<br>(IMGT) | HCDR3 | ARGVKSLGVSEIDY |
| SEQ ID NO: 274 | VH | QVQLVQSGAEVKKPGASVKVSCKASGYTFTSYDIIWVRQA<br>TGQGLEWMGRMNPTGGNTDYVPKFQGRVTMTRDISLSTAY<br>MELRSLTSEDTAVFYCARGVKSLGVSEIDYWGQGTLVTVS<br>S |

TABLE 2-continued

Anti-Polyoma virus Antibodies

| SEQ ID NO: 275 | DNA VH | CAGGTGCAGCTGGTGCAGTCTGGGGCTGAGGTGAAGAAAC<br>CTGGGGCCTCAGTGAAGGTCTCCTGCAAGGCTTCTGGATA<br>CACCTTCACCAGTTATGATATCATCTGGGTGCGACAGGCC<br>ACTGGACAAGGGCTTGAGTGGATGGGAAGGATGAACCCTA<br>CCGGTGGTAACACAGACTATGTACCGAAGTTCCAGGGCAG<br>AGTCACCATGACCAGGGACATCTCCTTAAGTACAGCCTAC<br>ATGGAGCTGCGCAGCCTGACATCTGAGGACACGGCCGTGT<br>TTTACTGTGCGAGAGGCGTAAAGTCTTTAGGAGTTTCGGA<br>AATTGACTACTGGGGCCAGGGAACCCTGGTCACCGTCTCC<br>TCA |
|---|---|---|
| SEQ ID NO: 276 | Heavy<br>Chain | QVQLVQSGAEVKKPGASVKVSCKASGYTFTSYDIIWVRQA<br>TGQGLEWMGRMNPTGGNTDYVPKFQGRVTMTRDISLSTAY<br>MELRSLTSEDTAVFYCARGVKSLGVSEIDYWGQGTLVTVS<br>SASTKGPSVFPLAPSSKSTSGGTAALGCLVKDYFPEPVTV<br>SWNSGALTSGVHTFPAVLQSSGLYSLSSVVTVPSSSLGTQ<br>TYICNVNHKPSNTKVDKRVEPKSCDKTHTCPPCPAPELLG<br>GPSVFLFPPKPKDTLMISRTPEVTCVVVDVSHEDPEVKFN<br>WYVDGVEVHNAKTKPREEQYNSTYRVVSVLTVLHQDWLNG<br>KEYKCKVSNKALPAPIEKTISKAKGQPREPQVYTLPPSRE<br>EMTKNQVSLTCLVKGFYPSDIAVEWESNGQPENNYKTTPP<br>VLDSDGSFFLYSKLTVDKSRWQQGNVFSCSVMHEALHNHY<br>TQKSLSLSPGK |
| SEQ ID NO: 277 | DNA<br>Heavy<br>Chain | CAGGTGCAGCTGGTGCAGTCTGGGGCTGAGGTGAAGAAAC<br>CTGGGGCCTCAGTGAAGGTCTCCTGCAAGGCTTCTGGATA<br>CACCTTCACCAGTTATGATATCATCTGGGTGCGACAGGCC<br>ACTGGACAAGGGCTTGAGTGGATGGGAAGGATGAACCCTA<br>CCGGTGGTAACACAGACTATGTACCGAAGTTCCAGGGCAG<br>AGTCACCATGACCAGGGACATCTCCTTAAGTACAGCCTAC<br>ATGGAGCTGCGCAGCCTGACATCTGAGGACACGGCCGTGT<br>TTTACTGTGCGAGAGGCGTAAAGTCTTTAGGAGTTTCGGA<br>AATTGACTACTGGGGCCAGGGAACCCTGGTCACCGTCTCC<br>TCAGCCTCCACCAAGGGCCCATCGGTCTTCCCCCTGGCAC<br>CCTCCTCCAAGAGCACCTCTGGGGGCACAGCGGCCCTGGG<br>CTGCCTGGTCAAGGACTACTTCCCCGAACCGGTGACGGTG<br>TCGTGGAACTCAGGCGCCCTGACCAGCGGCGTGCACACCT<br>TCCCGGCTGTCCTACAGTCCTCAGGACTCTACTCCCTCAG<br>CAGCGTGGTGACCGTGCCCTCCAGCAGCTTGGGCACCCAG<br>ACCTACATCTGCAACGTGAACCACAAGCCCAGCAACACCA<br>AGGTGGACAAGAGAGTGGAGCCCAAGAGCTGCGACAAGAC<br>CCACACCTGCCCCCCCTGCCCAGCCCCAGAGCTGCTGGGC<br>GGACCCTCCGTGTTCCTGTTCCCCCCCAAGCCCAAGGACA<br>CCCTGATGATCAGCAGGACCCCCGAGGTGACCTGCGTGGT<br>GGTGGACGTGAGCCACGAGGACCCAGAGGTGAAGTTCAAC<br>TGGTACGTGGACGGCGTGGAGGTGCACAACGCCAAGACCA<br>AGCCCAGAGAGGAGCAGTACAACAGCACCTACAGGGTGGT<br>GTCCGTGCTGACCGTGCTGCACCAGGACTGGCTGAACGGC<br>AAGGAATACAAGTGCAAGGTCTCCAACAAGGCCCTGCCAG<br>CCCCCATCGAAAAGACCATCAGCAAGGCCAAGGGCCAGCC<br>ACGGGAGCCCCAGGTGTACACCCTGCCCCCCCTCCCGGGAG<br>GAGATGACCAAGAACCAGGTGTCCCTGACCTGTCTGGTGA<br>AGGGCTTCTACCCCAGCGACATCGCCGTGGAGTGGGAGAG<br>CAACGGCCAGCCCGAGAACAACTACAAGACCACCCCCCCA<br>GTGCTGGACAGCGACGGCAGCTTCTTCCTGTACAGCAAGC<br>TGACCGTGGACAAGTCCAGGTGGCAGCAGGGCAACGTGTT<br>CAGCTGCAGCGTGATGCACGAGGCCCTGCACAACCACTAC<br>ACCCAGAAGAGCCTGAGCCTGTCCCCCGGCAAG |
| SEQ ID NO: 278<br>(Combined) | LCDR1 | SGSTSNIANNYVL |
| SEQ ID NO: 279<br>(Combined) | LCDR2 | DNNKRPS |
| SEQ ID NO: 280<br>(Combined) | LCDR3 | GTWDNSLSVGV |
| SEQ ID NO: 281<br>(Kabat) | LCDR1 | SGSTSNIANNYVL |
| SEQ ID NO: 282<br>(Kabat) | LCDR2 | DNNKRPS |
| SEQ ID NO: 283<br>(Kabat) | LCDR3 | GTWDNSLSVGV |

TABLE 2-continued

Anti-Polyoma virus Antibodies

| SEQ ID NO: 284 (Chothia) | LCDR1 | STSNIANNY |
|---|---|---|
| SEQ ID NO: 285 (Chothia) | LCDR2 | DNN |
| SEQ ID NO: 286 (Chothia) | LCDR3 | WDNSLSVG |
| SEQ ID NO: 287 (IMGT) | LCDR1 | TSNIANNY |
| SEQ ID NO: 288 (IMGT) | LCDR2 | DNN |
| SEQ ID NO: 289 (IMGT) | LCDR3 | GTWDNSLSVGV |
| SEQ ID NO: 290 | VL | QSALTQPPSVSAAPGQKVTISCSGSTSNIANNYVLWYQQL PGTAPKLLIYDNNKRPSGIPDRFSGSKSGTSATLGITGLQ TADEADYYCGTWDNSLSVGVFGGGTKLTVL |
| SEQ ID NO: 291 | DNAVL | CAGTCTGCCCTGACTCAGCCTCCCTCAGTGTCTGCGGCCC CAGGACAGAAGGTCACCATCTCCTGCTCTGGAAGCACCTC CAACATTGCGAATAATTATGTCTTATGGTACCAGCAACTC CCAGGAACAGCCCCCAAACTCCTCATTTATGACAATAATA AGCGACCCTCAGGGATTCCTGACCGATTCTCCGGCTCCAA GTCTGGCACGTCAGCCACCCTGGGCATCACCGGACTCCAG ACTGCGGACGAGGCCGATTACTACTGCGGAACATGGGATA ACAGCCTGAGTGTTGGGGTGTTCGGCGGCGGGACCAAGTT GACCGTCCTA |
| SEQ ID NO: 292 | Light Chain | QSALTQPPSVSAAPGQKVTISCSGSTSNIANNYVLWYQQL PGTAPKLLIYDNNKRPSGIPDRFSGSKSGTSATLGITGLQ TADEADYYCGTWDNSLSVGVFGGGTKLTVLGQPKAAPSVT LFPPSSEELQANKATLVCLISDFYPGAVTVAWKADSSPVK AGVETTTPSKQSNNKYAASSYLSLTPEQWKSHRSYSCQVT HEGSTVEKTVAPTECS |
| SEQ ID NO: 293 | DNA Light Chain | CAGTCTGCCCTGACTCAGCCTCCCTCAGTGTCTGCGGCCC CAGGACAGAAGGTCACCATCTCCTGCTCTGGAAGCACCTC CAACATTGCGAATAATTATGTCTTATGGTACCAGCAACTC CCAGGAACAGCCCCCAAACTCCTCATTTATGACAATAATA AGCGACCCTCAGGGATTCCTGACCGATTCTCCGGCTCCAA GTCTGGCACGTCAGCCACCCTGGGCATCACCGGACTCCAG ACTGCGGACGAGGCCGATTACTACTGCGGAACATGGGATA ACAGCCTGAGTGTTGGGGTGTTCGGCGGCGGGACCAAGTT GACCGTCCTAGGTCAGCCCAAGGCTGCCCCCTCGGTCACT CTGTTCCCGCCCTCCTCTGAGGAGCTTCAAGCCAACAAGG CCACACTGGTGTGTCTCATAAGTGACTTCTACCCGGGAGC CGTGACAGTGGCCTGGAAGGCAGATAGCAGCCCCGTCAAG GCGGGAGTGGAGACCACCACACCCTCCAAACAAAGCAACA ACAAGTACGCCGCCAGCAGCTACCTGAGCCTGACGCCTGA GCAGTGGAAGTCCCACAGAAGCTACAGCTGCCAGGTCACC CACGAGGGCAGCACCGTGGAGAAAACCGTGGCCCCCACCG AGTGCAGC |

NOV527

| SEQ ID NO: 294 | Heavy Chain | MELGLCWLLLVAILKGVQCEVQLLESGGGLVQPGGSLRLS CAASGFIFRNYGMSWLRQAPGKGLEWVSAISGSGANTYYT DSVKGRFTISRDNSKNTLYLQIYSLTAEDTALYYCAKSKG DGGADAFDVWGQGTLVTVSSGSASAPTLFPLVSCENSPSD TSSVAVGCLAQDFLPDSITFSWKYKNNSDISSTRGFPSVL RGGKYAATSQVLLPSKDVMQGTDEHVVCKVQHPNGNKEKN VPLPVIAELPPKVSVFVPPRDGFFGNPRKSKLICQATGFS PRQIQVSWLREGKQVGSGVTTDQVQAEAKESGPTTYKVTS TLTIKESDWLGQSMFTCRVDHRGLTFQQNASSMCVPDQDT AIRVFAIPPSFASIFLTKSTKLTCLVTDLTTYDSVTISWT RQNGEAVKTHTNISESHPNATFSAVGEASICEDDWNSGER FTCTVTHTDLPSPLKQTISRPKGVALHRPDVYLLPPAREQ LNLRESATITCLVTGFSPADVFVQWMQRGQPLSPEKYVTS APMPEPQAPGRYFAHSILTVSEEEWNTGETYTCVVAHEAL PNRVTERTVDKSTGKPTLYNVSLVMSDTAGTCY |
| SEQ ID NO: 295 | Light chain | MRLPAQLLGLLLLWLPGAKCDIRMTQSPSTLSASVGDRVT ITCRASQSISRWLAWYQQKPGKAPKLLIYKASSLESGVPS RFSGSGSATEFTLTISSLQPDDFATYYCQQYNSFWTFGQG |

TABLE 2-continued

Anti-Polyoma virus Antibodies

|  |  |  | TKVEIKRTVAAPSVFIFPPPSDEQLKSGTASVVCLLNNFYP<br>REAKVQWKVDNALQSGNSQESVTEQDSKDSTYSLSSTLTL<br>SKADYEKHKVYACEVTHQGLSSPVTKSFNRGEC |

NOV280

| SEQ ID NO: 296 | Heavy<br>Chain | MELGLCWVFLVALLRGVQCQVQLVESGGGVVQPGRSLRLS<br>CAASGFTFSSYGMHWVRQAPGKGLEWVAVIWYDGSNKYYA<br>DSVKGRFT1SRDNSKNTLYLQMNSLRAEDTAVYYCARDPL<br>IVVVPAAIYYYYGMDVWGQGTTVTVSSGSASAPTLFPLVS<br>CENSPSDTSSVAVGCLAQDFLPDSITFSWKYKNNSDISST<br>RGFPSVLRGGKYAATSQVLLPSKDVMQGTDEHVVCKVQHP<br>NGNKEKNVPLPVIAELPPKVSVFVPPRDGFFGNPRKSKLI<br>CQATGFSPRQIQVSWLREGKQVGSGVTTDQVQAEAKESGP<br>TTYKVTSTLTIKESDWLGQSMFTCRVDHRGLTFQQNASSM<br>CVPDQDTAIRVFAIPPSFASIFLTKSTKLTCLVTDLTTYD<br>SVTISWTRQNGEAVKTHTNISESHPNATFSAVGEASICED<br>DWNSGERFTCTVTHTDLPSPLKQTISRPKGVALHRPDVYL<br>LPPAREQLNLRESATITCLVTGFSPADVFVQWMQRGQPLS<br>PEKYVTSAPMPEPQAPGRYFAHSILTVSEEEWNTGETYTC<br>VVAHEALPNRVTERTVDKSTGKPTLYNVSLVMSDTAGTCY |
| SEQ ID NO: 297 | Light<br>chain | MDMRVPAQLLGLLLLWLRGARCDIQMTQSPSSLSASVGDR<br>VTITCRTSQSISSYLNWYQQKPGKAPKLLIYAASSLQSGV<br>PSRFSGSGSGTDFTLTISSLQPEDFATYYCQQSYSTPITF<br>GQGTRLEIKRTVAAPSVFIFPPSDEQLKSGTASVVCLLNN<br>FYPREAKVQWKVDNALQSGNSQESVTEQDSKDSTYSLSST<br>LTLSKADYEKHKVYACEVTHQGLSSPVTKSFNRGEC |

NOV756

| SEQ ID NO: 298 | Heavy<br>Chain | MKHLWFFLLLVAAPRWVLSQLQLQESGPGLVKPSETLSLT<br>CTVSGGSISSSSYYWGWIRQPPGKGLEWIGSIYYSGSTYY<br>NPSLKSRVTISVDTSKNQFSLKLSSVTAADTAVYYCARLG<br>YYYYMDVWGKGTTVTVSSGSASAPTLFPLVSCENSPSDTS<br>SVAVGCLAQDFLPDSITFSWKYKNNSDISSTRGFPSVLRG<br>GKYAATSQVLLPSKDVMQGTDEHVVCKVQHPNGNKEKNVP<br>LPVIAELPPKVSVFVPPRDGFFGNPRKSKLICQATGFSPR<br>QIQVSWLREGKQVGSGVTTDQVQAEAKESGPTTYKVTSTL<br>TIKESDWLGQSMFTCRVDHRGLTFQQNASSMCVPDQDTAI<br>RVFAIPPSFASIFLTKSTKLTCLVTDLTTYDSVTISWTRQ<br>NGEAVKTHTNISESHPNATFSAVGEASICEDDWNSGERFT<br>CTVTHTDLPSPLKQTISRPKGVALHRPDVYLLPPAREQLN<br>LRESATITCLVTGFSPADVFVQWMQRGQPLSPEKYVTSAP<br>MPEPQAPGRYFAHSILTVSEEEWNTGETYTCVVAHEALPN<br>RVTERTVDKSTGKPTLYNVSLVMSDTAGTCY |
| SEQ ID NO: 299 | Light<br>chain | MVLQTQVFISLLLLWISGAYGDIVMTQSPDSLAVSLGERAT<br>INCKSSQSVLYSSNNKNYLAWYQQKPGQPPKLLIYWASTR<br>ESGVPDRFSGSGSGTDFTLTISSLQAEDVAVYYCQQYYST<br>PPTFGGGTKVEIKRTVAAPSVFIFPPSDEQLKSGTASVVC<br>LLNNFYPREAKVQWKVDNALQSGNSQESVTEQDSKDSTYS<br>LSSTLTLSKADYEKHKVYACEVTHQGLSSPVTKSFNRGEC |

NON252

| SEQ ID NO: 300 | Heavy<br>Chain | MEFGLSWVFLVAILKGVQCEVQVVESGGGLVQPGESLRLS<br>CAASGFTFSNYFMHWVRQAPGMGLEWVARINTDGSVTMYA<br>DSVKGRFTISRDNAKNTVYLQMNSLRAEDTAVYYCVRPNS<br>VHDKLLENWGQGTLVTVSSGSASAPTLFPLVSCENSPSDT<br>SSVAVGCLAQDFLPDSITFSWKYKNNSDISSTRGFPSVLR<br>GGKYAATSQVLLPSKDVMQGTDEHVVCKVQHPNGNKEKNV<br>PLPVIAELPPKVSVFVPPRDGFFGNPRKSKLICQATGFSP<br>RQIQVSWLREGKQVGSGVTTDQVQAEAKESGPTTYKVTST<br>LTIKESDWLGQSMFTCRVDHRGLTFQQNASSMCVPDQDTA<br>IRVFAIPPSFASIFLTKSTKLTCLVTDLTTYDSVTISWTR<br>QNGEAVKTHTNISESHPNATFSAVGEASICEDDWNSGERF<br>TCTVTHTDLPSPLKQTISRPKGVALHRPDVYLLPPAREQL<br>NLRESATITCLVTGFSPADVFVQWMQRGQPLSPEKYVTSA<br>PMPEPQAPGRYFAHSILTVSEEEWNTGETYTCVVAHEALP<br>NRVTERTVDKSTGKPTLYNVSLVMSDTAGTCY |
| SEQ ID NO: 301 | Light<br>chain | MRLPAQLLGLLLLWLPGAKCDIQMTQSPSTLSASVGDRVT<br>ITCRASQSISSWLAWYQQKPGKAPKLLINKASSLESGVPS<br>RFSGSGSGTEFTLTINSLQPDDFATYYCQQYYTYSSYRFG<br>QGTKLEIKRTVAAPSVFIFPPSDEQLKSGTASVVCLLNNF<br>YPREAKVQWKVDNALQSGNSQESVTEQDSKDSTYSLSSTL<br>TLSKADYEKHKVYACEVTHQGLSSPVTKSFNRGEC |

TABLE 2-continued

Anti-Polyoma virus Antibodies

NOV157

| SEQ ID NO: 302 | Heavy Chain | MSVSFLLLVAAPRWVLSQQQLQESGPGLVKPSETLSLTCX VSGGSISSSSYYWGWIRQPPGKGLEWIGSIYYRGSTYYNP SLRSRVTASVDTSRNQFSLRLSSVTAADTAVYYCARSYCS GSCYAVGAFDMWGQGTMVTVSSGSASAPTLFPLVSCENSP SDTSSVAVGCLAQDFLPDSITFSWKYKNNSDISSTRGFPS VLRGGKYAATSQVLLPSKDVMQGTDEHVVCKVQHPNGNKE KNVPLPVIAELPPKVSVFVPPRDGFFGNPRKSKLICQATG FSPRQIQVSWLREGKQVGSGVTTDQVQAEAKESGPTTYKV TSTLTIKESDWLGQSMFTCRVDHRGLTFQQNASSMCVPDQ DTAIRVFAIPPSFASIFLTKSTKLTCLVTDLTTYDSVTIS WTRQNGEAVKTHTNISESHPNATFSAVGEASICEDDWNSG ERFTCTVTHTDLPSPLKQTISRPKGVALHRPDVYLLPPAR EQLNLRESATITCLVTGFSPADVFVQWMQRGQPLSPEKYV TSAPMPEPQAPGRYFAHSILTVSEEEWNTGETYTCVVAHE ALPNRVTERTVDKSTGKPTLYNVSLVMSDTAGTCY |
|---|---|---|
| SEQ ID NO: 303 | Light chain | MAWTPLLFLTLLLHCTGSLSQLVLTQSPSASASLGASVKL TCTLSSGHSSHAIAWHQQQPEKGPRYLIKLNSDGSHNKGD GIPDRFSGSSSGAERYLTISSLQSEDEADYYCQTWDTGIV VFGGGTKLTVLGQPKAAPSVTLFPPSSEELQANKATLVCL ISDFYPGAVTVAWKADSSPVKAGVETTTPSKQSNNKYAAS SYLSLTPEQWKSHRSYSCQVTHEGSTVEKTVAPTECS |

NOV882

| SEQ ID NO: 304 | Heavy Chain | MEFGLSWVFLVALLRGVQCQVQLVESGGGVVQPGRSLRLS CAASGFTFSSYAMHWVRQAPGKGLEWVAVISYDGSNKYYA DSVKGRFT1SRDNSKNTLYLQMNSLRAEDTAVYYCARDFR GWGGGSGGSCGYWGQGTLVTVSSGSASAPTLFPLVSCENS PSDTSSVAVGCLAQDFLPDSITFSWKYKNNSDISSTRGFP SVLRGGKYAATSQVLLPSKDVMQGTDEHVVCKVQHPNGNK EKNVPLPVIAELPPKVSVFVPPRDGFFGNPRKSKLICQAT GFSPRQIQVSWLREGKQVGSGVTTDQVQAEAKESGPTTYK VTSTLTIKESDWLGQSMFTCRVDHRGLTFQQNASSMCVPD QDTAIRVFAIPPSFASIFLTKSTKLTCLVTDLTTYDSVTI SWTRQNGEAVKTHTNISESHPNATFSAVGEASICEDDWNS GERFTCTVTHTDLPSPLKQTISRPKGVALHRPDVYLLPPA REQLNLRESATITCLVTGFSPADVFVQWMQRGQPLSPEKY VTSAPMPEPQAPGRYFAHSILTVSEEEWNTGETYTCVVAH EALPNRVTERTVDKSTGKPTLYNVSLVMSDTAGTCY |
|---|---|---|
| SEQ ID NO: 305 | Light chain | MALTPLLLTLLAHCTGSWANFMLTQPHSVSESPGKTVTIS CTRSSGSIASNYVQWYQQRPGSSPTTVIYEDNQRPSGVPD RFSGSIDSSSNSASLTISGLKTEDEADYYCQSYDSSNLYV FGTGTKVTVLGQPKANPTVTLFPPSSEELQANKATLVCLI SDFYPGAVTVAWKADGSPVKAGVETTKPSKQSNNKYAASS YLSLTPEQWKSHRSYSCQVTHEGSTVEKTVAPTECS |

NOV578

| SEQ ID NO: 306 | Heavy Chain | MEFGLSWVFLVAIIKGVQCQVQLVESGGGLVKPGGSLRLS CAASGFTFSDYFMSWVRQTPGKGLEWLSYMSSDGTIIHHA DSLKGRFTISRDNAKNSLFLQMNTLRAEDTAVYYCATHIL ETTIAAFEIWGRGTMVIVSSASTKGPSVFPLAPCSRSTSE STAALGCLVKDYFPEPVTVSWNSGALTSGVHTFPAVLQSS GLYSLSSVVTVPSSNFGTQTYICNVNHKPSNTKVDKRVEP KSCDKTHTCPPCPAPELLGGPSVFLFPPKPKDTLMISRTP EVTCVVVDVSHEDPEVKFNWYVDGVEVHNAKTKPREEQYN STYRVVSVLTVLHQDWLNGKEYKCKVSNKALPAPIEKTIS KAKGQPREPQVYTLPPSREEMTKNQVSLTCLVKGFYPSDI AVEWESNGQPENNYKTTPPVLDSDGSFFLYSKLTVDKSRW QQGNVFSCSVMHEALHNHYTQKSLSLSPGK |
|---|---|---|
| SEQ ID NO: 307 | Light chain | MVLQTQVFISLLLWIAGAYGDIVMTQSPDSLALSLGERAT INCRSSHSVLYRSNNNNYVAWYQQKPGQPPRLLIYWASNR ASGVPDRFSGSGSGTDFTLTISSLQPEDAAVYFCQQILDT PFTFGPGTKVEIKRTVAAPSVFIFPPSDEQLKSGTASVVC LLNNFYPREAKVQWKVDNALQSGNSQESVTEQDSKDSTYS LSSTLTLSKADYEKHKVYACEVTHQGLSSPVTKSFNRGEC |

NOV265

| SEQ ID NO: 308 | Heavy Chain | MEFGLSWLFLVATLKGVQCEVQLLESGGGLMQPGGSXRLS CAASGFTFRSYAMNWVRQAPGKGLEWVSTISGNGGTTYYA DSVRGRFTISRDNSKNTLFLQMNSLRAEDTAIYYCAQGEP |
|---|---|---|

TABLE 2-continued

Anti-Polyoma virus Antibodies

WSGYLEPLFASWGQGTLVTVSSASTKGPSVFPLAPCSRST
SGGTAALGCLVKDYFPEPVTVSWNSGALTSGVHTFPAVLQ
SSGLYSLSSVVTVPSSSLGTQTYICNVNHKPSNTKVDKRV
EPKSCDKTHTCPPCPAPELLGGPSVFLFPPKPKDTLMISR
TPEVTCVVVDVSHEDPEVKFNWYVDGVEVHNAKTKPREEQ
YNSTYRVVSVLTVLHQDWLNGKEYKCKVSNKALPAPIEKT
ISKAKGQPREPQVYTLPPSREEMTKNQVSLTCLVKGFYPS
DIAVEWESNGQPENNYKTTPPVLDSDGSFFLYSKLTVDKS
RWQQGNVFSCSVMHEALHNHYTQKSLSLSPGK

SEQ ID NO: 309    Light      MAWTPLWLTLLTLCIGSVVSSELTQDPAVSVALGQTVRIT
                  chain      CQGDSLRNFYASWYQQKPGQAPVLVIYGKNNRPSGIPDRF
                             SGSSSGNTVSLTITGAQAEDDADYYCNSRDSSGNHVIFGG
                             GTKLTVLGQPKAAPSVTLFPPSSEELQANKATLVCLISDF
                             YPGAVTVAWKADSSPVKAGVETTTPSKQSNNKYAASSYLS
                             LTPEQWKSHRSYSCQVTHEGSTVEKTVAPTECS

NOV612

SEQ ID NO: 310    Heavy      MELGLCWVFLVAILEGVQCEVQLVESGGGLVHPGGSLRLS
                  Chain      CAASGFTFRTYIMNWVRQAPGKGLEWISYISASSGTIYYA
                             DSVKGRFTISRDNAKNSLYLQMNSLRAEDTAVYYCARDLD
                             CSGGTCYDGFDSWGHGTLVTVSSSSTKGPSVFPLAPSSKS
                             TSGGTAALGCLVKDYFPEPVTVSWNSGALTSGVHTFPAVL
                             QSSGLYSLSSVVTVPSSSLGTQTYICNVNHKPSNTKVDKR
                             VEPKSCDKTHTCPPCPAPELLGGPSVFLFPPKPKDTLMIS
                             RTPEVTCVVVDVSHEDPEVKFNWYVDGVEVHNAKTKPREE
                             QYNSTYRVVSVLTVLHQDWLNGKEYKCKVSNKALPAPIEK
                             TISKAKGQPREPQVYTLPPSREEMTKNQVSLTCLVKGFYP
                             SDIAVEWESNGQPENNYKTTPPVLDSDGSFFLYSKLTVDK
                             SRWQQGNVFSCSVMHEALHNHYTQKSLSLSPGK SEQ ID NO: 311    Light      MAWTPLFLGVLAYCTGSVASYELTQPPSLSVSPGQTASIT
                  chain      CSGDKLGDKYACWYQQRPGQSPVLVIYQDTKRPSGIPERF
                             SGSNSGNTATLTISGTQAMDEADYYCQAWDSSTAVFGGGT
                             RLTVLGQPKAAPSVTLFPPSSEELQANKATLVCLISDFYP
                             GAVTVAWKADSSPVKAGVETTTPSKQSNNKYAASSYLSLT
                             PEQWKSHRSYSCQVTHEGSTVEKTVAPTECS

NOV773

SEQ ID NO: 312    Heavy      MEFGLSWIFLLAILKGVQCEVQLVESGGGLVQPGRSLRLS
                  Chain      CAASGFNFDNYAMHWVRQVPGKGLEWVSGINWNSGYEGYA
                             DSVKGRFTISRDNAQNSLYLQMDSLRTDDTALYYCTKDTI
                             AAVGRGAFDIWGQGTKVTVSSASTKGPSVFPLAPCSRSTS
                             GGTAALGCLVKDYFPEPVTVSWNSGALTSGVHTFPAVLQS
                             SGLYSLSSVVTVPSSSLGTQTYICNVNHKPSNTKVDKRVE
                             PKSCDKTHTCPPCPAPELLGGPSVFLFPPKPKDTLMISRT
                             PEVTCVVVDVSHEDPEVKFNWYVDGVEVHNAKTKPREEQY
                             NSTYRVVSVLTVLHQDWLNGKEYKCKVSNKALPAPIEKTI
                             SKAKGQPREPQVYTLPPSREEMTKNQVSLTCLVKGFYPSD
                             IAVEWESNGQPENNYKTTPPVLDSDGSFFLYSKLTVDKSR
                             WQQGNVFSCSVMHEALHNHYTQKSLSLSPGK SEQ ID NO: 313    Light      MAWIPLLLGLLSHCTGSVTSYVLTQPPSVSVAPGKTAMIT
                  chain      CGGNKIGGKSVHWYQQKPGQAPVLVISYDSDRPSGIPQRF
                             SGSNSGNTATLTISRVEAGDEADYYCQVWDTSSVHRVFGG
                             GTKLTVLGQPKAAPSVTLFPPSSEELQANKATLVCLISDF
                             YPGAVTVAWKADSSPVKAGVETTTPSKQSNNKYAASSYLS
                             LTPEQWKSHRSYSCQVTHEGSTVEKTVAPTECS

NOV738

SEQ ID NO: 314    Heavy      MKHLWFFLLLVAAPRWVLSQLQLRESGPGLVKPSETLSLT
                  Chain      CSVSGDSISRSSDYWGWIRQPPGRGLEWIGSIYRTGSTYY
                             NPSLSSRVTISVDTSKSQFSLSLSSVTAADTALYYCARVR
                             HDYVWGSIYYYGMDVWGQGTTVTVSSPSTKGPSVFPLAPC
                             SRSTSGGTAALGCLVKDYFPEPVTVSWNSGALTSGVHTFP
                             AVLQSSGLYSLSSVVTVPSSSLGTQTYICNVNHKPSNTKV
                             DKRVEPKSCDKTHTCPPCPAPELLGGPSVFLFPPKPKDTL
                             MISRTPEVTCVWDVSHEDPEVKFNWYVDGVEVHNAKTKP
                             REEQYNSTYRVVSVLTVLHQDWLNGKEYKCKVSNKALPAP
                             IEKTISKAKGQPREPQVYTLPPSREEMTKNQVSLTCLVKG
                             FYPSDIAVEWESNGQPENNYKTTPPVLDSDGSFFLYSKLT
                             VDKSRWQQGNVFSCSVMHEALHNHYTQKSLSLSPGK TABLE 2-continued Anti-Polyoma virus Antibodies

| SEQ ID NO: 315 | Light chain | MAWSPLLLTQGTGSWAQSALTQPRSVSGSPGQSVTISCTG TGSDVGGYTYVSWYQQHPDKAPKLVIYDVTKRPSGVPDRF SGSKSGNTASLTISGLRADDEADYYCCSYAGRYSWVFGGG TKLTVLGQPKAAPSVTLFPPSSEELQANKATLVCLISDFY PGAVTVAWKADSSPVKAGVETTTPSKQSNNKYAASSYLSL TPEQWKSHRSYSCQVTHEGSTVEKTVAPTECS |
|---|---|---|

NOV151

| SEQ ID NO: 316 | Heavy Chain | MEFGLSWLFLVAILKGVHCEVDLLESGGGLIQPGGSLRLS CAASGFTFRNYAMNWVRQVPGKGLEWVSSVSGSGGTTYYA DSVKGRFSISRDNSKNTLYLQMNGLRAGDTAIYYCAKGEA WSGYLEPLCDFWGHGTLVTVSSASTKGPSVFPLAPSSKST SGGTAALGCLVKDYFPEPVTVSWNSGALTSGVHTFPAVLQ SSGLYSLSSVVTVPSSSLGTQTYICNVNHKPSNTKVDKRV EPKSCDKTHTCPPCPAPELLGGPSVFLFPPKPKDTLMISR TPEVTCVVVDVSHEDPEVKFNWYVDGVEVHNAKTKPREEQ YNSTYRVVSVLTVLHQDWLNGKEYKCKVSNKALPAPIEKT ISKAKGQPREPQVYTLPPSREEMTKNQVSLTCLVKGFYPS DIAVEWESNGQPENNYKTTPPVLDSDGSFFLYSKLTVDKS RWQQGNVFSCSVMHEALHNHYTQKSLSLSPGK |
|---|---|---|
| SEQ ID NO: 317 | Light chain | MALTPLWLTLLTLCIGSVVSSELTQDPAVSVALGQTVRIT CQGDSLRDFYGSWYQQKPGQAPVLVNFGYNNRPSGIPDRF SGSRSGNTASLTITGAQAEDEADYYCNSRDISGNRVVFGG GTKLTVVGQPEAAPSVTLFPPSSEELQANKATLVCLISDF YPGAVTVAWKADSSPVKAGVETTTPSKQSNNKYAASSYLS LTPEQWKSHRSYSCQVTHEGSTVEKTVAPTECS |

NOV212

| SEQ ID NO: 318 | Heavy Chain | MKHLWFFLLLVAAPRWVLSQLQLQESGSGLVRPSQTLSLT CAVSGASISSGGYSWSWIRQPPGKGLEWIGYIYHSGSTSY NPSLKSRVTISEDKSNNQFSLKLSSVTAADTAVYYCARVW ASFYYGSWTPPTWFDPWGPGTLVTVSSASTKGPSVFPLAP CSRSTSGGTAALGCLVKDYFPEPVTVSWNSGALTSGVHTF PAVLQSSGLYSLSSVVTVPSSSLGTQTYICNVNHKPSNTK VDKRVEPKSCDKTHTCPPCPAPELLGGPSVFLFPPKPKDT LMISRTPEVTCVVVDVSHEDPEVKFNWYVDGVEVHNAKTK PREEQYNSTYRVVSVLTVLHQDWLNGKEYKCKVSNKALPA PIEKTISKAKGQPREPQVYTLPPSREEMTKNQVSLTCLVK GFYPSDIAVEWESNGQPENNYKTTPPVLDSDGSFFLYSKL TVDKSRWQQGNVFSCSVMHEALHNHYTQKSLSLSPGK |
|---|---|---|
| SEQ ID NO: 319 | Light chain | MAWIPLLLTQGTGSWAQSALTQPRSVSGSPGQSVTISCTG TGSNVGGYTYVSWYQQHPGKAPKLLIYDVSKRPSGVPDRF SGSKSGNTASLTISGLQADDEADYHCCSYAGGYTLVFGGG TKLTVLGQPKAAPSVTLFPPSSEELQANKATLVCLISDFY PGAVTVAWKADSSPVKAGVETTTPSKQSNNKYAASSYLSL TPEQWKSHRSYSCQVTHEGSTVEKTVAPTECS |

NOV624

| SEQ ID NO: 320 | Heavy Chain | MELGLSWVFLVAILEGVQCEVQLVESGGGLVQPGGSLRLS CSASGFTFRSYIINWVRQAPGKGLEWVSYISGSSGTKNYA DSVKGRFTISRDNAKNSVYLQMNSLRAEDTAVYYCARDLD CSGGSCYDGMDVWGQGTTVTVSSASTKGPSVFPLAPCSRS TSGGTAALGCLVKDYFPEPVTVSWNSGALTSGVHTFPAVL QSSGLYSLSSVVTVPSSSLGTQTYICNVNHKPSNTKVDKR VEPKSCDKTHTCPPCPAPELLGGPSVFLFPPKPKDTLMIS RTPEVTCVVVDVSHEDPEVKFNWYVDGVEVHNAKTKPREE QYNSTYRVVSVLTVLHQDWLNGKEYKCKVSNKALPAPIEK TISKAKGQPREPQVYTLPPSREEMTKNQVSLTCLVKGFYP SDIAVEWESNGQPENNYKTTPPVLDSDGSFFLYSKLTVDK SRWQQGNVFSCSVMHEALHNHYTQKSLSLSPGK |
|---|---|---|
| SEQ ID NO: 321 | Light chain | MAWTPLLLGVLAYCTGSVASFELTQPPSVSVSPGQTASIT CSGDKLGHHYAYWFQQRPGQSPVLVIYQHTKRPSGIPERF SGSKSGNTATLTISGTQAMDEADYYCQAWDSSTYVVFGGG TKVTVLGQPKAAPSVTLFPPSSEELQANKATLVCLISDFY PGAVTVAWKADSSPVKAGVETTTPSKQSNNKYAASSYLSL TPEQWKSHRSYSCQVTHEGSTVEKTVAPTECS |

NOV696

| SEQ ID NO: 322 | Heavy Chain | MKHLWFFLLLVAAPRWVLSQVQLQESGPGLVKPSQTLSLT CSVSGGSISSGSHYWSWIRQPAGEALEWIGRTYTSGRTSY NPSLKSRVTISVDTSKNQFSLKLTSVTAADTAVYYCARNS |
|---|---|---|

TABLE 2-continued

Anti-Polyoma virus Antibodies

RIYGGYELFDIWGQGTMVTVSSASTKGPSVFPLAPSSKST
SGGTAALGCLVKDYFPEPVTVSWNSGALTSGVHTFPAVLQ
SSGLYSLSSVVTVPSSSLGTQTYICNVNHKPSNTKVDKRV
EPKSCDKTHTCPPCPAPELLGGPSVFLFPPKPKDTLMISR
TPEVTCVVVDVSHEDPEVKFNWYVDGVEVHNAKTKPREEQ
YNSTYRVVSVLTVLHQDWLNGKEYKCKVSNKALPAPIEKT
ISKAKGQPREPQVYTLPPSREEMTKNQVSLTCLVKGFYPS
DIAVEWESNGQPENNYKTTPPVLDSDGSFFLYSKLTVDKS
RWQQGNVFSCSVMHEALHNHYTQKSLSLSPGK

SEQ ID NO: 323    Light      MAWTPLLLGLLSHCTGSLTSYVLTQPPSVSVAPGKTARIP
                  chain      CGGDNIGNKGVHWYQQKSGQAPVLLIHYDSDRPSGIPERF
                             SGSNSGNTATLSISRVELGDEADYYCQVWDTSSDQPVFGG
                             GTKLTVLGQPKAAPSVTLFPPSSEELQANKATLVCLISDF
                             YPGAVTVAWKADSSPVKAGVETTTPSKQSNNKYAASSYLS
                             LTPEQWKSHRSYSCQVTHEGSTVEKTVAPTECS

NOV474

SEQ ID NO: 324    Heavy      MEFGLSWVFLVAILEGVQCEVQLVESGGGLVQPGGSLRLS
                  Chain      CAASGFTFRSYMMNWVRQAPGKGLEWVSYISGSGGTKYYV
                             DSVKGRFTISRDNAKNSLYLQMHSLRAEDTAVYYCARDLD
                             CSGGTCYDGMDVWGQGTTVTVSSASTKGPSVFPLAPCSRS
                             TSGGTAALGCLVKDYFPEPVTVSWNSGALTSGVHTFPAVL
                             QSSGLYSLSSVVTVPSSSLGTQTYICNVNHKPSNTKVDKR
                             VEPKSCDKTHTCPPCPAPELLGGPSVFLFPPKPKDTLMIS
                             RTPEVTCVVVDVSHEDPEVKFNWYVDGVEVHNAKTKPREE
                             QYNSTYRVVSVLTVLHQDWLNGKEYKCKVSNKALPAPIEK
                             TISKAKGQPREPQVYTLPPSREEMTKNQVSLTCLVKGFYP
                             SDIAVEWESNGQPENNYKTTPPVLDSDGSFFLYSKLTVDK
                             SRWQQGNVFSCSVMHEALHNHYTQKSLSLSPGK SEQ ID NO: 325    Light      MAWAPLLLGVLAYCTGSVASYELIQPPSVSVSPGQTASIT
                  chain      CSGDKLGNKYVYWFQHRPGQSPVLVIYQHTKRPSGIPERF
                             SGSKSGNTATLIISGTQAMDEADYYCQAWDSSVVIFGGGT
                             KLTVLGQPKAAPSVTLFPPSSEELQANKATLVCLISDFYP
                             GAVTVAWKADSSPVKAGVETTTPSKQSNNKYAASSYLSLT
                             PEQWKSHRSYSCQVTHEGSTVEKTVAPTECS

NOV126

SEQ ID NO: 326    Heavy      MKHLWFFLLLVAAPRWVLSQLQLQESGPGLVKPSETLSLT
                  Chain      CSVSGDSISRSSDYWGWIRQPPGRGLEWIGSIYRTGSTYY
                             NPSLSSRVTISVDTSKSQFSLSLSSVTAADTALYYCARVR
                             HDYVWGSIYYYGMDVWGQGTTVTVSSPSTKGPSVFPLAPC
                             SRSTSGGTAALGCLVKDYFPEPVTVSWNSGALTSGVHTFP
                             AVLQSSGLYSLSSVVTVPSSSLGTQTYICNVNHKPSNTKV
                             DKRVEPKSCDKTHTCPPCPAPELLGGPSVFLFPPKPKDTL
                             MISRTPEVTCVVVDVSHEDPEVKFNWYVDGVEVHNAKTKP
                             REEQYNSTYRVVSVLTVLHQDWLNGKEYKCKVSNKALPAP
                             IEKTISKAKGQPREPQVYTLPPSREEMTKNQVSLTCLVKG
                             FYPSDIAVEWESNGQPENNYKTTPPVLDSDGSFFLYSKLT
                             VDKSRWQQGNVFSCSVMHEALHNHYTQKSLSLSPGK SEQ ID NO: 327    Light      MAWIPLLLTQGTGSWAQSALTQPRSVSGSPGQSVTISCTG
                  chain      TGSDVGGYTYVSWYQQHPDKAPKLVIYDVTKRPSGVPDRF
                             SGSKSGNTASLTISGLRADDEADYYCCSYAGRYSWVFGGG
                             TKLTVLGQPKAAPSVTLFPPSSEELQANKATLVCLISDFY
                             PGAVTVAWKADSSPVKAGVETTTPSKQSNNKYAASSYLSL
                             TPEQWKSHRSYSCQVTHEGSTVEKTVAPTECS

NOV128

SEQ ID NO: 328    Heavy      MDWTWRILFLVAAATGAHSQVQLVQSGAEVKKPGASVKVS
                  Chain      CKTSGYTFTAYHLHWVRQTPGQGLEWMGWINPNSGGTNYA
                             LKFQGRVTVTRDTSISTVYMELTRLRSDDTAVYYCAREKE
                             PLMASYYYYGMDVWGQGTTVTVSSASTKGPSVFPLAPCSR
                             STSGGTAALGCLVKDYFPEPVTVSWNSGALTSGVHTFPAV
                             LQSSGLYSLSSVVTVPSSSLGTQTYICNVNHKPSNTKVDK
                             RVEPKSCDKTHTCPPCPAPELLGGPSVFLFPPKPKDTLMI
                             SRTPEVTCVVVDVSHEDPEVKFNWYVDGVEVHNAKTKPRE
                             EQYNSTYRVVSVLTVLHQDWLNGKEYKCKVSNKALPAPIE
                             KTISKAKGQPREPQVYTLPPSREEMTKNQVSLTCLVKGFY
                             PSDIAVEWESNGQPENNYKTTPPVLDSDGSFFLYSKLTVD
                             KSRWQQGNVFSCSVMHEALHNHYTQKSLSLSPGK SEQ ID NO: 329    Light      MAWAPLWLTLLTLCIGSVVSSEVTQDPAVSVALGQTVRIT
                  chain      CQGDSLRNYYTRWYQQKPGQAPVLVIYRENNRPSGIPDRF TABLE 2-continued Anti-Polyoma virus Antibodies SGSSSGNTASLTITGAQAEDEADYYCTSRATNTDHLVFGG
GTKLTVLGQPKAAPSVTLFPPSSEELQANKATLVCLISDF
YPGAVTVAWKADSSPVKAGVETTTPSKQSNNKYAASSYLS
LTPEQWKSHRSYSCQVTHEGSTVEKTVAPTECS

NOV265

| SEQ ID NO: 330 | Heavy Chain | MKHLWFFLLLVAAPRWVLSQLQLQESGSGLVRPSQTLSLT<br>CAVSGASINSGGYSWSWIRQPPGKGLEWIGYIYHSGSTSY<br>NPSLKSRVTISEDRSKNQFSLKLSSVTAADTAVYYCARVW<br>ASFYYGSWTPPTWLDPWGPGTLVTVSSASTKGPSVFPLAP<br>CSRSTSGGTAALGCLVKDYFPEPVTVSWNSGALTSGVHTF<br>PAVLQSSGLYSLSSVVTVPSSSLGTQTYICNVNHKPSNTK<br>VDKRVEPKSCDKTHTCPPCPAPELLGGPSVFLFPPKPKDT<br>LMISRTPEVTCVVVDVSHEDPEVKFNWYVDGVEVHNAKTK<br>PREEQYNSTYRVVSVLTVLHQDWLNGKEYKCKVSNKALPA<br>PIEKTISKAKGQPREPQVYTLPPSREEMTKNQVSLTCLVK<br>GFYPSDIAVEWESNGQPENNYKTTPPVLDSDGSFFLYSKL<br>TVDKSRWQQGNVFSCSVMHEALHNHYTQKSLSLSPGK |
|---|---|---|
| SEQ ID NO: 331 | Light chain | MAWSPLLLTQGTGSWAQSALTQPRSVSGSPGQSVTISCTG<br>TGSDVGGYTYVSWYQQHPGKAPKLMIYDVSKRPSGVPDRF<br>SGSKSGNTASLTISGLQADDEADYYCCSYAGGYTLVFGGG<br>TKLTVLGQPKAAPSVTLFPPSSEELQANKATLVCLISDFY<br>PGAVTVAWKADSSPVKAGVETTTPSKQSNNKYAASSYLSL<br>TPEQWKSHRSYSCQVTHEGSTVEKTVAPTECS |

NOV864

| SEQ ID NO: 332 | Heavy Chain | MEFGLSWIFLLAILKGVQCEVQLVESGGGLVQPGRSLRLS<br>CAASGFNFDNYAMHWVRQVPGKGLEWVSGINWNSGYEAYA<br>DSVKGRFIISRDNAQNSLYLQMNSLRADDTAFYYCTKDTI<br>AAVGRGAFDIWGQGTGVSVSPASTKGPSVFPLAPCSRSTS<br>GGTAALGCLVKDYFPEPVTVSWNSGALTSGVHTFPAVLQS<br>SGLYSLSSVVTVPSSSLGTQTYICNVNHKPSNTKVDKRVE<br>PKSCDKTHTCPPCPAPELLGGPSVFLFPPKPKDTLMISRT<br>PEVTCVVVDVSHEDPEVKFNWYVDGVEVHNAKTKPREEQY<br>NSTYRVVSVLTVLHQDWLNGKEYKCKVSNKALPAPIEKTI<br>SKAKGQPREPQVYTLPPSREEMTKNQVSLTCLVKGFYPSD<br>IAVEWESNGQPENNYKTTPPVLDSDGSFFLYSKLTVDKSR<br>WQQGNVFSCSVMHEALHNHYTQKSLSLSPGK |
|---|---|---|
| SEQ ID NO: 333 | Light chain | MAWIPLLLGLLSHCTGSVTSYLLTQPPSVSVAPGKTAMIT<br>CGGSKIGGKSVHWYQQKPGQAPVLVISYDSDRPSGIPKRF<br>SGSNSGNTATLTISGVEAGDEADYYCQVWDSSNVHRVFGG<br>GTKLTVLSQPKAAPSVTLFPPSSEELQANKATLVCLISDF<br>YPGAVTVAWKADSSPVKAGVETTTPSKQSNNKYAASSYLS<br>LTPEQWKSHRSYSCQVTHEGSTVEKTVAPTECS |

NOV618

| SEQ ID NO: 334 | Heavy Chain | MKHLWFFLLLVAAPRWVLSQLQLQESGPGLVKPSETLSLT<br>CSVSGDSISRSSDYWGWIRQPPGRGLEWIGSIYRTGSTYY<br>NPSLSSRVTISVDTSKSQFSLSLSSVTAADTALYYCARVR<br>HDYVWGSIYYYGMDVWGQGTTVTVSSSPTKGPSVFPLAPC<br>SRSTSGGTAALGCLVKDYFPEPVTVSWNSGALTSGVHTFP<br>AVLQSSGLYSLSSVVTVPSSSLGTQTYICNVNHKPSNTKV<br>DKRVEPKSCDKTHTCPPCPAPELLGGPSVFLFPPKPKDTL<br>MISRTPEVTCVVVDVSHEDPEVKFNWYVDGVEVHNAKTKP<br>REEQYNSTYRVVSVLTVLHQDWLNGKEYKCKVSNKALPAP<br>IEKTISKAKGQPREPQVYTLPPSREEMTKNQVSLTCLVKG<br>FYPSDIAVEWESNGQPENNYKTTPPVLDSDGSFFLYSKLT<br>VDKSRWQQGNVFSCSVMHEALHNHYTQKSLSLSPGK |
|---|---|---|
| SEQ ID NO: 335 | Light chain | MAWIPLLLTQGTGSWAQSALTQPRSVSGSPGQSVTISCTG<br>TGSDVGGYTYVSWYQQHPDKAPKLVIYDVTKRPSGVPDRF<br>SGSKSGNTASLTISGLRADDEADYYCCSYAGQPKAAPSVT<br>LFPPSSEELQANKATLVCLISDFYPGAVTVAWKADSSPVK<br>AGVETTTPSKQSNNKYAASSYLSLTPEQWKSHRSYSCQVT<br>HEGSTVEKTVAPTECS |

NOV430

| SEQ ID NO: 336 | Heavy Chain | MELGLCWVFLVAILEGVQCEVQLVESGGGLVQPGGSLRLS<br>CSASGFTFRSYIINWVRQAPGKGLEWSYISGSSGTKNYA<br>DSVKGRFTISRDNAKNSVYLQMNSLRAEDTAVYYCARDLD<br>CSGGSCYDGMDVWGQGTTVTVSSASTKGPSVFPLAPCSRS<br>TSGGTAALGCLVKDYFPEPVTVSWNSGALTSGVHTFPAVL |

TABLE 2-continued

Anti-Polyoma virus Antibodies

|  |  |  |
|---|---|---|
|  |  | QSSGLYSLSSVVTVPSSSLGTQTYICNVNHKPSNTKVDKR VEPKSCDKTHTCPPCPAPELLGGPSVFLFPPKPKDTLMIS RTPEVTCVVVDVSHEDPEVKFNWYVDGVEVHNAKTKPREE QYNSTYRVVSVLTVLHQDWLNGKEYKCKVSNKALPAPIEK TISKAKGQPREPQVYTLPPSREEMTKNQVSLTCLVKGFYP SDIAVEWESNGQPENNYKTTPPVLDSDGSFFLYSKLTVDK SRWQQGNVFSCSVMHEALHNHYTQKSLSLSPGK |
| SEQ ID NO: 337 | Light chain | MAWTPLFLGVLAYCTGSVASFELTQPPSVSVSPGQTASIT CSGDKLGHHYAYWFQQRPGQSPVLVIYQHTKRPSGIPERF SGSKSGNTATLTISGTQAMDEADYYCQAWDSSTYVVFGGG TKLTVLGQPKAAPSVTLFPPSSEELQANKATLVCLISDFY PGAVTVAWKADSSPVKAGVETTTPSKQSNNKYAASSYLSL TPEQWKSHRSYSCQVTHEGSTVEKTVAPTECS |

NOV270

| SEQ ID NO: 338 | Heavy Chain | MELGLCWVFLVAILEGVQCEVQLVESGGGLVQPGGSLRLS CAASGFTFRSYMMNWVRQAPGKGLEWVSYISGSGGTKYYV DSVKGRFTISRDNAKNSLYLQMHSLRAEDTAVYYCARDLD CSGGTCYDGMDVWGQGTTVTVSSASTKGPSVFPLAPCSRS TSGGTAALGCLVKDYFPEPVTVSWNSGALTSGVHTFPAVL QSSGLYSLSSVVTVPSSSLGTQTYICNVNHKPSNTKVDKR VEPKSCDKTHTCPPCPAPELLGGPSVFLFPPKPKDTLMIS RTPEVTCVVVDVSHEDPEVKFNWYVDGVEVHNAKTKPREE QYNSTYRVVSVLTVLHQDWLNGKEYKCKVSNKALPAPIEK TISKAKGQPREPQVYTLPPSREEMTKNQVSLTCLVKGFYP SDIAVEWESNGQPENNYKTTPPVLDSDGSFFLYSKLTVDK SRWQQGNVFSCSVMHEALHNHYTQKSLSLSPGK |
|---|---|---|
| SEQ ID NO: 339 | Light chain | MAWIPLFLGVLAYCTGSVASYELTQPPSVSVSPGQTASIT CSGDKLGHKYVYWFQHRPGQSPVLVIYQHTKRPSGIPERF SGSKSGNTATLTISGTQALDEADYYCQAWDSSVVIFGGGT KLTVLGQPKAAPSVTLFPPSSEELQANKATLVCLISDFYP GAVTVAWKADSSPVKAGVETTTPSKQSNNKYAASSYLSLT PEQWKSHRSYSCQVTHEGSTVEKTVAPTECS |

NOV024

| SEQ ID NO: 340 | Heavy Chain | MDWTWRILFLVAAVTGAHSQVQLVQSGPEVKRPGASVKVS CKASGYTLTTSSIHWVRQAPGQRLEWMGWINTGNDNTMYS QKFQGRVLITTDTSASTAYLELRSLRSEDTAVFYCARGPL PYYYDSSGPLDYWGQGTLVTVSSASTKGPSVFPLAPSSKS TSGGTAALGCLVKDYFPEPVTVSWNSGALTSGVHTFPAVL QSSGLYSLSSVVTVPSSSLGTQTYICNVNHKPSNTKVDKR VEPKSCDKTHTCPPCPAPELLGGPSVFLFPPKPKDTLMIS RTPEVTCVVVDVSHEDPEVKFNWYVDGVEVHNAKTKPREE QYNSTYRVVSVLTVLHQDWLNGKEYKCKVSNKALPAPIEK TISKAKGQPREPQVYTLPPSREEMTKNQVSLTCLVKGFYP SDIAVEWESNGQPENNYKTTPPVLDSDGSFFLYSKLTVDK SRWQQGNVFSCSVMHEALHNHYTQKSLSLSPGK |
|---|---|---|
| SEQ ID NO: 341 | Light chain | MAWIPLLLGLLSHCTGSVTSYVLTQPPSVSVAPGKTATFT CGGDNIGTKSVHWYRQKPGQAPVLVVYDDSDRPSGDPERF SGSNSGNTATLTISRVEAGDEADYFCQVWISSRDHPVFGE GTRLTVLGQPKAAPSVTLFPPSSEELQANKATLVCLISDF YPGAVTVAWKADSSPVKAGVETTTPSKQSNNKYAASSYLS LTPEQWKSHRSYSCQVTHEGSTVEKTVAPTECS |

NOV650

| SEQ ID NO: 342 | Heavy Chain | MDWTWRILFLVAAATGAHSQVQLVQSGAEVKKPGASVKVS CKTSGYTFTAYHMHWVRQAPGQGLEWMGWINPNSGGTNYA QNFQGRVTVTRDTSISTVYMELTRLRSDDTAVYYCARERE PLMASYYYYGMDVWGQGTTVTVSSASTKGPSVFPLAPCSR STSGGTAALGCLVKDYFPEPVTVSWNSGALTSGVHTFPAV LQSSGLYSLSSVVTVPSSSLGTQTYICNVNHKPSNTKVDK RVEPKSCDKTHTCPPCPAPELLGGPSVFLFPPKPKDTLMI SRTPEVTCVVVDVSHEDPEVKFNWYVDGVEVHNAKTKPRE EQYNSTYRVVSVLTVLHQDWLNGKEYKCKVSNKALPAPIE KTISKAKGQPREPQVYTLPPSREEMTKNQVSLTCLVKGFY PSDIAVEWESNGQPENNYKTTPPVLDSDGSFFLYSKLTVD KSRWQQGNVFSCSVMHEALHNHYTQKSLSLSPGK |
|---|---|---|
| SEQ ID NO: 343 | Light chain | MAWATLLLTLCIGSVVSSEVTQDPAVSVALGQTVRITCQG DSLRNYYTRWYQQKPGQAPILVIYRENNRPSGIPDRFSGS NSGNTASLTITGAQAEDEADYYCTSRASGSDHLVFGGGTK LTVLGQPKAAPSVTLFPPSSEELQANKATLVCLISDFYPG |

TABLE 2-continued

Anti-Polyoma virus Antibodies

|  |  |  | AVTVAWKADSSPVKAGVETTTPSKQSNNKYAASSYLSLTP<br>EQWKSHRSYSCQVTHEGSTVEKTVAPTECS |
|---|---|---|---|
| NOV605 |  |  |  |
| SEQ ID NO: 344 | Heavy<br>Chain | | MDWTWRILFLVAAATGAHSRVQLVQSGAEVKKPGASVKVS<br>CKASGYTFTAYHMHWVRQAPGQGLEWMGWINPNSGGTNYA<br>QRFQGRVTMTRDTSSSTAYMDLTRLRSDDTAVYYCARERE<br>PLMASFYHYGLGVWGQGTTVAVSSASTKGPSVFPLAPCSR<br>STSGGTAALGCLVKDYFPEPVTVSWNSGALTSGVHTFPAV<br>LQSSGLYSLSSVVTVPSSSLGTQTYICNVNHKPSNTKVDK<br>RVEPKSCDKTHTCPPCPAPELLGGPSVFLFPPKPKDTLMI<br>SRTPEVTCVVVDVSHEDPEVKFNWYVDGVEVHNAKTKPRE<br>EQYNSTYRVVSVLTVLHQDWLNGKEYKCKVSNKALPAPIE<br>KTISKAKGQPREPQVYTLPPSREEMTKNQVSLTCLVKGFY<br>PSDIAVEWESNGQPENNYKTTPPVLDSDGSFFLYSKLTVD<br>KSRWQQGNVFSCSVMHEALHNHYTQKSLSLSPGK |
| SEQ ID NO: 345 | Light<br>chain | | MAWTPLLTLCIGSGGSSELTQDPAVSVALGQTVTITCQGD<br>SLRIYYASWYQQKPGQAPILVIYDTNKRPSGIPDRFSGSS<br>SGNTASLTITGAQAEDEAEYYCDSRDSSGDHLLFGGGTRV<br>TVLGQPKAAPSVTLFPPSSEELQANKATLVCLISDFYPGA<br>VTVAWKADSSPVKAGVETTTPSKQSNNKYAASSYLSLTPE<br>QWKSHRSYSCQVTHEGSTVEKTVAPTECS |
| NOV922 |  |  |  |
| SEQ ID NO: 346 | Heavy<br>Chain | | MKHLWFFLLLVAAPRWVLSQLQLQESGPGLVKPSETLSLT<br>CSVSGDSISRSSDYWGWIRQPPGRGLEWIGSIYRTGSTYY<br>NPSLSSRVTISVDTSKSQFSLSLSSVTAADTALYYCARVR<br>HDYVWGSIYYYGMDVWGQGTTVTVSSPSTKGPSVFPLAPC<br>SRSTSGGTAALGCLVKDYFPEPVTVSWNSGALTSGVHTFP<br>AVLQSSGLYSLSSVVTVPSSSLGTQTYICNVNHKPSNTKV<br>DKRVEPKSCDKTHTCPPCPAPELLGGPSVFLFPPKPKDTL<br>MISRTPEVTCVVVDVSHEDPEVKFNWYVDGVEVHNAKTKP<br>REEQYNSTYRVVSVLTVLHQDWLNGKEYKCKVSNKALPAP<br>IEKTISKAKGQPREPQVYTLPPSREEMTKNQVSLTCLVKG<br>FYPSDIAVEWESNGQPENNYKTTPPVLDSDGSFFLYSKLT<br>VDKSRWQQGNVFSCSVMHEALHNHYTQKSLSLSPGK |
| SEQ ID NO: 347 | Light<br>chain | | MAWTVLLLSLLTQGTGSWAQSALTQPRSVSGSPGQSVTIS<br>CTGTGSDVGGYTYVSWYQQHPDKAPKLVIYDVTKRPSGVP<br>DRFSGSKSGNTASLTISGLRADDEADYYCCSYAGRYSWVF<br>GGGTKLTVLGQPKAAPSVTLFPPSSEELQANKATLVCLIS<br>DFYPGAVTVAWKADSSPVKAGVETTTPSKQSNNKYAASSY<br>LSLTPEQWKSHRSYSCQVTHEGSTVEKTVAPTECS |
| NOV152 |  |  |  |
| SEQ ID NO: 348 | Heavy<br>Chain | | MDWTWRILFLVAAATGAHSQVQLVQSGAEVKKPGASVKVS<br>CKTSGYTFTAYHMHWVRQAPGQGLEWMGWINPNSGGTNYA<br>QKFQGRVTVTRDTSISTVYMELTRLRSDDTAVYYCARERE<br>PLMASYYYYGMDVWGQGTTVTVSSASTKGPSVFPLAPCSR<br>STSGGTAALGCLVKDYFPEPVTVSWNSGALTSGVHTFPAV<br>LQSSGLYSLSSVVTVPSSSLGTQTYICNVNHKPSNTKVDK<br>RVEPKSCDKTHTCPPCPAPELLGGPSVFLFPPKPKDTLMI<br>SRTPEVTCVVVDVSHEDPEVKFNWYVDGVEVHNAKTKPRE<br>EQYNSTYRVVSVLTVLHQDWLNGKEYKCKVSNKALPAPIE<br>KTISKAKGQPREPQVYTLPPSREEMTKNQVSLTCLVKGFY<br>PSDIAVEWESNGQPENNYKTTPPVLDSDGSFFLYSKLTVD<br>KSRWQQGNVFSCSVMHEALHNHYTQKSLSLSPGK |
| SEQ ID NO: 349 | Light<br>chain | | MAWIPLWLTLLTLCIGSVVSSEVTQDPAVSVALGQTVRIT<br>CQGDSLRNYYTRWYQQKPGQAPVLVIYRENNRPSGIPDRF<br>SGSSSGNTASLTITGAQAEDEADYYCTSRASSTDHLVFGG<br>GTKLTVLGQPKAAPSVTLFPPSSEELQANKATLVCLISDF<br>YPGAVTVAWKADSSPVKAGVETTTPSKQSNNKYAASSYLS<br>LTPEQWKSHRSYSCQVTHEGSTVEKTVAPTECS |
| NOV229 |  |  |  |
| SEQ ID NO: 350 | Heavy<br>Chain | | MELGLSWLFLVATLKGVQCEVQLLESGGGLMQPGGSLRLS<br>CAASGFTFRSYAMNWVRQAPGKGLEWVSTISGNGGTTYYA<br>DSVRGRFTISRDNSKNTLFLQMNSLRAEDTAIYYCAQGEP<br>WSGYLEPLFASWGQGTLVTVSSASTKGPSVFPLAPCSRST<br>SGGTAALGCLVKDYFPEPVTVSWNSGALTSGVHTFPAVLQ<br>SSGLYSLSSVVTVPSSSLGTQTYICNVNHKPSNTKVDKRV<br>EPKSCDKTHTCPPCPAPELLGGPSVFLFPPKPKDTLMISR |

TABLE 2-continued

Anti-Polyoma virus Antibodies

|  |  |  |
|---|---|---|
|  |  | TPEVTCVVVDVSHEDPEVKFNWYVDGVEVHNAKTKPREEQ<br>YNSTYRVVSVLTVLHQDWLNGKEYKCKVSNKALPAPIEKT<br>ISKAKGQPREPQVYTLPPSREEMTKNQVSLTCLVKGFYPS<br>DIAVEWESNGQPENNYKTTPPVLDSDGSFFLYSKLTVDKS<br>RWQQGNVFSCSVMHEALHNHYTQKSLSLSPGK |
| SEQ ID NO: 351 | Light<br>chain | MALTPLWLTLLTPCIGSVVSSELTQDPAVSVALGQTVRIT<br>CQGDSLRNFYASWYQQKPGQAPVLVIYGKNNRPSGIPDRF<br>SGSSSGNTVSLTITGAQAEDDADYYCNSRDSSGNHVIFGG<br>GTKLTVLGQPKAAPSVTLFPPSSEELQANKATLVCLISDF<br>YPGAVTVAWKADSSPVKAGVETTTPSKQSNNKYAASSYLS<br>LTPEQWKSHRSYSCQVTHEGSTVEKTVAPTECS |

NOV099

|  |  |  |
|---|---|---|
| SEQ ID NO: 352 | Heavy<br>Chain | MELGLRWVFLVAILEGVHCEVQLVESGGGLVKPGGSLRLS<br>CAASGFTFSSYSMNWVRQAPGKGLEWVSSISTSKNYKKYA<br>DSVKGRFTISRDNAENSLYLQMNSLRAEDTAIYYCARVDY<br>DYIWGSYREKAMDVWGHGTTVTVSSASTKGPSVFPLAPCS<br>RSTSGGTAALGCLVKDYFPEPVTVSWNSGALTSGVHTFPA<br>VLQSSGLYSLSSVVTVPSSSLGTQTYICNVNHKPSNTKVD<br>KRVEPKSCDKTHTCPPCPAPELLGGPSVFLFPPKPKDTLM<br>ISRTPEVTCVVVDVSHEDPEVKFNWYVDGVEVHNAKTKPR<br>EEQYNSTYRVVSVLTVLHQDWLNGKEYKCKVSNKALPAPI<br>EKTISKAKGQPREPQVYTLPPSREEMTKNQVSLTCLVKGF<br>YPSDIAVEWESNGQPENNYKTTPPVLDSDGSFFLYSKLTV<br>DKSRWQQGNVFSCSVMHEALHNHYTQKSLSLSPGK |
| SEQ ID NO: 353 | Light<br>chain | MAWSPLLLTQGTGSWAQSALTQPRSVSGSPGQSVTISCTG<br>TGSDVGGYNYVSWYQQHPGKAPKVIIYDVSKRPSGVPDRF<br>SGSKSGNTASLTISGLQAEDEADYHCCSYAGTYTWVFGGG<br>TKVTVLGQPKAAPSVTLFPPSSEELQANKATLVCLISDFY<br>PGAVTVAWKADSSPVKAGVETTTPSKQSNNKYAASSYLSL<br>TPEQWKSHRSYSCQVTHEGSTVEKTVAPTECS |

NOV160

|  |  |  |
|---|---|---|
| SEQ ID NO: 354 | Heavy<br>Chain | MEFGLRWLFLVAILKGVQCEVQLLESGGGSVQPGGSLRLS<br>CAASGFTFRNYAMNWVRQSPGKGLEWVSTISGTGGTTYYA<br>DSVKGRFSISRDNSRNTLYLNMNNLRVEDTAIYYCAKGEP<br>WSNYLEPLFDHWGQGTLVTVSSASTKGPSVFPLAPSSKST<br>SGGTAALGCLVKDYFPEPVTVSWNSGALTSGVHTFPAVLQ<br>SSGLYSLSSVVTVPSSSLGTQTYICNVNHKPSNTKVDKRV<br>EPKSCDKTHTCPPCPAPELLGGPSVFLFPPKPKDTLMISR<br>TPEVTCVVVDVSHEDPEVKFNWYVDGVEVHNAKTKPREEQ<br>YNSTYRVVSVLTVLHQDWLNGKEYKCKVSNKALPAPIEKT<br>ISKAKGQPREPQVYTLPPSREEMTKNQVSLTCLVKGFYPS<br>DIAVEWESNGQPENNYKTTPPVLDSDGSFFLYSKLTVDKS<br>RWQQGNVFSCSVMHEALHNHYTQKSLSLSPGK |
| SEQ ID NO: 355 | Light<br>chain | MALTPLLLTLCIGSVVSSELTQDPAVSVALGQTVRITCQG<br>DSLRNFYATWYQQKPGQAPVFVMYDKTNRPSGIPDRFSGS<br>RSGNTAYLTITGAQAEDEADYYCNSRDSSGNYVIFGGGTK<br>LTVLGQPKAAPSVTLFPPSSEELQANKATLVCLISDFYPG<br>AVTVAWKADSSPVKAGVETTTPSKQSNNKYAASSYLSLTP<br>EQWKSHRSYSCQVTHEGSTVEKTVAPTECS |

NOV904

|  |  |  |
|---|---|---|
| SEQ ID NO: 356 | Heavy<br>Chain | MDWTWRILFLVAAATGAHSQVQLVQSGAEVMRPGASLKVS<br>CKASGYSFTMYSIHWVRQAPGHRLEWMGWINAANGNTIYS<br>QNFQGRVTISRDTSATTAHMELGSLRSEDTAVYFCARGPI<br>PYYYDHSGPFDYWGQGTLVTVSSASTKGPSVFPLAPCSRS<br>TSGGTAALGCLVKDYFPEPVTVSWNSGALTSGVHTFPAVL<br>QSSGLYSLSSVVTVPSSSLGTQTYICNVNHKPSNTKVDKR<br>VEPKSCDKTHTCPPCPAPELLGGPSVFLFPPKPKDTLMIS<br>RTPEVTCVVVDVSHEDPEVKFNWYVDGVEVHNAKTKPREE<br>QYNSTYRVVSVLTVLHQDWLNGKEYKCKVSNKALPAPIEK<br>TISKAKGQPREPQVYTLPPSREEMTKNQVSLTCLVKGFYP<br>SDIAVEWESNGQPENNYKTTPPVLDSDGSFFLYSKLTVDK<br>SRWQQGNVFSCSVMHEALHNHYTQKSLSLSPGK |
| SEQ ID NO: 357 | Light<br>chain | MEAPAQLLFLLLLWLPDTTGEIVMTQSPPTLSVSPGERAI<br>LSCRASQSVSSDLAWYQQAGQAPRLLIYGASTRATGIPP<br>RFSGSGSGTEFTLTISSLQSEDFAVYYCQQYNKWVTFGGG<br>TKVEIKRTVAAPSVFIFPPSDEQLKSGTASVVCLLNNFYP<br>REAKVQWKVDNALQSGNSQESVTEQDSKDSTYSLSSTLTL<br>SKADYEKHKVYACEVTHQGLSSPVTKSFNRGEC |

TABLE 2-continued

Anti-Polyoma virus Antibodies

NOV972

| SEQ ID NO: 358 | Heavy Chain | MDWTWRILFLVAAATGAHSQVQLVQSGAEVKKPGASVKVS CRTSGYTFTAYHMHWVRQAPGQGLEWMGWINPNSGGTNYA QKFQGRVTVTRDTSLRTVYMEVTSLRSDDTAVYYCARERE PLMASYYYYGLDVWGQGTTVTVSSASTKGPSVFPLAPCSR STSGGTAALGCLVKDYFPEPVTVSWNSGALTSGVHTFPAV LQSSGLYSLSSVVTVPSSSLGTQTYICNVNHKPSNTKVDK RVEPKSCDKTHTCPPCPAPELLGGPSVFLFPPKPKDTLMI SRTPEVTCVVVDVSHEDPEVKFNWYVDGVEVHNAKTKPRE EQYNSTYRVVSVLTVLHQDWLNGKEYKCKVSNKALPAPIE KTISKAKGQPREPQVYTLPPSREEMTKNQVSLTCLVKGFY PSDIAVEWESNGQPENNYKTTPPVLDSDGSFFLYSKLTVD KSRWQQGNVFSCSVMHEALHNHYTQKSLSLSPGK |
|---|---|---|
| SEQ ID NO: 359 | Light chain | MAWAPLWLTLLTLCIGSVVSSEVTQDPAVSVALGQTVRIT CQGDSLRNYYTRWYQQKPGQAPILVIYRENNRPSGIPDRF SGTNSGNTASLTITGAQAEDEADYYCTSRASGTDHLVFGR GTKLTVLGQPKAAPSVTLFPPSSEELQANKATLVCLISDF YPGAVTVAWKADSSPVKAGVETTTPSKQSNNKYAASSYLS LTPEQWKSHRSYSCQVTHEGSTVEKTVAPTECS |

NOV364

| SEQ ID NO: 360 | Heavy Chain | MDWTWRILFLVAAATGAHSQVQLVQSGAEVKKPGASVKVS CKTSGYAFTAFHLHWVRQAPGQGLEWMGWINPNSGDTNYA QKFQGRVTVTRDTSISTVYMELTRLRSDDTAVYYCARERE PLMASYYYYGMDVWGQGTTVTVSSASTKGPSVFPLAPCSR STSGGTAALGCLVKDYFPEPVTVSWNSGALTSGVHTFPAV LQSSGLYSLSSVVTVPSSSLGTQTYICNVNHKPSNTKVDK RVEPKSCDKTHTCPPCPAPELLGGPSVFLFPPKPKDTLMI SRTPEVTCVVVDVSHEDPEVKFNWYVDGVEVHNAKTKPRE EQYNSTYRVVSVLTVLHQDWLNGKEYKCKVSNKALPAPIE KTISKAKGQPREPQVYTLPPSREEMTKNQVSLTCLVKGFY PSDIAVEWESNGQPENNYKTTPPVLDSDGSFFLYSKLTVD KSRWQQGNVFSCSVMHEALHNHYTQKSLSLSPGK |
|---|---|---|
| SEQ ID NO: 361 | Light chain | MAWAPLLLTLCIGSVVSSEVTQDPAVSVALGQTVRITCQG DSLRKYYTRWYQQKPGQAPVLVIYRENNRPSGIPDRFSGS SSGNTASLTITGAQAEDEADYYCSSRASSTDHLVFGGGTK LTVLGQPKAAPSVTLFPPSSEELQANKATLVCLISDFYPG AVTVAWKADSSPVKAGVETTTPSKQSNNKYAASSYLSLTP EQWKSHRSYSCQVTHEGSTVEKTVAPTECS |

NOV742

| SEQ ID NO: 362 | Heavy Chain | MKHLWFFLLLVAAPRWVLSQLQLQESGPGLVKPSETLSLT CSVSGDSISRSSDYWGWIRQPPGRGLEWIGSIYRTGSTYY NPSLSSRVTISVDTSKSQFSLSLSSVTAADTALYYCARVR HDYVWGSIYYYGMDVWGQGTTVTVSSPSTKGPSVFPLAPC SRSTSGGTAALGCLVKDYFPEPVTVSWNSGALTSGVHTFP AVLQSSGLYSLSSVVTVPSSSLGTQTYICNVNHKPSNTKV DKRVEPKSCDKTHTCPPCPAPELLGGPSVFLFPPKPKDTL MISRTPEVTCVVVDVSHEDPEVKFNWYVDGVEVHNAKTKP REEQYNSTYRVVSVLTVLHQDWLNGKEYKCKVSNKALPAP IEKTISKAKGQPREPQVYTLPPSREEMTKNQVSLTCLVKG FYPSDIAVEWESNGQPENNYKTTPPVLDSDGSFFLYSKLT VDKSRWQQGNVFSCSVMHEALHNHYTQKSLSLSPGK |
|---|---|---|
| SEQ ID NO: 363 | Light chain | MAWXXXXXSXLTQGTGSWARSALTQPRSVSGXPGQSVTIS CTGTGSDVGGYTYVSWYQQHPDKAPKLVIYDVTKRPSGVP DRFSGSKSGNTASLTISGLRADDEADYYCCSYAGRYSWVF GGGTKLTVLGQPKAAPSVTLFPPSSEELQANKATLVCLIS DFYPGAVTVAWKADSSPVKAGVETTTPSKQSNNKYAASSY LSLTPEQWKSHRSYSCQVTHEGSTVEKTVAPTECS |

NOV706

| SEQ ID NO: 364 | Heavy Chain | MKHLWFFLLLVAAPRWVLSQVQLQESGPGLVKPSQTLSLT CTVSGGSISSGSHYWSWIRQPAGKGLEWIGRIYTSGRNSY NPSLKSRVTISVDTFKNQFSLKVSSVTAADTAVYYCARNN RIYGGYELFDIWGQGTTVTVSSASTKGPSVFPLAPSSKST SGGTAALGCLVKDYFPEPVTVSWNSGALTSGVHTFPAVLQ SSGLYSLSSVVTVPSSSLGTQTYICNVNHKPSNTKVDKRV EPKSCDKTHTCPPCPAPELLGGPSVFLFPPKPKDTLMISR TPEVTCVVVDVSHEDPEVKFNWYVDGVEVHNAKTKPREEQ YNSTYRVVSVLTVLHQDWLNGKEYKCKVSNKALPAPIEKT |
|---|---|---|

TABLE 2-continued

Anti-Polyoma virus Antibodies

|  |  |  |
|---|---|---|
|  |  | ISKAKGQPREPQVYTLPPSREEMTKNQVSLTCLVKGFYPS DIAVEWESNGQPENNYKTTPPVLDSDGSFFLYSKLTVDKS RWQQGNVFSCSVMHEALHNHYTQKSLSLSPGK |
| SEQ ID NO: 365 | Light chain | MAWSPLLLGLLSHCTVSVTSFVLTQPPSVSVAPGKTARFS CGGDNIGSKPVHWYQQKPGQAPALVIYYDSDRPSGIPERF SGSNSGNTATLTISRVEAGDEADYYCQVWDTSGDHPVFGG GTKLTVLGQPKAAPSVTLFPPSSEELQANKATLVCLISDF YPGAVTVAWKADSSPVKAGVETTTPSKQSNNKYAASSYLS LTPEQWKSHRSYSCQVTHEGSTVEKTVAPTECS |
| NOV420 |  |  |
| SEQ ID NO: 366 | Heavy Chain | MELGLCWVFLVAILEGVHCEVQLVESGGGLVKPGGSLRLS CAASGFTFSSYSMNWVRQAPGKGLEWVSSISTSKNYKKYA DSVKGRFTISRDNAENSLYLQMNSLRAEDTAIYYCARVDY DYIWGSYREKAMDVWGHGTTVTVSSASTKGPSVFPLAPCS RSTSGGTAALGCLVKDYFPEPVTVSWNSGALTSGVHTFPA VLQSSGLYSLSSVVTVPSSSLGTQTYICNVNHKPSNTKVD KRVEPKSCDKTHTCPPCPAPELLGGPSVFLFPPKPKDTLM ISRTPEVTCVVVDVSHEDPEVKFNWYVDGVEVHNAKTKPR EEQYNSTYRVVSVLTVLHQDWLNGKEYKCKVSNKALPAPI EKTISKAKGQPREPQVYTLPPSREEMTKNQVSLTCLVKGF YPSDIAVEWESNGQPENNYKTTPPVLDSDGSFFLYSKLTV DKSRWQQGNVFSCSVMHEALHNHYTQKSLSLSPGK |
| SEQ ID NO: 367 | Light chain | MAWIPLLLTQGTGSWAQSALTQPRSVSGSPGQSVTISCTG TGSDVGGYNYVSWYQQHPGKAPKVIIYDVSKRPSGVPDRF SGSKSGNTASLTISGLQAEDEADYHCCSYAGTYTWVFGGG TKVTVLGQPKAAPSVTLFPPSSEELQANKATLVCLISDFY PGAVTVAWKADSSPVKAGVETTTPSKQSNNKYAASSYLSL TPEQWKSHRSYSCQVTHEGSTVEKTVAPTECS |
| NOV504 |  |  |
| SEQ ID NO: 368 | Heavy Chain | MDWTWRVFCLLAVAPGVHSQVQLVQSGAEVKKPGASVRVS CKASGYTFTNYYMHWVRQAPGQGLEWTGIVNPSGGSTNYA QKLQGRVTMTIDTSTSTVYMELNSLTSEDTAVYYCARARK HYFGSGTDYKGRYTAHALDLWGQGTMVIVSSASTKGPSVF FLAPSSKSTSGGTAALGCLVKDYFPEPVTVSWNSGALTSG VHTFPAVLQSSGLYSLSSVVTVPSSSLGTQTYICNVNHKP SNTKVDKRVEPKSCDKTHTCPPCPAPELLGGPSVFLFPPK PKDTLMISRTPEVTCVVVDVSHEDPEVKFNWYVDGVEVHN AKTKPREEQYNSTYRVVSVLTVLHQDWLNGKEYKCKVSNK ALPAPIEKTISKAKGQPREPQVYTLPPSREEMTKNQVSLT CLVKGFYPSDIAVEWESNGQPENNYKTTPPVLDSDGSFFL YSKLTVDKSRWQQGNVFSCSVMHEALHNHYTQKSLSLSPG K |
| SEQ ID NO: 369 | Light chain | MVLQTQVFISLLLWISGAYGDIVMTQSPDSLAVSLGERAT INCKSSQSLLYTSNNKNYLAWYQQKAGQPPKLLIYWASTR ESGVPDRFSGSGSGTDFTLTISSLQSEDVAVYYCQQYYST PQTFGQGTKVEIKRTVAAPSVFIFPPSDEQLKSGTASVVC LLNNFYPREAKVQWKVDNALQSGNSQESVTEQDSKDSTYS LSSTLTLSKADYEKHKVYACEVTHQGLSSPVTKSFNRGEC |
| NOV647 |  |  |
| SEQ ID NO: 370 | Heavy Chain | MKHLWFFLLLVAAPRWVLSQVQLQESGPRLVKPSQTLSLT CSVSGGTVRTGDYYWSWIRQPPGKGLEWIGFIHYSGSTYY NPSLKSRVTISLDTSRNQFSLKLSSVTAADTAVYFCARIY YDSSGYLHSLKIIDSWGQGTLVTVSSASTKGPSVFPLAPC SRSTSGGTAALGCLVKDYFPEPVTVSWNSGALTSGVHTFP AVLQSSGLYSLSSVVTVPSSSLGTQTYICNVNHKPSNTKV DKRVEPKSCDKTHTCPPCPAPELLGGPSVFLFPPKPKDTL MISRTPEVTCVVVDVSHEDPEVKFNWYVDGVEVHNAKTKP REEQYNSTYRVVSVLTVLHQDWLNGKEYKCKVSNKALPAP IEKTISKAKGQPREPQVYTLPPSREEMTKNQVSLTCLVKG FYPSDIAVEWESNGQPENNYKTTPPVLDSDGSFFLYSKLT VDKSRWQQGNVFSCSVMHEALHNHYTQKSLSLSPGK |
| SEQ ID NO: 371 | Heavy Chain | MRLPAQLLFLLLLWLPDTTGEIVLTQSPATLSASPGERAT LSCRASQSVSSNLAWYRQKPGQSPRLLIYGASARATGIPA RFGGSGSGTEFTLTISSLQSEDFAVYYCQQYNNWPLTFGG GTKVEIKRTVAAPSVFIFPPSDEQLKSGTASVVCLLNNFY PREAKVQWKVDNALQSGNSQESVTEQDSKDSTYSLSSTLT LSKADYEKHKVYACEVTHQGLSSPVTKSFNRGEC |

TABLE 2-continued

Anti-Polyoma virus Antibodies

NOV329

| SEQ ID NO: 372 | Heavy Chain | MDWTWRILFLVAAATGAHSQVQLVQSGTEVKKPGASVKVS CKASGYTFNKYAMNWVRQAPGQRLEWMGYINADNGNTKYS QKFRDRVTITRDTSASIVYMELRSLRSEDTAMYYCARDGG WSTTVNNQPYYGMDVWGQGTTVTVSSASTKGPSVFPLAP SSKSTSGGTAALGCLVKDYFPEPVTVSWNSGALTSGVHTF PAVLQSSGLYSLSSVVTVPSSSLGTQTYICNVNHKPSNTK VDKRVEPKSCDKTHTCPPCPAPELLGGPSVFLFPPKPKDT LMISRTPEVTCVVVDVSHEDPEVKFNWYVDGVEVHNAKTK PREEQYNSTYRVVSVLTVLHQDWLNGKEYKCKVSNKALPA PIEKTISKAKGQPREPQVYTLPPSREEMTKNQVSLTCLVK GFYPSDIAVEWESNGQPENNYKTTPPVLDSDGSFFLYSKL TVDKSRWQQGNVFSCSVMHEALHNHYTQKSLSLSPGK |
|---|---|---|
| SEQ ID NO: 373 | Light chain | MRLLAQLLFLLLLWLPDTTGEIVLTQSPGTLSLSPGERAT LSCRASQFVGSKYMAWYQQKPGQAPRLLIYGASSRATGIP DRFSGSGSGTDFTLTISRLEPEDFAVYYCQQFGSSPPMYA FGQGTKLEIKRTVAAPSVFIFPPSDEQLKSGTASVVCLLN NFYPREAKVQWKVDNALQSGNSQESVTEQDSKDSTYSLSS TLTLSKADYEKHKVYACEVTHQGLSSPVTKSFNRGEC |

NOV631

| SEQ ID NO: 374 | Heavy Chain | MKHLWFFLLLVAVPRWVLSQVQLQESGPRLVKPSQTLSLT CTVSGGSISSGDYYWSWIRQAPGTGLEWIGFIYNTETTYY SPSLRSRVSMSLDTSKNQFSLKLSSVTAADTAVYYCARER RPSHYDSGGYSLDYWGQGTLVTVSSASTKGPSVFPLAPSS KSTSGGTAALGCLVKDYFPEPVTVSWNSGALTSGVHTFPA VLQSSGLYSLSSVVTVPSSSLGTQTYICNVNHKPSNTKVD KRVEPKSCDKTHTCPPCPAPELLGGPSVFLFPPKPKDTLM ISRTPEVTCVVVDVSHEDPEVKFNWYVDGVEVHNAKTKPR EEQYNSTYRVVSVLTVLHQDWLNGKEYKCKVSNKALPAPI EKTISKAKGQPREPQVYTLPPSREEMTKNQVSLTCLVKGF YPSDIAVEWESNGQPENNYKTTPPVLDSDGSFFLYSKLTV DKSRWQQGNVFSCSVMHEALHNHYTQKSLSLSPGK |
|---|---|---|
| SEQ ID NO: 375 | Light chain | MEAPAQLLFLLLLWLPDSTGEIVMTQSPATLSVSPGERAT LSCRASQSVSSNLAWYQQKPGQAPRLLIYGASTRATGIPA RFSGSGSGTEFTLAISSLQSEDFALYYCQQYNNWPRTFGQ GTKVEIKRTVAAPSVFIFPPSDEQLKSGTASVVCLLNNFY PREAKVQWKVDNALQSGNSQESVTEQDSKDSTYSLSSTLT LSKADYEKHKVYACEVTHQGLSSPVTKSFNRGEC |

NOV055

| SEQ ID NO: 376 | Heavy Chain | MELGLCWVFLVAILEGVQCEVQLVESGGGLVKPGGSLRLS CAASGFTFSTYSMNWVRQAPGKGLEWVSSISSSGTYTYYA DSVKGRFTISRDNAKDSLYLQMNSLRADDTAVYYCARAPY DYGDYRGGRYFDLWGRGSLVTVSSASTKGPSVFPLAPCSR STSGGTAALGCLVKDYFPEPVTVSWNSGALTSGVHTFPAV LQSSGLYSLSSVVTVPSSSLGTQTYICNVNHKPSNTKVDK RVEPKSCDKTHTCPPCPAPELLGGPSVFLFPPKPKDTLMI SRTPEVTCVVVDVSHEDPEVKFNWYVDGVEVHNAKTKPRE EQYNSTYRVVSVLTVLHQDWLNGKEYKCKVSNKALPAPIE KTISKAKGQPREPQVYTLPPSREEMTKNQVSLTCLVKGFY PSDIAVEWESNGQPENNYKTTPPVLDSDGSFFLYSKLTVD KSRWQQGNVFSCSVMHEALHNHYTQKSLSLSPGK |
|---|---|---|
| SEQ ID NO: 377 | Light chain | MRLPAQLLFLLLLWLPDTTGEIVMTQSPATLSVSPGERAT LSCRASQSVSSKLAWYQQKPGQAPRLLIFGASTRATGIPA RFSGSGSGTEFTLTISSLQSEDFAVYYCQQYNNWPRTFGQ GTKVEIKRTVAAPSVFIFPPSDEQLKSGTASVVCLLNNFY PREAKVQWKVDNALQSGNSQESVTEQDSKDSTYSLSSTLT LSKADYEKHKVYACEVTHQGLSSPVTKSFNRGEC |

NOV224

| SEQ ID NO: 378 | Heavy Chain | MDTLCSTLLLLTIPSWVLSQITLKESGPTLVKPTQTLMLT CTFSGFSLSTSGVGVGWIRQPPGKALEWLAFIYWNTDKRY NPSLKTRLTITKDTSKTQVVLTMTNLDPVDTGTYYCVHHD GYLAEYFNHWGQGTLVTVSSASTKGPSVFPLAPSSKSTSG GTAALGCLVKDYFPEPVTVSWNSGALTSGVHTFPPAVLQSS GLYSLSSVVTVPSSSLGTQTYICNVNHKPSNTKVDKRVEP KSCDKTHTCPPCPAPELLGGPSVFLFPPKPKDTLMISRTP EVTCVVVDVSHEDPEVKFNWYVDGVEVHNAKTKPREEQYN STYRVVSVLTVLHQDWLNGKEYKCKVSNKALPAPIEKTIS KAKGQPREPQVYTLPPSREEMTKNQVSLTCLVKGFYPSDI |
|---|---|---|

TABLE 2-continued

Anti-Polyoma virus Antibodies

|  |  | AVEWESNGQPENNYKTTPPVLDSDGSFFLYSKLTVDKSRW<br>QQGNVFSCSVMHEALHNHYTQKSLSLSPGK |
|---|---|---|
| SEQ ID NO: 379 | Light<br>chain | MALTPLLLTLLIHCTGSWAQSVLTQPPSVSAAPGQRVTIS<br>CSGTTSNIGNYYVSWYQEVPGTAPKLLIYDNVKRPSGIPD<br>RFSASKSGTSATLGISGLQTGDEADYYCGTWDGRLSAWVF<br>GGGTKLTVLGQPKAAPSVTLFPPSSEELQANKATLVCLIS<br>DFYPGAVTVAWKADSSPVKAGVETTTPSKQSNNKYAASSY<br>LSLTPEQWKSHRSYSCQVTHEGSTVEKTVAPTECS |

NOV998

| SEQ ID NO: 380 | Heavy<br>Chain | MKHLWFFLLLVAAPRWVLSQVQLQQWGAGLLRPSETLSLT<br>CGVSGGALSGYIWSWIRQPPGKGLEWIGEINHSGTTNYSP<br>SLKSRVTISVDTSKNHFSLRLSSVTAADSAMYYCARGGVR<br>NWQLGPALDFWGQGTLVTVSSASTKGPSVFPLAPSSKSTS<br>GGTAALGCLVKDYFPEPVTVSWNSGALTSGVHTFPAVLQS<br>SGLYSLSSVVTVPSSSLGTQTYICNVNHKPSNTKVDKRVE<br>PKSCDKTHTCPPCPAPELLGGPSVFLFPPKPKDTLMISRT<br>PEVTCVVVDVSHEDPEVKFNWYVDGVEVHNAKTKPREEQY<br>NSTYRVVSVLTVLHQDWLNGKEYKCKVSNKALPAPIEKTI<br>SKAKGQPREPQVYTLPPSREEMTKNQVSLTCLVKGFYPSD<br>IAVEWESNGQPENNYKTTPPVLDSDGSFFLYSKLTVDKSR<br>WQQGNVFSCSVMHEALHNHYTQKSLSLSPGK |
|---|---|---|
| SEQ ID NO: 381 | Light<br>chain | MRLPAQLLGLLLLWLPGARCAIQLTQSPSSLSASVGDRVT<br>ITCRASQDISSFLAWFQQKPGRAPKLLLYAASTLQSGVPS<br>RFSGSGSGTDFSLTIGSLQPEDFATYYCQSLNNYPRSFTF<br>GPGTKVDIKRTVAAPSVFIFPPSDEQLKSGTASVVCLLNN<br>FYPREAKVQWKVDNALQSGNSQESVTEQDSKDSTYSLSST<br>LTLSKADYEKHKVYACEVTHQGLSSPVTKSFNRGEC |

NOV484

| SEQ ID NO: 382 | Heavy<br>Chain | MKHLWFFLLLVAAPRWVLSQVQLQESGPGLVKPSETLSLT<br>CSVSGDSMASDYWSWIRQPPGKGLEWIGYVSYSGTTYYIP<br>SLKSRVTISLDRSRTQFSLKVTSVTSADTAVYYCARGRRG<br>HSSGGWGIEFFHQWGQGTLVTVSPASTKGPSVFPLAPSSK<br>STSGGTAALGCLVKDYFPEPVTVSWNSGALTSGVHTFPAV<br>LQSSGLYSLRSVVTVPSSSLGTQTYICNVNHKPSNTKVDK<br>RVEPKSCDKTHTCPPCPAPELLGGPSVFLFPPKPKDTLMI<br>SRTPEVTCVVVDVSHEDPEVKFNWYVDGVEVHNAKTKPRE<br>EQYNSTYRVVSVLTVLHQDWLNGKEYKCKVSNKALPAPIE<br>KTISKAKGQPREPQVYTLPPSREEMTKNQVSLTCLVKGFY<br>PSDIAVEWESNGQPENNYKTTPPVLDSDGSFFLYSKLTVD<br>KSRWQQGNVFSCSVMHEALHNHYTQKSLSLSPGK |
|---|---|---|
| SEQ ID NO: 383 | Light<br>chain | MEAPAQLLFLLLLWLPDTTGEIVMTQSPPTLSVSPGERAT<br>LSCRASQSVSSDLAWYQQQAGQAPRLLIYDASTRATGIPP<br>RFSGSGSGTEFTLTISSLQSEDFAVYYCQQYNKWVTFGGG<br>TKVEIKRTVAAPSVFIFPPSDEQLKSGTASVVCLLNNFYP<br>REAKVQWKVDNALQSGNSQESVTEQDSKDSTYSLSSTLTL<br>SKADYEKHKVYACEVTHQGLSSPVTKSFNRGEC |

NOV178

| SEQ ID NO: 384 | Heavy<br>Chain | MDWTWRILFLVAAATGAHSQVQLVQSGAEVMRPGASLKVS<br>CKASGYSFTMYSIHWVRQAPGHRLEWMGWINAANGNTIYS<br>QNFQGRVTISRDTSATTAHMELGSLRSEDTAVYFCARGPI<br>PYYYDHSGPFDYWGQGTLVTVSSASTKGPSVFPLAPCSRS<br>TSGGTAALGCLVKDYFPEPVTVSWNSGALTSGVHTFPAVL<br>QSSGLYSLSSVVTVPSSSLGTQTYICNVNHKPSNTKVDKR<br>VEPKSCDKTHTCPPCPAPELLGGPSVFLFPPKPKDTLMIS<br>RTPEVTCVVVDVSHEDPEVKFNWYVDGVEVHNAKTKPREE<br>QYNSTYRVVSVLTVLHQDWLNGKEYKCKVSNKALPAPIEK<br>TISKAKGQPREPQVYTLPPSREEMTKNQVSLTCLVKGFYP<br>SDIAVEWESNGQPENNYKTTPPVLDSDGSFFLYSKLTVDK<br>SRWQQGNVFSCSVMHEALHNHYTQKSLSLSPGK |
|---|---|---|
| SEQ ID NO: 385 | Light<br>chain | MEAPAQLLFLLLLWLPDTTGEIVMTQSPPTLSVSPGERAI<br>LSCRASQSVSSDLAWYQQQAGQAPRLLIYGASTRATGIPP<br>RFSGSGSGTEFTLTISSLQSEDFAVYYCQQYNKWVTFGGG<br>TKVEIKRTVAAPSVFIFPPSDEQLKSGTASVVCLLNNFYP<br>REAKVQWKVDNALQSGNSQESVTEQDSKDSTYSLSSTLTL<br>SKADYEKHKVYACEVTHQGLSSPVTKSFNRGEC |

Other antibodies of the present disclosure include those where the amino acids or nucleic acids encoding the amino acids have been mutated; yet have at least 60, 70, 80, 90 or 95 percent identity to the sequences described in Table 2. In some aspects, it includes mutant amino acid sequences wherein no more than 1, 2, 3, 4 or 5 amino acids have been mutated in the variable regions when compared with the variable regions depicted in the sequence described in Table 2, while retaining substantially the same therapeutic activity.

Since each of these antibodies can bind to VP1, the VH, VL, full length light chain, and full length heavy chain sequences (amino acid sequences and the nucleotide sequences encoding the amino acid sequences) can be "mixed and matched" to create other VP1-binding antibodies. Such "mixed and matched" VP1-binding antibodies can be tested using the binding assays known in the art (e.g., ELISAs, and other assays described in the Example section). When these chains are mixed and matched, a VH sequence from a particular VH/VL pairing should be replaced with a structurally similar VH sequence. Likewise a full length heavy chain sequence from a particular full length heavy chain/full length light chain pairing should be replaced with a structurally similar full length heavy chain sequence. Likewise, a VL sequence from a particular VH/VL pairing should be replaced with a structurally similar VL sequence. Likewise, a full length light chain sequence from a particular full length heavy chain/full length light chain pairing should be replaced with a structurally similar full length light chain sequence. Accordingly, in one aspect, the disclosure provides for an isolated monoclonal antibody or antigen binding region thereof having: a heavy chain variable region comprising an amino acid sequence selected from the group consisting of SEQ ID NO: 18, 50, 82, 114, 146, 178, 210, 242 and 274 (Table 2); and a light chain variable region comprising an amino acid sequence selected from the group consisting of SEQ ID NO: 34, 66, 98, 130, 162, 194, 226, 258 and 290 (Table 2); wherein the antibody specifically binds to BK or JC virus.

In another aspect, the disclosure provides (i) an isolated monoclonal antibody having: a full length heavy chain comprising an amino acid sequence selected from Table 2 and a full length light chain comprising an amino acid sequence selected from Table 2, with the sequences optimized for expression in a mammalian cell. In similar aspect, the disclosure provides (i) an isolated monoclonal antibody having: a full length heavy chain comprising an amino acid sequence that has been optimized for expression in a mammalian cell, selected from the group consisting of SEQ ID NOs: 20, 52, 84, 116, 148, 180, 212, 244 and 276 (Table 2) and a full length light chain comprising an amino acid sequence that has been optimized for expression in a mammalian cell, selected from the group consisting of SEQ ID NOs: 36, 68, 100, 132, 164, 196, 228, 260 and 292 (Table 2) or (ii) a functional protein comprising an antigen binding portion thereof.

In another aspect, the present disclosure provides BK or JC virus binding antibodies that comprise the heavy chain and light chain CDR1s, CDR2s and CDR3s as described in Table 2, or combinations thereof. The amino acid sequences of the VH CDR1s of the antibodies are shown in SEQ ID NOs: 9, 41, 73, 105, 137, 169, 201, 233 and 265. The amino acid sequences of the VH CDR2s of the antibodies and are shown in SEQ ID NOs: 10, 42, 74, 106, 138, 170, 202, 234 and 266. The amino acid sequences of the VH CDR3s of the antibodies are shown in SEQ ID NOs: 11, 43, 75, 107, 139, 171, 203, 235 and 267. The amino acid sequences of the VL CDR1s of the antibodies are shown in SEQ ID NOs: 25, 57, 89, 121, 153, 185, 217, 249 and 281. The amino acid sequences of the VL CDR2s of the antibodies are shown in SEQ ID NOs 26, 58, 90, 122, 154, 186, 218, 250 and 282. The amino acid sequences of the VL CDR3s of the antibodies are shown in SEQ ID NOs: 27, 59, 91, 123, 155, 187, 219, 251 and 283.

Given that each of these antibodies can bind to BK or JC virus and that antigen-binding specificity is provided primarily by the CDR1, 2 and 3 regions, the VH CDR1, 2 and 3 sequences and VL CDR1, 2 and 3 sequences can be "mixed and matched" (i.e., CDRs from different antibodies can be mixed and matched, although each antibody must contain a VH CDR1, 2 and 3 and a VL CDR1, 2 and 3 to create other VP1-binding binding molecules. Such "mixed and matched" VP1-binding antibodies can be tested using the binding assays known in the art and those described in the Examples (e.g., ELISAs). When VH CDR sequences are mixed and matched, the CDR1, CDR2 and/or CDR3 sequence from a particular VH sequence should be replaced with a structurally similar CDR sequence(s). Likewise, when VL CDR sequences are mixed and matched, the CDR1, CDR2 and/or CDR3 sequence from a particular VL sequence should be replaced with a structurally similar CDR sequence(s). It will be readily apparent to the ordinarily skilled artisan that novel VH and VL sequences can be created by substituting one or more VH and/or VL CDR region sequences with structurally similar sequences from the CDR sequences shown herein for monoclonal antibodies of the present disclosure.

Accordingly, the present disclosure provides an isolated monoclonal antibody or antigen binding region thereof comprising a heavy chain CDR1 comprising an amino acid sequence selected from the group consisting of SEQ ID NOs: 9, 41, 73, 105, 137, 169, 201, 233 and 265; a heavy chain CDR2 comprising an amino acid sequence selected from the group consisting of SEQ ID NOs: 10, 42, 74, 106, 138, 170, 202, 234 and 266; a heavy chain CDR3 comprising an amino acid sequence selected from the group consisting of SEQ ID NOs:11, 43, 75, 107, 139, 171, 203, 235 and 267; a light chain CDR1 comprising an amino acid sequence selected from the group consisting of SEQ ID NOs: 25, 57, 89, 121, 153, 185, 217, 249 and 281; a light chain CDR2 comprising an amino acid sequence selected from the group consisting of SEQ ID NOs: 26, 58, 90, 122, 154, 186, 218, 250 and 282; and a light chain CDR3 comprising an amino acid sequence selected from the group consisting of SEQ ID NOs:27, 59, 91, 123, 155, 187, 219, 251 and 283; wherein the antibody specifically binds to BK or JC virus.

In certain aspects, an antibody that specifically binds to BK or JC virus is an antibody or antibody fragment (e.g., antigen binding fragment) that is described in Table 2.

1. Identification of Antibodies

The present disclosure provides antibodies and antibody fragments (e.g., antigen binding fragments) that bind to BK or JC virus. In certain aspects the antibodies and antibody fragments can bind to the same epitope within all four BKV serotypes and/or JCV.

The present disclosure also provides antibodies and antibody fragments (e.g., antigen binding fragments) that bind to the same epitope as do the anti-BK or JC antibodies described in Table 2. Additional antibodies and antibody fragments (e.g., antigen binding fragments) can therefore be identified based on their ability to cross-compete (e.g., to competitively inhibit the binding of, in a statistically significant manner) with other antibodies in binding assays. The ability of a test antibody to inhibit the binding of antibodies and antibody fragments (e.g., antigen binding fragments) of the present disclosure to BK or JC virus demonstrates that the test antibody can compete with that antibody or antibody fragment (e.g., antigen binding fragments) for binding to BK or JC virus; such an antibody may, according to non-limiting theory, bind to the same or a related (e.g., a structurally similar or spatially proximal) epitope on BK or JC virus as the antibody or antibody fragment (e.g., antigen binding fragments) with which it competes. In a certain aspect, the antibody that binds to the same epitope on BK or JC virus as the antibodies or antibody fragments (e.g., antigen binding fragments) of the present disclosure is a human or humanized monoclonal antibody. Such human or humanized monoclonal antibodies can be prepared and isolated as described herein.

2. Further Alteration of the Framework of Fc Region

The present disclosure disclosed specific anti-BK or JC virus antibodies. These antibodies comprise modified antibodies or antigen binding fragments thereof that further comprise modifications to framework residues within VH and/or VL, e.g. to improve the properties of the antibody. Typically such framework modifications are made to decrease the immunogenicity of the antibody. For example, one approach is to "back-mutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "back-mutated" to the germline sequence by, for example, site-directed mutagenesis. Such "back-mutated" antibodies are also intended to be encompassed.

Another type of framework modification involves mutating one or more residues within the framework region, or even within one or more CDR regions, to remove T-cell epitopes to thereby reduce the potential immunogenicity of the antibody. This approach is also referred to as "deimmunization" and is described in further detail in U.S. Patent Publication No. 2003/0153043 by Carr et al.

In addition or alternative to modifications made within the framework or CDR regions, antibodies can be engineered to include modifications within the Fc region, typically to alter one or more functional properties of the antibody, such as serum half-life, complement fixation, Fc receptor binding, and/or antigen-dependent cellular cytotoxicity. Furthermore, an antibody can be chemically modified (e.g., one or more chemical moieties can be attached to the antibody) or be modified to alter its glycosylation, again to alter one or more functional properties of the antibody. Each of these aspects is described in further detail below.

In one aspect, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another aspect, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In yet other aspects, the Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in, e.g., U.S. Pat. Nos. 5,624,821 and 5,648,260, both by Winter et al.

In another aspect, one or more amino acids selected from amino acid residues can be replaced with a different amino acid residue such that the antibody has altered C1q binding and/or reduced or abolished complement dependent cytotoxicity (CDC). This approach is described in, e.g., U.S. Pat. No. 6,194,551 by Idusogie et al.

In another aspect, one or more amino acid residues are altered to thereby alter the ability of the antibody to fix complement. This approach is described in, e.g., the PCT Publication WO 94/29351 by Bodmer et al. In a specific aspect, one or more amino acids of an antibody or antigen binding fragment thereof of the present disclosure are replaced by one or more allotypic amino acid residues, for the IgG1 subclass and the kappa isotype. Allotypic amino acid residues also include, but are not limited to, the constant region of the heavy chain of the IgG1, IgG2, and IgG3 subclasses as well as the constant region of the light chain of the kappa isotype as described by Jefferis et al., MAbs. 1:332-338 (2009).

In yet another aspect, the Fc region is modified to increase the ability of the antibody to mediate antibody dependent cellular cytotoxicity (ADCC) and/or to increase the affinity of the antibody for an Fcγ receptor by modifying one or more amino acids. This approach is described in, e.g., the PCT Publication WO 00/42072 by Presta. Moreover, the binding sites on human IgG1 for FcγRI, FcγRII, FcγRIII and FcRn have been mapped and variants with improved binding have been described (see Shields et al., J. Biol. Chem. 276:6591-6604, 2001).

In still another aspect, the glycosylation of an antibody is modified. For example, an aglycosylated antibody can be made (i.e., the antibody lacks glycosylation). Glycosylation can be altered to, for example, increase the affinity of the antibody for "antigen." Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in, e.g., U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies to thereby produce an antibody with altered glycosylation. For example, EP 1,176,195 by Hang et al. describes a cell line with a functionally disrupted FUT8 gene, which encodes a fucosyl transferase, such that antibodies expressed in such a cell line exhibit hypofucosylation. PCT Publication WO 03/035835 by Presta describes a variant CHO cell line, Lecl3 cells, with reduced ability to attach fucose to Asn (297)-linked carbohydrates, also resulting in hypofucosylation of antibodies expressed in that host cell (see also Shields et al., (2002) J. Biol. Chem. 277:26733-26740). PCT Publication WO 99/54342 by Umana et at describes cell lines engineered to express glycoprotein-modifying glycosyl transferases (e.g., beta(1,4)-N acetylglucosaminyltransferase III (GnTIII)) such that antibodies expressed in the engineered cell lines exhibit increased bisecting GlcNac structures which results in increased ADCC activity of the antibodies (see also Umana et al., Nat. Biotech. 17:176-180, 1999).

In another aspect, the antibody is modified to increase its biological half-life. Various approaches are possible. For example, one or more of the following mutations can be introduced: T252L, T254S, T256F, as described in U.S. Pat. No. 6,277,375 to Ward. Alternatively, to increase the biological half-life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In order to minimize the ADCC activity of an antibody, specific mutations in the Fc region result in "Fc silent" antibodies that have minimal interaction with effector cells. In general, the "IgG Fc region" is used to define the C-terminal region of an immunoglobulin heavy chain, including native sequence Fc region and variant Fc regions. The human IgG heavy chain Fc region is generally defined as comprising the amino acid residue from position C226 or from P230 to the carboxyl-terminus of the IgG antibody. The numbering of residues in the Fc region is that of the EU index of Kabat. The C-terminal lysine (residue K447) of the Fc region may be removed, for example, during production or purification of the antibody.

Silenced effector functions can be obtained by mutation in the Fc region of the antibodies and have been described in the art: LALA and N297A (Strohl, W., 2009, Curr. Opin. Biotechnol. vol. 20(6):685-691); and D265A (Baudino et al., 2008, J. Immunol. 181: 6664-69) see also Heusser et al., WO2012065950. Examples of silent Fc lgG1 antibodies are the LALA mutant comprising L234A and L235A mutation in the lgG1 Fc amino acid sequence. Another example of a silent lgG1 antibody is the DAPA (D265A, P329A) mutation (U.S. Pat. No. 6,737,056). Another silent lgG1 antibody comprises the N297A mutation, which results in aglycosylated/non-glycosylated antibodies.

Fc silent antibodies result in no or low ADCC activity, meaning that an Fc silent antibody exhibits an ADCC activity that is below 50% specific cell lysis (low ADCC activity), or that is below 1% specific cell lysis (no ADCC activity).

3. Production of the Antibodies

Anti-BK or JC virus antibodies and antibody fragments (e.g., antigen binding fragments) thereof can be produced by any means known in the art, including but not limited to, recombinant expression, chemical synthesis, and enzymatic digestion of antibody tetramers, whereas full-length monoclonal antibodies can be obtained by, e.g., hybridoma or recombinant production. Recombinant expression can be from any appropriate host cells known in the art, for example, mammalian host cells, bacterial host cells, yeast host cells, insect host cells, etc.

The disclosure further provides polynucleotides encoding the antibodies described herein, e.g., polynucleotides encoding heavy or light chain variable regions or segments comprising the complementarity determining regions as described herein. In some aspects, the polynucleotide encoding the heavy chain variable regions has at least 85%, 89%, 90%, 91%, 92%, 93%, 94%, 95%, 96%, 97%, 98%, 99%, or 100% nucleic acid sequence identity with a polynucleotide selected from the group consisting of SEQ ID NOs: 19, 51, 83, 115, 147, 179, 211, 243 and 275. In some aspects, the polynucleotide encoding the light chain variable regions has at least 85%, 89%, 90%, 91%, 92%, 93%, 94%, 95%, 96%, 97%, 98%, 99%, or 100% nucleic acid sequence identity with a polynucleotide selected from the group consisting of SEQ ID NOs: 35, 67, 99, 131, 163, 195, 227, 259 and 291.

In some aspects, the polynucleotide encoding the heavy chain has at least 85%, 89%, 90%, 91%, 92%, 93%, 94%, 95%, 96%, 97%, 98%, 99%, or 100% nucleic acid sequence identity with a polynucleotide of SEQ ID NO: 21, 53, 85, 117, 149, 181, 213, 245 and 277. In some aspects, the polynucleotide encoding the light chain has at least 85%, 89%, 90%, 91%, 92%, 93%, 94%, 95%, 96%, 97%, 98%, 99%, or 100% nucleic acid sequence identity with a polynucleotide of SEQ ID NO: 37, 69, 101, 133, 165, 197, 229, 261 and 293.

The polynucleotides of the present disclosure can encode only the variable region sequence of an anti-BK or JC virus antibody. They can also encode both a variable region and a constant region of the antibody. Some of the polynucleotide sequences encode a polypeptide that comprises variable regions of both the heavy chain and the light chain of one of an exemplified anti-BK or JC virus antibody. Some other polynucleotides encode two polypeptide segments that respectively are substantially identical to the variable regions of the heavy chain and the light chain of one of the mouse antibodies.

The polynucleotide sequences can be produced by de novo solid-phase DNA synthesis or by PCR mutagenesis of an existing sequence encoding an anti-BK or JC virus antibody or its binding fragment. Direct chemical synthesis of nucleic acids can be accomplished by methods known in the art, such as the phosphotriester method of Narang et al., Meth. Enzymol. 68:90, 1979; the phosphodiester method of Brown et al., Meth. Enzymol. 68:109, 1979; the diethylphosphoramidite method of Beaucage et al., Tetra. Lett., 22:1859, 1981; and the solid support method of U.S. Pat. No. 4,458,066. Introducing mutations to a polynucleotide sequence by PCR can be performed as described in, e.g., PCR Technology: Principles and Applications for DNA Amplification, H. A. Erlich (Ed.), Freeman Press, NY, NY, 1992; PCR Protocols: A Guide to Methods and Applications, Innis et al. (Ed.), Academic Press, San Diego, CA, 1990; Mattila et al., Nucleic Acids Res. 19:967, 1991; and Eckert et al., PCR Methods and Applications 1:17, 1991.

Also provided in the present disclosure are expression vectors and host cells for producing the anti-BK or JC virus antibodies described above. Various expression vectors can be employed to express the polynucleotides encoding the anti-BK or JC virus antibody chains or binding fragments. Both viral-based and nonviral expression vectors can be used to produce the antibodies in a mammalian host cell. Nonviral vectors and systems include plasmids, episomal vectors, typically with an expression cassette for expressing a protein or RNA, and human artificial chromosomes (see, e.g., Harrington et al., Nat Genet 15:345, 1997). For example, nonviral vectors useful for expression of the anti-BK or JC virus polynucleotides and polypeptides in mammalian (e.g., human) cells include pThioHis A, B & C, pcDNA3.1/His, pEBVHis A, B & C (Invitrogen, San Diego, CA), MPSV vectors, and numerous other vectors known in the art for expressing other proteins. Useful viral vectors include vectors based on retroviruses, adenoviruses, adeno-associated viruses, herpes viruses, vectors based on SV40, papilloma virus, HBP Epstein Barr virus, vaccinia virus vectors and Semliki Forest virus (SFV). See, Brent et al., supra; Smith, Annu. Rev. Microbiol. 49:807, 1995; and Rosenfeld et al., Cell 68:143, 1992.

The choice of expression vector depends on the intended host cells in which the vector is to be expressed. Typically, the expression vectors contain a promoter and other regulatory sequences (e.g., enhancers) that are operably linked to the polynucleotides encoding an anti-BK or JC virus antibody chain or fragment. In some aspects, an inducible promoter is employed to prevent expression of inserted sequences except under inducing conditions. Inducible promoters include, e.g., arabinose, lacZ, metallothionein promoter or a heat shock promoter. Cultures of transformed organisms can be expanded under non-inducing conditions without biasing the population for coding sequences whose expression products are better tolerated by the host cells. In addition to promoters, other regulatory elements may also be required or desired for efficient expression of an anti-VP1 antibody chain or fragment. These elements typically include an ATG initiation codon and adjacent ribosome binding site or other sequences. In addition, the efficiency of expression may be enhanced by the inclusion of enhancers appropriate to the cell system in use (see, e.g., Scharf et al., Results Probl. Cell Differ. 20:125, 1994; and Bittner et al., Meth. Enzymol., 153:516, 1987). For example, the SV40 enhancer or CMV enhancer may be used to increase expression in mammalian host cells.

The expression vectors may also provide a secretion signal sequence position to form a fusion protein with polypeptides encoded by inserted anti-BK antibody sequences. More often, the inserted anti-BK antibody sequences are linked to a signal sequences before inclusion in the vector. Vectors to be used to receive sequences encoding anti-BK antibody light and heavy chain variable domains sometimes also encode constant regions or parts thereof. Such vectors allow expression of the variable regions as fusion proteins with the constant regions thereby leading to production of intact antibodies or fragments thereof. Typically, such constant regions are human.

The host cells for harboring and expressing the anti-BK or JC antibody chains can be either prokaryotic or eukaryotic. E. coli is one prokaryotic host useful for cloning and expressing the polynucleotides of the present disclosure. Other microbial hosts suitable for use include bacilli, such as Bacillus subtilis, and other enterobacteriaceae, such as Salmonella, Serratia, and various Pseudomonas species. In these prokaryotic hosts, one can also make expression vectors, which typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters typically control expression, optionally with an operator sequence, and have ribosome binding site sequences and the like, for initiating and completing transcription and translation. Other microbes, such as yeast, can also be employed to express anti-VP1 polypeptides. Insect cells in combination with baculovirus vectors can also be used.

In other aspects, mammalian host cells are used to express and produce the anti-VP1 polypeptides of the present disclosure. For example, they can be either a hybridoma cell line expressing endogenous immunoglobulin genes (e.g., the myeloma hybridoma clones as described in the Examples) or a mammalian cell line harboring an exogenous expression vector. These include any normal mortal or normal or abnormal immortal animal or human cell. For example, a number of suitable host cell lines capable of secreting intact immunoglobulins have been developed, including the CHO cell lines, various COS cell lines, HeLa cells, myeloma cell lines, transformed B-cells and hybridomas. The use of mammalian tissue cell culture to express polypeptides is discussed generally in, e.g., Winnacker, From Genes to Clones, VCH Publishers, N.Y., N. Y., 1987. Expression vectors for mammalian host cells can include expression control sequences, such as an origin of replication, a promoter, and an enhancer (see, e.g., Queen et al., Immunol. Rev. 89:49-68, 1986), and necessary processing information sites, such as ribosome binding sites, RNA splice sites, polyadenylation sites, and transcriptional terminator sequences. These expression vectors usually contain promoters derived from mammalian genes or from mammalian viruses. Suitable promoters may be constitutive, cell type-specific, stage-specific, and/or modulatable or regulatable. Useful promoters include, but are not limited to, the metallothionein promoter, the constitutive adenovirus major late promoter, the dexamethasone-inducible MMTV promoter, the SV40 promoter, the MRP polIII promoter, the constitutive MPSV promoter, the tetracycline-inducible CMV promoter (such as the human immediate-early CMV promoter), the constitutive CMV promoter, and promoter-enhancer combinations known in the art.

Methods for introducing expression vectors containing the polynucleotide sequences of interest vary depending on the type of cellular host. For example, calcium chloride transfection is commonly utilized for prokaryotic cells, whereas calcium phosphate treatment or electroporation may be used for other cellular hosts (see generally Sambrook et al., supra). Other methods include, e.g., electroporation, calcium phosphate treatment, liposome-mediated transformation, injection and microinjection, ballistic methods, virosomes, immunoliposomes, polycation:nucleic acid conjugates, naked DNA, artificial virions, fusion to the herpes virus structural protein VP22 (Elliot and O'Hare, Cell 88:223, 1997), agent-enhanced uptake of DNA, and ex vivo transduction. For long-term, high-yield production of recombinant proteins, stable expression will often be desired. For example, cell lines which stably express anti-BK or JC virus antibody chains or binding fragments can be prepared using expression vectors which contain viral origins of replication or endogenous expression elements and a selectable marker gene. Following introduction of the vector, cells may be allowed to grow for 1-2 days in an enriched media before they are switched to selective media. The purpose of the selectable marker is to confer resistance to selection, and its presence allows growth of cells which successfully express the introduced sequences in selective media. Resistant, stably transfected cells can be proliferated using tissue culture techniques appropriate to the cell type. Therapeutic and Diagnostic Uses The antibodies, antibody fragments (e.g., antigen binding fragments) of the present disclosure are useful in a variety of applications including, but not limited to, polyoma viral infection and disease. In certain aspects, the antibodies, antibody fragments (e.g., antigen binding fragments), and are useful for neutralizing BKV or JCV infection and the prevention or treatment of BK virus nephropathy, for example, BKVAN). The methods of use can be in vitro, ex vivo, or in vivo methods.

In one aspect, the antibodies, antibody fragments (e.g., antigen binding fragments), are useful for detecting the presence of BKV in a biological sample. The term "detecting" as used herein encompasses quantitative or qualitative detection. In certain aspects, a biological sample comprises a cell or tissue. In certain aspects, such tissues include normal and/or cancerous tissues that express BKV at higher levels relative to other tissues.

In one aspect, the present disclosure provides a method of detecting the presence of BK or JC virus in a biological sample. In certain aspects, the method comprises contacting the biological sample with an anti-BK or JC virus antibody under conditions permissive for binding of the antibody to the antigen, and detecting whether a complex is formed between the antibody and the antigen. The biological sample can include, without limitation, urine or blood samples.

Also included is a method of diagnosing a disorder associated with expression of BK or JC virus. In certain aspects, the method comprises contacting a test cell with an anti-BK or JC virus antibody; determining the level of expression (either quantitatively or qualitatively) of BK or JC virus in the test cell by detecting binding of the antibody to the BK or JC virus; and comparing the level of infection in the test cell with the level of infection of BK or JC virus in a control cell (e.g., a normal cell of the same tissue origin as the test cell or a non-virus infected cell), wherein a higher level of presence of BK or JC virus in the test cell as compared to the control cell indicates the presence of a disorder associated with infection with BK or JC virus. In certain aspects, the test cell is obtained from an individual suspected of having a BK or JC virus infection.

In certain aspects, a method of diagnosis or detection, such as those described above, comprises detecting binding of an BK or JC virus antibody to a virus infected cell. An exemplary assay for detecting binding of an anti-BK or JC virus antibody to a BK or JC virus infected cell is a "FACS" assay.

Certain other methods can be used to detect binding of anti-BK or JC virus antibodies. Such methods include, but are not limited to, antigen-binding assays that are well known in the art, such as Western blots, radioimmunoassays, ELISA (enzyme linked immunosorbent assay), "sandwich" immunoassays, immunoprecipitation assays, fluorescent immunoassays, protein A immunoassays, and immunohistochemistry (IHC).

In certain aspects, anti-BK or JC virus antibodies are labeled. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction.

In certain aspects, anti-BK or JC virus antibodies are immobilized on an insoluble matrix. Immobilization entails separating the anti-BK or JC virus antibody from any BKV or JCV proteins that remains free in solution. This conventionally is accomplished by either insolubilizing the anti-BK or JC antibody before the assay procedure, as by adsorption to a water-insoluble matrix or surface (Bennich et al, U.S. Pat. No. 3,720,760), or by covalent coupling (for example, using glutaraldehyde cross-linking), or by insolubilizing the anti-BK or JC antibody after formation of a complex between the anti-BK or JC antibody and BKV or JCV protein, e.g., by immunoprecipitation.

Any of the above aspects of diagnosis or detection can be carried out using an anti-BK or JC antibody of the present disclosure in place of or in addition to another anti-BK or JC antibody.

In one aspect, the disclosure provides for a method of treating, reducing the likelihood of or ameliorating a disease comprising administering the antibodies, antibody fragments (e.g., antigen binding fragments), to a patient, thereby treating the disease. In certain aspects, the disease treated with the antibodies, antibody fragments (e.g., antigen binding fragments), is a BK viral or JC viral infection. Examples of BKV and JCV diseases which can be treated and/or prevented include, but are not limited to, nephropathy, hemorrhagic cystitis, Progressive Multifocal Leukoencephalopathy (PML), interstitial kidney disease, ureteral stenosis, granule cell neuronopathy (GCN), vasculitis, colitis, retinitis, meningitis, and immune reconstitution inflammatory syndrome (IRIS). In certain aspects, the infection is characterized by BKV or JCV expressing cells to which the anti-BK or JC antibodies, antibody fragments (e.g., antigen binding fragments) can specifically bind.

The present disclosure provides for methods of treating BK viral infection and BKVAN comprising administering a therapeutically effective amount of the antibodies, antibody fragments (e.g., antigen binding fragments). In certain aspects, the subject is a human.

In certain aspects, the method of reducing BK viral infection comprises administering to a subject a therapeutically effective amount of antibodies or antibody fragments (e.g., antigen binding fragments). In certain aspects, the subject is a human. In certain aspects, the subject is immunosuppressed. For immunosuppressed subjects, the amount of immunosuppression can be increased or decreased due to the therapeutic effects of the anti-BK antibodies.

In certain aspects, the transplanted tissue is infected with BK virus to which the anti-BK antibody binds. As the incidence of BK infection in the general population is high, there is a high probability that in the case of kidney transplantation, the patient accepting the kidney is BK virus positive or the donor providing the kidney is BK virus positive or both are BK virus positive. In order to prevent BKVAN, anti-BK antibodies can be administered to the kidney transplant recipient, before and/or after the kidney transplant procedure, depending on the seropositivity of the kidney donor or transplant recipient. In another aspect, the anti-BK antibodies can be administered to the patient when virus is detected in the urine (viruria), or when virus is detected in the blood (viremia).

For the treatment of BK or JC viral infection, the appropriate dosage of the antibodies, or antibody fragments (e.g., antigen binding fragments), depend on various factors, such as the type of infection to be treated, the severity and course of the infection, the responsiveness of the infection, the generation of viral resistance to therapy, previous therapy, patient's clinical history, and so on. The antibody can be administered one time or over a series of treatments lasting from several days to several months, or until a cure is effected or a diminution of the infection is achieved (e.g., reduction in viruria or viral damage to the kidney). Optimal dosing schedules can be calculated from measurements of drug accumulation in the body of the patient and will vary depending on the relative potency of an individual antibody or antibody fragment (e.g., antigen binding fragment). In certain aspects, dosage is from 0.01 mg to 10 mg (e.g., 0.01 mg, 0.05 mg, 0.1 mg, 0.5 mg, 1 mg, 2 mg, 3 mg, 4 mg, 5 mg, 7 mg, 8 mg, 9 mg, or 10 mg) per kg of body weight, and can be given once or more daily, weekly, monthly or yearly. In certain aspects, the antibody or antibody fragment (e.g., antigen binding fragment), of the present disclosure is given once every two weeks or once every three weeks. The treating physician can estimate repetition rates for dosing based on measured half-life and concentrations of the antibody in bodily fluids or tissues.

Combination Therapy

In certain instances, the antibody or antibody fragment (e.g., antigen binding fragment), of the present disclosure is combined with other therapeutic agents, such as other antiviral agents, anti-allergic agents, anti-nausea agents (or anti-emetics), pain relievers, cytoprotective agents, immunosuppressants and combinations thereof.

The term "pharmaceutical combination" as used herein refers to either a fixed combination in one dosage unit form, or non-fixed combination or a kit of parts for the combined administration where two or more therapeutic agents may be administered independently at the same time or separately within time intervals, especially where these time intervals allow that the combination partners show a cooperative, e.g. synergistic effect.

The term "combination therapy" refers to the administration of two or more therapeutic agents to treat a therapeutic condition or infection described in the present disclosure. Such administration encompasses co-administration of these therapeutic agents in a substantially simultaneous manner, such as in a single capsule having a fixed ratio of active ingredients. Alternatively, such administration encompasses co-administration in multiple, or in separate containers (e.g., capsules, powders, and liquids) for each active ingredient. Powders and/or liquids may be reconstituted or diluted to a desired dose prior to administration. In addition, such administration also encompasses use of each type of therapeutic agent in a sequential manner, either at approximately the same time or at different times. In either case, the treatment regimen will provide beneficial effects of the drug combination in treating the conditions or disorders described herein.

The combination therapy can provide "synergy" and prove "synergistic", i.e., the effect achieved when the active ingredients used together is greater than the sum of the effects that results from using the compounds separately. A synergistic effect can be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect can be attained when the compounds are administered or delivered sequentially, e.g., by different injections in separate syringes. In general, during alternation therapy, an effective dosage of each active ingredient is administered sequentially, i.e., serially, whereas in combination therapy, effective dosages of two or more active ingredients are administered together.

In one aspect, the present disclosure provides a method of treating BKV or JCV infection by administering to a subject in need thereof an antibody in together with immunosuppressant therapies. The anti-BK or JC antibodies will act prophylactically to neutralize BKV or JCV primary infection or viral reactivation resulting from the immunosuppressant therapy prior to or post-transplantation. Examples of immunosuppressant therapy include, but are not limited to; a monophosphate dehydrogenase inhibitor, a purine synthesis inhibitor, a calcineurin inhibitor or an mTOR inhibitor.

Specific examples of immunosuppressive therapeutics include but are not limited to; mycophenolate mofetil (MMF), mycophenolate sodium, azathioprine, tacrolimus, sirolimus and cyclosporine.

Pharmaceutical Compositions

To prepare pharmaceutical or sterile compositions including anti-BK or JC antibodies, the antibodies of the present disclosure are mixed with a pharmaceutically acceptable carrier or excipient. The compositions can additionally contain one or more other therapeutic agents that are suitable for neutralizing BKV or JCV infection.

Formulations of therapeutic and diagnostic agents can be prepared by mixing with physiologically acceptable carriers, excipients, or stabilizers in the form of, e.g., lyophilized powders, slurries, aqueous solutions, lotions, or suspensions (see, e.g., Hardman et al., Goodman and Gilman's The Pharmacological Basis of Therapeutics, McGraw-Hill, New York, N.Y., 2001; Gennaro, Remington: The Science and Practice of Pharmacy, Lippincott, Williams, and Wilkins, New York, N.Y., 2000; Avis, et al. (eds.), Pharmaceutical Dosage Forms: Parenteral Medications, Marcel Dekker, N Y, 1993; Lieberman, et al. (eds.), Pharmaceutical Dosage Forms: Tablets, Marcel Dekker, N Y, 1990; Lieberman, et al. (eds.) Pharmaceutical Dosage Forms: Disperse Systems, Marcel Dekker, N Y, 1990; Weiner and Kotkoskie, Excipient Toxicity and Safety, Marcel Dekker, Inc., New York, N.Y., 2000).

In a specific aspect, the anti-BK or JC antibody is a lyophilisate in a vial containing the antibody. The lyophilisate can be reconstituted with water or a pharmaceutical carrier suitable for injection. For subsequent intravenous administration, the obtained solution will usually be further diluted into a carrier solution.

The antibodies disclosed herein are useful in the neutralization of BKV or JCV in tissue transplant patients who can be immunosuppressed, so a pharmaceutical carrier of sucrose and human albumin as used previously in bone marrow transplant patients receiving CytoGam® can be used (DeRienzo et al. Pharmacotherapy 2000; 20:1175-8). Alternatively, the anti-BK or JC antibodies can be introduced into transplant patients via a pharmaceutical carrier as described for another anti-viral antibody, Synagis®, as described in WO2003/105894. In this publication, the pharmaceutical carrier was comprised of histidine and/or glycine, a saccharide (e.g. sucrose) and a polyol (e.g. polysorbate).

Selecting an administration regimen for a therapeutic depends on several factors, including the severity of the infection, the level of symptoms, and the accessibility of the target cells in the biological matrix. In certain aspects, an administration regimen maximizes the amount of therapeutic delivered to the patient consistent with an acceptable level of side effects. Accordingly, the amount of biologic delivered depends in part on the particular entity and the severity of the condition being treated. Guidance in selecting appropriate doses of antibodies, cytokines, and small molecules are available (see, e.g., Wawrzynczak, Antibody Therapy, Bios Scientific Pub. Ltd, Oxfordshire, UK, 1996; Kresina (ed.), Monoclonal Antibodies, Cytokines and Arthritis, Marcel Dekker, New York, N.Y., 1991; Bach (ed.), Monoclonal Antibodies and Peptide Therapy in Autoimmune Diseases, Marcel Dekker, New York, N.Y., 1993; Baert et al., New Engl. J. Med. 348:601-608, 2003; Milgrom et al., New Engl. J. Med. 341:1966-1973, 1999; Slamon et al., New Engl. J. Med. 344:783-792, 2001; Beniaminovitz et al., New Engl. J. Med. 342:613-619, 2000; Ghosh et al., New Engl. J. Med. 348:24-32, 2003; Lipsky et al., New Engl. J. Med. 343:1594-1602, 2000).

Determination of the appropriate dose is made by the clinician, e.g., using parameters or factors known or suspected in the art to affect treatment or predicted to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., infusion reactions.

Actual dosage levels of the active ingredients in the pharmaceutical compositions with the anti-BK antibodies can be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the neutralizing activity of the antibodies, the route of administration, the time of administration, the half-life of the antibody in the patient, the duration of the treatment, other drugs, compounds and/or materials used in combination with the particular compositions employed, the age, sex, weight, condition, general health and prior medical history of the patient being treated, and like factors known in the medical arts.

Compositions comprising antibodies or fragments thereof can be provided by continuous infusion, or by doses at intervals of, e.g., one day, one week, or 1-7 times per week. Doses can be provided intravenously, subcutaneously, topically, orally, nasally, rectally, intramuscular, intracerebrally, or by inhalation. A specific dose protocol is one involving the maximal dose or dose frequency that avoids significant undesirable side effects.

For the antibodies described herein, the dosage administered to a patient may be 0.0001 mg/kg to 100 mg/kg of the patient's body weight. The dosage may be between 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg to 0.25 mg/kg, 0.0001 to 0.15 mg/kg, 0.0001 to 0.10 mg/kg, 0.001 to 0.5 mg/kg, 0.01 to 0.25 mg/kg or 0.01 to 0.10 mg/kg of the patient's body weight. The dosage of the antibodies or fragments thereof can be calculated using the patient's weight in kilograms (kg) multiplied by the dose to be administered in mg/kg.

Doses of the antibodies then can be repeated and the administrations may be separated by at least 1 day, 2 days, 3 days, 5 days, 10 days, 15 days, 30 days, 45 days, 2 months, 75 days, 3 months, or at least 6 months.

An effective amount for a particular patient may vary depending on factors such as the condition being treated, the overall health of the patient, the method, route and dose of administration and the severity of side effects (see, e.g., Maynard et al., A Handbook of SOPs for Good Clinical Practice, Interpharm Press, Boca Raton, Fla., 1996; Dent, Good Laboratory and Good Clinical Practice, Urch Publ., London, UK, 2001).

The route of administration may be by, e.g., topical or cutaneous application, injection or infusion by intravenous, intraperitoneal, intracerebral, intramuscular, intraocular, intraarterial, intracerebrospinal, intralesional, or by sustained release systems or an implant (see, e.g., Sidman et al., Biopolymers 22:547-556, 1983; Langer et al., J. Biomed. Mater. Res. 15:167-277, 1981; Langer, Chem. Tech. 12:98-105, 1982; Epstein et al., Proc. Natl. Acad. Sci. USA 82:3688-3692, 1985; Hwang et al., Proc. Natl. Acad. Sci.

USA 77:4030-4034, 1980; U.S. Pat. Nos. 6,350,466 and 6,316,024). Where necessary, the composition may also include a solubilizing agent or a local anesthetic such as lidocaine to ease pain at the site of the injection, or both. In addition, pulmonary administration can also be employed, e.g., by use of an inhaler or nebulizer, and formulation with an aerosolizing agent. See, e.g., U.S. Pat. Nos. 6,019,968, 5,985,320, 5,985,309, 5,934,272, 5,874,064, 5,855,913, 5,290,540, and 4,880,078; and PCT Publication Nos. WO 92/19244, WO 97/32572, WO 97/44013, WO 98/31346, and WO 99/66903, each of which is incorporated herein by reference their entirety.

A composition of the present disclosure can also be administered via one or more routes of administration using one or more of a variety of methods known in the art. As will be appreciated by the skilled artisan, the route and/or mode of administration will vary depending upon the desired results. Selected routes of administration for the antibodies include intravenous, intramuscular, intradermal, intraperitoneal, subcutaneous, spinal or other parenteral routes of administration, for example by injection or infusion. Parenteral administration may represent modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, a composition of the present disclosure can be administered via a non-parenteral route, such as a topical, epidermal or mucosal route of administration, for example, intranasally, orally, vaginally, rectally, sublingually or topically. In one aspect, the antibodies of the present disclosure are administered by infusion. In another aspect, the antibodies are administered subcutaneously.

If the antibodies of the present disclosure are administered in a controlled release or sustained release system, a pump may be used to achieve controlled or sustained release (see Langer, supra; Sefton, CRC Crit. Ref Biomed. Eng. 14:20, 1987; Buchwald et al., Surgery 88:507, 1980; Saudek et al., N. Engl. J. Med. 321:574, 1989). Polymeric materials can be used to achieve controlled or sustained release of the therapies of the antibodies (see e.g., Medical Applications of Controlled Release, Langer and Wise (eds.), CRC Pres., Boca Raton, Fla., 1974; Controlled Drug Bioavailability, Drug Product Design and Performance, Smolen and Ball (eds.), Wiley, New York, 1984; Ranger and Peppas, J. Macromol. Sci. Rev. Macromol. Chem. 23:61, 1983; see also Levy et al., Science 228:190, 1985; During et al., Ann. Neurol. 25:351, 1989; Howard et al., J. Neurosurg. 7 1:105, 1989; U.S. Pat. Nos. 5,679,377; 5,916,597; 5,912,015; 5,989,463; 5,128,326; PCT Publication No. WO 99/15154; and PCT Publication No. WO 99/20253. Examples of polymers used in sustained release formulations include, but are not limited to, poly(2-hydroxy ethyl methacrylate), poly (methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In one aspect, the polymer used in a sustained release formulation is inert, free of leachable impurities, stable on storage, sterile, and biodegradable. A controlled or sustained release system can be placed in proximity of the prophylactic or therapeutic target, thus requiring only a fraction of the systemic dose (see, e.g., Goodson, in Medical Applications of Controlled Release, supra, vol. 2, pp. 115-138, 1984).

Controlled release systems are discussed in the review by Langer, Science 249:1527-1533, 1990). Any technique known to one of skill in the art can be used to produce sustained release formulations comprising one or more antibodies of the present disclosure. See, e.g., U.S. Pat. No. 4,526,938, PCT publication WO 91/05548, PCT publication WO 96/20698, Ning et al., Radiotherapy & Oncology 39:179-189, 1996; Song et al., PDA Journal of Pharmaceutical Science & Technology 50:372-397, 1995; Cleek et al., Pro. Int'l. Symp. Control. Rel. Bioact. Mater. 24:853-854, 1997; and Lam et al., Proc. Int'l. Symp. Control Rel. Bioact. Mater. 24:759-760, 1997, each of which is incorporated herein by reference in their entirety.

If the antibodies of the disclosure are administered topically, they can be formulated in the form of an ointment, cream, transdermal patch, lotion, gel, spray, aerosol, solution, emulsion, or other form well-known to one of skill in the art. See, e.g., Remington's Pharmaceutical Sciences and Introduction to Pharmaceutical Dosage Forms, 19th ed., Mack Pub. Co., Easton, Pa. (1995). For non-sprayable topical dosage forms, viscous to semi-solid or solid forms comprising a carrier or one or more excipients compatible with topical application and having a dynamic viscosity, in some instances, greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, in some instances, in combination with a solid or liquid inert carrier, is packaged in a mixture with a pressurized volatile (e.g., a gaseous propellant, such as freon) or in a squeeze bottle. Moisturizers or humectants can also be added to pharmaceutical compositions and dosage forms if desired. Examples of such additional ingredients are well-known in the art.

If the compositions comprising the antibodies are administered intranasally, it can be formulated in an aerosol form, spray, mist or in the form of drops. In particular, prophylactic or therapeutic agents for use according to the present disclosure can be conveniently delivered in the form of an aerosol spray presentation from pressurized packs or a nebulizer, with the use of a suitable propellant (e.g., dichlorodifluoromethane, trichlorofluoromethane, dichlorotetrafluoroethane, carbon dioxide or other suitable gas). In the case of a pressurized aerosol the dosage unit may be determined by providing a valve to deliver a metered amount. Capsules and cartridges (composed of, e.g., gelatin) for use in an inhaler or insufflator may be formulated containing a powder mix of the compound and a suitable powder base such as lactose or starch.

Methods for co-administration or treatment with a second therapeutic agent, e.g., an immunosuppressant, a cytokine, steroid, chemotherapeutic agent, antibiotic, or radiation, are known in the art (see, e.g., Hardman et al., (eds.) (2001) Goodman and Gilman's The Pharmacological Basis of Therapeutics, 10th ed., McGraw-Hill, New York, N.Y.; Poole and Peterson (eds.) (2001) Pharmacotherapeutics for Advanced Practice: A Practical Approach, Lippincott, Williams & Wilkins, Phila., Pa.; Chabner and Longo (eds.) (2001) Cancer Chemotherapy and Biotherapy, Lippincott, Williams & Wilkins, Phila., Pa.). An effective amount of therapeutic may decrease the symptoms by at least 10%; by at least 20%; at least about 30%; at least 40%, or at least 50%.

Additional therapies (e.g., prophylactic or therapeutic agents), which can be administered in combination with the anti-BK antibodies may be administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours apart from the anti-VP1 antibodies of the present disclosure. The two or more therapies may be administered within one same patient visit.

In certain aspects, anti-BK antibodies can be formulated to ensure proper distribution in vivo. For example, the blood-brain barrier (BBB) excludes many highly hydrophilic compounds. To ensure that the anti-BK antibodies cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., Ranade, (1989) J. Clin. Pharmacol. 29:685). Exemplary targeting moieties include folate or biotin (see, e.g., U.S. Pat. No. 5,416,016 to Low et al.); mannosides (Umezawa et al., (1988) Biochem. Biophys. Res. Commun. 153:1038); antibodies (Bloeman et al., (1995) FEBS Lett. 357:140; Owais et al., (1995) Antimicrob. Agents Chemother. 39:180); surfactant protein A receptor (Briscoe et al., (1995) Am. J. Physiol. 1233:134); p 120 (Schreier et al, (1994) J. Biol. Chem. 269:9090); see also K. Keinanen; M. L. Laukkanen (1994) FEBS Lett. 346:123; J. J. Killion; I. J. Fidler (1994) Immunomethods 4:273.

The present disclosure provides protocols for the administration of pharmaceutical composition comprising antibodies alone or in combination with other therapies to a subject in need thereof. The combination therapies (e.g., prophylactic or therapeutic agents) can be administered concomitantly or sequentially to a subject. The therapy (e.g., prophylactic or therapeutic agents) of the combination therapies can also be cyclically administered. Cycling therapy involves the administration of a first therapy (e.g., a first prophylactic or therapeutic agent) for a period of time, followed by the administration of a second therapy (e.g., a second prophylactic or therapeutic agent) for a period of time and repeating this sequential administration, i.e., the cycle, in order to reduce the development of resistance to one of the therapies (e.g., agents) to avoid or reduce the side effects of one of the therapies (e.g., agents), and/or to improve, the efficacy of the therapies.

The therapies (e.g., prophylactic or therapeutic agents) of the combination therapies of the disclosure can be administered to a subject concurrently. The term "concurrently" is not limited to the administration of therapies (e.g., prophylactic or therapeutic agents) at exactly the same time, but rather it is meant that a pharmaceutical composition comprising antibodies or fragments thereof are administered to a subject in a sequence and within a time interval such that the antibodies can act together with the other therapy(ies) to provide an increased benefit than if they were administered otherwise. For example, each therapy may be administered to a subject at the same time or sequentially in any order at different points in time; however, if not administered at the same time, they should be administered sufficiently close in time so as to provide the desired therapeutic or prophylactic effect. Each therapy can be administered to a subject separately, in any appropriate form and by any suitable route. In various aspects, the therapies (e.g., prophylactic or therapeutic agents) are administered to a subject less than 15 minutes, less than 30 minutes, less than 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, 24 hours apart, 48 hours apart, 72 hours apart, or 1 week apart. In other aspects, two or more therapies (e.g., prophylactic or therapeutic agents) are administered to a within the same patient visit.

The prophylactic or therapeutic agents of the combination therapies can be administered to a subject in the same pharmaceutical composition. Alternatively, the prophylactic or therapeutic agents of the combination therapies can be administered concurrently to a subject in separate pharmaceutical compositions. The prophylactic or therapeutic agents may be administered to a subject by the same or different routes of administration.

EXAMPLES

Example 1: Generation of Anti-BK or JC Virus Antibodies

B cells expressing anti-BKV and/or anti-JCV antibodies were lysed and the VH (heavy) and VL (light) chains were amplified by RT-PCR and subsequently sequenced and analyzed to identify critical post translational modification (PTM) sites. Plasmids of the VH and VL chains were then transfected in a CHO mammalian cell line in an IgG1 backbone vector for expression of the full IgG1 antibodies.

Example 2: Binding of Anti-BKV Antibodies to VLPs (ELISA)

The binding of antibodies to VLPs were analyzed by ELISA. Briefly, Nunc MaxiSorp 384-well plates (Thermo Scientific) were coated with 100 ng/well BKV VLPs to BK serotype I (ST1) or serotype IV (ST4) overnight. Antibodies were serially diluted in PBS with 0.5% BSA and allowed to bind antigen-coated plates for 2 hours. Plates were washed with PBS and then incubated with secondary antibody (HRP-conjugated goat anti-human IgG, Southern Biotech #2040-01) diluted 1:6000 in 0.5% BSA in PBS for 1 hour. Plates were washed with PBS and tetramethylbenzidine (TMB) microwell peroxidase substrate (SeramunBlau Fast, Seramun, Germany) was used to develop the reactions. The results of ELISA binding can be seen in FIG. 1. For example, the antibody NOV530 bound to both BKV ST1 and BKV ST4. Antibody NOV638 bound only to BKV ST1.

Example 3: Neutralization of Viral Infection Anti-BKV Antibodies

Infectious BKV serotype I (ST1) and chimeric viruses representing serotype II (ST2), III (ST3), and IV (ST4) were pre-incubated with purified antibodies for 1 hour to allow for binding and neutralization. Primary renal proximal tubule epithelial (RPTE) cells (ATCC, cat #PCS-400-010) were then exposed to the virus-antibody mixture for 4 hours, replaced with fresh medium, and incubated for 48 hours to allow for viral entry and gene expression. Cells were fixed with 4% paraformaldehyde and analyzed by immunofluorescence to detect TAg expression (Calbiochem DP02, pAb416 mouse anti-SV40 TAg antibody). The immunofluorescence was analyzed by high content image analysis using the Cellomics ArrayScan® VTI HCS Reader to quantify the percent of BKV-infected cells (TAg-positive, DAP1-positive), with data presented as percent inhibition of infection relative to untreated control wells. Data are presented as EC50, the concentration of antibody at which virus infection is neutralized by 50%, relative to untreated control wells.

Physiologically, antibodies exert several functions which help inhibit a progressing pathogenic reaction, one of which is to directly block the ability of a virus to bind and/or enter its target cell. These "neutralizing" antibodies typically represent only a subset of antigen-binding Ig. Most of the monoclonal IgG anti-BKV antibodies disclosed herein were able to neutralize at least BKV ST1 in a primary renal cell infection assay, while several were also able to neutralize additional BKV subtypes and/or the related JC virus (FIG. 1). For example, antibody NOV638 was able to bind and neutralize BKV ST1, while antibody NOV530 was able to bind and neutralize all four serotypes of BK virus and also showed a sub-nanomolar EC50 of JCV (FIG. 1).

Example 4: BK Virus and Virus-Like Particle (VLP) Generation

Genomic clones of BKV ST1 were obtained from ATCC (pBR322-BKV MM, cat #45026; pBR322-BKV Dunlop, cat #45025). Infectious genomic clones of chimeric viruses for ST2, ST3 and ST4 were generated using the cloning strategy described previously (Broekema et al, Virology 2010 407: 368-373). Briefly, unique restriction sites (SacII, PmlI) were introduced into BKV serotype I genomes flanking the VP1-VP2-VP3 coding region using site-directed mutagenesis. The coding region for VP1 from ST2 isolate SB (GenBank Accession CAA79596.1), serotype III isolate AS (GenBank Accession AAA46882.1) and ST4 isolate ITA-4 (GenBank Accession BAF75132) were synthesized in the context of VP2/VP3 coding region from the ST1 isolates (Genewiz, La Jolla, CA), such that the synthesized fragments encompassed the SacII-PmlI region to be used for swap combinations as described in Broekema et al., supra. The resulting chimeric genomic clones were then used to generate high titer infectious viral stocks in primary renal proximal tubule epithelial (RPTE) cells (ATCC, cat #PCS-400-010) as previously described (Abend et al, J. Virology 2007 81:272-279).

VLPs representing each of the four BKV serotypes were generated by expression of VP1 in Sf9 insect cells and extracted from frozen cell pellets from 1 L cultures by microtip sonication (3×45 second pulses, rest 5 min between pulses on ice), isolation by pelleting VLPs through a 20% sucrose cushion (116,000 g for 2.5 hours), and purification by anion exchange with a 5 ml GE HiTrap Q HP column (GE Healthcare, Pittsburgh, PA) followed by purification using a 10 ml Capto™ Core700 (GE Healthcare, Pittsburgh, PA) resin-based size exclusion column, and finally purification on a GE Sephacryl S500 26/60 (GE Healthcare, Pittsburgh, PA) size exclusion column. The prepared VLPs were used in ELISA and SET based binding assays.

Example 5: Affinity Measurements of Anti-BK Antibodies (SET Assay)

Solution equilibration titration (SET) assay was used to determine the interaction affinities ($K_d$) of antibodies with BKV VLPs from all four serotypes. Antibodies were assayed at 1 pM concentration (constant), VLPs were serially diluted from a starting concentration of 10 nM. Antibody:VLP solution was incubated overnight, then assayed for unbound antibody using an MSD array plate (Meso Scale Discovery Cat #L21XA, Rockville MD) coated with VLPs. The $K_d$ was determined by fitting the plot with a 1:1 fit model (according to Piehler et al. J. Immunol. Methods. 1997; 201(2):189-206).

Figures 2A, 2B:
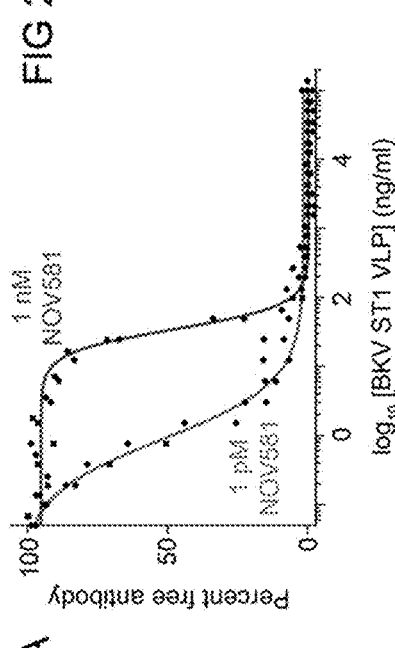
FIG. 2A shows a 4-parameter fitting of a $K_d$-controlled curve (based on the low concentration of the antibody NOV581), and a fitting of a stoichiometry-controlled curve.
FIG. 2B shows the $K_d$ in pM for three antibodies across all four BK serotypes.

Sample curve set used for affinity determination via SET of an anti-BKV monoclonal IgG (clone NOV581) against VLPs of the BKV ST1 is shown in FIG. 2A. The lower curve is a 4-parameter fitting of a $K_d$-controlled curve (based on the low concentration of the antibody NOV581), while the upper curve is a fitting of a stoichiometry-controlled curve (higher constant antibody concentration for estimating the effective ligand concentration). Signal strengths were normalized to initial conditions without BKV VLPs in solution ("100% free antibody").

In FIG. 2B, the binding affinity was determined of cross-neutralizing monoclonal anti-BKV IgG antibodies against BKV virus-like particles (VLPs). All antibodies tested had $K_d$ values below 50 pM against BKV ST1. In this assay, antibody NOV581 had significant affinity to BKV serotypes 1, 2 and 3, but not 4. In contrast, antibody NOV530 had significant affinity to all four serotypes (FIG. 2B).

Example 6: Cryo Electron Microscopy

Figure 3A:
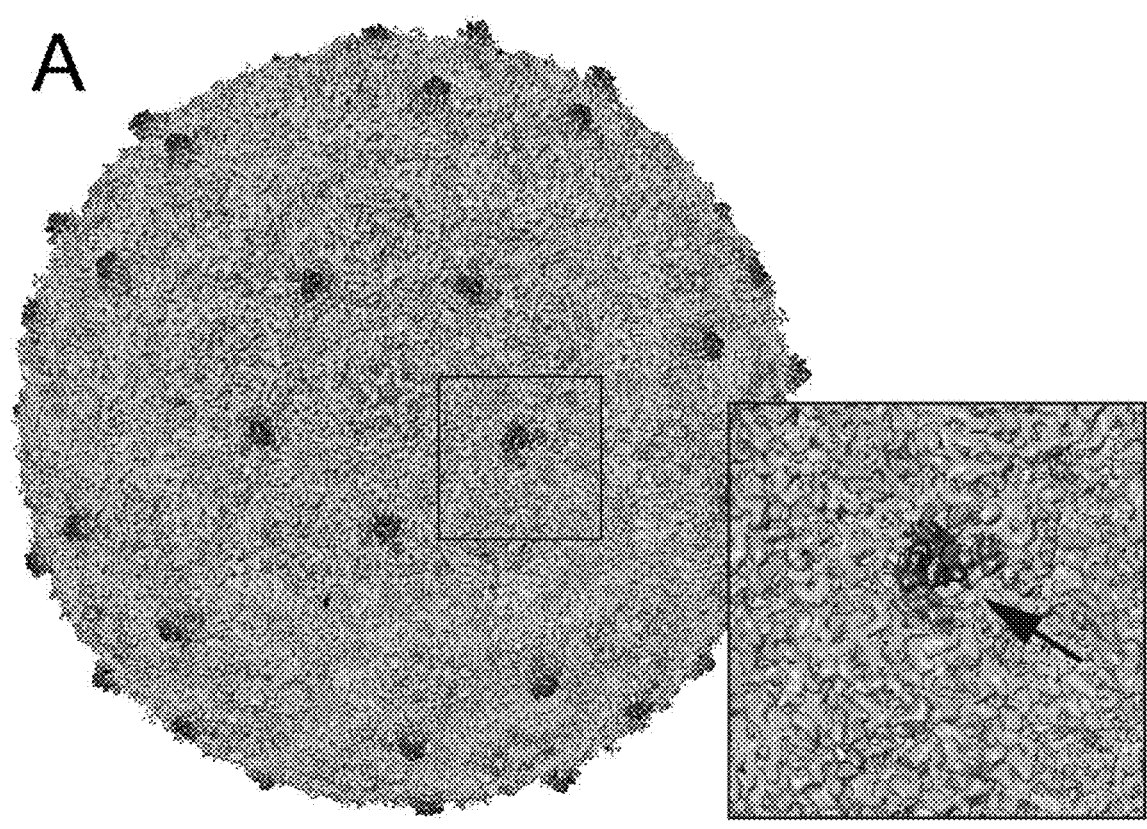
FIG. 3A shows cryo-electron microscopy structure of the interaction between BKV and a cross-neutralizing antibody. It is a 4.24 Å-resolution EM map of BKV ST1 VLP in complex with an scFv of the NOV530 polyomavirus cross-neutralizing antibody. Bound antibody fragments (marked area, black arrow) appear around the viral capsid at the junctions between capsid pentamers. Inset: magnified view of the single scFv bound to its epitope.
Figure 3B:
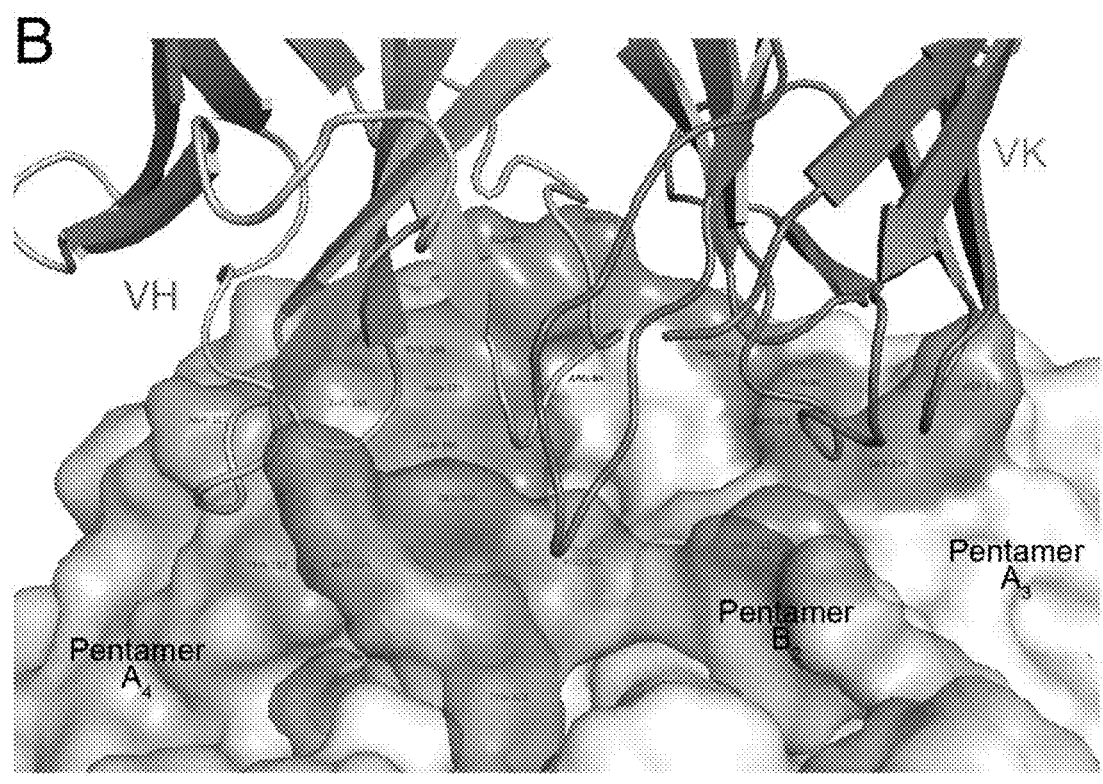
FIG. 3B is a surface and ribbon visualization of the virus-like particle and antibody chains, respectively, of density map-fitted structure models comprising the quaternary viral epitope for NOV530. Individual VP1 monomers from the VLP capsid are labeled to represent their geometric orientation within their respective pentamers. Adjacent pentamers contributing to the epitope are labelled "Pentamer A" (VP1 chains) and "Pentamer B." The VH, heavy chain variable domain and the VK, kappa light chain variable domain are respectively labeled.
Figure 3C:
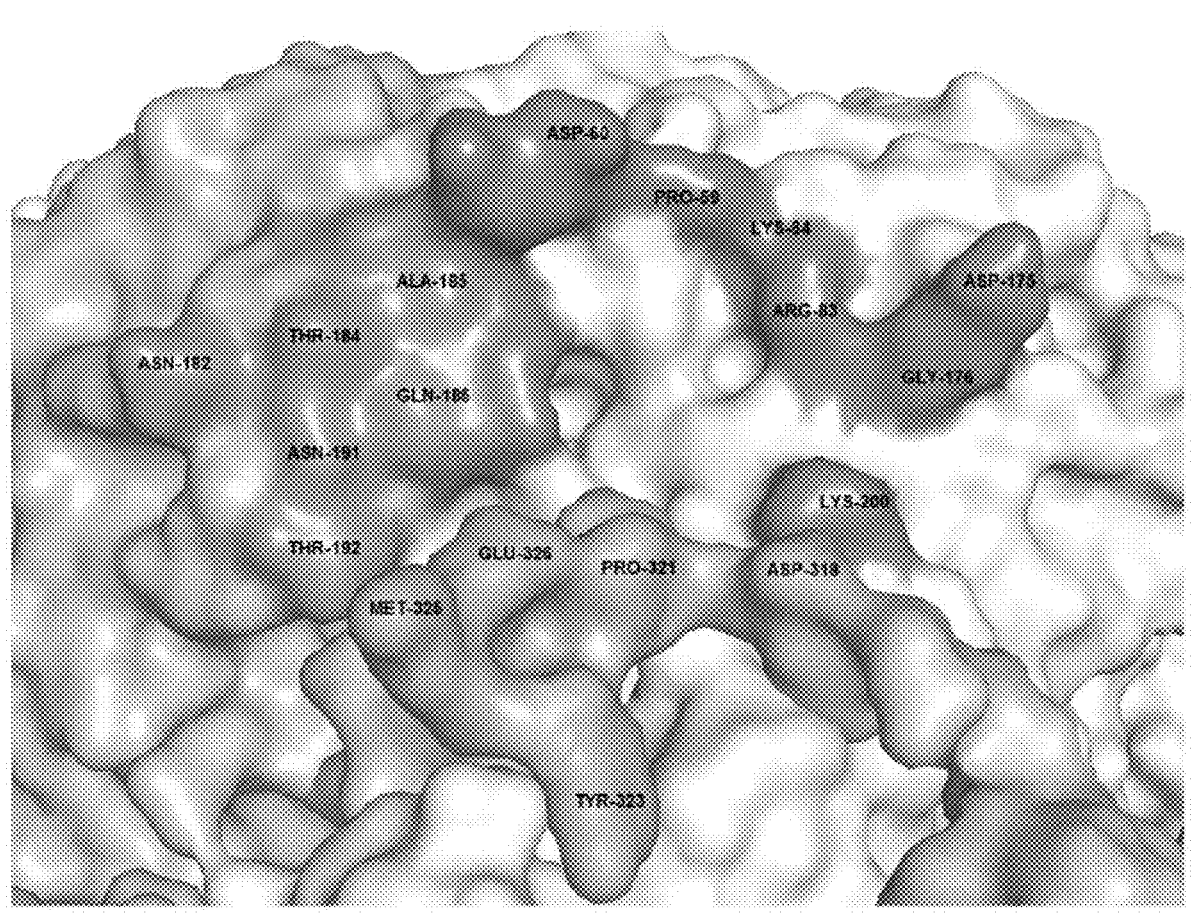
FIG. 3C is an enlargement of FIG. 3B highlighting the critical contact residues.
Figure 3G:
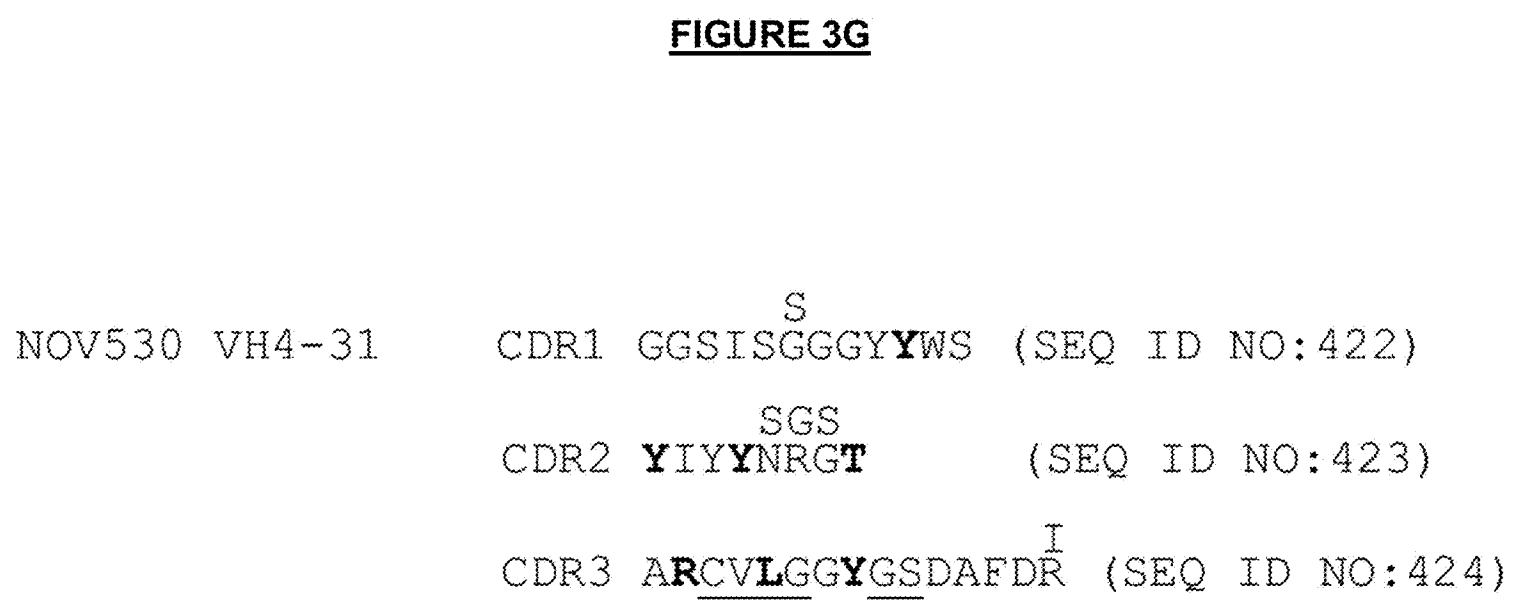

To understand the mechanism by which the isolated cross-neutralizing antibodies effectively inhibit infection by multiple polyomavirus strains, we performed cryo-electron microscopy (cryoEM) on BKV ST1 VLPs complexed with a single-chain variable fragment (scFv) format of the cross-neutralizing IgG NOV530, and obtained a class-averaged density map at a resolution of 4.24 Å (FIG. 3A). We were able to model the capsid structure of the VLP, including the interlocking pentameric subunits joined together via the C-termini of individual VP1 monomers. Surprisingly, this quaternary structure forms the basis for the complex viral epitope bound by NOV530 (FIG. 3B-C), with three VP1 subunits contributing amino acid residues. In total, 20 viral residues are predicted to be within 5 Å of the antibody; these residues are highly conserved across polyomavirus species, with 3 showing conservative homology and the remaining 17 identical in JCV (FIGS. 3D-F). Interacting positions from the antibody are spread throughout the heavy and light chains, with contributions from both germline-encoded (CDR1 and CDR2) and somatically recombined (CDR3) loops (FIGS. 3G-H). Identifying the complex binding site of NOV530 to the BKV capsid protein would have been impossible with any other method due to its quaternary structural requirement. This binding modality raises additional interesting questions about the mechanism of viral neutralization by NOV530; for example, it is possible that the antibody locks together capsid subunits, thereby blocking viral uncoating processes post-entry. Potential escape mutations may occur only at the cost of reduced virion stability. Indeed, mutations to three amino acid residues within the NOV530 epitope (E61, R64, and R83) have previously been reported to drastically reduce viral fitness, likely due to their effect on receptor binding and capsid structural integrity (Dugan A. S. et al., Identification of amino acid residues in BK virus VP1 that are critical for viability and growth. J Virol 81, 11798-11808 (2007)).

CryoEM Methodologies

BKV ST1 VLPs were incubated with the scFv fragment of NOV530 (360 scFv molecules per VLP, total protein concentration of 1 mg/ml) at room temperature for 1 hour. The sample was then concentrated 10-fold. 4.0 µL of the concentrated VLP-scFv complex was applied onto the grid (R1.2/1.3, Cu 300 mesh, Quantifoil Micro Tools GmbH, Grosslöbichau, Germany) coated with an additional thin amorphous carbon layer. Grids were vitrified using a Leica EM GP plunger. Images were acquired with a Cs-corrected FEI Titan Krios TEM operated at 300 kV equipped with a Quantum-LS Gatan Image Filter (GIF) and recorded on a Gatan K2-Summit direct electron detector (Gatan GmbH). Images were collected automatically (with EPU, Thermo Fisher) in electron-counting mode (nominal post-GIF magnification of ×105,000 and calibrated pixel size of 1.12 Å). Exposures of 7 s were dose-fractionated into 40 frames. The total exposure dose was ~40 e−/Å2. Defocus values varied from −0.8 to −2.5 µm.

The cryoEM data was imaged by using the following protocol. The stage drift and beam-induced motion during exposure were pre-processed and aligned using a pipeline (StackGUJ) that automates whole-image drift correction using UNBLUR (Grant, T and Grigorieff N. Measuring the optimal exposure for single particle cryo-EM using a 2.6 Å reconstruction of rotavirus VP6 (eLife. 4(e06980):1-19 (2015)). Contrast transfer function (CTF) parameters were estimated using the program CTFFIND4 (Mindell J A, and Grigorieff N. Accurate determination of local defocus and specimen tilt in electron microscopy. J. Struct. Biol. 142: 334-347 (2003)). Particles were automatically picked up on each micrograph using GAUTOMATCH. A total of 1,400 micrographs were acquired from which 6000 particles were extracted for processing using the Relion software package (Scheres, S. H. RELION: implementation of a Bayesian approach to cryo-EM structure determination. J. Struct. Biol. 180, 519-530, doi:10.1016/j.jsb.2012.09.006 (2012)). Particle sorting included two cycles of reference-free 2D classification. The 5000 particles in the best 2D classes were used for 3D refinement. A sphere was used as an initial model for 3D refinement. We performed particle-based beam-induced movement correction and radiation-damage weighting (known as particle polishing, see Scheres, S. H., Beam-induced motion correction for sub-megadalton cryo-EM particles. Elife 3, e03665, doi:10.7554/eLife.03665 (2014)) on the first 20 frames (corresponding to a total dose of ~20 e−/Å2). The resulting 5000 polished particles gave rise to a reconstruction with an overall resolution of 4.5 Å. Auto-refinement of polished particles with a soft mask around BK-VLP_scFv complex resulted in a 4.24 Å resolution map. The resolution values reported are based on the gold-standard Fourier shell correlation curve (FSC) at 0.143 criterion (Scheres, S. H. RELION: implementation of a Bayesian approach to cryo-EM structure determination. J. Struct. Biol. 180, 519-530, doi:10.1016/j.jsb.2012.09.006 (2012)). The cryo-EM structure of BK virion and crystal structure of scFv (PDB ID codes 5FUA and 4UT7 respectively) were manually fitted into the final cryo-EM map using the program Coot (Emsley P. et al., Features and development of Coot. Acta Crystallogr D Biol Crystallogr 66:486-501 (2010)). The resultant atomic model was subjected to multiple cycles of model rebuilding using the program Coot (Emsley P. et al., supra) and real space refinement against the map using the program Phenix (Adams P D, et al. PHENIX: A comprehensive Python-based system for macromolecular structure solution. Acta Crystallogr D Biol Crystallogr 66:213-221(2010)). This process resulted an atomic model of the pentamer and scFv complex that fit well into the cryo-EM density. Structural illustrations were prepared with PyMOL (available from Schrodinger).

Example 7: Formulation

The anti-BK or JC virus antibodies described herein are monoclonal antibodies, IgG1 isotype with kappa or lambda light chains, and can be lyophilized. These antibodies are soluble and stable in a histidine-sucrose formulation buffer for 4 weeks. In addition, anti-VP1 antibodies were soluble at >200 mg/ml as minimally formulated drug substance (e.g., in histidine buffer in the absence of stabilizers).

For subsequent intravenous administration, the obtained solution will usually be further diluted into a carrier solution to the ready-to-use antibody solution for infusion.

Important stability-indicating analytical methods to select the most stable formulation encompassed, amongst others, size-exclusion chromatography to determine aggregation levels, subvisible particulate matter testing, and potency testing.

It is understood that the examples and aspects described herein are for illustrative purposes only and that various modifications or changes in light thereof will be suggested to persons skilled in the art and are to be included within the spirit and purview of this application and scope of the appended claims.

What is claimed is:

1. An isolated antibody or antigen binding fragment thereof that binds VP1, wherein said antibody comprises:
   (i) a heavy chain that comprises SEQ ID NO:294, and a light chain that comprises SEQ ID NO: 295;
   (ii) a heavy chain that comprises SEQ ID NO:296, and a light chain that comprises SEQ ID NO: 297;
   (iii) a heavy chain that comprises SEQ ID NO:298, and a light chain that comprises SEQ ID NO: 299;
   (iv) a heavy chain that comprises SEQ ID NO:300, and a light chain that comprises SEQ ID NO: 301;
   (v) a heavy chain that comprises SEQ ID NO:302, and a light chain that comprises SEQ ID NO: 303; or
   (vi) a heavy chain that comprises SEQ ID NO:304, and a light chain that comprises SEQ ID NO: 305.

2. The antibody or antigen binding fragment thereof of claim 1, wherein the antibody or antigen binding fragment thereof is a monoclonal antibody, or a single chain antibody (scFv).

3. The antibody or antigen binding fragment thereof of claim 1 wherein the antibody or antigen binding fragment thereof has reduced glycosylation or no glycosylation or is hypofucosylated.

4. A pharmaceutical composition comprising the antibody or antigen binding fragment thereof of claim 1 and a pharmaceutically acceptable carrier.

5. A pharmaceutical composition comprising a plurality of antibodies or antigen binding fragments thereof of claim 1, wherein at least 0.05%, 0.1%, 0.5%, 1%, 2%, 3%, or 5% of the antibodies or antigen binding fragment thereof in the composition have an $\alpha$2,3-linked sialic acid residue.

6. A pharmaceutical composition comprising a plurality of antibodies or antigen binding fragments thereof of claim 1, wherein none of the antibodies or antigen binding fragments thereof comprise a bisecting GlcNAc.

7. A diagnostic reagent comprising the antibody or antigen binding fragment thereof of claim 1, wherein the antibody or antigen binding fragment thereof is labeled.

8. The diagnostic reagent of claim 7, wherein the label is selected from the group consisting of a radiolabel, a fluorophore, a chromophore, an imaging agent, and a metal ion.

* * * * *

SEQUENCE LISTING

```
Sequence total quantity: 427
SEQ ID NO: 1              moltype = AA  length = 362
FEATURE                   Location/Qualifiers
source                    1..362
                          mol_type = protein
                          organism = Human polyomavirus BKV
SEQUENCE: 1
MAPTKRKGEC PGAAPKKPKE PVQVPKLLIK GGVEVLEVKT GVDAITEVEC FLNPEMGDPD  60
ENLRGFSLKL SAENDFSSDS PERKMLPCYS TARIPLPNLN EDLTCGNLLM WEAVTVQTEV  120
IGITSMLNLH AGSQKVHEHG GGKPIQGSNF HFFAVGGDPL EMQGVLMNYR TKYPEGTITP  180
KNPTAQSQVM NTDHKAYLDK NNAYPVECWI PDPSRNENTR YFGTFTGGEN VPPVLHVTNT  240
ATTVLLDEQG VGPLCKADSL YVSAADICGL FTNSSGTQQW RGLARYFKIR LRKRSVKNPY  300
PISFLLSDLI NRRTQRVDGQ PMYGMESQVE EVRVFDGTER LPGDPDMIRY IDKQGQLQTK  360
ML                                                                362

SEQ ID NO: 2              moltype = AA  length = 362
FEATURE                   Location/Qualifiers
source                    1..362
                          mol_type = protein
                          organism = Human polyomavirus BKV
SEQUENCE: 2
MAPTKRKGEC PGAAPKKPKE PVQVPKLLIK GGVEVLEVKT GVDAITEVEC FLNPEMGDPD  60
DNLRGYSLKL TAENAFDSDS PDKKMLPCYS TARIPLPNLN EDLTCGNLLM WEAVTVKTEV  120
IGITSMLNLH AGSQKVHENG GGKPVQGSNF HFFAVGGDPL EMQGVLMNYR TKYPQGTITP  180
KNPTAQSQVM NTDHKAYLDK NNAYPVECWI PDPSRNENTR YFGTYTGGEN VPPVLHVTNT  240
ATTVLLDEQG VGPLCKADSL YVSAADICGL FTNSSGTQQW RGLARYFKIR LRKRSVKNPY  300
PISFLLSDLI NRRTQKVDGQ PMYGMESQVE EVRVFDGTEQ LPGDPDMIRY IDRQGQLQTK  360
MV                                                                362

SEQ ID NO: 3              moltype = AA  length = 362
FEATURE                   Location/Qualifiers
source                    1..362
                          mol_type = protein
                          organism = Human polyomavirus BKV
SEQUENCE: 3
MAPTKRKGEC PGAAPKKPKE PVQVPKLLIK GGVEVLEVKT GVDAITEVEC FLNPEMGDPD  60
DHLRGYSQHL SAENAFDSDS PDKKMLPCYS TARIPLPNLN EDLTCGNLLM WEAVTVKTEV  120
IGITSMLNLH AGSQKVHENG GGKPVQGSNF HFFAVGGDPL EMQGVLMNYR TKYPQGTITP  180
KNPTAQSQVM NTDHKAYLDK NNAYPVECWI PDPSKNENTR YFGTYTGGEN VPPVLHVTNT  240
ATTVLLDEQG VGPLCKADSL YVSAADICGL FTNSSGTQQW RGLARYFKIR LRKRSVKNPY  300
PISFLLSDLI NRRTQKVDGQ PMYGMESQVE EVRVFDGTEQ LPGDPDMIRY IDRQGQLQTK  360
MV                                                                362

SEQ ID NO: 4              moltype = AA  length = 362
FEATURE                   Location/Qualifiers
source                    1..362
                          mol_type = protein
                          organism = Human polyomavirus BKV
SEQUENCE: 4
MAPTKRKGEC PGAAPKKPKE PVQVPKLLIK GGVEVLEVKT GVDAITEVEC FLNPEMGDPD  60
NDLRGYSLRL TAETAFDSDS PDRKMLPCYS TARIPLPNLN EDLTCGNLLM WEAVTVKTEV  120
IGITSMLNLH AGSQKVHENG GGKPIQGSNF HFFAVGGDPL EMQGVLMNYR TKYPEGTVTP  180
KNPTAQSQVM NTDHKAYLDK NNAYPVECWI PDPSRNENTR YFGTYTGGEN VPPVLHVTNT  240
ATTVLLDEQG VGPLCKADSL YVSAADICGL FTNSSGTQQW RGLPRYFKIR LRKRSVKNPY  300
PISFLLSDLI NRRTQRVDGQ PMYGMESQVE EVRVFDGTEQ LPGDPDMIRY IDRQGQLQTK  360
MV                                                                362
```

```
SEQ ID NO: 5              moltype = AA   length = 354
FEATURE                  Location/Qualifiers
source                   1..354
                         mol_type = protein
                         organism = Human polyomavirus JCV
SEQUENCE: 5
MAPTKRKGER KDPVQVPKLL IRGGVEVLEV KTGVDSITEV ECFLTPEMGD PDEHLRGFSK  60
SISISDTFES DSPNKDMLPC YSVARIPLPN LNEDLTCGNI LMWEAVTLKT EVIGVTTLMN  120
VHSNGQATHD NGAGKPVQGT SFHFFSVGGE ALELQGVVFN YRTKYPDGTI FPKNATVQSQ  180
VMNTEHKAYL DKNKAYPVEC WVPDPTRNEN TRYFGTLTGG ENVPPVLHIT NTATTVLLDE  240
FGVGPLCKGD NLYLSAVDVC GMFTNRSGSQ QWRGLSRYFK VQLRKRRVKN PYPISFLLTD  300
LINRRTPRVD GQPMYGMDAQ VEEVRVFEGT EELPGDPDMM RYVDRYGQLQ TKML         354

SEQ ID NO: 6              moltype = AA   length = 12
FEATURE                  Location/Qualifiers
source                   1..12
                         mol_type = protein
                         organism = synthetic construct
SEQUENCE: 6
GGSISGGGYY WS                                                       12

SEQ ID NO: 7              moltype = AA   length = 16
FEATURE                  Location/Qualifiers
source                   1..16
                         mol_type = protein
                         organism = synthetic construct
SEQUENCE: 7
YIYYNRGTYY NPALKS                                                   16

SEQ ID NO: 8              moltype = AA   length = 13
FEATURE                  Location/Qualifiers
source                   1..13
                         mol_type = protein
                         organism = synthetic construct
SEQUENCE: 8
CVLGGYGSDA FDR                                                      13

SEQ ID NO: 9              moltype = AA   length = 7
FEATURE                  Location/Qualifiers
source                   1..7
                         mol_type = protein
                         organism = synthetic construct
SEQUENCE: 9
GGGYYWS                                                             7

SEQ ID NO: 10             moltype = AA   length = 16
FEATURE                  Location/Qualifiers
source                   1..16
                         mol_type = protein
                         organism = synthetic construct
SEQUENCE: 10
YIYYNRGTYY NPALKS                                                   16

SEQ ID NO: 11             moltype = AA   length = 13
FEATURE                  Location/Qualifiers
source                   1..13
                         mol_type = protein
                         organism = synthetic construct
SEQUENCE: 11
CVLGGYGSDA FDR                                                      13

SEQ ID NO: 12             moltype = AA   length = 9
FEATURE                  Location/Qualifiers
source                   1..9
                         mol_type = protein
                         organism = synthetic construct
SEQUENCE: 12
GGSISGGGY                                                           9

SEQ ID NO: 13             moltype = AA   length = 5
FEATURE                  Location/Qualifiers
source                   1..5
                         mol_type = protein
                         organism = synthetic construct
SEQUENCE: 13
YYNRG                                                               5

SEQ ID NO: 14             moltype = AA   length = 13
```

-continued

```
FEATURE            Location/Qualifiers
source             1..13
                   mol_type = protein
                   organism = synthetic construct
SEQUENCE: 14
CVLGGYGSDA FDR                                                        13

SEQ ID NO: 15      moltype = AA  length = 10
FEATURE            Location/Qualifiers
source             1..10
                   mol_type = protein
                   organism = synthetic construct
SEQUENCE: 15
GGSISGGGYY                                                            10

SEQ ID NO: 16      moltype = AA  length = 7
FEATURE            Location/Qualifiers
source             1..7
                   mol_type = protein
                   organism = synthetic construct
SEQUENCE: 16
IYYNRGT                                                               7

SEQ ID NO: 17      moltype = AA  length = 15
FEATURE            Location/Qualifiers
source             1..15
                   mol_type = protein
                   organism = synthetic construct
SEQUENCE: 17
ARCVLGGYGS DAFDR                                                      15

SEQ ID NO: 18      moltype = AA  length = 123
FEATURE            Location/Qualifiers
source             1..123
                   mol_type = protein
                   organism = synthetic construct
SEQUENCE: 18
QVQLQESGPG LVKPSQTLSL TCTVSGGSIS GGGYYWSWIR QHPGKGLEFI GYIYYNRGTY    60
YNPALKSRLT ISVDTSKNDF SLKLSSVSAA DTAVYYCARC VLGGYGSDAF DRWGQGTTVT    120
VAS                                                                  123

SEQ ID NO: 19      moltype = DNA  length = 369
FEATURE            Location/Qualifiers
source             1..369
                   mol_type = other DNA
                   organism = synthetic construct
SEQUENCE: 19
caggtgcagc tgcaggagtc gggcccagga ctggtgaagc cttcacagac cctgtccctc    60
acctgcactg tctctggtgg ctccatcagc ggtggtggtt actactggag ctggatccgc    120
cagcacccag gaaagggcct ggagttcatt ggatacatat attataatag gggcacctac    180
tacaatccgg ccctcaagag tcgacttacc atatcagtag acacctctaa gaatgacttc    240
tccctgaagc tgagctctgt gagtgccgcg gacacggccg tgtattactg tgcgagatgt    300
gtccttggtg gctacggttc tgatgctttt gataggtggg gccaagggac aacggtcacc    360
gtcgcttca                                                            369

SEQ ID NO: 20      moltype = AA  length = 453
FEATURE            Location/Qualifiers
source             1..453
                   mol_type = protein
                   organism = synthetic construct
SEQUENCE: 20
QVQLQESGPG LVKPSQTLSL TCTVSGGSIS GGGYYWSWIR QHPGKGLEFI GYIYYNRGTY    60
YNPALKSRLT ISVDTSKNDF SLKLSSVSAA DTAVYYCARC VLGGYGSDAF DRWGQGTTVT    120
VASASTKGPS VFPLAPCSRS TSGGTAALGC LVKDYFPEPV TVSWNSGALT SGVHTFPTVL    180
QSSGLYSLSS VVTVPSSSLG TQTYICNVNH KPSNTKVDKR VEPKSCDKTH TCPPCPAPEL    240
LGGPSVFLFP PKPKDTLMIS RTPEVTCVVV DVSHEDPEVK FNWYVDGVEV HNAKTKPREE    300
QYNSTYRVVS VLTVLHQDWL NGKEYKCKVS NKALPAPIEK TISKAKGQPR EPQVYTLPPS    360
REEMTKNQVS LTCLVKGFYP SDIAVEWESN GQPENNYKTT PPVLDSDGSF FLYSKLTVDK    420
SRWQQGNVFS CSVMHEALHN HYTQKSLSLS PGK                                 453

SEQ ID NO: 21      moltype = DNA  length = 1359
FEATURE            Location/Qualifiers
source             1..1359
                   mol_type = other DNA
                   organism = synthetic construct
SEQUENCE: 21
caggtgcagc tgcaggagtc gggcccagga ctggtgaagc cttcacagac cctgtccctc    60
acctgcactg tctctggtgg ctccatcagc ggtggtggtt actactggag ctggatccgc    120
cagcacccag gaaagggcct ggagttcatt ggatacatat attataatag gggcacctac    180
```

```
tacaatccgg ccctcaagag tcgacttacc atatcagtag acacctctaa gaatgacttc      240
tccctgaagc tgagctctgt gagtgccgcg gacacggccg tgtattactg tgcgagatgt      300
gtccttggtg gctacggttc tgatgctttt gataggtggg gccaagggac aacggtcacc      360
gtcgcttcag cttccaccaa gggcccatcg gtcttccccc tggcgccctg ctccaggagc      420
acctctgggg gcacagcggc cctgggctgc ctggtcaagg actacttccc cgaaccggtg      480
acggtgtcgt ggaactcagg cgccctgacc agcggcgtgc acaccttccc gactgtccta      540
cagtcctcag gactctactc cctcagcagc gtggtgaccg tgccctccag cagcttgggc      600
acccagacct acatctgcaa cgtgaaccac aagcccagca acaccaaggt ggacaagaga      660
gtggagccca agagctgcga caagacccac acctgccccc cctgcccagc cccagagctc      720
ctgggcggac cctccgtgtt cctgttcccc cccaagccca aggacaccct gatgatcagc      780
aggacccccg aggtgacctg cgtggtggtg gacgtgagcc acgaggaccc agaggtgaag      840
ttcaactggt acgtggacgg cgtggaggtg cacaacgcca agaccaagcc cagagaggag      900
cagtacaaca gcacctacag ggtggtgtcc gtgctgaccg tgctgcacca ggactggctg      960
aacggcaagg aatacaagtg caaggtctcc aacaaggccc tgccagcccc catcgaaaag     1020
accatcagca aggccaaggg ccagccacgg gagccccagg tgtacaccct gccccctcc      1080
cgggaggaga tgaccaagaa ccaggtgtcc ctgacctgtc tggtgaaggg cttctacccc     1140
agcgacatcg ccgtggagtg ggagagcaac ggccagcccg agaacaacta caagaccacc     1200
cccccagtgc tggacagcga cggcagcttc ttcctgtaca gcaagctgac cgtggacaag     1260
tccaggtggc agcagggcaa cgtgttcagc tgcagcgtga tgcacgaggc cctgcacaac     1320
cactacaccc agaagagcct gagcctgtcc cccggcaag                            1359
```

```
SEQ ID NO: 22               moltype = AA   length = 11
FEATURE                     Location/Qualifiers
source                      1..11
                            mol_type = protein
                            organism = synthetic construct
SEQUENCE: 22
RASQSVSSHL A                                                          11

SEQ ID NO: 23               moltype = AA   length = 7
FEATURE                     Location/Qualifiers
source                      1..7
                            mol_type = protein
                            organism = synthetic construct
SEQUENCE: 23
DASSRAN                                                               7

SEQ ID NO: 24               moltype = AA   length = 11
FEATURE                     Location/Qualifiers
source                      1..11
                            mol_type = protein
                            organism = synthetic construct
SEQUENCE: 24
QQRSSWPPSL T                                                          11

SEQ ID NO: 25               moltype = AA   length = 11
FEATURE                     Location/Qualifiers
source                      1..11
                            mol_type = protein
                            organism = synthetic construct
SEQUENCE: 25
RASQSVSSHL A                                                          11

SEQ ID NO: 26               moltype = AA   length = 7
FEATURE                     Location/Qualifiers
source                      1..7
                            mol_type = protein
                            organism = synthetic construct
SEQUENCE: 26
DASSRAN                                                               7

SEQ ID NO: 27               moltype = AA   length = 11
FEATURE                     Location/Qualifiers
source                      1..11
                            mol_type = protein
                            organism = synthetic construct
SEQUENCE: 27
QQRSSWPPSL T                                                          11

SEQ ID NO: 28               moltype = AA   length = 7
FEATURE                     Location/Qualifiers
source                      1..7
                            mol_type = protein
                            organism = synthetic construct
SEQUENCE: 28
SQSVSSH                                                               7

SEQ ID NO: 29               moltype =    length =
SEQUENCE: 29
```

```
000

SEQ ID NO: 30           moltype = AA   length = 8
FEATURE                 Location/Qualifiers
source                  1..8
                        mol_type = protein
                        organism = synthetic construct
SEQUENCE: 30
RSSWPPSL                                                            8

SEQ ID NO: 31           moltype = AA   length = 6
FEATURE                 Location/Qualifiers
source                  1..6
                        mol_type = protein
                        organism = synthetic construct
SEQUENCE: 31
QSVSSH                                                              6

SEQ ID NO: 32           moltype = AA   length = 10
FEATURE                 Location/Qualifiers
source                  1..10
                        mol_type = protein
                        organism = synthetic construct
SEQUENCE: 32
DASSRANGIP                                                          10

SEQ ID NO: 33           moltype = AA   length = 11
FEATURE                 Location/Qualifiers
source                  1..11
                        mol_type = protein
                        organism = synthetic construct
SEQUENCE: 33
QQRSSWPPSL T                                                        11

SEQ ID NO: 34           moltype = AA   length = 109
FEATURE                 Location/Qualifiers
source                  1..109
                        mol_type = protein
                        organism = synthetic construct
SEQUENCE: 34
EIVLTQSPVT LSLSPGERAI LSCRASQSVS SHLAWYQQKP GQAPRLLIYD ASSRANGIPA   60
RFSGSGSGTD FTLTISSLAP EDFAVYYCQQ RSSWPPSLTF GGGTKVEIR              109

SEQ ID NO: 35           moltype = DNA   length = 327
FEATURE                 Location/Qualifiers
source                  1..327
                        mol_type = other DNA
                        organism = synthetic construct
SEQUENCE: 35
gaaattgtgt tgacacagtc cccagtcacc ctgtctttgt ctccagggga aagagccatc   60
ctctcctgta gggccagtca gagtgttagc agccacttag cctggtacca acagaagcct  120
ggccaggctc ccaggctcct catctatgat gcatccagca gggccaatgg catcccagcc  180
aggttcagtg gcagtgggtc tgggacagac ttcactctca ccatcagcag cctagcgcct  240
gaagattttg cagtttatta ctgtcagcag cgtagcagct ggcctccgtc cctcactttc  300
ggcggaggga ccaaggtgga gatcaga                                      327

SEQ ID NO: 36           moltype = AA   length = 216
FEATURE                 Location/Qualifiers
source                  1..216
                        mol_type = protein
                        organism = synthetic construct
SEQUENCE: 36
EIVLTQSPVT LSLSPGERAI LSCRASQSVS SHLAWYQQKP GQAPRLLIYD ASSRANGIPA   60
RFSGSGSGTD FTLTISSLAP EDFAVYYCQQ RSSWPPSLTF GGGTKVEIRR TVAAPSVFIF  120
PPSDEQLKSG TASVVCLLNN FYPREAKVQW KVDNALQSGN SQESVTEQDS KDSTYSLSST  180
LTLSKADYEK HKVYACEVTH QGLSSPVTKS FNRGEC                            216

SEQ ID NO: 37           moltype = DNA   length = 648
FEATURE                 Location/Qualifiers
source                  1..648
                        mol_type = other DNA
                        organism = synthetic construct
SEQUENCE: 37
gaaattgtgt tgacacagtc cccagtcacc ctgtctttgt ctccagggga aagagccatc   60
ctctcctgta gggccagtca gagtgttagc agccacttag cctggtacca acagaagcct  120
ggccaggctc ccaggctcct catctatgat gcatccagca gggccaatgg catcccagcc  180
aggttcagtg gcagtgggtc tgggacagac ttcactctca ccatcagcag cctagcgcct  240
gaagattttg cagtttatta ctgtcagcag cgtagcagct ggcctccgtc cctcactttc  300
ggcggaggga ccaaggtgga gatcagacga actgtggctg caccatctgt cttcatcttc  360
```

-continued

```
ccgccatctg atgagcagtt gaaatctgga actgcctctg ttgtgtgcct gctgaataac    420
ttctatccca gagaggccaa agtacagtgg aaggtggaca acgccctgca gagcggcaac    480
agccaggaga gcgtcaccga gcaggacagc aaggactcca cctacagcct gagcagcacc    540
ctgaccctga gcaaggccga ctacgagaag cataaggtgt acgcctgcga ggtgacccac    600
cagggcctgt ccagccccgt gaccaagagc ttcaacaggg gcgagtgc                 648

SEQ ID NO: 38               moltype = AA   length = 10
FEATURE                     Location/Qualifiers
source                      1..10
                            mol_type = protein
                            organism = synthetic construct
SEQUENCE: 38
GFTFRSYMMN                                                             10

SEQ ID NO: 39               moltype = AA   length = 17
FEATURE                     Location/Qualifiers
source                      1..17
                            mol_type = protein
                            organism = synthetic construct
SEQUENCE: 39
YISGSGGTKY YVDSVKG                                                     17

SEQ ID NO: 40               moltype = AA   length = 15
FEATURE                     Location/Qualifiers
source                      1..15
                            mol_type = protein
                            organism = synthetic construct
SEQUENCE: 40
DLDCSGGTCY DGMDV                                                       15

SEQ ID NO: 41               moltype = AA   length = 5
FEATURE                     Location/Qualifiers
source                      1..5
                            mol_type = protein
                            organism = synthetic construct
SEQUENCE: 41
SYMMN                                                                  5

SEQ ID NO: 42               moltype = AA   length = 17
FEATURE                     Location/Qualifiers
source                      1..17
                            mol_type = protein
                            organism = synthetic construct
SEQUENCE: 42
YISGSGGTKY YVDSVKG                                                     17

SEQ ID NO: 43               moltype = AA   length = 15
FEATURE                     Location/Qualifiers
source                      1..15
                            mol_type = protein
                            organism = synthetic construct
SEQUENCE: 43
DLDCSGGTCY DGMDV                                                       15

SEQ ID NO: 44               moltype = AA   length = 7
FEATURE                     Location/Qualifiers
source                      1..7
                            mol_type = protein
                            organism = synthetic construct
SEQUENCE: 44
GFTFRSY                                                                7

SEQ ID NO: 45               moltype = AA   length = 6
FEATURE                     Location/Qualifiers
source                      1..6
                            mol_type = protein
                            organism = synthetic construct
SEQUENCE: 45
SGSGGT                                                                 6

SEQ ID NO: 46               moltype = AA   length = 15
FEATURE                     Location/Qualifiers
source                      1..15
                            mol_type = protein
                            organism = synthetic construct
SEQUENCE: 46
DLDCSGGTCY DGMDV                                                       15

SEQ ID NO: 47               moltype = AA   length = 8
```

```
FEATURE                Location/Qualifiers
source                 1..8
                       mol_type = protein
                       organism = synthetic construct
SEQUENCE: 47
GFTFRSYM                                                                        8

SEQ ID NO: 48          moltype = AA  length = 8
FEATURE                Location/Qualifiers
source                 1..8
                       mol_type = protein
                       organism = synthetic construct
SEQUENCE: 48
ISGSGGTK                                                                        8

SEQ ID NO: 49          moltype = AA  length = 17
FEATURE                Location/Qualifiers
source                 1..17
                       mol_type = protein
                       organism = synthetic construct
SEQUENCE: 49
ARDLDCSGGT CYDGMDV                                                             17

SEQ ID NO: 50          moltype = AA  length = 124
FEATURE                Location/Qualifiers
source                 1..124
                       mol_type = protein
                       organism = synthetic construct
SEQUENCE: 50
EVQLVESGGG LVQPGGSLRL SCAASGFTFR SYMMNWVRQA PGKGLEWVSY ISGSGGTKYY    60
VDSVKGRFTI SRDNAKNSLY LQMHSLRAED TAVYYCARDL DCSGGTCYDG MDVWGQGTTV   120
TVSS                                                                          124

SEQ ID NO: 51          moltype = DNA  length = 372
FEATURE                Location/Qualifiers
source                 1..372
                       mol_type = other DNA
                       organism = synthetic construct
SEQUENCE: 51
gaggtgcagc tggtggagtc gggggggaggc ttggtacagc ctggggggtc cctgagactc    60
tcctgtgcag cctctggatt caccttcagg agttatatga tgaattgggt ccgccaggct   120
ccagggaagg ggctggagtg ggtttcatat attagtggta gtggtggaac caaatactac   180
gtagactctg tgaagggccg attcaccata tccagagaca acgccaagaa ctcactgtat   240
ctgcaaatgc acagcctgag agccgaggac acggctgtgt attactgtgc gagagatctc   300
gattgcagtg gtgggacctg ctacgacggt atggacgtct ggggccaagg gaccacggtc   360
accgtctcct ca                                                          372

SEQ ID NO: 52          moltype = AA  length = 454
FEATURE                Location/Qualifiers
source                 1..454
                       mol_type = protein
                       organism = synthetic construct
SEQUENCE: 52
EVQLVESGGG LVQPGGSLRL SCAASGFTFR SYMMNWVRQA PGKGLEWVSY ISGSGGTKYY    60
VDSVKGRFTI SRDNAKNSLY LQMHSLRAED TAVYYCARDL DCSGGTCYDG MDVWGQGTTV   120
TVSSASTKGP SVFPLAPCSR STSGGTAALG CLVKDYFPEP VTVSWNSGAL TSGVHTFPAV   180
LQSSGLYSLS SVVTVPSSSL GTQTYICNVN HKPSNTKVDK RVEPKSCDKT HTCPPCPAPE   240
LLGGPSVFLF PPKPKDTLMI SRTPEVTCVV VDVSHEDPEV KFNWYVDGVE VHNAKTKPRE   300
EQYNSTYRVV SVLTVLHQDW LNGKEYKCKV SNKALPAPIE KTISKAKGQP REPQVYTLPP   360
SREEMTKNQV SLTCLVKGFY PSDIAVEWES NGQPENNYKT TPPVLDSDGS FFLYSKLTVD   420
KSRWQQGNVF SCSVMHEALH NHYTQKSLSL SPGK                                 454

SEQ ID NO: 53          moltype = DNA  length = 1362
FEATURE                Location/Qualifiers
source                 1..1362
                       mol_type = other DNA
                       organism = synthetic construct
SEQUENCE: 53
gaggtgcagc tggtggagtc gggggggaggc ttggtacagc ctggggggtc cctgagactc    60
tcctgtgcag cctctggatt caccttcagg agttatatga tgaattgggt ccgccaggct   120
ccagggaagg ggctggagtg ggtttcatat attagtggta gtggtggaac caaatactac   180
gtagactctg tgaagggccg attcaccata tccagagaca acgccaagaa ctcactgtat   240
ctgcaaatgc acagcctgag agccgaggac acggctgtgt attactgtgc gagagatctc   300
gattgcagtg gtgggacctg ctacgacggt atggacgtct ggggccaagg gaccacggtc   360
accgtctcct cagcttccac caagggccca tcggtcttcc ccctggcgcc ctgctccagg   420
agcacctctg ggggcacagc ggccctgggc tgcctggtca aggactactt ccccgaaccg   480
gtgacggtgt cgtggaactc aggcgccctg accagcggcg tgcacacctt cccggctgtc   540
ctacagtcct caggactcta ctccctcagc agcgtggtga ccgtgccctc cagcagcttg   600
ggcacccaga cctacatctg caacgtgaac cacaagccca gcaacaccaa ggtggacaag   660
```

```
agagtggagc ccaagagctg cgacaagacc cacacctgcc ccccctgccc agccccagag   720
ctgctgggcg gaccctccgt gttcctgttc cccccaagc ccaaggacac cctgatgatc   780
agcaggaccc ccgaggtgac ctgcgtggtg gtggacgtga gccacgagga cccagaggtg   840
aagttcaact ggtacgtgga cggcgtggag gtgcacaacg ccaagaccaa gcccagagag   900
gagcagtaca acagcaccta cagggtggtg tccgtgctga ccgtgctgca ccaggactgg   960
ctgaacggca aggaatacaa gtgcaaggtc tccaacaagg ccctgccagc ccccatcgaa   1020
aagaccatca gcaaggccaa gggccagcca cgggagcccc aggtgtacac cctgcccccc   1080
tcccgggagg agatgaccaa gaaccaggtg tccctgacct gtctggtgaa gggcttctac   1140
cccagcgaca tcgccgtgga gtgggagagc aacggccagc ccgagaacaa ctacaagacc   1200
acccccccag tgctggacag cgacggcagc ttcttcctgt acagcaagct gaccgtggac   1260
aagtccaggt ggcagcaggg caacgtgttc agctgcagcg tgatgcacga ggccctgcac   1320
aaccactaca cccagaagag cctgagcctg tcccccggca ag                    1362
```

```
SEQ ID NO: 54          moltype = AA   length = 11
FEATURE                Location/Qualifiers
source                 1..11
                       mol_type = protein
                       organism = synthetic construct
SEQUENCE: 54
SGDKLGNKYV Y                                                       11

SEQ ID NO: 55          moltype = AA   length = 7
FEATURE                Location/Qualifiers
source                 1..7
                       mol_type = protein
                       organism = synthetic construct
SEQUENCE: 55
QHTKRPS                                                            7

SEQ ID NO: 56          moltype = AA   length = 9
FEATURE                Location/Qualifiers
source                 1..9
                       mol_type = protein
                       organism = synthetic construct
SEQUENCE: 56
QAWDSSIVI                                                          9

SEQ ID NO: 57          moltype = AA   length = 11
FEATURE                Location/Qualifiers
source                 1..11
                       mol_type = protein
                       organism = synthetic construct
SEQUENCE: 57
SGDKLGNKYV Y                                                       11

SEQ ID NO: 58          moltype = AA   length = 7
FEATURE                Location/Qualifiers
source                 1..7
                       mol_type = protein
                       organism = synthetic construct
SEQUENCE: 58
QHTKRPS                                                            7

SEQ ID NO: 59          moltype = AA   length = 9
FEATURE                Location/Qualifiers
source                 1..9
                       mol_type = protein
                       organism = synthetic construct
SEQUENCE: 59
QAWDSSIVI                                                          9

SEQ ID NO: 60          moltype = AA   length = 7
FEATURE                Location/Qualifiers
source                 1..7
                       mol_type = protein
                       organism = synthetic construct
SEQUENCE: 60
DKLGNKY                                                            7

SEQ ID NO: 61          moltype =    length =
SEQUENCE: 61
000

SEQ ID NO: 62          moltype = AA   length = 6
FEATURE                Location/Qualifiers
source                 1..6
                       mol_type = protein
                       organism = synthetic construct
SEQUENCE: 62
```

```
WDSSIV                                                             6

SEQ ID NO: 63          moltype = AA   length = 6
FEATURE                Location/Qualifiers
source                 1..6
                       mol_type = protein
                       organism = synthetic construct
SEQUENCE: 63
KLGNKY                                                             6

SEQ ID NO: 64          moltype =    length =
SEQUENCE: 64
000

SEQ ID NO: 65          moltype = AA   length = 9
FEATURE                Location/Qualifiers
source                 1..9
                       mol_type = protein
                       organism = synthetic construct
SEQUENCE: 65
QAWDSSIVI                                                          9

SEQ ID NO: 66          moltype = AA   length = 106
FEATURE                Location/Qualifiers
source                 1..106
                       mol_type = protein
                       organism = synthetic construct
SEQUENCE: 66
SYELTQPPSV SVSPGQTATI TCSGDKLGNK YVYWFQHRPG QSPVLVIYQH TKRPSGIPER  60
FSGSNSGNTA TLTISGTQAM DEADYYCQAW DSSIVIFGGG TKLTVL                 106

SEQ ID NO: 67          moltype = DNA   length = 318
FEATURE                Location/Qualifiers
source                 1..318
                       mol_type = other DNA
                       organism = synthetic construct
SEQUENCE: 67
tcctatgagc tgactcagcc accctcagtg tccgtgtccc ctggacagac agccaccatc  60
acctgctctg gagataaaatt gggtaataaa tatgtttact ggtttcagca caggccaggc  120
cagtcccctg tgctggtcat ctatcaacat accaagcggc cctcaggat ccctgagcga  180
ttctctggct ccaactctgg gaacacagcc actctgacca tcagcgggac ccaggctatg  240
gatgaggctg actattactg tcaggcgtgg gacagtagca ttgtgatatt cggcggaggg  300
accaagctga ccgtccta                                                318

SEQ ID NO: 68          moltype = AA   length = 212
FEATURE                Location/Qualifiers
source                 1..212
                       mol_type = protein
                       organism = synthetic construct
SEQUENCE: 68
SYELTQPPSV SVSPGQTATI TCSGDKLGNK YVYWFQHRPG QSPVLVIYQH TKRPSGIPER  60
FSGSNSGNTA TLTISGTQAM DEADYYCQAW DSSIVIFGGG TKLTVLGQPK AAPSVTLFPP  120
SSEELQANKA TLVCLISDFY PGAVTVAWKA DSSPVKAGVE TTTPSKQSNN KYAASSYLSL  180
TPEQWKSHRS YSCQVTHEGS TVEKTVAPTE CS                                212

SEQ ID NO: 69          moltype = DNA   length = 636
FEATURE                Location/Qualifiers
source                 1..636
                       mol_type = other DNA
                       organism = synthetic construct
SEQUENCE: 69
tcctatgagc tgactcagcc accctcagtg tccgtgtccc ctggacagac agccaccatc  60
acctgctctg gagataaaatt gggtaataaa tatgtttact ggtttcagca caggccaggc  120
cagtcccctg tgctggtcat ctatcaacat accaagcggc cctcaggat ccctgagcga  180
ttctctggct ccaactctgg gaacacagcc actctgacca tcagcgggac ccaggctatg  240
gatgaggctg actattactg tcaggcgtgg gacagtagca ttgtgatatt cggcggaggg  300
accaagctga ccgtcctagg tcagcccaag gctgcccct cggtcactct gttcccgccc  360
tcctctgagg agcttcaagc caacaaggcc acactggtgt gtctcataag tgacttctac  420
ccgggagccg tgacagtggc ctggaaggca gatagcagcc ccgtcaaggc gggagtggag  480
accaccacac cctccaaaca aagcaacaac aagtacgccg ccagcagcta cctgagcctg  540
acccccgagc agtggaagag ccacagaagc tacagctgcc aggtcaccca cgagggcagc  600
accgtggaga aaaccgtggc ccccaccgag tgcagc                            636

SEQ ID NO: 70          moltype = AA   length = 10
FEATURE                Location/Qualifiers
source                 1..10
                       mol_type = protein
                       organism = synthetic construct
SEQUENCE: 70
```

-continued

```
GYTFTAYYMH                                                                        10

SEQ ID NO: 71          moltype = AA   length = 17
FEATURE                Location/Qualifiers
source                 1..17
                       mol_type = protein
                       organism = synthetic construct SEQUENCE: 71
WINPNTGVTN FAQKFQG                                                                 17

SEQ ID NO: 72          moltype = AA   length = 16
FEATURE                Location/Qualifiers
source                 1..16
                       mol_type = protein
                       organism = synthetic construct SEQUENCE: 72
DRDASMASYY YYGMDV                                                                  16

SEQ ID NO: 73          moltype = AA   length = 5
FEATURE                Location/Qualifiers
source                 1..5
                       mol_type = protein
                       organism = synthetic construct SEQUENCE: 73
AYYMH                                                                              5

SEQ ID NO: 74          moltype = AA   length = 17
FEATURE                Location/Qualifiers
source                 1..17
                       mol_type = protein
                       organism = synthetic construct SEQUENCE: 74
WINPNTGVTN FAQKFQG                                                                 17

SEQ ID NO: 75          moltype = AA   length = 16
FEATURE                Location/Qualifiers
source                 1..16
                       mol_type = protein
                       organism = synthetic construct SEQUENCE: 75
DRDASMASYY YYGMDV                                                                  16

SEQ ID NO: 76          moltype = AA   length = 7
FEATURE                Location/Qualifiers
source                 1..7
                       mol_type = protein
                       organism = synthetic construct SEQUENCE: 76
GYTFTAY                                                                            7

SEQ ID NO: 77          moltype = AA   length = 6
FEATURE                Location/Qualifiers
source                 1..6
                       mol_type = protein
                       organism = synthetic construct SEQUENCE: 77
NPNTGV                                                                             6

SEQ ID NO: 78          moltype = AA   length = 16
FEATURE                Location/Qualifiers
source                 1..16
                       mol_type = protein
                       organism = synthetic construct SEQUENCE: 78
DRDASMASYY YYGMDV                                                                  16

SEQ ID NO: 79          moltype = AA   length = 8
FEATURE                Location/Qualifiers
source                 1..8
                       mol_type = protein
                       organism = synthetic construct SEQUENCE: 79
GYTFTAYY                                                                           8

SEQ ID NO: 80          moltype = AA   length = 8
FEATURE                Location/Qualifiers
source                 1..8
                       mol_type = protein
                       organism = synthetic construct
```

-continued

```
SEQUENCE: 80
INPNTGVT                                                                        8

SEQ ID NO: 81            moltype = AA  length = 18
FEATURE                  Location/Qualifiers
source                   1..18
                         mol_type = protein
                         organism = synthetic construct
SEQUENCE: 81
ARDRDASMAS YYYYGMDV                                                             18

SEQ ID NO: 82            moltype = AA  length = 125
FEATURE                  Location/Qualifiers
source                   1..125
                         mol_type = protein
                         organism = synthetic construct
SEQUENCE: 82
QVQLVQSGAE VKKPGASVKV SCKASGYTFT AYYMHWVRQA PGQGLEWMGW INPNTGVTNF   60
AQKFQGRVTM TRDTSIGTAY IELSWLRSDD TAVYYCARDR DASMASYYYY GMDVWGQGTT   120
VTVSS                                                                          125

SEQ ID NO: 83            moltype = DNA  length = 375
FEATURE                  Location/Qualifiers
source                   1..375
                         mol_type = other DNA
                         organism = synthetic construct
SEQUENCE: 83
caggtgcagc tggtgcagtc tggggctgag gtgaagaagc ctgggggcctc agtgaaggtc   60
tcctgcaagg cttctggata caccttcacc gcctattata tgcactgggt gcgacaggcc   120
cctggacaag ggcttgagtg gatgggctgg atcaaccta acactggtgt cacaaacttt   180
gcacagaagt ttcagggcag ggtcaccatg accagggaca cgtccatcgg cacagcctac   240
attgaattga gctggctgag atctgacgac acggccgtgt attactgtgc gagggatagg   300
gatgcatcta tggcctccta ctactactac ggtatggacg tctgggggcca agggaccacg   360
gtcaccgtct cctca                                                              375

SEQ ID NO: 84            moltype = AA  length = 455
FEATURE                  Location/Qualifiers
source                   1..455
                         mol_type = protein
                         organism = synthetic construct
SEQUENCE: 84
QVQLVQSGAE VKKPGASVKV SCKASGYTFT AYYMHWVRQA PGQGLEWMGW INPNTGVTNF   60
AQKFQGRVTM TRDTSIGTAY IELSWLRSDD TAVYYCARDR DASMASYYYY GMDVWGQGTT   120
VTVSSASTKG PSVFPLAPCS RSTSGGTAAL GCLVKDYFPE PVTVSWNSGA LTSGVHTFPA   180
VLQSSGLYSL SSVVTVPSSS LGTQTYICNV NHKPSNTKVD KRVEPKSCDK THTCPPCPAP   240
ELLGGPSVFL FPPKPKDTLM ISRTPEVTCV VVDVSHEDPE VKFNWYVDGV EVHNAKTKPR   300
EEQYNSTYRV VSVLTVLHQD WLNGKEYKCK VSNKALPAPI EKTISKAKGQ PREPQVYTLP   360
PSREEMTKNQ VSLTCLVKGF YPSDIAVEWE SNGQPENNYK TTPPVLDSDG SFFLYSKLTV   420
DKSRWQQGNV FSCSVMHEAL HNHYTQKSLS LSPGK                                        455

SEQ ID NO: 85            moltype = DNA  length = 1365
FEATURE                  Location/Qualifiers
source                   1..1365
                         mol_type = other DNA
                         organism = synthetic construct
SEQUENCE: 85
caggtgcagc tggtgcagtc tggggctgag gtgaagaagc ctgggggcctc agtgaaggtc   60
tcctgcaagg cttctggata caccttcacc gcctattata tgcactgggt gcgacaggcc   120
cctggacaag ggcttgagtg gatgggctgg atcaaccta acactggtgt cacaaacttt   180
gcacagaagt ttcagggcag ggtcaccatg accagggaca cgtccatcgg cacagcctac   240
attgaattga gctggctgag atctgacgac acggccgtgt attactgtgc gagggatagg   300
gatgcatcta tggcctccta ctactactac ggtatggacg tctgggggcca agggaccacg   360
gtcaccgtct cctcagcttc caccaagggc ccatcggtct tccccctggc gccctgctcc   420
aggagcacct ctgggggcac agcggccctg ggctgcctgg tcaaggacta cttccccgaa   480
ccggtgacgg tgtcgtggaa ctcaggcgcc ctgaccagcg gcgtgcacac cttcccggct   540
gtcctacagt cctcaggact ctactccctc agcagcgtgg tgaccgtgcc ctccagcagc   600
ttgggcaccc agacctacat ctgcaacgtg aaccacaagc ccagcaacac caaggtggac   660
aagagagtgg agcccaagag ctgcgacaag acccacacct gcccccccctg cccagcccca   720
gagctgctgg gcggaccctc cgtgttcctg ttcccccccca agcccaagga caccctgatg   780
atcagcagga cccccgaggt gacctgcgtg gtggtggacg tgagccacga ggacccagag   840
gtgaagttca actggtacgt ggacggcgtg gaggtgcaca cgccaagac caagcccaga   900
gaggagcagt acaacagcac ctacagggtg gtgtccgtgc tgaccgtgct gcaccaggac   960
tggctgaacg gcaaggaata caagtgcaag gtctccaaca aggccctgcc agcccccatc   1020
gaaaagacca tcagcaaggc caagggccag ccacggagac cccaggtgta caccctgccc   1080
ccctcccggg aggagatgac caagaaccag gtgtccctga cctgtctggt gaagggcttc   1140
tacccccagcg acatcgccgt ggagtgggag agcaacggcc agccagagaa caactacaag   1200
accacccccc cagtgctgga cagcgacggc agcttcttcc tgtacagcaa gctgaccgtg   1260
gacaagtcca gtggcagca gggcaacgtg ttcagctgca cgtgatgca cgaggccctg   1320
cacaaccact acacccagaa gagcctgagc ctgtcccccg gcaag                             1365
```

-continued

```
SEQ ID NO: 86           moltype = AA   length = 13
FEATURE                 Location/Qualifiers
source                  1..13
                        mol_type = protein
                        organism = synthetic construct

SEQUENCE: 86
SGSSSNIGNN YVS                                                  13

SEQ ID NO: 87           moltype = AA   length = 7
FEATURE                 Location/Qualifiers
source                  1..7
                        mol_type = protein
                        organism = synthetic construct

SEQUENCE: 87
DNYKRPS                                                         7

SEQ ID NO: 88           moltype = AA   length = 11
FEATURE                 Location/Qualifiers
source                  1..11
                        mol_type = protein
                        organism = synthetic construct

SEQUENCE: 88
GTWDRSLSAV V                                                    11

SEQ ID NO: 89           moltype = AA   length = 13
FEATURE                 Location/Qualifiers
source                  1..13
                        mol_type = protein
                        organism = synthetic construct

SEQUENCE: 89
SGSSSNIGNN YVS                                                  13

SEQ ID NO: 90           moltype = AA   length = 7
FEATURE                 Location/Qualifiers
source                  1..7
                        mol_type = protein
                        organism = synthetic construct

SEQUENCE: 90
DNYKRPS                                                         7

SEQ ID NO: 91           moltype = AA   length = 11
FEATURE                 Location/Qualifiers
source                  1..11
                        mol_type = protein
                        organism = synthetic construct

SEQUENCE: 91
GTWDRSLSAV V                                                    11

SEQ ID NO: 92           moltype = AA   length = 9
FEATURE                 Location/Qualifiers
source                  1..9
                        mol_type = protein
                        organism = synthetic construct

SEQUENCE: 92
SSSNIGNNY                                                       9

SEQ ID NO: 93           moltype =    length =
SEQUENCE: 93
000

SEQ ID NO: 94           moltype = AA   length = 8
FEATURE                 Location/Qualifiers
source                  1..8
                        mol_type = protein
                        organism = synthetic construct

SEQUENCE: 94
WDRSLSAV                                                        8

SEQ ID NO: 95           moltype = AA   length = 8
FEATURE                 Location/Qualifiers
source                  1..8
                        mol_type = protein
                        organism = synthetic construct

SEQUENCE: 95
SSNIGNNY                                                        8

SEQ ID NO: 96           moltype =    length =
SEQUENCE: 96
```

-continued

000

```
SEQ ID NO: 97          moltype = AA  length = 11
FEATURE                Location/Qualifiers
source                 1..11
                       mol_type = protein
                       organism = synthetic construct
SEQUENCE: 97
GTWDRSLSAV V                                                     11

SEQ ID NO: 98          moltype = AA  length = 110
FEATURE                Location/Qualifiers
source                 1..110
                       mol_type = protein
                       organism = synthetic construct
SEQUENCE: 98
QSVLTQPPSV SAAAGQKVTI SCSGSSSNIG NNYVSWYQHL PGTAPKLLIY DNYKRPSGIP  60
DRFSGSKSGT SATLGITGLQ TGDEADYYCG TWDRSLSAVV FGGGTKLTVL           110

SEQ ID NO: 99          moltype = DNA  length = 330
FEATURE                Location/Qualifiers
source                 1..330
                       mol_type = other DNA
                       organism = synthetic construct
SEQUENCE: 99
cagtctgtgc tgacgcagcc gccctcagtg tctgcggccg caggacagaa ggtcaccatc  60
tcctgctctg gaagcagttc caacattggg aataattatg tatcctggta ccagcacctc  120
ccaggaacag cccccaaact cctcatttat gacaattata agcgaccctc agggattcct  180
gaccgattct ctggctccaa gtctggcacg tcagccaccc tgggcatcac cggactccag  240
actggggacg aggccgacta ttattgcgga acatgggata ggagcctgag tgctgtggta  300
ttcggcggag ggaccaagct gaccgtccta                                  330

SEQ ID NO: 100         moltype = AA  length = 216
FEATURE                Location/Qualifiers
source                 1..216
                       mol_type = protein
                       organism = synthetic construct
SEQUENCE: 100
QSVLTQPPSV SAAAGQKVTI SCSGSSSNIG NNYVSWYQHL PGTAPKLLIY DNYKRPSGIP  60
DRFSGSKSGT SATLGITGLQ TGDEADYYCG TWDRSLSAVV FGGGTKLTVL GQPKAAPSVT  120
LFPPSSEELQ ANKATLVCLI SDFYPGAVTV AWKADSSPVK AGVETTTPSK QSNNKYAASS  180
YLSLTPEQWK SHRSYSCQVT HEGSTVEKTV APTECS                          216

SEQ ID NO: 101         moltype = DNA  length = 648
FEATURE                Location/Qualifiers
source                 1..648
                       mol_type = other DNA
                       organism = synthetic construct
SEQUENCE: 101
cagtctgtgc tgacgcagcc gccctcagtg tctgcggccg caggacagaa ggtcaccatc  60
tcctgctctg gaagcagttc caacattggg aataattatg tatcctggta ccagcacctc  120
ccaggaacag cccccaaact cctcatttat gacaattata agcgaccctc agggattcct  180
gaccgattct ctggctccaa gtctggcacg tcagccaccc tgggcatcac cggactccag  240
actggggacg aggccgacta ttattgcgga acatgggata ggagcctgag tgctgtggta  300
ttcggcggag ggaccaagct gaccgtccta ggtcagccca aggctgcccc ctcggtcact  360
ctgttcccgc cctcctctga ggagcttcaa gccaacaagg ccacactggt gtgtctcata  420
agtgacttct acccgggagc cgtgacagtg gcctggaagg cagatagcag ccccgtcaag  480
gcgggagtgg agaccaccac accctccaaa caaagcaaca acaagtacgc cgccagcagc  540
tatctgagcc tgacgcctga gcagtggaag tcccacagaa gctacagctg ccaggtcacc  600
cacgagggca gcaccgtgga gaaaaccgtg gcccccaccg agtgcagc              648

SEQ ID NO: 102         moltype = AA  length = 10
FEATURE                Location/Qualifiers
source                 1..10
                       mol_type = protein
                       organism = synthetic construct
SEQUENCE: 102
GYRFTSHWIS                                                       10

SEQ ID NO: 103         moltype = AA  length = 17
FEATURE                Location/Qualifiers
source                 1..17
                       mol_type = protein
                       organism = synthetic construct
SEQUENCE: 103
RIDPSDSYIK YSPSFQG                                               17

SEQ ID NO: 104         moltype = AA  length = 12
FEATURE                Location/Qualifiers
```

-continued

```
source                    1..12
                          mol_type = protein
                          organism = synthetic construct
SEQUENCE: 104
LGYSSGWYYF DY                                                              12

SEQ ID NO: 105            moltype = AA   length = 5
FEATURE                   Location/Qualifiers
source                    1..5
                          mol_type = protein
                          organism = synthetic construct
SEQUENCE: 105
SHWIS                                                                      5

SEQ ID NO: 106            moltype = AA   length = 17
FEATURE                   Location/Qualifiers
source                    1..17
                          mol_type = protein
                          organism = synthetic construct
SEQUENCE: 106
RIDPSDSYIK YSPSFQG                                                         17

SEQ ID NO: 107            moltype = AA   length = 12
FEATURE                   Location/Qualifiers
source                    1..12
                          mol_type = protein
                          organism = synthetic construct
SEQUENCE: 107
LGYSSGWYYF DY                                                              12

SEQ ID NO: 108            moltype = AA   length = 7
FEATURE                   Location/Qualifiers
source                    1..7
                          mol_type = protein
                          organism = synthetic construct
SEQUENCE: 108
GYRFTSH                                                                    7

SEQ ID NO: 109            moltype = AA   length = 6
FEATURE                   Location/Qualifiers
source                    1..6
                          mol_type = protein
                          organism = synthetic construct
SEQUENCE: 109
DPSDSY                                                                     6

SEQ ID NO: 110            moltype = AA   length = 12
FEATURE                   Location/Qualifiers
source                    1..12
                          mol_type = protein
                          organism = synthetic construct
SEQUENCE: 110
LGYSSGWYYF DY                                                              12

SEQ ID NO: 111            moltype = AA   length = 8
FEATURE                   Location/Qualifiers
source                    1..8
                          mol_type = protein
                          organism = synthetic construct
SEQUENCE: 111
GYRFTSHW                                                                   8

SEQ ID NO: 112            moltype = AA   length = 8
FEATURE                   Location/Qualifiers
source                    1..8
                          mol_type = protein
                          organism = synthetic construct
SEQUENCE: 112
IDPSDSYI                                                                   8

SEQ ID NO: 113            moltype = AA   length = 14
FEATURE                   Location/Qualifiers
source                    1..14
                          mol_type = protein
                          organism = synthetic construct
SEQUENCE: 113
ARLGYSSGWY YFDY                                                           14

SEQ ID NO: 114            moltype = AA   length = 121
```

-continued

```
FEATURE                  Location/Qualifiers
source                   1..121
                         mol_type = protein
                         organism = synthetic construct
SEQUENCE: 114
EVQLVQSGAE VKKPGESLRI SCKGSGYRFT SHWISWVRQM PGKGLEWVAR IDPSDSYIKY   60
SPSFQGHVTI SADKSTSTAF LQWSSLKASD TAMYYCARLG YSSGWYYFDY WGQGTLVTVS  120
S                                                                  121

SEQ ID NO: 115           moltype = DNA   length = 363
FEATURE                  Location/Qualifiers
source                   1..363
                         mol_type = other DNA
                         organism = synthetic construct
SEQUENCE: 115
gaagtgcagc tggtgcagtc tggagcagag gtgaaaaagc ccggggagtc tctgaggatc   60
tcttgtaagg gttctggata caggtttacc agccactgga tcagctgggt gcgccagatg  120
cccgggaaag gcctggagtg ggtggcgagg attgatccta gtgactctta tatcaagtac  180
agcccgtcct tccaaggcca cgtcaccatc tcagctgaca agtccaccag cacagccttc  240
ctgcagtgga gcagcctgaa ggcctcggac accgccatgt attactgtgc gagactaggg  300
tatagcagtg gctggtacta ttttgactac tggggccagg gaaccctggt caccgtctcc  360
tca                                                                363

SEQ ID NO: 116           moltype = AA   length = 451
FEATURE                  Location/Qualifiers
source                   1..451
                         mol_type = protein
                         organism = synthetic construct
SEQUENCE: 116
EVQLVQSGAE VKKPGESLRI SCKGSGYRFT SHWISWVRQM PGKGLEWVAR IDPSDSYIKY   60
SPSFQGHVTI SADKSTSTAF LQWSSLKASD TAMYYCARLG YSSGWYYFDY WGQGTLVTVS  120
SASTKGPSVF PLAPCSRSTS GGTAALGCLV KDYFPEPVTV SWNSGALTSG VHTFPAVLQS  180
SGLYSLSSVV TVPSSSLGTQ TYICNVNHKP SNTKVDKRVE PKSCDKTHTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRE  360
EMTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                 451

SEQ ID NO: 117           moltype = DNA   length = 1353
FEATURE                  Location/Qualifiers
source                   1..1353
                         mol_type = other DNA
                         organism = synthetic construct
SEQUENCE: 117
gaagtgcagc tggtgcagtc tggagcagag gtgaaaaagc ccggggagtc tctgaggatc   60
tcttgtaagg gttctggata caggtttacc agccactgga tcagctgggt gcgccagatg  120
cccgggaaag gcctggagtg ggtggcgagg attgatccta gtgactctta tatcaagtac  180
agcccgtcct tccaaggcca cgtcaccatc tcagctgaca agtccaccag cacagccttc  240
ctgcagtgga gcagcctgaa ggcctcggac accgccatgt attactgtgc gagactaggg  300
tatagcagtg gctggtacta ttttgactac tggggccagg gaaccctggt caccgtctcc  360
tcagcttcca ccaagggccc atcggtcttc cccctggcgc cctgctccag gagcacctct  420
gggggcacag cggccctggg ctgcctggtc aaggactact ccccgaacc  ggtgacggtg  480
tcgtggaact caggcgccct gaccagcggc gtgcacacct tcccggctgt cctacagtcc  540
tcaggactct actccctcag cagcgtggtg accgtgccct ccagcagctt gggcacccag  600
acctacatct gcaacgtgaa ccacaagccc agcaacaccaa aggtggacaa gagagtggag  660
cccaagagct gcgacaagac ccacacctgc cccccctgcc cagccccaga gctgctgggc  720
ggaccctccg tgttcctgtt ccccccaag  cccaaggaca ccctgatgat cagcaggacc  780
cccgaggtga cctgcgtggt ggtggacgtg agccacgagg acccagaggt gaagttcaac  840
tggtacgtgg acggcgtgga ggtgcacaac gccaagacca gcccagagga ggagcagtac  900
aacagcacct acagggtggt gtccgtgctg accgtgctgc accaggactg gctgaacggc  960
aaggaataca agtgcaaggt ctccaacaag gccctgccag ccccatcga  aaagaccatc 1020
agcaaggcca agggccagcc acgggagccc caggtgtaca ccctgccccc ctcccgggag 1080
gagatgacca gaaccaggt  gtccctgacc tgtctggtga agggcttcta ccccagcgac 1140
atcgccgtgg agtgggagag caacggccag cccgagaaca actacaagac cacccccccca 1200
gtgctggaca cgcacggcag cttcttcctg tacagcaagc tgaccgtgga caagtccagg 1260
tggcagcagg gcaacgtgtt cagctgcagc gtgatgcacg aggccctgca caaccactac 1320
acccagaaga gcctgagcct gtccccggc  aag                              1353

SEQ ID NO: 118           moltype = AA   length = 13
FEATURE                  Location/Qualifiers
source                   1..13
                         mol_type = protein
                         organism = synthetic construct
SEQUENCE: 118
SGSRTNIGSN AVN                                                      13

SEQ ID NO: 119           moltype = AA   length = 7
FEATURE                  Location/Qualifiers
source                   1..7
```

-continued

```
                              mol_type = protein
                              organism = synthetic construct
SEQUENCE: 119
SSDQRPS                                                            7

SEQ ID NO: 120       moltype = AA  length = 11
FEATURE              Location/Qualifiers
source               1..11
                     mol_type = protein
                     organism = synthetic construct
SEQUENCE: 120
AAWDDSLHGW V                                                       11

SEQ ID NO: 121       moltype = AA  length = 13
FEATURE              Location/Qualifiers
source               1..13
                     mol_type = protein
                     organism = synthetic construct
SEQUENCE: 121
SGSRTNIGSN AVN                                                     13

SEQ ID NO: 122       moltype = AA  length = 7
FEATURE              Location/Qualifiers
source               1..7
                     mol_type = protein
                     organism = synthetic construct
SEQUENCE: 122
SSDQRPS                                                            7

SEQ ID NO: 123       moltype = AA  length = 11
FEATURE              Location/Qualifiers
source               1..11
                     mol_type = protein
                     organism = synthetic construct
SEQUENCE: 123
AAWDDSLHGW V                                                       11

SEQ ID NO: 124       moltype = AA  length = 9
FEATURE              Location/Qualifiers
source               1..9
                     mol_type = protein
                     organism = synthetic construct
SEQUENCE: 124
SRTNIGSNA                                                          9

SEQ ID NO: 125       moltype =   length =
SEQUENCE: 125
000

SEQ ID NO: 126       moltype = AA  length = 8
FEATURE              Location/Qualifiers
source               1..8
                     mol_type = protein
                     organism = synthetic construct
SEQUENCE: 126
WDDSLHGW                                                           8

SEQ ID NO: 127       moltype = AA  length = 8
FEATURE              Location/Qualifiers
source               1..8
                     mol_type = protein
                     organism = synthetic construct
SEQUENCE: 127
RTNIGSNA                                                           8

SEQ ID NO: 128       moltype =   length =
SEQUENCE: 128
000

SEQ ID NO: 129       moltype = AA  length = 11
FEATURE              Location/Qualifiers
source               1..11
                     mol_type = protein
                     organism = synthetic construct
SEQUENCE: 129
AAWDDSLHGW V                                                       11

SEQ ID NO: 130       moltype = AA  length = 110
FEATURE              Location/Qualifiers
```

-continued

```
source                    1..110
                          mol_type = protein
                          organism = synthetic construct
SEQUENCE: 130
SPVLTQPPSA SGTPGQRVTI SCSGSRTNIG SNAVNWYQQV PGTAPKLLIY SSDQRPSGVS   60
DRFSGSKSGT SGSLAISGLQ SEDETDYYCA AWDDSLHGWV FGGGTKLTVL             110

SEQ ID NO: 131            moltype = DNA   length = 330
FEATURE                   Location/Qualifiers
source                    1..330
                          mol_type = other DNA
                          organism = synthetic construct
SEQUENCE: 131
tcgcctgtgc tgactcagcc gccctcagcg tctgggaccc ccgggcagag ggtcaccatc   60
tcttgttctg gaagcaggac caacatcgga agtaatgctg taaactggta ccagcaggtc   120
ccaggaacgg cccccaaact cctcatctat agtagtgatc agcggccctc aggggtctct   180
gaccgattct ctggctccaa gtctggcacc tcaggctccc tggccatcag tggcctccag   240
tctgaggatg aaactgatta ttactgtgca gcatgggatg acagcctgca tggttgggtg   300
ttcggcggag ggaccaagct gaccgtccta                                    330

SEQ ID NO: 132            moltype = AA   length = 216
FEATURE                   Location/Qualifiers
source                    1..216
                          mol_type = protein
                          organism = synthetic construct
SEQUENCE: 132
SPVLTQPPSA SGTPGQRVTI SCSGSRTNIG SNAVNWYQQV PGTAPKLLIY SSDQRPSGVS   60
DRFSGSKSGT SGSLAISGLQ SEDETDYYCA AWDDSLHGWV FGGGTKLTVL GQPKAAPSVT   120
LFPPSSEELQ ANKATLVCLI SDFYPGAVTV AWKADSSPVK AGVETTTPSK QSNNKYAASS   180
YLSLTPEQWK SHRSYSCQVT HEGSTVEKTV APTECS                             216

SEQ ID NO: 133            moltype = DNA   length = 648
FEATURE                   Location/Qualifiers
source                    1..648
                          mol_type = other DNA
                          organism = synthetic construct
SEQUENCE: 133
tcgcctgtgc tgactcagcc gccctcagcg tctgggaccc ccgggcagag ggtcaccatc   60
tcttgttctg gaagcaggac caacatcgga agtaatgctg taaactggta ccagcaggtc   120
ccaggaacgg cccccaaact cctcatctat agtagtgatc agcggccctc aggggtctct   180
gaccgattct ctggctccaa gtctggcacc tcaggctccc tggccatcag tggcctccag   240
tctgaggatg aaactgatta ttactgtgca gcatgggatg acagcctgca tggttgggtg   300
ttcggcggag ggaccaagct gaccgtccta ggtcagccca aggctgcccc ctcggtcact   360
ctgttcccgc cctcctctga ggagcttcaa gccaacaagg ccacactggt gtgtctcata   420
agtgacttct acccgggagc cgtgacagtg gcctggaagg cagatagcag ccccgtcaag   480
gcgggagtgg agaccaccac accctccaaa caaagcaaca caagtacgc cgccagcagc   540
tacctgagcc tgacccccga gcagtggaag agccacagaa gctacagctg ccaggtcacc   600
cacgagggca gcaccgtgga gaaaaccgtg gccccaccg agtgcagc                648

SEQ ID NO: 134            moltype = AA   length = 10
FEATURE                   Location/Qualifiers
source                    1..10
                          mol_type = protein
                          organism = synthetic construct
SEQUENCE: 134
GYRFTSHWIS                                                          10

SEQ ID NO: 135            moltype = AA   length = 17
FEATURE                   Location/Qualifiers
source                    1..17
                          mol_type = protein
                          organism = synthetic construct
SEQUENCE: 135
RIDPSDSYTK YSPSFQG                                                  17

SEQ ID NO: 136            moltype = AA   length = 12
FEATURE                   Location/Qualifiers
source                    1..12
                          mol_type = protein
                          organism = synthetic construct
SEQUENCE: 136
LGYHSGWYYF DY                                                       12

SEQ ID NO: 137            moltype = AA   length = 5
FEATURE                   Location/Qualifiers
source                    1..5
                          mol_type = protein
                          organism = synthetic construct
SEQUENCE: 137
```

-continued

```
SHWIS                                                     5

SEQ ID NO: 138            moltype = AA  length = 17
FEATURE                   Location/Qualifiers
source                    1..17
                          mol_type = protein
                          organism = synthetic construct
SEQUENCE: 138
RIDPSDSYTK YSPSFQG                                        17

SEQ ID NO: 139            moltype = AA  length = 12
FEATURE                   Location/Qualifiers
source                    1..12
                          mol_type = protein
                          organism = synthetic construct
SEQUENCE: 139
LGYHSGWYYF DY                                             12

SEQ ID NO: 140            moltype = AA  length = 7
FEATURE                   Location/Qualifiers
source                    1..7
                          mol_type = protein
                          organism = synthetic construct
SEQUENCE: 140
GYRFTSH                                                   7

SEQ ID NO: 141            moltype = AA  length = 6
FEATURE                   Location/Qualifiers
source                    1..6
                          mol_type = protein
                          organism = synthetic construct
SEQUENCE: 141
DPSDSY                                                    6

SEQ ID NO: 142            moltype = AA  length = 12
FEATURE                   Location/Qualifiers
source                    1..12
                          mol_type = protein
                          organism = synthetic construct
SEQUENCE: 142
LGYHSGWYYF DY                                             12

SEQ ID NO: 143            moltype = AA  length = 8
FEATURE                   Location/Qualifiers
source                    1..8
                          mol_type = protein
                          organism = synthetic construct
SEQUENCE: 143
GYRFTSHW                                                  8

SEQ ID NO: 144            moltype = AA  length = 8
FEATURE                   Location/Qualifiers
source                    1..8
                          mol_type = protein
                          organism = synthetic construct
SEQUENCE: 144
IDPSDSYT                                                  8

SEQ ID NO: 145            moltype = AA  length = 14
FEATURE                   Location/Qualifiers
source                    1..14
                          mol_type = protein
                          organism = synthetic construct
SEQUENCE: 145
ARLGYHSGWY YFDY                                           14

SEQ ID NO: 146            moltype = AA  length = 121
FEATURE                   Location/Qualifiers
source                    1..121
                          mol_type = protein
                          organism = synthetic construct
SEQUENCE: 146
QVQLVESGAE VKKPGESLRI SCKGSGYRFT SHWISWVRQM PGKGLEWVAR IDPSDSYTKY  60
SPSFQGHVTI STDKSTSTAY LHWSSLKASD TAMYYCARLG YHSGWYYFDY WGQGTLVTVS  120
S                                                        121

SEQ ID NO: 147            moltype = DNA  length = 363
FEATURE                   Location/Qualifiers
source                    1..363
```

```
                      mol_type = other DNA
                      organism = synthetic construct
SEQUENCE: 147
caggtgcagc tggttggagtc tggagcagag gtgaaaaagc ccggggagtc tctgaggatc      60
tcctgtaagg gttctggata caggtttacc agccactgga tcagctgggt gcgccagatg     120
cccgggaaag gcctggagtg ggtggcgagg attgatccta gtgactctta taccaagtac     180
agcccgtcct ccaaggcca cgtcaccatc tcaactgaca agtccaccag cacagcctac     240
ctgcactgga gcagcctgaa ggcctcggac accgccatgt attactgtgc gagactaggg     300
tatcacagtg gctggtacta cttttgactac tggggccagg gaaccctggt caccgtctcc     360
tca                                                                    363

SEQ ID NO: 148        moltype = AA  length = 451
FEATURE               Location/Qualifiers
source                1..451
                      mol_type = protein
                      organism = synthetic construct
SEQUENCE: 148
QVQLVESGAE VKKPGESLRI SCKGSGYRFT SHWISWVRQM PGKGLEWVAR IDPSDSYTKY      60
SPSFQGHVTI STDKSTSTAY LHWSSLKASD TAMYYCARLG YHSGWYYFDY WGQGTLVTVS     120
SASTKGPSVF PLAPCSRSTS GGTAALGCLV KDYFPEPVTV SWNSGALTSG VHTFPAVLQS     180
SGLYSLSSVV TVPSSSLGTQ TYICNVNHKP SNTKVDKRVE PKSCDKTHTC PPCPAPELLG     240
GPSVFLPPPK PKDTLMISRT PEVTCVVVDV SHEDPEVKFN WYVDGVEVHN AKTKPREEQY     300
NSTYRVVSVL TVLHQDWLNG KEYKCKVSNK ALPAPIEKTI SKAKGQPREP QVYTLPPSRE     360
EMTKNQVSLT CLVKGFYPSD IAVEWESNGQ PENNYKTTPP VLDSDGSFFL YSKLTVDKSR     420
WQQGNVFSCS VMHEALHNHY TQKSLSLSPG K                                    451

SEQ ID NO: 149        moltype = DNA  length = 1353
FEATURE               Location/Qualifiers
source                1..1353
                      mol_type = other DNA
                      organism = synthetic construct
SEQUENCE: 149
caggtgcagc tggttggagtc tggagcagag gtgaaaaagc ccggggagtc tctgaggatc      60
tcctgtaagg gttctggata caggtttacc agccactgga tcagctgggt gcgccagatg     120
cccgggaaag gcctggagtg ggtggcgagg attgatccta gtgactctta taccaagtac     180
agcccgtcct ccaaggcca cgtcaccatc tcaactgaca agtccaccag cacagcctac     240
ctgcactgga gcagcctgaa ggcctcggac accgccatgt attactgtgc gagactaggg     300
tatcacagtg gctggtacta cttttgactac tggggccagg gaaccctggt caccgtctcc     360
tcagcttcca ccaagggccc atcggtcttc cccctggcgc cctgctccag gagcacctct     420
gggggcacag cggccctggg ctgcctggtc aaggactact ccccgaacc ggtgacggtg     480
tcgtggaact caggcgccct gaccagcggc gtgcacacct tcccggctgt cctacagtcc     540
tcaggactct actccctcag cagcgtggtg accgtgccct ccagcagctt gggcacccag     600
acctacatct gcaacgtgaa ccacaagccc agcaacacca aggtggacaa gagagtggac     660
cccaagagct gcgacaagac ccacacctgc ccccccgc cagccccaga gctgctgggc     720
ggaccctccg tgttcctgtt ccccccaag cccaaggaca ccctgatgat cagcaggacc     780
cccgaggtga cctgcgtggt ggtggacgtg agccacgagg acccagaggt gaagttcaac     840
tggtacgtgg acggcgtgga ggtgcacaac gccaagacaa agcccagaga ggagcagtac     900
aacagcacct acaggtggt gtccgtgctg accgtgctgc accaggactg gctgaacggc     960
aaggaataca gtgcaaggt ctccaacaag gccctgccag ccccatcga aaagaccatc    1020
agcaaggcca agggccagcc acgggagccc caggtgtaca ccctgccccc ctcccgggag    1080
gagatgacca gaaccaggt gtccctgacc tgtctggtga agggcttcta cccagcgac    1140
atcgccgtgg agtgggagag caacggccag cccgagaaca actacaagac cacccccca    1200
gtgctggaca cgacggcag cttcttcctg tacagcaagc tgaccgtgga caagtccagg    1260
tggcagcagg gcaacgtgtt cagctgcagc gtgatgcacg aggccctgca caaccactac    1320
acccagaaga gcctgagcct gtcccccggc aag                                1353

SEQ ID NO: 150        moltype = AA  length = 13
FEATURE               Location/Qualifiers
source                1..13
                      mol_type = protein
                      organism = synthetic construct
SEQUENCE: 150
SGSSSNIGSN AVN                                                          13

SEQ ID NO: 151        moltype = AA  length = 7
FEATURE               Location/Qualifiers
source                1..7
                      mol_type = protein
                      organism = synthetic construct
SEQUENCE: 151
SSDQRPS                                                                  7

SEQ ID NO: 152        moltype = AA  length = 11
FEATURE               Location/Qualifiers
source                1..11
                      mol_type = protein
                      organism = synthetic construct
SEQUENCE: 152
AAWDDSLHGW I                                                            11
```

-continued

```
SEQ ID NO: 153            moltype = AA   length = 13
FEATURE                   Location/Qualifiers
source                    1..13
                          mol_type = protein
                          organism = synthetic construct
SEQUENCE: 153
SGSSSNIGSN AVN                                                    13

SEQ ID NO: 154            moltype = AA   length = 7
FEATURE                   Location/Qualifiers
source                    1..7
                          mol_type = protein
                          organism = synthetic construct
SEQUENCE: 154
SSDQRPS                                                           7

SEQ ID NO: 155            moltype = AA   length = 11
FEATURE                   Location/Qualifiers
source                    1..11
                          mol_type = protein
                          organism = synthetic construct
SEQUENCE: 155
AAWDDSLHGW I                                                      11

SEQ ID NO: 156            moltype = AA   length = 9
FEATURE                   Location/Qualifiers
source                    1..9
                          mol_type = protein
                          organism = synthetic construct
SEQUENCE: 156
SSSNIGSNA                                                         9

SEQ ID NO: 157            moltype =    length =
SEQUENCE: 157
000

SEQ ID NO: 158            moltype = AA   length = 8
FEATURE                   Location/Qualifiers
source                    1..8
                          mol_type = protein
                          organism = synthetic construct
SEQUENCE: 158
WDDSLHGW                                                          8

SEQ ID NO: 159            moltype = AA   length = 8
FEATURE                   Location/Qualifiers
source                    1..8
                          mol_type = protein
                          organism = synthetic construct
SEQUENCE: 159
SSNIGSNA                                                          8

SEQ ID NO: 160            moltype =    length =
SEQUENCE: 160
000

SEQ ID NO: 161            moltype = AA   length = 11
FEATURE                   Location/Qualifiers
source                    1..11
                          mol_type = protein
                          organism = synthetic construct
SEQUENCE: 161
AAWDDSLHGW I                                                      11

SEQ ID NO: 162            moltype = AA   length = 110
FEATURE                   Location/Qualifiers
source                    1..110
                          mol_type = protein
                          organism = synthetic construct
SEQUENCE: 162
QSALTQPPSA SGTPGQRVTI SCSGSSSNIG SNAVNWYQQL PGTAPKLLIY SSDQRPSGVP  60
DRFSGSKSGT SGSLAISGLH SEDETDYYCA AWDDSLHGWI FGGGTKLTVI            110

SEQ ID NO: 163            moltype = DNA   length = 330
FEATURE                   Location/Qualifiers
source                    1..330
                          mol_type = other DNA
                          organism = synthetic construct
```

```
SEQUENCE: 163
cagtctgccc tgactcagcc accctcagcg tctgggaccc ccgggcagag ggtcaccatc    60
tcttgttctg gaagcagctc caacatcgga agtaatgctg taaactggta ccagcagctc   120
ccaggaacgg cccccaaact cctcatctat agtagtgatc agcggccctc aggggtccct   180
gaccgattct ctggctccaa gtctggcacc tcaggctccc tggccatcag tgggctccac   240
tctgaggatg agactgatta ttactgtgca gcatgggatg acagcctgca tggttggata   300
ttcggcggag ggaccaagct gaccgtcata                                     330

SEQ ID NO: 164          moltype = AA   length = 216
FEATURE                 Location/Qualifiers
source                  1..216
                        mol_type = protein
                        organism = synthetic construct
SEQUENCE: 164
QSALTQPPSA SGTPGQRVTI SCSGSSSNIG SNAVNWYQQL PGTAPKLLIY SSDQRPSGVP     60
DRFSGSKSGT SGSLAISGLH SEDETDYYCA AWDDSLHGWI FGGGTKLTVI GQPKAAPSVT    120
LFPPSSEELQ ANKATLVCLI SDFYPGAVTV AWKADSSPVK AGVETTTPSK QSNNKYAASS    180
YLSLTPEQWK SHRSYSCQVT HEGSTVEKTV APTECS                             216

SEQ ID NO: 165          moltype = DNA   length = 648
FEATURE                 Location/Qualifiers
source                  1..648
                        mol_type = other DNA
                        organism = synthetic construct
SEQUENCE: 165
cagtctgccc tgactcagcc accctcagcg tctgggaccc ccgggcagag ggtcaccatc    60
tcttgttctg gaagcagctc caacatcgga agtaatgctg taaactggta ccagcagctc   120
ccaggaacgg cccccaaact cctcatctat agtagtgatc agcggccctc aggggtccct   180
gaccgattct ctggctccaa gtctggcacc tcaggctccc tggccatcag tgggctccac   240
tctgaggatg agactgatta ttactgtgca gcatgggatg acagcctgca tggttggata   300
ttcggcggag ggaccaagct gaccgtcata ggtcagccca aggctgcccc ctcggtcact   360
ctgttcccgc cctcctctga ggagcttcaa gccaacaagg ccacactggt gtgtctcata   420
agtgacttct acccgggagc cgtgacagtg gcctggaagg cagatagcag ccccgtcaag   480
gcgggagtgg agaccaccac accctccaaa caaagcaaca acaagtacgc cgccagcagc   540
tacctgagcc tgacgcctga gcagtggaag tcccacagaa gctacagctg ccaggtcacc   600
cacgagggca gcaccgtgga gaaaaccgtg gcccccaccg agtgcagc                648

SEQ ID NO: 166          moltype = AA   length = 12
FEATURE                 Location/Qualifiers
source                  1..12
                        mol_type = protein
                        organism = synthetic construct
SEQUENCE: 166
GASISSGSDY WS                                                        12

SEQ ID NO: 167          moltype = AA   length = 16
FEATURE                 Location/Qualifiers
source                  1..16
                        mol_type = protein
                        organism = synthetic construct
SEQUENCE: 167
RIYTSGRNSY NPSLKS                                                    16

SEQ ID NO: 168          moltype = AA   length = 13
FEATURE                 Location/Qualifiers
source                  1..13
                        mol_type = protein
                        organism = synthetic construct
SEQUENCE: 168
NSRRYGGYDL FDV                                                       13

SEQ ID NO: 169          moltype = AA   length = 7
FEATURE                 Location/Qualifiers
source                  1..7
                        mol_type = protein
                        organism = synthetic construct
SEQUENCE: 169
SGSDYWS                                                              7

SEQ ID NO: 170          moltype = AA   length = 16
FEATURE                 Location/Qualifiers
source                  1..16
                        mol_type = protein
                        organism = synthetic construct
SEQUENCE: 170
RIYTSGRNSY NPSLKS                                                    16

SEQ ID NO: 171          moltype = AA   length = 13
FEATURE                 Location/Qualifiers
```

-continued

```
source                    1..13
                          mol_type = protein
                          organism = synthetic construct
SEQUENCE: 171
NSRRYGGYDL FDV                                              13

SEQ ID NO: 172            moltype = AA  length = 9
FEATURE                   Location/Qualifiers
source                    1..9
                          mol_type = protein
                          organism = synthetic construct
SEQUENCE: 172
GASISSGSD                                                   9

SEQ ID NO: 173            moltype = AA  length = 5
FEATURE                   Location/Qualifiers
source                    1..5
                          mol_type = protein
                          organism = synthetic construct
SEQUENCE: 173
YTSGR                                                       5

SEQ ID NO: 174            moltype = AA  length = 13
FEATURE                   Location/Qualifiers
source                    1..13
                          mol_type = protein
                          organism = synthetic construct
SEQUENCE: 174
NSRRYGGYDL FDV                                              13

SEQ ID NO: 175            moltype = AA  length = 10
FEATURE                   Location/Qualifiers
source                    1..10
                          mol_type = protein
                          organism = synthetic construct
SEQUENCE: 175
GASISSGSDY                                                  10

SEQ ID NO: 176            moltype = AA  length = 7
FEATURE                   Location/Qualifiers
source                    1..7
                          mol_type = protein
                          organism = synthetic construct
SEQUENCE: 176
IYTSGRN                                                     7

SEQ ID NO: 177            moltype = AA  length = 15
FEATURE                   Location/Qualifiers
source                    1..15
                          mol_type = protein
                          organism = synthetic construct
SEQUENCE: 177
ARNSRRYGGY DLFDV                                            15

SEQ ID NO: 178            moltype = AA  length = 123
FEATURE                   Location/Qualifiers
source                    1..123
                          mol_type = protein
                          organism = synthetic construct
SEQUENCE: 178
QVQLQESGPG LVKPSQTLSL TCTVSGASIS SGSDYWSWIR QPAGKGLEWI GRIYTSGRNS   60
YNPSLKSRVT IAVDTSKNQF SLKLSSVSAT DTAVYYCARN SRRYGGYDLF DVWGQGTMVT  120
VSS                                                              123

SEQ ID NO: 179            moltype = DNA  length = 369
FEATURE                   Location/Qualifiers
source                    1..369
                          mol_type = other DNA
                          organism = synthetic construct
SEQUENCE: 179
caggtgcagc tgcaggagtc gggcccagga ctggtgaagc cttcacagac cctgtccctc   60
acctgcactg tctctggtgc ctccatcagc agtggtagtg actactggag ctggatccgg  120
cagcccgccg ggaagggact gggagtggatt gggcgtatct ataccagtgg gaggaacagc  180
tacaacccct ccctcaagag tcgagtcacc atagcagtag acacgtccaa gaaccagttc  240
tccctgaagc tgagtagtgt gagtgccaca gacacggccg tgtattactg tgcgaggaat  300
agcagaagat atggtggcta cgatctgttt gatgtctggg gccaagggac aatggtcacc  360
gtctcttca                                                         369

SEQ ID NO: 180            moltype = AA  length = 453
```

```
FEATURE                 Location/Qualifiers
source                  1..453
                        mol_type = protein
                        organism = synthetic construct
SEQUENCE: 180
QVQLQESGPG LVKPSQTLSL TCTVSGASIS SGSDYWSWIR QPAGKGLEWI GRIYTSGRNS   60
YNPSLKSRVT IAVDTSKNQF SLKLSSVSAT DTAVYYCARN SRRYGGYDLF DVWGQGTMVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKR VEPKSCDKTH TCPPCPAPEL  240
LGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
REEMTKNQVS LTCLVKGFYP SDIAVEWESN GQPENNYKTT PPVLDSDGSF FLYSKLTVDK  420
SRWQQGNVFS CSVMHEALHN HYTQKSLSLS PGK                                453

SEQ ID NO: 181         moltype = DNA  length = 1359
FEATURE                Location/Qualifiers
source                 1..1359
                       mol_type = other DNA
                       organism = synthetic construct
SEQUENCE: 181
caggtgcagc tgcaggagtc gggcccagga ctggtgaagc cttcacagac cctgtccctc   60
acctgcactg tctctggtgc ctccatcagc agtggtagtg actactggag ctggatccgg  120
cagcccgccg ggaagggact ggagtggatt gggcgtatct ataccagtgg gaggaacagc  180
tacaacccct ccctcaagag tcgagtcacc atagcagtag acacgtccaa gaaccagttc  240
tccctgaagc tgagtagtgt gagtgccaca gacacggccg tgtattactg tgcgaggaat  300
agcagaagat atggtggcta cgatctgttt gatgtctggg gccaaggac aatggtcacc  360
gtctcttcag cctccaccaa gggcccatcg gtcttccccc tggcaccctc ctccaagagc  420
acctctgggg gcacagcggc cctgggctgc ctggtcaagg actacttccc cgaaccggtg  480
acggtgtcgt ggaactcagg cgccctgacc agcggcgtgc acaccttccc ggctgtccta  540
cagtcctcag gactctactc cctcagcagc gtggtgaccg tgccctccag cagcttgggc  600
acccagacct acatctgcaa cgtgaaccac aagcccagca acaccaaggt ggacaagaga  660
gtggagccca gagctgcga caagaccac acctgcccc cctgcccagc cccagagctg  720
ctgggcggac cctccgtgtt cctgttcccc cccaagccca aggacaccct gatgatcagc  780
aggacccccg aggtgacctg cgtggtggtg gacgtgagcc acgaggaccc agaggtgaag  840
ttcaactggt acgtggacgg cgtggaggtg cacaacgcca agacaagcc cagagaggag  900
cagtacaaca gcacctacag ggtggtgtcc gtgctgaccg tgctgcacca ggactggctg  960
aacggcaagg aatacaagtg caaggtctcc aacaaggccc tgccagcccc catcgaaaag 1020
accatcagca aggccaaggg ccagccacgg gagccccagg tgtacaccct gccccctcc 1080
cgggaggaga tgaccaagaa ccaggtgtcc ctgacctgtc tggtgaaggg cttctaccc 1140
agcgacatcg ccgtggagtg ggagagcaac ggccagcccg agaacaacta caagaccacc 1200
cccccagtgc tggacagcga cggcagcttc ttcctgtaca gcaagctgac cgtggacaag 1260
tccaggtggc agcagggcaa cgtgttcagc tgcagcgtga tgcacgaggc cctgcacaac 1320
cactacaccc agaagagcct gagcctgtcc cccggcaag                          1359

SEQ ID NO: 182         moltype = AA  length = 11
FEATURE                Location/Qualifiers
source                 1..11
                       mol_type = protein
                       organism = synthetic construct
SEQUENCE: 182
GGNNIGSKSV H                                                          11

SEQ ID NO: 183         moltype = AA  length = 7
FEATURE                Location/Qualifiers
source                 1..7
                       mol_type = protein
                       organism = synthetic construct
SEQUENCE: 183
YDGDRPS                                                                7

SEQ ID NO: 184         moltype = AA  length = 11
FEATURE                Location/Qualifiers
source                 1..11
                       mol_type = protein
                       organism = synthetic construct
SEQUENCE: 184
QVWDTSSDHP V                                                          11

SEQ ID NO: 185         moltype = AA  length = 11
FEATURE                Location/Qualifiers
source                 1..11
                       mol_type = protein
                       organism = synthetic construct
SEQUENCE: 185
GGNNIGSKSV H                                                          11

SEQ ID NO: 186         moltype = AA  length = 7
FEATURE                Location/Qualifiers
source                 1..7
```

-continued

```
                              mol_type = protein
                              organism = synthetic construct
SEQUENCE: 186
YDGDRPS                                                                    7

SEQ ID NO: 187          moltype = AA  length = 11
FEATURE                 Location/Qualifiers
source                  1..11
                        mol_type = protein
                        organism = synthetic construct
SEQUENCE: 187
QVWDTSSDHP V                                                               11

SEQ ID NO: 188          moltype = AA  length = 7
FEATURE                 Location/Qualifiers
source                  1..7
                        mol_type = protein
                        organism = synthetic construct
SEQUENCE: 188
NNIGSKS                                                                    7

SEQ ID NO: 189          moltype =   length =
SEQUENCE: 189
000

SEQ ID NO: 190          moltype = AA  length = 8
FEATURE                 Location/Qualifiers
source                  1..8
                        mol_type = protein
                        organism = synthetic construct
SEQUENCE: 190
WDTSSDHP                                                                   8

SEQ ID NO: 191          moltype = AA  length = 6
FEATURE                 Location/Qualifiers
source                  1..6
                        mol_type = protein
                        organism = synthetic construct
SEQUENCE: 191
NIGSKS                                                                     6

SEQ ID NO: 192          moltype =   length =
SEQUENCE: 192
000

SEQ ID NO: 193          moltype = AA  length = 11
FEATURE                 Location/Qualifiers
source                  1..11
                        mol_type = protein
                        organism = synthetic construct
SEQUENCE: 193
QVWDTSSDHP V                                                               11

SEQ ID NO: 194          moltype = AA  length = 108
FEATURE                 Location/Qualifiers
source                  1..108
                        mol_type = protein
                        organism = synthetic construct
SEQUENCE: 194
SYVLTQPPSV SEAPGKTARI TCGGNNIGSK SVHWYQQKPG QAPVLVIYYD GDRPSGIPER   60
FSGSNSGNTA TLTISRVEAG DEADYYCQVW DTSSDHPVFG GGTKLTVL              108

SEQ ID NO: 195          moltype = DNA  length = 324
FEATURE                 Location/Qualifiers
source                  1..324
                        mol_type = other DNA
                        organism = synthetic construct
SEQUENCE: 195
tcctatgtgc tgactcagcc accctcagtg tcagaggccc caggaaagac ggccaggatt   60
acctgtgggg gaaacaacat tggaagtaaa agtgtgcact ggtaccagca gaagccaggc  120
caggcccctg tgctggtcat ctattatgat ggcgaccggc cctcaggat ccctgagcga  180
ttctctggct ccaactctgg gaacacggcc accctgacca tcagcagggt cgaagccggg  240
gatgaggccg actattactg tcaggtgtgg gatactagta gtgatcaccc ggtgttcggc  300
ggagggacca agctgaccgt ccta                                          324

SEQ ID NO: 196          moltype = AA  length = 214
FEATURE                 Location/Qualifiers
source                  1..214
                        mol_type = protein
```

```
                            organism = synthetic construct
SEQUENCE: 196
SYVLTQPPSV SEAPGKTARI TCGGNNIGSK SVHWYQQKPG QAPVLVIYYD GDRPSGIPER    60
FSGSNSGNTA TLTISRVEAG DEADYYCQVW DTSSDHPVFG GGTKLTVLGQ PKAAPSVTLF   120
PPSSEELQAN KATLVCLISD FYPGAVTVAW KADSSPVKAG VETTTPSKQS NNKYAASSYL   180
SLTPEQWKSH RSYSCQVTHE GSTVEKTVAP TECS                               214

SEQ ID NO: 197             moltype = DNA   length = 642
FEATURE                    Location/Qualifiers
source                     1..642
                           mol_type = other DNA
                           organism = synthetic construct
SEQUENCE: 197
tcctatgtgc tgactcagcc accctcagtg tcagaggccc caggaaagac ggccaggatt    60
acctgtgggg gaaacaacat tggaagtaaa agtgtgcact ggtaccagca gaagccaggc   120
caggcccctg tgctggtcat ctattatgat ggcgaccggc cctcagggat ccctgagcga   180
ttctctggct ccaactctgg gaacacggcc accctgacca tcagcagggt cgaagccggg   240
gatgaggccg actattactg tcaggtgtgg gatactagta gtgatcaccc ggtgttcggc   300
ggagggacca agctgaccgt cctaggtcag cccaaggctg ccccctcggt cactctgttc   360
ccgcccctcct ctgaggagct tcaagccaac aaggccacac tggtgtgtct cataagtgac   420
ttctacccgg gagccgtgac agtggcctgg aaggcagata gcagccccgt caaggcggga   480
gtggagacca ccacaccctc caaacaaagc aacaacaagt acgccgccag cagctacctg   540
agcctgaccc ccgagcagtg gaagagccac agaagctaca gctgccaggt cacccacgag   600
ggcagcaccg tggagaaaac cgtggccccc accgagtgca gc                     642

SEQ ID NO: 198             moltype = AA   length = 10
FEATURE                    Location/Qualifiers
source                     1..10
                           mol_type = protein
                           organism = synthetic construct
SEQUENCE: 198
GFTFSGYNMH                                                          10

SEQ ID NO: 199             moltype = AA   length = 17
FEATURE                    Location/Qualifiers
source                     1..17
                           mol_type = protein
                           organism = synthetic construct
SEQUENCE: 199
YISNSGRTIY YADSVKG                                                  17

SEQ ID NO: 200             moltype = AA   length = 14
FEATURE                    Location/Qualifiers
source                     1..14
                           mol_type = protein
                           organism = synthetic construct
SEQUENCE: 200
DRDPQWLGND ALQI                                                     14

SEQ ID NO: 201             moltype = AA   length = 5
FEATURE                    Location/Qualifiers
source                     1..5
                           mol_type = protein
                           organism = synthetic construct
SEQUENCE: 201
GYNMH                                                               5

SEQ ID NO: 202             moltype = AA   length = 17
FEATURE                    Location/Qualifiers
source                     1..17
                           mol_type = protein
                           organism = synthetic construct
SEQUENCE: 202
YISNSGRTIY YADSVKG                                                  17

SEQ ID NO: 203             moltype = AA   length = 14
FEATURE                    Location/Qualifiers
source                     1..14
                           mol_type = protein
                           organism = synthetic construct
SEQUENCE: 203
DRDPQWLGND ALQI                                                     14

SEQ ID NO: 204             moltype = AA   length = 7
FEATURE                    Location/Qualifiers
source                     1..7
                           mol_type = protein
                           organism = synthetic construct
SEQUENCE: 204
```

-continued

```
GFTFSGY                                                        7

SEQ ID NO: 205        moltype = AA  length = 6
FEATURE               Location/Qualifiers
source                1..6
                      mol_type = protein
                      organism = synthetic construct
SEQUENCE: 205
SNSGRT                                                         6

SEQ ID NO: 206        moltype = AA  length = 14
FEATURE               Location/Qualifiers
source                1..14
                      mol_type = protein
                      organism = synthetic construct
SEQUENCE: 206
DRDPQWLGND ALQI                                               14

SEQ ID NO: 207        moltype = AA  length = 8
FEATURE               Location/Qualifiers
source                1..8
                      mol_type = protein
                      organism = synthetic construct
SEQUENCE: 207
GFTFSGYN                                                       8

SEQ ID NO: 208        moltype = AA  length = 8
FEATURE               Location/Qualifiers
source                1..8
                      mol_type = protein
                      organism = synthetic construct
SEQUENCE: 208
ISNSGRTI                                                       8

SEQ ID NO: 209        moltype = AA  length = 16
FEATURE               Location/Qualifiers
source                1..16
                      mol_type = protein
                      organism = synthetic construct
SEQUENCE: 209
ARDRDPQWLG NDALQI                                             16

SEQ ID NO: 210        moltype = AA  length = 123
FEATURE               Location/Qualifiers
source                1..123
                      mol_type = protein
                      organism = synthetic construct
SEQUENCE: 210
QVQLVESGGG LVQPGGSLRL SCVASGFTFS GYNMHWVRQA PGKGLEWVSY ISNSGRTIYY   60
ADSVKGRFTL SRDNAKNSLY LQMNSLRAED TAVYFCARDR DPQWLGNDAL QIWGQGTMVT  120
VSS                                                              123

SEQ ID NO: 211        moltype = DNA  length = 369
FEATURE               Location/Qualifiers
source                1..369
                      mol_type = other DNA
                      organism = synthetic construct
SEQUENCE: 211
caggtgcagc tggtggagtc tgggggaggc ttggtacagc ctggggggtc cctgaggctc   60
tcctgtgtag cctctggatt caccttcagt ggctataaca tgcactgggt ccgccaggct  120
ccagggaagg ggctggagtg ggtctcatac attagtaata gtggtagaac catatactac  180
gcagactctg tgaagggccg attcaccctg tccagagaca acgccaagaa ctcactgtat  240
ctgcagatga acagcctgag agccgaggac acggctgtct attttgtgc gagagatcgg  300
gatccccagt ggctgggaaa tgatgctctt caaatctggg gccaagggac aatggtcacc  360
gtctcttca                                                        369

SEQ ID NO: 212        moltype = AA  length = 453
FEATURE               Location/Qualifiers
source                1..453
                      mol_type = protein
                      organism = synthetic construct
SEQUENCE: 212
QVQLVESGGG LVQPGGSLRL SCVASGFTFS GYNMHWVRQA PGKGLEWVSY ISNSGRTIYY   60
ADSVKGRFTL SRDNAKNSLY LQMNSLRAED TAVYFCARDR DPQWLGNDAL QIWGQGTMVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKR VEPKSCDKTH TCPPCPAPEL  240
LGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
REEMTKNQVS LTCLVKGFYP SDIAVEWESN GQPENNYKTT PPVLDSDGSF FLYSKLTVDK  420
```

SRWQQGNVFS CSVMHEALHN HYTQKSLSLS PGK                                    453

SEQ ID NO: 213          moltype = DNA   length = 1359
FEATURE                 Location/Qualifiers
source                  1..1359
                        mol_type = other DNA
                        organism = synthetic construct
SEQUENCE: 213
caggtgcagc tggtggagtc tggggggaggc ttggtacagc ctggggggtc cctgaggctc  60
tcctgtgtag cctctggatt caccttcagt ggctataaca tgcactgggt ccgccaggct  120
ccagggaagg ggctggagtg ggtctctac attagtaata gtggtagaac catatactac  180
gcagactctg tgaagggccg attcaccctg tccagagaca acgccaagaa ctcactgtat  240
ctgcagatga acagcctgag agccgaggac acggctgtct atttttgtgc gagagatcgg  300
gatccccagt ggctgggaaa tgatgctctt caaatctggg gccaagggac aatggtcacc  360
gtctcttcag cctccaccaa gggcccatcg gtcttccccc tggcaccctc ctccaagagc  420
acctctgggg gcacagcggc cctgggctgc ctggtcaagg actacttccc cgaaccggtg  480
acggtgtcgt ggaactcagg cgccctgacc agcggcgtgc acaccttccc ggctgtccta  540
cagtcctcag gactctactc cctcagcagc gtggtgaccg tgccctccag cagcttgggc  600
acccagacct acatctgcaa cgtgaatcac aagcccagca acaccaaggt ggacaagaga  660
gtggagccca gagctgcga caagacccac acctgccccc cctgcccagc cccagagctg  720
ctgggcggac cctccgtgtt cctgttcccc cccaagccca aggacaccct gatgatcagc  780
aggacccccg aggtgacctg cgtggtggtg gacgtgagcc acgaggacc gagggtgaag  840
ttcaactggt acgtggacgg cgtggaggtg cacaacgcca agaccaagcc cagagaggag  900
cagtacaaca gcacctacag ggtggtgtcc gtgctgaccg tgctgcacca ggactggctg  960
aacggcaagg aatacaagtg caaggtctcc aacaaggccc tgccagcccc catcgaaaag  1020
accatcagca aggccaaggg ccagccacgg gagccccagg tgtacaccct gcccccctcc  1080
cgggaggaga tgaccaagaa ccaggtgtcc ctgacctgtc tggtgaaggg cttctacccc  1140
agcgacatcg ccgtggagtg ggagagcaac ggccagcccg agaacaacta caagaccacc  1200
cccccagtgc tggacagcga cggcagcttc ttcctgtaca gcaagctgac cgtggacaag  1260
tccaggtggc agcagggcaa cgtgttcagc tgcagcgtga tgcacgaggc cctgcacaac  1320
cactacaccc agaagagcct gagcctgtcc cccggcaag                          1359

SEQ ID NO: 214          moltype = AA   length = 12
FEATURE                 Location/Qualifiers
source                  1..12
                        mol_type = protein
                        organism = synthetic construct
SEQUENCE: 214
RASQSVSSGY LA                                                          12

SEQ ID NO: 215          moltype = AA   length = 7
FEATURE                 Location/Qualifiers
source                  1..7
                        mol_type = protein
                        organism = synthetic construct
SEQUENCE: 215
GASSRAT                                                                7

SEQ ID NO: 216          moltype = AA   length = 9
FEATURE                 Location/Qualifiers
source                  1..9
                        mol_type = protein
                        organism = synthetic construct
SEQUENCE: 216
QQYGTSRKT                                                              9

SEQ ID NO: 217          moltype = AA   length = 12
FEATURE                 Location/Qualifiers
source                  1..12
                        mol_type = protein
                        organism = synthetic construct
SEQUENCE: 217
RASQSVSSGY LA                                                          12

SEQ ID NO: 218          moltype = AA   length = 7
FEATURE                 Location/Qualifiers
source                  1..7
                        mol_type = protein
                        organism = synthetic construct
SEQUENCE: 218
GASSRAT                                                                7

SEQ ID NO: 219          moltype = AA   length = 9
FEATURE                 Location/Qualifiers
source                  1..9
                        mol_type = protein
                        organism = synthetic construct
SEQUENCE: 219
QQYGTSRKT                                                              9

```
SEQ ID NO: 220          moltype = AA   length = 8
FEATURE                 Location/Qualifiers
source                  1..8
                        mol_type = protein
                        organism = synthetic construct
SEQUENCE: 220
SQSVSSGY                                                                  8

SEQ ID NO: 221          moltype =    length =
SEQUENCE: 221
000

SEQ ID NO: 222          moltype = AA   length = 6
FEATURE                 Location/Qualifiers
source                  1..6
                        mol_type = protein
                        organism = synthetic construct
SEQUENCE: 222
YGTSRK                                                                    6

SEQ ID NO: 223          moltype = AA   length = 7
FEATURE                 Location/Qualifiers
source                  1..7
                        mol_type = protein
                        organism = synthetic construct
SEQUENCE: 223
QSVSSGY                                                                   7

SEQ ID NO: 224          moltype =    length =
SEQUENCE: 224
000

SEQ ID NO: 225          moltype = AA   length = 9
FEATURE                 Location/Qualifiers
source                  1..9
                        mol_type = protein
                        organism = synthetic construct
SEQUENCE: 225
QQYGTSRKT                                                                 9

SEQ ID NO: 226          moltype = AA   length = 108
FEATURE                 Location/Qualifiers
source                  1..108
                        mol_type = protein
                        organism = synthetic construct
SEQUENCE: 226
EIVLTQSPGT LSLSPGERAT LSCRASQSVS SGYLAWYQQK PGQAPRLLIY GASSRATGIP   60
DRFSGSGSGT DFTLTISRLE PEDFAVYYCQ QYGTSRKTFG QGTKVEIK              108

SEQ ID NO: 227          moltype = DNA   length = 324
FEATURE                 Location/Qualifiers
source                  1..324
                        mol_type = other DNA
                        organism = synthetic construct
SEQUENCE: 227
gaaattgttt tgacgcagtc tccaggcacc ctgtctttgt ctccagggga aagagccacc   60
ctctcctgca gggccagtca gagtgttagc agtggctact tagcctggta tcagcagaaa  120
cctggccagg ctcccaggct cctcatctat ggtgcatcca gcagggccac tggcatccca  180
gacaggttca gtggcagtgg gtctgggaca gacttcactc tcaccatcag cagactggag  240
cctgaagatt ttgcagtgta ttattgtcag cagtatggta cctcacgtaa gacgttcggc  300
caagggacca aggtggaaat caaa                                          324

SEQ ID NO: 228          moltype = AA   length = 215
FEATURE                 Location/Qualifiers
source                  1..215
                        mol_type = protein
                        organism = synthetic construct
SEQUENCE: 228
EIVLTQSPGT LSLSPGERAT LSCRASQSVS SGYLAWYQQK PGQAPRLLIY GASSRATGIP   60
DRFSGSGSGT DFTLTISRLE PEDFAVYYCQ QYGTSRKTFG QGTKVEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                             215

SEQ ID NO: 229          moltype = DNA   length = 645
FEATURE                 Location/Qualifiers
source                  1..645
                        mol_type = other DNA
                        organism = synthetic construct
```

```
SEQUENCE: 229
gaaattgttt tgacgcagtc tccaggcacc ctgtctttgt ctccagggga aagagccacc    60
ctctcctgca gggccagtca gagtgttagc agtggctact tagcctggta tcagcagaaa   120
cctggccagg ctcccaggct ccctcatctat ggtgcatcca gcagggccac tggcatccca   180
gacaggttca gtggcagtgg gtctgggaca gacttcactc tcaccatcag cagactggag   240
cctgaagatt ttgcagtgta ttattgtcag cagtatggta cctcacgtaa gacgttcggc   300
caagggacca aggtggaaat caaacgaact gtggctgcac catctgtctt catcttcccg   360
ccatctgatg agcagttgaa atctggaact gcctctgttg tgtgcctgct gaataacttc   420
tatcccagag aggccaaagt acagtggaag gtggacaacg ccctgcagag cggcaacagc   480
caggagagcg tcaccgagca ggacagcaag gactccacct acagcctgag cagcaccctg   540
accctgagca aggccgacta cgagaagcat aaggtgtacg cctgcgaggt gacccaccag   600
ggcctgtcca gccccgtgac caagagcttc aacaggggcg agtgc              645

SEQ ID NO: 230        moltype = AA  length = 10
FEATURE               Location/Qualifiers
source                1..10
                      mol_type = protein
                      organism = synthetic construct
SEQUENCE: 230
GGSISGYYWS                                                          10

SEQ ID NO: 231        moltype = AA  length = 16
FEATURE               Location/Qualifiers
source                1..16
                      mol_type = protein
                      organism = synthetic construct
SEQUENCE: 231
LIYESGSANY NPSLKS                                                   16

SEQ ID NO: 232        moltype = AA  length = 11
FEATURE               Location/Qualifiers
source                1..11
                      mol_type = protein
                      organism = synthetic construct
SEQUENCE: 232
RVRGWSYGMD V                                                        11

SEQ ID NO: 233        moltype = AA  length = 5
FEATURE               Location/Qualifiers
source                1..5
                      mol_type = protein
                      organism = synthetic construct
SEQUENCE: 233
GYYWS                                                                5

SEQ ID NO: 234        moltype = AA  length = 16
FEATURE               Location/Qualifiers
source                1..16
                      mol_type = protein
                      organism = synthetic construct
SEQUENCE: 234
LIYESGSANY NPSLKS                                                   16

SEQ ID NO: 235        moltype = AA  length = 11
FEATURE               Location/Qualifiers
source                1..11
                      mol_type = protein
                      organism = synthetic construct
SEQUENCE: 235
RVRGWSYGMD V                                                        11

SEQ ID NO: 236        moltype = AA  length = 7
FEATURE               Location/Qualifiers
source                1..7
                      mol_type = protein
                      organism = synthetic construct
SEQUENCE: 236
GGSISGY                                                              7

SEQ ID NO: 237        moltype = AA  length = 5
FEATURE               Location/Qualifiers
source                1..5
                      mol_type = protein
                      organism = synthetic construct
SEQUENCE: 237
YESGS                                                                5

SEQ ID NO: 238        moltype = AA  length = 11
FEATURE               Location/Qualifiers
```

```
source                  1..11
                        mol_type = protein
                        organism = synthetic construct
SEQUENCE: 238
RVRGWSYGMD V                                                                11

SEQ ID NO: 239          moltype = AA   length = 8
FEATURE                 Location/Qualifiers
source                  1..8
                        mol_type = protein
                        organism = synthetic construct
SEQUENCE: 239
GGSISGYY                                                                    8

SEQ ID NO: 240          moltype = AA   length = 7
FEATURE                 Location/Qualifiers
source                  1..7
                        mol_type = protein
                        organism = synthetic construct
SEQUENCE: 240
IYESGSA                                                                     7

SEQ ID NO: 241          moltype = AA   length = 13
FEATURE                 Location/Qualifiers
source                  1..13
                        mol_type = protein
                        organism = synthetic construct
SEQUENCE: 241
ARRVRGWSYG MDV                                                              13

SEQ ID NO: 242          moltype = AA   length = 119
FEATURE                 Location/Qualifiers
source                  1..119
                        mol_type = protein
                        organism = synthetic construct
SEQUENCE: 242
QVQLVQSGPG LVKPSETLSL TCSVSGGSIS GYYWSWIRQP PGKGLEWIGL IYESGSANYN  60
PSLKSRVTIS LDTSKNQFSL KLKSVTAADT AVYYCARRVR GWSYGMDVWG QGTTVAVSS   119

SEQ ID NO: 243          moltype = DNA   length = 357
FEATURE                 Location/Qualifiers
source                  1..357
                        mol_type = other DNA
                        organism = synthetic construct
SEQUENCE: 243
caggtgcagc tggtgcagtc tggcccagga ctggtgaagc cttcggagac cctgtccctc  60
acctgcagtg tctctggtgg ctccatcagt ggttactact ggagctggat ccggcagccc  120
ccagggaagg gactggagtg gatcggctta atttatgaga gtgggagcgc caactacaat  180
ccctccctca agagtcgagt caccatatcg ctagacacgt ccaagaatca gttctccctg  240
aagctgaagt ctgtgaccgc cgcggacacg gccgtgtatt actgtgcgag acgagtccgt  300
ggctggtctt acggtatgga cgtctggggc caagggacca cggtcgccgt ctcctca     357

SEQ ID NO: 244          moltype = AA   length = 449
FEATURE                 Location/Qualifiers
source                  1..449
                        mol_type = protein
                        organism = synthetic construct
SEQUENCE: 244
QVQLVQSGPG LVKPSETLSL TCSVSGGSIS GYYWSWIRQP PGKGLEWIGL IYESGSANYN  60
PSLKSRVTIS LDTSKNQFSL KLKSVTAADT AVYYCARRVR GWSYGMDVWG QGTTVAVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKRVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                     449

SEQ ID NO: 245          moltype = DNA   length = 1347
FEATURE                 Location/Qualifiers
source                  1..1347
                        mol_type = other DNA
                        organism = synthetic construct
SEQUENCE: 245
caggtgcagc tggtgcagtc tggcccagga ctggtgaagc cttcggagac cctgtccctc  60
acctgcagtg tctctggtgg ctccatcagt ggttactact ggagctggat ccggcagccc  120
ccagggaagg gactggagtg gatcggctta atttatgaga gtgggagcgc caactacaat  180
ccctccctca agagtcgagt caccatatcg ctagacacgt ccaagaatca gttctccctg  240
aagctgaagt ctgtgaccgc cgcggacacg gccgtgtatt actgtgcgag acgagtccgt  300
ggctggtctt acggtatgga cgtctggggc caagggacca cggtcgccgt ctcctcagcc  360
```

-continued

```
tccaccaagg gcccatcggt cttccccctg gcaccctcct ccaagagcac ctctgggggc   420
acagcggccc tgggctgcct ggtcaaggac tacttccccg aaccggtgac ggtgtcgtgg   480
aactcaggcg ccctgaccag cggcgtgcac accttcccgg ctgtcctaca gtcctcagga   540
ctctactccc tcagcagcgt ggtgaccgtg ccctccagca gcttgggcac ccagacctac   600
atctgcaacg tgaaccacaa gcccagcaac accaaggtg acaagagagt ggagcccaag   660
agctgcgaca gacccacac ctgcccccc tgcccagccc cagagctgct gggcggaccc   720
tccgtgttcc tgttcccccc caagcccaag gacaccctga tgatcagcag gacccccgag   780
gtgacctgcg tggtggtgga cgtgagccac gaggacccag aggtgaagtt caactggtac   840
gtggacggcg tggaggtgca caacgccaag accaagccca gagaggagca gtacaacagc   900
acctacaggg tggtgtccgt gctgaccgtg ctgcaccagg actggctgaa cggcaaggaa   960
tacaagtgca aggtctccaa caaggccctg ccagccccca tcgaaaagac catcagcaag   1020
gccaagggcc agccacggga gccccaggtg tacaccctgc cccctcccg ggaggagatg   1080
accaagaacc aggtgtccct gacctgtctg gtgaagggct tctaccccag cgacatcgcc   1140
gtggagtggg agagcaacgg ccagcccgag aacaactaca agacaccccc cccagtgctg   1200
gacagcgacg gcagcttctt cctgtacagc aagctgaccg tggacaagtc caggtggcag   1260
cagggcaacg tgttcagctg cagcgtgatg cacgaggccc tgcacaacca ctacacccag   1320
aagagcctga gcctgtcccc cggcaag   1347
```

```
SEQ ID NO: 246        moltype = AA   length = 12
FEATURE               Location/Qualifiers
source                1..12
                      mol_type = protein
                      organism = synthetic construct
SEQUENCE: 246
RASQILSSSF LA                                              12

SEQ ID NO: 247        moltype = AA   length = 7
FEATURE               Location/Qualifiers
source                1..7
                      mol_type = protein
                      organism = synthetic construct
SEQUENCE: 247
AASSRAT                                                    7

SEQ ID NO: 248        moltype = AA   length = 10
FEATURE               Location/Qualifiers
source                1..10
                      mol_type = protein
                      organism = synthetic construct
SEQUENCE: 248
QHYGSSPPWT                                                 10

SEQ ID NO: 249        moltype = AA   length = 12
FEATURE               Location/Qualifiers
source                1..12
                      mol_type = protein
                      organism = synthetic construct
SEQUENCE: 249
RASQILSSSF LA                                              12

SEQ ID NO: 250        moltype = AA   length = 7
FEATURE               Location/Qualifiers
source                1..7
                      mol_type = protein
                      organism = synthetic construct
SEQUENCE: 250
AASSRAT                                                    7

SEQ ID NO: 251        moltype = AA   length = 10
FEATURE               Location/Qualifiers
source                1..10
                      mol_type = protein
                      organism = synthetic construct
SEQUENCE: 251
QHYGSSPPWT                                                 10

SEQ ID NO: 252        moltype = AA   length = 8
FEATURE               Location/Qualifiers
source                1..8
                      mol_type = protein
                      organism = synthetic construct
SEQUENCE: 252
SQILSSSF                                                   8

SEQ ID NO: 253        moltype =    length =
SEQUENCE: 253
000

SEQ ID NO: 254        moltype = AA   length = 7
```

```
FEATURE              Location/Qualifiers
source               1..7
                     mol_type = protein
                     organism = synthetic construct
SEQUENCE: 254
YGSSPPW                                                             7

SEQ ID NO: 255       moltype = AA  length = 7
FEATURE              Location/Qualifiers
source               1..7
                     mol_type = protein
                     organism = synthetic construct
SEQUENCE: 255
QILSSSF                                                             7

SEQ ID NO: 256       moltype =    length =
SEQUENCE: 256
000

SEQ ID NO: 257       moltype = AA  length = 10
FEATURE              Location/Qualifiers
source               1..10
                     mol_type = protein
                     organism = synthetic construct
SEQUENCE: 257
QHYGSSPPWT                                                          10

SEQ ID NO: 258       moltype = AA  length = 109
FEATURE              Location/Qualifiers
source               1..109
                     mol_type = protein
                     organism = synthetic construct
SEQUENCE: 258
DIVLTQSPGT LSLSPGETAT LSCRASQILS SSFLAWFQQI PGQAPRLLIY AASSRATGIP  60
DRFSGSGSGT DFSLTISRLE PEDFAVYYCQ HYGSSPPWTF GQGTKVEIK             109

SEQ ID NO: 259       moltype = DNA  length = 327
FEATURE              Location/Qualifiers
source               1..327
                     mol_type = other DNA
                     organism = synthetic construct
SEQUENCE: 259
gatattgtgt tgacgcagtc tccaggcacc ctgtctttgt ctccagggga gacagccacc  60
ctctcctgca gggccagtca gattcttagc agcagcttct tagcctggtt ccagcagata 120
cctggccagg ctcccagact cctcatctat gctgcatcca gcagggccac tggcatccca 180
gacaggttca gtggcagtgg gtctgggaca gacttcagtc tcaccatcag cagactggag 240
cctgaagatt ttgcagtgta ttactgtcag cactatggta gctcacctcc ttggacgttc 300
ggccaaggga ccaaggtgga aatcaaa                                     327

SEQ ID NO: 260       moltype = AA  length = 216
FEATURE              Location/Qualifiers
source               1..216
                     mol_type = protein
                     organism = synthetic construct
SEQUENCE: 260
DIVLTQSPGT LSLSPGETAT LSCRASQILS SSFLAWFQQI PGQAPRLLIY AASSRATGIP  60
DRFSGSGSGT DFSLTISRLE PEDFAVYYCQ HYGSSPPWTF GQGTKVEIKR TVAAPSVFIF 120
PPSDEQLKSG TASVVCLLNN FYPREAKVQW KVDNALQSGN SQESVTEQDS KDSTYSLSST 180
LTLSKADYEK HKVYACEVTH QGLSSPVTKS FNRGEC                           216

SEQ ID NO: 261       moltype = DNA  length = 648
FEATURE              Location/Qualifiers
source               1..648
                     mol_type = other DNA
                     organism = synthetic construct
SEQUENCE: 261
gatattgtgt tgacgcagtc tccaggcacc ctgtctttgt ctccagggga gacagccacc  60
ctctcctgca gggccagtca gattcttagc agcagcttct tagcctggtt ccagcagata 120
cctggccagg ctcccagact cctcatctat gctgcatcca gcagggccac tggcatccca 180
gacaggttca gtggcagtgg gtctgggaca gacttcagtc tcaccatcag cagactggag 240
cctgaagatt ttgcagtgta ttactgtcag cactatggta gctcacctcc ttggacgttc 300
ggccaaggga ccaaggtgga aatcaaacga actgtggctg caccatctgt cttcatcttc 360
ccgccatctg atgagcagtt gaaatctgga actgcctctg ttgtgtgcct gctgaataac 420
ttctatccca gagaggccaa agtacagtgg aaggtggaca acgccctgca gagcggcaac 480
agccaggaga gcgtcaccga gcaggacagc aaggactcca cctacagcct gagcagcacc 540
ctgaccctga gcaaggccga ctacgagaag cataaggtgt acgcctgcga ggtgacccac 600
cagggcctgt ccagccccgt gaccaagagc ttcaacaggg gcgagtgc              648

SEQ ID NO: 262       moltype = AA  length = 10
```

-continued

```
FEATURE            Location/Qualifiers
source             1..10
                   mol_type = protein
                   organism = synthetic construct
SEQUENCE: 262
GYTFTSYDII                                                    10

SEQ ID NO: 263     moltype = AA  length = 17
FEATURE            Location/Qualifiers
source             1..17
                   mol_type = protein
                   organism = synthetic construct
SEQUENCE: 263
RMNPTGGNTD YVPKFQG                                            17

SEQ ID NO: 264     moltype = AA  length = 12
FEATURE            Location/Qualifiers
source             1..12
                   mol_type = protein
                   organism = synthetic construct
SEQUENCE: 264
GVKSLGVSEI DY                                                 12

SEQ ID NO: 265     moltype = AA  length = 5
FEATURE            Location/Qualifiers
source             1..5
                   mol_type = protein
                   organism = synthetic construct
SEQUENCE: 265
SYDII                                                         5

SEQ ID NO: 266     moltype = AA  length = 17
FEATURE            Location/Qualifiers
source             1..17
                   mol_type = protein
                   organism = synthetic construct
SEQUENCE: 266
RMNPTGGNTD YVPKFQG                                            17

SEQ ID NO: 267     moltype = AA  length = 12
FEATURE            Location/Qualifiers
source             1..12
                   mol_type = protein
                   organism = synthetic construct
SEQUENCE: 267
GVKSLGVSEI DY                                                 12

SEQ ID NO: 268     moltype = AA  length = 7
FEATURE            Location/Qualifiers
source             1..7
                   mol_type = protein
                   organism = synthetic construct
SEQUENCE: 268
GYTFTSY                                                       7

SEQ ID NO: 269     moltype = AA  length = 6
FEATURE            Location/Qualifiers
source             1..6
                   mol_type = protein
                   organism = synthetic construct
SEQUENCE: 269
NPTGGN                                                        6

SEQ ID NO: 270     moltype = AA  length = 12
FEATURE            Location/Qualifiers
source             1..12
                   mol_type = protein
                   organism = synthetic construct
SEQUENCE: 270
GVKSLGVSEI DY                                                 12

SEQ ID NO: 271     moltype = AA  length = 8
FEATURE            Location/Qualifiers
source             1..8
                   mol_type = protein
                   organism = synthetic construct
SEQUENCE: 271
GYTFTSYD                                                      8
```

-continued

```
SEQ ID NO: 272        moltype = AA   length = 8
FEATURE               Location/Qualifiers
source                1..8
                      mol_type = protein
                      organism = synthetic construct
SEQUENCE: 272
MNPTGGNT                                                                    8

SEQ ID NO: 273        moltype = AA   length = 14
FEATURE               Location/Qualifiers
source                1..14
                      mol_type = protein
                      organism = synthetic construct
SEQUENCE: 273
ARGVKSLGVS EIDY                                                             14

SEQ ID NO: 274        moltype = AA   length = 121
FEATURE               Location/Qualifiers
source                1..121
                      mol_type = protein
                      organism = synthetic construct
SEQUENCE: 274
QVQLVQSGAE VKKPGASVKV SCKASGYTFT SYDIIWVRQA TGQGLEWMGR MNPTGGNTDY   60
VPKFQGRVTM TRDISLSTAY MELRSLTSED TAVFYCARGV KSLGVSEIDY WGQGTLVTVS   120
S                                                                          121

SEQ ID NO: 275        moltype = DNA   length = 363
FEATURE               Location/Qualifiers
source                1..363
                      mol_type = other DNA
                      organism = synthetic construct
SEQUENCE: 275
caggtgcagc tggtgcagtc tggggctgag gtgaagaaac ctggggcctc agtgaaggtc   60
tcctgcaagg cttctggata caccttcacc agttatgata tcatctgggt gcgacaggcc   120
actggacaag ggcttgagtg gatgggaagg atgaaccca ccggtggtaa cacagactat    180
gtaccgaagt tccagggcag agtcaccatg accaggaca tctccttaag tacagcctac    240
atggagctgc gcagcctgac atctgaggac acggccgtgt tttactgtgc gagaggcgta   300
aagtctttag gagtttcgga aattgactac tggggccagg gaaccctggt caccgtctcc   360
tca                                                                        363

SEQ ID NO: 276        moltype = AA   length = 451
FEATURE               Location/Qualifiers
source                1..451
                      mol_type = protein
                      organism = synthetic construct
SEQUENCE: 276
QVQLVQSGAE VKKPGASVKV SCKASGYTFT SYDIIWVRQA TGQGLEWMGR MNPTGGNTDY   60
VPKFQGRVTM TRDISLSTAY MELRSLTSED TAVFYCARGV KSLGVSEIDY WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKRVE PKSCDKTHTC PPCPAPELLG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVYTLPPSRE   360
EMTKNQVSLT CLVKGFYPSD IAVEWESNGQ PENNYKTTPP VLDSDGSFFL YSKLTVDKSR   420
WQQGNVFSCS VMHEALHNHY TQKSLSLSPG K                                          451

SEQ ID NO: 277        moltype = DNA   length = 1353
FEATURE               Location/Qualifiers
source                1..1353
                      mol_type = other DNA
                      organism = synthetic construct
SEQUENCE: 277
caggtgcagc tggtgcagtc tggggctgag gtgaagaaac ctggggcctc agtgaaggtc   60
tcctgcaagg cttctggata caccttcacc agttatgata tcatctgggt gcgacaggcc   120
actggacaag ggcttgagtg gatgggaagg atgaaccca ccggtggtaa cacagactat    180
gtaccgaagt tccagggcag agtcaccatg accaggaca tctccttaag tacagcctac    240
atggagctgc gcagcctgac atctgaggac acggccgtgt tttactgtgc gagaggcgta   300
aagtctttag gagtttcgga aattgactac tggggccagg gaaccctggt caccgtctcc   360
tcagcctcca ccaagggccc atcggtcttc ccctggcac cctcctccaa gagcacctct    420
gggggcacag cggccctggg ctgcctggtc aaggactact ccccgaacc ggtgacggtg     480
tcgtggaact caggcgccct gaccagcggc gtgcacacct tcccggctgt cctacagtcc    540
tcaggactct actccctcag cagcgtggtg accgtgccct ccagcagctt gggcacccag    600
acctacatct gcaacgtgaa ccacaagccc agcaacacca aggtggacaa gagagttgag    660
cccaagagct gcgacaagac ccacacctgc cccccctgcc cagccccaga gctgctgggc    720
ggaccctcg tgttcctgtt cccccccaag cccaaggaca ccctcatgat cagcaggacc     780
cccgaggtga cctgcgtggt ggtggacgtg agccacgagg acccagaggt gaagttcaac    840
tggtacgtgg acggcgtgga ggtgcacaac gccaagacca gcccagaga ggagcagtac     900
aacagcacct acaggtggtg gtccgtgctg accgtgctgc accaggactg gctgaacggc    960
aaggaataca agtgcaaggt ctccaacaag gccctgccag ccccatcga aaagaccatc     1020
agcaaggcca agggccagcc acgggagccc caggtgtaca ccctgccccc ctcccgggag   1080
```

-continued

```
gagatgacca agaaccaggt gtccctgacc tgtctggtga agggcttcta ccccagcgac   1140
atcgccgtgg agtgggagag caacggccag cccgagaaca actacaagac cacccccca    1200
gtgctggaca gcgacggcag cttcttcctg tacagcaagc tgaccgtgga caagtccagg   1260
tggcagcagg gcaacgtgtt cagctgcagc gtgatgcacg aggccctgca caaccactac   1320
acccagaaga gcctgagcct gtccccggc  aag                                1353

SEQ ID NO: 278            moltype = AA   length = 13
FEATURE                   Location/Qualifiers
source                    1..13
                          mol_type = protein
                          organism = synthetic construct SEQUENCE: 278
SGSTSNIANN YVL                                                       13

SEQ ID NO: 279            moltype = AA   length = 7
FEATURE                   Location/Qualifiers
source                    1..7
                          mol_type = protein
                          organism = synthetic construct SEQUENCE: 279
DNNKRPS                                                              7

SEQ ID NO: 280            moltype = AA   length = 11
FEATURE                   Location/Qualifiers
source                    1..11
                          mol_type = protein
                          organism = synthetic construct SEQUENCE: 280
GTWDNSLSVG V                                                         11

SEQ ID NO: 281            moltype = AA   length = 13
FEATURE                   Location/Qualifiers
source                    1..13
                          mol_type = protein
                          organism = synthetic construct SEQUENCE: 281
SGSTSNIANN YVL                                                       13

SEQ ID NO: 282            moltype = AA   length = 7
FEATURE                   Location/Qualifiers
source                    1..7
                          mol_type = protein
                          organism = synthetic construct SEQUENCE: 282
DNNKRPS                                                              7

SEQ ID NO: 283            moltype = AA   length = 11
FEATURE                   Location/Qualifiers
source                    1..11
                          mol_type = protein
                          organism = synthetic construct SEQUENCE: 283
GTWDNSLSVG V                                                         11

SEQ ID NO: 284            moltype = AA   length = 9
FEATURE                   Location/Qualifiers
source                    1..9
                          mol_type = protein
                          organism = synthetic construct SEQUENCE: 284
STSNIANNY                                                            9

SEQ ID NO: 285            moltype =    length =
SEQUENCE: 285
000

SEQ ID NO: 286            moltype = AA   length = 8
FEATURE                   Location/Qualifiers
source                    1..8
                          mol_type = protein
                          organism = synthetic construct SEQUENCE: 286
WDNSLSVG                                                             8

SEQ ID NO: 287            moltype = AA   length = 8
FEATURE                   Location/Qualifiers
source                    1..8
                          mol_type = protein
                          organism = synthetic construct
```

```
SEQUENCE: 287
TSNIANNY                                                              8

SEQ ID NO: 288          moltype =    length =
SEQUENCE: 288
000

SEQ ID NO: 289          moltype = AA   length = 11
FEATURE                 Location/Qualifiers
source                  1..11
                        mol_type = protein
                        organism = synthetic construct
SEQUENCE: 289
GTWDNSLSVG V                                                          11

SEQ ID NO: 290          moltype = AA   length = 110
FEATURE                 Location/Qualifiers
source                  1..110
                        mol_type = protein
                        organism = synthetic construct
SEQUENCE: 290
QSALTQPPSV SAAPGQKVTI SCSGSTSNIA NNYVLWYQQL PGTAPKLLIY DNNKRPSGIP     60
DRFSGSKSGT SATLGITGLQ TADEADYYCG TWDNSLSVGV FGGGTKLTVL              110

SEQ ID NO: 291          moltype = DNA   length = 330
FEATURE                 Location/Qualifiers
source                  1..330
                        mol_type = other DNA
                        organism = synthetic construct
SEQUENCE: 291
cagtctgccc tgactcagcc tccctcagtg tctgcggccc caggacagaa ggtcaccatc     60
tcctgctctg gaagcacctc caacattgcg aataattatg tcttatggta ccagcaactc    120
ccaggaacag cccccaaact cctcatttat gacaataata agcgaccctc agggattcct    180
gaccgattct ccggctccaa gtctggcacg tcagccaccc tgggcatcac cggactccag    240
actgcggacg aggccgatta ctactgcgga acatgggata acagcctgag tgttggggtg    300
ttcggcggcg ggaccaagtt gaccgtccta                                     330

SEQ ID NO: 292          moltype = AA   length = 216
FEATURE                 Location/Qualifiers
source                  1..216
                        mol_type = protein
                        organism = synthetic construct
SEQUENCE: 292
QSALTQPPSV SAAPGQKVTI SCSGSTSNIA NNYVLWYQQL PGTAPKLLIY DNNKRPSGIP     60
DRFSGSKSGT SATLGITGLQ TADEADYYCG TWDNSLSVGV FGGGTKLTVL GQPKAAPSVT    120
LFPPSSEELQ ANKATLVCLI SDFYPGAVTV AWKADSSPVK AGVETTTPSK QSNNKYAASS    180
YLSLTPEQWK SHRSYSCQVT HEGSTVEKTV APTECS                             216

SEQ ID NO: 293          moltype = DNA   length = 648
FEATURE                 Location/Qualifiers
source                  1..648
                        mol_type = other DNA
                        organism = synthetic construct
SEQUENCE: 293
cagtctgccc tgactcagcc tccctcagtg tctgcggccc caggacagaa ggtcaccatc     60
tcctgctctg gaagcacctc caacattgcg aataattatg tcttatggta ccagcaactc    120
ccaggaacag cccccaaact cctcatttat gacaataata agcgaccctc agggattcct    180
gaccgattct ccggctccaa gtctggcacg tcagccaccc tgggcatcac cggactccag    240
actgcggacg aggccgatta ctactgcgga acatgggata acagcctgag tgttggggtg    300
ttcggcggcg ggaccaagtt gaccgtccta ggtcagccca aggctgcccc ctcggtcact    360
ctgttcccgc cctcctctga ggagcttcaa gccaacaagg ccacactggt gtgtctcata    420
agtgacttct acccgggagc cgtgacagtg gcctggaagg cagatagcag ccccgtcaag    480
gcgggagtgg agaccaccac acctccaaa caaagcaaca caagtacgc cgccagcagc     540
tacctgagcc tgacgcctga gcagtggaag tcccacaaa gctacagctg ccaggtcacc    600
cacgagggca gcaccgtgga gaaaaccgtg gccccaccg agtgcagc                 648

SEQ ID NO: 294          moltype = AA   length = 593
FEATURE                 Location/Qualifiers
source                  1..593
                        mol_type = protein
                        organism = synthetic construct
SEQUENCE: 294
MELGLCWLLL VAILKGVQCE VQLLESGGGL VQPGGSLRLS CAASGFIFRN YGMSWLRQAP     60
GKGLEWVSAI SGSGANTYYT DSVKGRFTIS RDNSKNTLYL QIYSLTAEDT ALYYCAKSKG    120
DGGADAFDVW GQGTLVTVSS GSASAPTLFP LVSCENSPSD TSSVAVGCLA QDFLPDSITF    180
SWKYKNNSDI SSTRGFPSVL RGGKYAATSQ VLLPSKDVMQ GTDEHVVCKV QHPNGNKEKN    240
VPLPVIAELP PKVSVFVPPR DGFFGNPRKS KLICQATGFS PRQIQVSWLR EGKQVGSGVT    300
TDQVQAEAKE SGPTTYKVTS TLTIKESDWL GQSMFTCRVD HRGLTFQQNA SSMCVPDQDT    360
AIRVFAIPPS FASIFLTKST KLTCLVTDLT TYDSVTISWT RQNGEAVKTH TNISESHPNA    420
```

```
TFSAVGEASI CEDDWNSGER FTCTVTHTDL PSPLKQTISR PKGVALHRPD VYLLPPAREQ  480
LNLRESATIT CLVTGFSPAD VFVQWMQRGQ PLSPEKYVTS APMPEPQAPG RYFAHSILTV  540
SEEEWNTGET YTCVVAHEAL PNRVTERTVD KSTGKPTLYN VSLVMSDTAG TCY         593

SEQ ID NO: 295             moltype = AA   length = 233
FEATURE                    Location/Qualifiers
source                     1..233
                           mol_type = protein
                           organism = synthetic construct
SEQUENCE: 295
MRLPAQLLGL LLLWLPGAKC DIRMTQSPST LSASVGDRVT ITCRASQSIS RWLAWYQQKP  60
GKAPKLLIYK ASSLESGVPS RFSGSGSATE FTLTISSLQP DDFATYYCQQ YNSFWTFGQG  120
TKVEIKRTVA APSVFIFPPS DEQLKSGTAS VVCLLNNFYP REAKVQWKVD NALQSGNSQE  180
SVTEQDSKDS TYSLSSTLTL SKADYEKHKV YACEVTHQGL SSPVTKSFNR GEC         233

SEQ ID NO: 296             moltype = AA   length = 600
FEATURE                    Location/Qualifiers
source                     1..600
                           mol_type = protein
                           organism = synthetic construct
SEQUENCE: 296
MELGLCWVFL VALLRGVQCQ VQLVESGGGV VQPGRSLRLS CAASGFTFSS YGMHWVRQAP  60
GKGLEWVAVI WYDGSNKYYA DSVKGRFTIS RDNSKNTLYL QMNSLRAEDT AVYYCARDPL  120
IVVVPAAIYY YYGMDVWGQG TTVTVSSGSA SAPTLFPLVS CENSPSDTSS VAVGCLAQDF  180
LPDSITFSWK YKNNSDISST RGFPSVLRGG KYAATSQVLL PSKDVMQGTD EHVVCKVQHP  240
NGNKEKNVPL PVIAELPPKV SVFVPPRDGF FGNPRKSKLI CQATGFSPRQ IQVSWLREGK  300
QVGSGVTTDQ VQAEAKESGP TTYKVTSTLT IKESDWLGQS MFTCRVDHRG LTFQQNASSM  360
CVPDQDTAIR VFAIPPSFAS IFLTKSTKLT CLVTDLTTYD SVTISWTRQN GEAVKTHTNI  420
SESHPNATFS AVGEASICED DWNSGERFTC TVTHTDLPSP LKQTISRPKG VALHRPDVYL  480
LPPAREQLNL RESATITCLV TGFSPADVFV QWMRGQPLS PEKYVTSAPM PEPQAPGRYF   540
AHSILTVSEE EWNTGETYTC VVAHEALPNR VTERTVDKST GKPTLYNVSL VMSDTAGTCY  600

SEQ ID NO: 297             moltype = AA   length = 236
FEATURE                    Location/Qualifiers
source                     1..236
                           mol_type = protein
                           organism = synthetic construct
SEQUENCE: 297
MDMRVPAQLL GLLLLWLRGA RCDIQMTQSP SSLSASVGDR VTITCRTSQS ISSYLNWYQQ  60
KPGKAPKLLI YAASSLQSGV PSRFSGSGSG TDFTLTISSL QPEDFATYYC QQSYSTPITF  120
GQGTRLEIKR TVAAPSVFIF PPSDEQLKSG TASVVCLLNN FYPREAKVQW KVDNALQSGN  180
SQESVTEQDS KDSTYSLSST LTLSKADYEK HKVYACEVTH QGLSSPVTKS FNRGEC      236

SEQ ID NO: 298             moltype = AA   length = 591
FEATURE                    Location/Qualifiers
source                     1..591
                           mol_type = protein
                           organism = synthetic construct
SEQUENCE: 298
MKHLWFFLLL VAAPRWVLSQ LQLQESGPGL VKPSETLSLT CTVSGGSISS SSYYWGWIRQ  60
PPGKGLEWIG SIYYSGSTYY NPSLKSRVTI SVDTSKNQFS LKLSSVTAAD TAVYYCARLG  120
YYYYMDVWGK GTTVTVSSGS ASAPTLFPLV SCENSPSDTS SVAVGCLAQD FLPDSITFSW  180
KYKNNSDISS TRGFPSVLRG GKYAATSQVL PSKDVMQGT DEHVVCKVQH PNGNKEKNVP   240
LPVIAELPPK VSVFVPPRDG FFGNPRKSKL ICQATGFSPR QIQVSWLREG KQVGSGVTTD  300
QVQAEAKESG PTTYKVTSTL TIKESDWLGQ SMFTCRVDHR GLTFQQNASS MCVPDQDTAI  360
RVFAIPPSFA SIFLTKSTKL TCLVTDLTTY DSVTISWTRQ NGEAVKTHTN ISESHPNATF  420
SAVGEASICE DDWNSGERFT CTVTHTDLPS PLKQTISRPK GVALHRPDVY LLPPAREQLN  480
LRESATITCL VTGFSPADVF VQWMRGQPL SPEKYVTSAP MPEPQAPGRY FAHSILTVSE   540
EEWNTGETYT CVVAHEALPN RVTERTVDKS TGKPTLYNVS LVMSDTAGTC Y           591

SEQ ID NO: 299             moltype = AA   length = 240
FEATURE                    Location/Qualifiers
source                     1..240
                           mol_type = protein
                           organism = synthetic construct
SEQUENCE: 299
MVLQTQVFIS LLLWISGAYG DIVMTQSPDS LAVSLGERAT INCKSSQSVL YSSNNKNYLA  60
WYQQKPGQPP KLLIYWASTR ESGVPDRFSG SGSGTDFTLT ISSLQAEDVA VYYCQQYYST  120
PPTFGGGTKV EIKRTVAAPS VFIFPPSDEQ LKSGTASVVC LLNNFYPREA KVQWKVDNAL  180
QSGNSQESVT EQDSKDSTYS LSSTLTLSKA DYEKHKVYAC EVTHQGLSSP VTKSFNRGEC  240

SEQ ID NO: 300             moltype = AA   length = 592
FEATURE                    Location/Qualifiers
source                     1..592
                           mol_type = protein
                           organism = synthetic construct
SEQUENCE: 300
MEFGLSWVFL VAILKGVQCE VQVVESGGGL VQPGESLRLS CAASGFTFSN YFMHWVRQAP  60
GMGLEWVARI NTDGSVTMYA DSVKGRFTIS RDNAKNTVYL QMNSLRAEDT AVYYCVRPNS  120
```

```
VHDKLLENWG QGTLVTVSSG SASAPTLFPL VSCENSPSDT SSSVAVGCLAQ DFLPDSITFS  180
WKYKNNSDIS STRGFPSVLR GGKYAATSQV LLPSKDVMQG TDEHVVCKVQ HPNGNKEKNV  240
PLPVIAELPP KVSVFVPPRD GFFGNPRKSK LICQATGFSP RQIQVSWLRE GKQVGSGVTT  300
DQVQAEAKES GPTTYKVTST LTIKESDWLG QSMFTCRVDH RGLTFQQNAS SMCVPDQDTA  360
IRVFAIPPSF ASIFLTKSTK LTCLVTDLTT YDSVTISWTR QNGEAVKTHT NISESHPNAT  420
FSAVGEASIC EDDWNSGERF TCTVTHTDLP SPLKQTISRP KGVALHRPDV YLLPPAREQL  480
NLRESATITC LVTGFSPADV FVQWMQRGQP LSPEKYVTSA PMPEPQAPGR YFAHSILTVS  540
EEEWNTGETY TCVVAHEALP NRVTERTVDK STGKPTLYNV SLVMSDTAGT CY          592
```

```
SEQ ID NO: 301           moltype = AA  length = 235
FEATURE                  Location/Qualifiers
source                   1..235
                         mol_type = protein
                         organism = synthetic construct
SEQUENCE: 301
MRLPAQLLGL LLLWLPGAKC DIQMTQSPST LSASVGDRVT ITCRASQSIS SWLAWYQQKP  60
GKAPKLLINK ASSLESGVPS RFSGSGSGTE FTLTINSLQP DDFATYYCQQ YYTYSSYRFG  120
QGTKLEIKRT VAAPSVFIFP PSDEQLKSGT ASVVCLLNNF YPREAKVQWK VDNALQSGNS  180
QESVTEQDSK DSTYSLSSTL TLSKADYEKH KVYACEVTHQ GLSSPVTKSF NRGEC       235
```

```
SEQ ID NO: 302           moltype = AA  length = 595
FEATURE                  Location/Qualifiers
VARIANT                  40
                         note = X can be any amino acid
source                   1..595
                         mol_type = protein
                         organism = synthetic construct
SEQUENCE: 302
MSVSFLLLVA APRWVLSQQQ LQESGPGLVK PSETLSLTCX VSGGSISSSS YYWGWIRQPP  60
GKGLEWIGSI YYRGSTYYNP SLRSRVTASV DTSRNQFSLR LSSVTAADTA VYYCARSYCS  120
GSCYAVGAFD MWGQGTMVTV SSGSASAPTL FPLVSCENSP SDTSSVAVGC LAQDFLPDSI  180
TFSWKYKNNS DISSTRGFPS VLRGGKYAAT SQVLLPSKDV MQGTDEHVVC KVQHPNGNKE  240
KNVPLPVIAE LPPKVSVFVP PRDGFFGNPR KSKLICQATG FSPRQIQVSW LREGKQVGSG  300
VTTDQVQAEA KESGPTTYKV TSTLTIKESD WLGQSMFTCR VDHRGLTFQQ NASSMCVPDQ  360
DTAIRVFAIP PSFASIFLTK STKLTCLVTD LTTYDSVTIS WTRQNGEAVK THTNISESHP  420
NATFSAVGEA SICEDDWNSG ERFTCTVTHT DLPSPLKQTI SRPKGVALHR PDVYLLPPAR  480
EQLNLRESAT ITCLVTGFSP ADVFVQWMQR GQPLSPEKYV TSAPMPEPQA PGRYFAHSIL  540
TVSEEEWNTG ETYTCVVAHE ALPNRVTERT VDKSTGKPTL YNVSLVMSDT AGTCY       595
```

```
SEQ ID NO: 303           moltype = AA  length = 237
FEATURE                  Location/Qualifiers
source                   1..237
                         mol_type = protein
                         organism = synthetic construct
SEQUENCE: 303
MAWTPLLFLT LLLHCTGSLS QLVLTQSPSA SASLGASVKL TCTLSSGHSS HAIAWHQQQP  60
EKGPRYLIKL NSDGSHNKGD GIPDRFSGSS SGAERYLTIS SLQSEDEADY YCQTWDTGIV  120
VFGGGTKLTV LGQPKAAPSV TLFPPSSEEL QANKATLVCL ISDFYPGAVT VAWKADSSPV  180
KAGVETTTPS KQSNNKYAAS SYLSLTPEQW KSHRSYSCQV THEGSTVEKT VAPTECS     237
```

```
SEQ ID NO: 304           moltype = AA  length = 596
FEATURE                  Location/Qualifiers
source                   1..596
                         mol_type = protein
                         organism = synthetic construct
SEQUENCE: 304
MEFGLSWVFL VALLRGVQCQ VQLVESGGGV VQPGRSLRLS CAASGFTFSS YAMHWVRQAP  60
GKGLEWVAVI SYDGSNKYYA DSVKGRFTIS RDNSKNTLYL QMNSLRAEDT AVYYCARDFR  120
GWGGGSGGSC GYWGQGTLVT VSSGSASAPT LFPLVSCENS PSDTSSVAVG CLAQDFLPDS  180
ITFSWKYKNN SDISSTRGFP SVLRGGKYAA TSQVLLPSKD VMQGTDEHVV CKVQHPNGNK  240
EKNVPLPVIA ELPPKVSVFV PPRDGFFGNP RKSKLICQAT GFSPRQIQVS WLREGKQVGS  300
GVTTDQVQAE AKESGPTTYK VTSTLTIKES DWLGQSMFTC RVDHRGLTFQ QNASSMCVPD  360
QDTAIRVFAI PPSFASIFLT KSTKLTCLVT DLTTYDSVTI SWTRQNGEAV KTHTNISESH  420
PNATFSAVGE ASICEDDWNS GERFTCTVTH TDLPSPLKQT ISRPKGVALH RPDVYLLPPA  480
REQLNLRESA TITCLVTGFS PADVFVQWMQ RGQPLSPEKY VTSAPMPEPQ APGRYFAHSI  540
LTVSEEEWNT GETYTCVVAH EALPNRVTER TVDKSTGKPT LYNVSLVMSD TAGTCY      596
```

```
SEQ ID NO: 305           moltype = AA  length = 236
FEATURE                  Location/Qualifiers
source                   1..236
                         mol_type = protein
                         organism = synthetic construct
SEQUENCE: 305
MALTPLLLTL LAHCTGSWAN FMLTQPHSVS ESPGKTVTIS CTRSSGSIAS NYVQWYQQRP  60
GSSPTTVIYE DNQRPSGVPD RFSGSIDSSS NSASLTISGL KTEDEADYYC QSYDSSNLYV  120
FGTGTKVTVL GQPKANPTVT LFPPSSEELQ ANKATLVCLI SDFYPGAVTV AWKADGSPVK  180
AGVETTKPSK QSNNKYAASS YLSLTPEQWK SHRSYSCQVT HEGSTVEKTV APTECS      236
```

```
SEQ ID NO: 306           moltype = AA  length = 470
```

```
FEATURE            Location/Qualifiers
source             1..470
                   mol_type = protein
                   organism = synthetic construct
SEQUENCE: 306
MEFGLSWVFL VAIIKGVQCQ VQLVESGGGL VKPGGSLRLS CAASGFTFSD YFMSWVRQTP   60
GKGLEWLSYM SSDGTIIHHA DSLKGRFTIS RDNAKNSLFL QMNTLRAEDT AVYYCATHIL   120
ETTIAAFEIW GRGTMVIVSS ASTKGPSVFP LAPCSRSTSE STAALGCLVK DYFPEPVTVS   180
WNSGALTSGV HTFPAVLQSS GLYSLSSVVT VPSSNFGTQT YICNVNHKPS NTKVDKRVEP   240
KSCDKTHTCP PCPAPELLGG PSVFLFPPKP KDTLMISRTP EVTCVVVDVS HEDPEVKFNW   300
YVDGVEVHNA KTKPREEQYN STYRVVSVLT VLHQDWLNGK EYKCKVSNKA LPAPIEKTIS   360
KAKGQPREPQ VYTLPPSREE MTKNQVSLTC LVKGFYPSDI AVEWESNGQP ENNYKTTPPV   420
LDSDGSFFLY SKLTVDKSRW QQGNVFSCSV MHEALHNHYT QKSLSLSPGK             470

SEQ ID NO: 307       moltype = AA  length = 240
FEATURE              Location/Qualifiers
source               1..240
                     mol_type = protein
                     organism = synthetic construct
SEQUENCE: 307
MVLQTQVFIS LLLWIAGAYG DIVMTQSPDS LALSLGERAT INCRSSHSVL YRSNNNNYVA   60
WYQQKPGQPP RLLIYWASNR ASGVPDRFSG SGSGTDFTLT ISSLQPEDAA VYFCQQILDT   120
PFTFGPGTKV EIKRTVAAPS VFIFPPSDEQ LKSGTASVVC LLNNFYPREA KVQWKVDNAL   180
QSGNSQESVT EQDSKDSTYS LSSTLTLSKA DYEKHKVYAC EVTHQGLSSP VTKSFNRGEC   240

SEQ ID NO: 308       moltype = AA  length = 472
FEATURE              Location/Qualifiers
VARIANT              37
                     note = X can be any amino acid
source               1..472
                     mol_type = protein
                     organism = synthetic construct
SEQUENCE: 308
MEFGLSWLFL VATLKGVQCE VQLLESGGGL MQPGGSXRLS CAASGFTFRS YAMNWVRQAP   60
GKGLEWVSTI SGNGGTTYYA DSVRGRFTIS RDNSKNTLFL QMNSLRAEDT AIYYCAQGEP   120
WSGYLEPLFA SWGQGTLVTV SSASTKGPSV FPLAPCSRST SGGTAALGCL VKDYFPEPVT   180
VSWNSGALTS GVHTFPAVLQ SSGLYSLSSV VTVPSSSLGT QTYICNVNHK PSNTKVDKRV   240
EPKSCDKTHT CPPCPAPELL GGPSVFLFPP KPKDTLMISR TPEVTCVVVD VSHEDPEVKF   300
NWYVDGVEVH NAKTKPREEQ YNSTYRVVSV LTVLHQDWLN GKEYKCKVSN KALPAPIEKT   360
ISKAKGQPRE PQVYTLPPSR EEMTKNQVSL TCLVKGFYPS DIAVEWESNG QPENNYKTTP   420
PVLDSDGSFF LYSKLTVDKS RWQQGNVFSC SVMHEALHNH YTQKSLSLSP GK           472

SEQ ID NO: 309       moltype = AA  length = 233
FEATURE              Location/Qualifiers
source               1..233
                     mol_type = protein
                     organism = synthetic construct
SEQUENCE: 309
MAWTPLWLTL LTLCIGSVVS SELTQDPAVS VALGQTVRIT CQGDSLRNFY ASWYQQKPGQ   60
APVLVIYGKN NRPSGIPDRF SGSSSGNTVS LTITGAQAED DADYYCNSRD SSGNHVIFGG   120
GTKLTVLGQP KAAPSVTLFP PSSEELQANK ATLVCLISDF YPGAVTVAWK ADSSPVKAGV   180
ETTTPSKQSN NKYAASSYLS LTPEQWKSHR SYSCQVTHEG STVEKTVAPT ECS          233

SEQ ID NO: 310       moltype = AA  length = 473
FEATURE              Location/Qualifiers
source               1..473
                     mol_type = protein
                     organism = synthetic construct
SEQUENCE: 310
MELGLCWVFL VAILEGVQCE VQLVESGGGL VHPGGSLRLS CAASGFTFRT YIMNWVRQAP   60
GKGLEWISYI SASSGTIYYA DSVKGRFTIS RDNAKNSLYL QMNSLRAEDT AVYYCARDLD   120
CSGGTCYDGF DSWGHGTLVT VSSSSTKGPS VFPLAPSSKS TSGGTAALGC LVKDYFPEPV   180
TVSWNSGALT SGVHTFPAVL QSSGLYSLSS VVTVPSSSLG TQTYICNVNH KPSNTKVDKR   240
VEPKSCDKTH TCPPCPAPEL LGGPSVFLFP PKPKDTLMIS RTPEVTCVVV DVSHEDPEVK   300
FNWYVDGVEV HNAKTKPREE QYNSTYRVVS VLTVLHQDWL NGKEYKCKVS NKALPAPIEK   360
TISKAKGQPR EPQVYTLPPS REEMTKNQVS LTCLVKGFYP SDIAVEWESN GQPENNYKTT   420
PPVLDSDGSF FLYSKLTVDK SRWQQGNVFS CSVMHEALHN HYTQKSLSLS PGK           473

SEQ ID NO: 311       moltype = AA  length = 231
FEATURE              Location/Qualifiers
source               1..231
                     mol_type = protein
                     organism = synthetic construct
SEQUENCE: 311
MAWTPLFLGV LAYCTGSVAS YELTQPPSLS VSPGQTASIT CSGDKLGDKY ACWYQQRPGQ   60
SPVLVIYQDT KRPSGIPERF SGSNSGNTAT LTISGTQAMD EADYYCQAWD SSTAVFGGGT   120
RLTVLGQPKA APSVTLFPPS SEELQANKAT LVCLISDFYP GAVTVAWKAD SSPVKAGVET   180
TTPSKQSNNK YAASSYLSLT PEQWKSHRSY SCQVTHEGST VEKTVAPTEC S             231
```

-continued

```
SEQ ID NO: 312            moltype = AA   length = 471
FEATURE                   Location/Qualifiers
source                    1..471
                          mol_type = protein
                          organism = synthetic construct
SEQUENCE: 312
MEFGLSWIFL LAILKGVQCE VQLVESGGGL VQPGRSLRLS CAASGFNFDN YAMHWVRQVP    60
GKGLEWVSGI NWNSGYEGYA DSVKGRFTIS RDNAQNSLYL QMDSLRTDDT ALYYCTKDTI   120
AAVGRGAFDI WGQGTKVTVS SASTKGPSVF PLAPCSRSTS GGTAALGCLV KDYFPEPVTV   180
SWNSGALTSG VHTFPAVLQS SGLYSLSSVV TVPSSSLGTQ TYICNVNHKP SNTKVDKRVE   240
PKSCDKTHTC PPCPAPELLG GPSVFLFPPK PKDTLMISRT PEVTCVVVDV SHEDPEVKFN   300
WYVDGVEVHN AKTKPREEQY NSTYRVVSVL TVLHQDWLNG KEYKCKVSNK ALPAPIEKTI   360
SKAKGQPREP QVYTLPPSRE EMTKNQVSLT CLVKGFYPSD IAVEWESNGQ PENNYKTTPP   420
VLDSDGSFFL YSKLTVDKSR WQQGNVFSCS VMHEALHNHY TQKSLSLSPG K            471

SEQ ID NO: 313            moltype = AA   length = 233
FEATURE                   Location/Qualifiers
source                    1..233
                          mol_type = protein
                          organism = synthetic construct
SEQUENCE: 313
MAWIPLLLGL LSHCTGSVTS YVLTQPPSVS VAPGKTAMIT CGGNKIGGKS VHWYQQKPGQ    60
APVLVISYDS DRPSGIPQRF SGSNSGNTAT LTISRVEAGD EADYYCQVWD TSSVHRVFGG   120
GTKLTVLGQP KAAPSVTLFP PSSEELQANK ATLVCLISDF YPGAVTVAWK ADSSPVKAGV   180
ETTTPSKQSN NKYAASSYLS LTPEQWKSHR SYSCQVTHEG STVEKTVAPT ECS          233

SEQ ID NO: 314            moltype = AA   length = 476
FEATURE                   Location/Qualifiers
source                    1..476
                          mol_type = protein
                          organism = synthetic construct
SEQUENCE: 314
MKHLWFFLLL VAAPRWVLSQ LQLRESGPGL VKPSETLSLT CSVSGDSISR SSDYWGWIRQ    60
PPGRGLEWIG SIYRTGSTYY NPSLSSRVTI SVDTSKSQFS LSLSSVTAAD TALYYCARVR   120
HDYVWGSIYY YGMDVWGQGT TVTVSSPSTK GPSVFPLAPC SRSTSGGTAA LGCLVKDYFP   180
EPVTVSWNSG ALTSGVHTFP AVLQSSGLYS LSSVVTVPSS SLGTQTYICN VNHKPSNTKV   240
DKRVEPKSCD KTHTCPPCPA PELLGGPSVF LFPPKPKDTL MISRTPEVTC VVVDVSHEDP   300
EVKFNWYVDG VEVHNAKTKP REEQYNSTYR VVSVLTVLHQ DWLNGKEYKC KVSNKALPAP   360
IEKTISKAKG QPREPQVYTL PPSREEMTKN QVSLTCLVKG FYPSDIAVEW ESNGQPENNY   420
KTTPPVLDSD GSFFLYSKLT VDKSRWQQGN VFSCSVMHEA LHNHYTQKSL SLSPGK       476

SEQ ID NO: 315            moltype = AA   length = 232
FEATURE                   Location/Qualifiers
source                    1..232
                          mol_type = protein
                          organism = synthetic construct
SEQUENCE: 315
MAWSPLLLTQ GTGSWAQSAL TQPRSVSGSP GQSVTISCTG TGSDVGGYTY VSWYQQHPDK    60
APKLVIYDVT KRPSGVPDRF SGSKSGNTAS LTISGLRADD EADYYCCSYA GRYSWVFGGG   120
TKLTVLGQPK AAPSVTLFPP SSEELQANKA TLVCLISDFY PGAVTVAWKA DSSPVKAGVE   180
TTTPSKQSNN KYAASSYLSL TPEQWKSHRS YSCQVTHEGS TVEKTVAPTE CS           232

SEQ ID NO: 316            moltype = AA   length = 472
FEATURE                   Location/Qualifiers
source                    1..472
                          mol_type = protein
                          organism = synthetic construct
SEQUENCE: 316
MEFGLSWLFL VAILKGVHCE VDLLESGGGL IQPGGSLRLS CAASGFTFRN YAMNWVRQVP    60
GKGLEWVSSV SGSGGTTYYA DSVKGRFSIS RDNSKNTLYL QMNGLRAGDT AIYYCAKGEA   120
WSGYLEPLCD FWGHGTLVTV SSASTKGPSV FPLAPSSKST SGGTAALGCL VKDYFPEPVT   180
VSWNSGALTS GVHTFPAVLQ SSGLYSLSSV VTVPSSSLGT QTYICNVNHK PSNTKVDKRV   240
EPKSCDKTHT CPPCPAPELL GGPSVFLFPP KPKDTLMISR TPEVTCVVVD VSHEDPEVKF   300
NWYVDGVEVH NAKTKPREEQ YNSTYRVVSL TVLHQDWLN GKEYKCKVSN KALPAPIEKT   360
ISKAKGQPRE PQVYTLPPSR EEMTKNQVSL TCLVKGFYPS DIAVEWESNG QPENNYKTTP   420
PVLDSDGSFF LYSKLTVDKS RWQQGNVFSC SVMHEALHNH YTQKSLSLSP GK           472

SEQ ID NO: 317            moltype = AA   length = 233
FEATURE                   Location/Qualifiers
source                    1..233
                          mol_type = protein
                          organism = synthetic construct
SEQUENCE: 317
MALTPLWLTL LTLCIGSVVS SELTQDPAVS VALGQTVRIT CQGDSLRDFY GSWYQQKPGQ    60
APVLVNFGYN NRPSGIPDRF SGSRSGNTAS LTITGAQAED EADYYCNSRD ISGNRVVFGG   120
GTKLTVVGQP EAAPSVTLFP PSSEELQANK ATLVCLISDF YPGAVTVAWK ADSSPVKAGV   180
ETTTPSKQSN NKYAASSYLS LTPEQWKSHR SYSCQVTHEG STVEKTVAPT ECS          233

SEQ ID NO: 318            moltype = AA   length = 477
```

```
FEATURE                 Location/Qualifiers
source                  1..477
                        mol_type = protein
                        organism = synthetic construct
SEQUENCE: 318
MKHLWFFLLL VAAPRWVLSQ LQLQESGSGL VRPSQTLSLT CAVSGASISS GGYSWSWIRQ  60
PPGKGLEWIG YIYHSGSTSY NPSLKSRVTI SEDKSNNQFS LKLSSVTAAD TAVYYCARVW  120
ASFYYGSWTP PTWFDPWGPG TLVTVSSAST KGPSVFPLAP CSRSTSGGTA ALGCLVKDYF  180
PEPVTVSWNS GALTSGVHTF PAVLQSSGLY SLSSVVTVPS SSLGTQTYIC NVNHKPSNTK  240
VDKRVEPKSC DKTHTCPPCP APELLGGPSV FLFPPKPKDT LMISRTPEVT CVVVDVSHED  300
PEVKFNWYVD GVEVHNAKTK PREEQYNSTY RVVSVLTVLH QDWLNGKEYK CKVSNKALPA  360
PIEKTISKAK GQPREPQVYT LPPSREEMTK NQVSLTCLVK GFYPSDIAVE WESNGQPENN  420
YKTTPPVLDS DGSFFLYSKL TVDKSRWQQG NVFSCSVMHE ALHNHYTQKS LSLSPGK  477

SEQ ID NO: 319          moltype = AA  length = 232
FEATURE                 Location/Qualifiers
source                  1..232
                        mol_type = protein
                        organism = synthetic construct
SEQUENCE: 319
MAWIPLLLTQ GTGSWAQSAL TQPRSVSGSP GQSVTISCTG TGSNVGGYTY VSWYQQHPGK  60
APKLLIYDVS KRPSGVPDRF SGSKSGNTAS LTISGLQADD EADYHCCSYA GGYTLVFGGG  120
TKLTVLGQPK AAPSVTLFPP SSEELQANKA TLVCLISDFY PGAVTVAWKA DSSPVKAGVE  180
TTTPSKQSNN KYAASSYLSL TPEQWKSHRS YSCQVTHEGS TVEKTVAPTE CS  232

SEQ ID NO: 320          moltype = AA  length = 473
FEATURE                 Location/Qualifiers
source                  1..473
                        mol_type = protein
                        organism = synthetic construct
SEQUENCE: 320
MELGLSWVFL VAILEGVQCE VQLVESGGGL VQPGGSLRLS CSASGFTFRS YIINWVRQAP  60
GKGLEWVSYI SGSSGTKNYA DSVKGRFTIS RDNAKNSVYL QMNSLRAEDT AVYYCARDLD  120
CSGGSCYDGM DVWGQGTTVT VSSASTKGPS VFPLAPCSRS TSGGTAALGC LVKDYFPEPV  180
TVSWNSGALT SGVHTFPAVL QSSGLYSLSS VVTVPSSSLG TQTYICNVNH KPSNTKVDKR  240
VEPKSCDKTH TCPPCPAPEL LGGPSVFLFP PKPKDTLMIS RTPEVTCVVV DVSHEDPEVK  300
FNWYVDGVEV HNAKTKPREE QYNSTYRVVS VLTVLHQDWL NGKEYKCKVS NKALPAPIEK  360
TISKAKGQPR EPQVYTLPPS REEMTKNQVS LTCLVKGFYP SDIAVEWESN GQPENNYKTT  420
PPVLDSDGSF FLYSKLTVDK SRWQQGNVFS CSVMHEALHN HYTQKSLSLS PGK  473

SEQ ID NO: 321          moltype = AA  length = 232
FEATURE                 Location/Qualifiers
source                  1..232
                        mol_type = protein
                        organism = synthetic construct
SEQUENCE: 321
MAWTPLLLGV LAYCTGSVAS FELTQPPSVS VSPGQTASIT CSGDKLGHHY AYWFQQRPGQ  60
SPVLVIYQHT KRPSGIPERF SGSKSGNTAT LTISGTQAMD EADYYCQAWD SSTYVVFGGG  120
TKVTVLGQPK AAPSVTLFPP SSEELQANKA TLVCLISDFY PGAVTVAWKA DSSPVKAGVE  180
TTTPSKQSNN KYAASSYLSL TPEQWKSHRS YSCQVTHEGS TVEKTVAPTE CS  232

SEQ ID NO: 322          moltype = AA  length = 472
FEATURE                 Location/Qualifiers
source                  1..472
                        mol_type = protein
                        organism = synthetic construct
SEQUENCE: 322
MKHLWFFLLL VAAPRWVLSQ VQLQESGPGL VKPSQTLSLT CSVSGGSISS GSHYWSWIRQ  60
PAGEALEWIG RTYTSGRTSY NPSLKSRVTI SVDTSKNQFS LKLTSVTAAD TAVYYCARNS  120
RIYGGYELFD IWGQGTMVTV SSASTKGPSV FPLAPSSKST SGGTAALGCL VKDYFPEPVT  180
VSWNSGALTS GVHTFPAVLQ SSGLYSLSSV VTVPSSSLGT QTYICNVNHK PSNTKVDKRV  240
EPKSCDKTHT CPPCPAPELL GGPSVFLFPP KPKDTLMISR TPEVTCVVVD VSHEDPEVKF  300
NWYVDGVEVH NAKTKPREEQ YNSTYRVVSV LTVLHQDWLN GKEYKCKVSN KALPAPIEKT  360
ISKAKGQPRE PQVYTLPPSR EEMTKNQVSL TCLVKGFYPS DIAVEWESNG QPENNYKTTP  420
PVLDSDGSFF LYSKLTVDKS RWQQGNVFSC SVMHEALHNH YTQKSLSLSP GK  472

SEQ ID NO: 323          moltype = AA  length = 233
FEATURE                 Location/Qualifiers
source                  1..233
                        mol_type = protein
                        organism = synthetic construct
SEQUENCE: 323
MAWTPLLLGL LSHCTGSLTS YVLTQPPSVS VAPGKTARIP CGGDNIGNKG VHWYQQKSGQ  60
APVLLIHYDS DRPSGIPERF SGSNSGNTAT LSISRVELGD EADYYCQVWD TSSDQPVFGG  120
GTKLTVLGQP KAAPSVTLFP PSSEELQANK ATLVCLISDF YPGAVTVAWK ADSSPVKAGV  180
ETTTPSKQSN NKYAASSYLS LTPEQWKSHR SYSCQVTHEG STVEKTVAPT ECS  233

SEQ ID NO: 324          moltype = AA  length = 473
FEATURE                 Location/Qualifiers
```

-continued

```
source                    1..473
                          mol_type = protein
                          organism = synthetic construct
SEQUENCE: 324
MEFGLSWVFL VAILEGVQCE VQLVESGGGL VQPGGSLRLS CAASGFTFRS YMMNWVRQAP  60
GKGLEWVSYI SGSGGGTKYYV DSVKGRFTIS RDNAKNSLYL QMHSLRAEDT AVYYCARDLD  120
CSGGTCYDGM DVWGQGTTVT VSSASTKGPS VFPLAPCSRS TSGGTAALGC LVKDYFPEPV  180
TVSWNSGALT SGVHTFPAVL QSSGLYSLSS VVTVPSSSLG TQTYICNVNH KPSNTKVDKR  240
VEPKSCDKTH TCPPCPAPEL LGGPSVFLFP PKPKDTLMIS RTPEVTCVVV DVSHEDPEVK  300
FNWYVDGVEV HNAKTKPREE QYNSTYRVVS VLTVLHQDWL NGKEYKCKVS NKALPAPIEK  360
TISKAKGQPR EPQVYTLPPS REEMTKNQVS LTCLVKGFYP SDIAVEWESN GQPENNYKTT  420
PPVLDSDGSF FLYSKLTVDK SRWQQGNVFS CSVMHEALHN HYTQKSLSLS PGK          473

SEQ ID NO: 325            moltype = AA  length = 231
FEATURE                   Location/Qualifiers
source                    1..231
                          mol_type = protein
                          organism = synthetic construct
SEQUENCE: 325
MAWAPLLLGV LAYCTGSVAS YELIQPPSVS VSPGQTASIT CSGDKLGNKY VYWFQHRPGQ  60
SPVLVIYQHT KRPSGIPERF SGSKSGNTAT LIISGTQAMD EADYYCQAWD SSVVIFGGGT  120
KLTVLGQPKA APSVTLFPPS SEELQANKAT LVCLISDFYP GAVTVAWKAD SSPVKAGVET  180
TTPSKQSNNK YAASSYLSLT PEQWKSHRSY SCQVTHEGST VEKTVAPTEC S           231

SEQ ID NO: 326            moltype = AA  length = 476
FEATURE                   Location/Qualifiers
source                    1..476
                          mol_type = protein
                          organism = synthetic construct
SEQUENCE: 326
MKHLWFFLLL VAAPRWVLSQ LQLQESGPGL VKPSETLSLT CSVSGDSISR SSDYWGWIRQ  60
PPGRGLEWIG SIYRTGSTYY NPSLSSRVTI SVDTSKSQFS LSLSSVTAAD TALYYCARVR  120
HDYVWGSIYY YGMDVWGQGT TVTVSSPSTK GPSVFPLAPC SRSTSGGTAA LGCLVKDYFP  180
EPVTVSWNSG ALTSGVHTFP AVLQSSGLYS LSSVVTVPSS SLGTQTYICN VNHKPSNTKV  240
DKRVEPKSCD KTHTCPPCPA PELLGGPSVF LFPPKPKDTL MISRTPEVTC VVVDVSHEDP  300
EVKFNWYVDG VEVHNAKTKP REEQYNSTYR VVSVLTVLHQ DWLNGKEYKC KVSNKALPAP  360
IEKTISKAKG QPREPQVYTL PPSREEMTKN QVSLTCLVKG FYPSDIAVEW ESNGQPENNY  420
KTTPPVLDSD GSFFLYSKLT VDKSRWQQGN VFSCSVMHEA LHNHYTQKSL SLSPGK      476

SEQ ID NO: 327            moltype = AA  length = 232
FEATURE                   Location/Qualifiers
source                    1..232
                          mol_type = protein
                          organism = synthetic construct
SEQUENCE: 327
MAWIPLLLTQ GTGSWAQSAL TQPRSVSGSP GQSVTISCTG TGSDVGGYTY VSWYQQHPDK  60
APKLVIYDVT KRPSGVPDRF SGSKSGNTAS LTISGLRADD AYYCCSYA GRYSWVFGGG   120
TKLTVLGQPK AAPSVTLFPP SSEELQANKA TLVCLISDFY PGAVTVAWKA DSSPVKAGVE  180
TTTPSKQSNN KYAASSYLSL TPEQWKSHRS YSCQVTHEGS TVEKTVAPTE CS          232

SEQ ID NO: 328            moltype = AA  length = 474
FEATURE                   Location/Qualifiers
source                    1..474
                          mol_type = protein
                          organism = synthetic construct
SEQUENCE: 328
MDWTWRILFL VAAATGAHSQ VQLVQSGAEV KKPGASVKVS CKTSGYTFTA YHLHWVRQTP  60
GQGLEWMGWI NPNSGGTNYA LKFQGRVTVT RDTSISTVYM ELTRLRSDDT AVYYCAREKE  120
PLMASYYYYG MDVWGQGTTV TVSSASTKGP SVFPLAPCSR STSGGTAALG CLVKDYFPEP  180
VTVSWNSGAL TSGVHTFPAV LQSSGLYSLS SVVTVPSSSL GTQTYICNVN HKPSNTKVDK  240
RVEPKSCDKT HTCPPCPAPE LLGGPSVFLF PPKPKDTLMI SRTPEVTCVV VDVSHEDPEV  300
KFNWYVDGVE VHNAKTKPRE EQYNSTYRVV SVLTVLHQDW LNGKEYKCKV SNKALPAPIE  360
KTISKAKGQP REPQVYTLPP SREEMTKNQV SLTCLVKGFY PSDIAVEWES NGQPENNYKT  420
TPPVLDSDGS FFLYSKLTVD KSRWQQGNVF SCSVMHEALH NHYTQKSLSL SPGK        474

SEQ ID NO: 329            moltype = AA  length = 233
FEATURE                   Location/Qualifiers
source                    1..233
                          mol_type = protein
                          organism = synthetic construct
SEQUENCE: 329
MAWAPLWLTL LTLCIGSVVS SEVTQDPAVS VALGQTVRIT CQGDSLRNYY TRWYQQKPGQ  60
APVLVIYREN NRPSGIPDRF SGSSSGNTAS LTITGAQAED EADYYCTSRA TNTDHLVFGG  120
GTKLTVLGQP KAAPSVTLFP PSSEELQANK ATLVCLISDF YPGAVTVAWK ADSSPVKAGV  180
ETTTPSKQSN NKYAASSYLS LTPEQWKSHR SYSCQVTHEG STVEKTVAPT ECS         233

SEQ ID NO: 330            moltype = AA  length = 477
FEATURE                   Location/Qualifiers
source                    1..477
```

-continued

```
                        mol_type = protein
                        organism = synthetic construct
SEQUENCE: 330
MKHLWFFLLL VAAPRWVLSQ LQLQESGSGL VRPSQTLSLT CAVSGASINS GGYSWSWIRQ    60
PPGKGLEWIG YIYHSGSTSY NPSLKSRVTI SEDRSKNQFS LKLSSVTAAD TAVYYCARVW   120
ASFYYGSWTP PTWLDPWGPG TLVTVSSAST KGPSVFPLAP CSRSTSGGTA ALGCLVKDYF   180
PEPVTVSWNS GALTSGVHTF PAVLQSSGLY SLSSVVTVPS SSLGTQTYIC NVNHKPSNTK   240
VDKRVEPKSC DKTHTCPPCP APELLGGPSV FLFPPKPKDT LMISRTPEVT CVVVDVSHED   300
PEVKFNWYVD GVEVHNAKTK PREEQYNSTY RVVSVLTVLH QDWLNGKEYK CKVSNKALPA   360
PIEKTISKAK GQPREPQVYT LPPSREEMTK NQVSLTCLVK GFYPSDIAVE WESNGQPENN   420
YKTTPPVLDS DGSFFLYSKL TVDKSRWQQG NVFSCSVMHE ALHNHYTQKS LSLSPGK      477

SEQ ID NO: 331         moltype = AA   length = 232
FEATURE                Location/Qualifiers
source                 1..232
                       mol_type = protein
                       organism = synthetic construct
SEQUENCE: 331
MAWSPLLLTQ GTGSWAQSAL TQPRSVSGSP GQSVTISCTG TGSDVGGYTY VSWYQQHPGK    60
APKLMIYDVS KRPSGVPDRF SGSKSGNTAS LTISGLQADD EADYYCCSYA GGYTLVFGGG   120
TKLTVLGQPK AAPSVTLFPP SSEELQANKA TLVCLISDFY PGAVTVAWKA DSSPVKAGVE   180
TTTPSKQSNN KYAASSYLSL TPEQWKSHRS YSCQVTHEGS TVEKTVAPTE CS           232

SEQ ID NO: 332         moltype = AA   length = 471
FEATURE                Location/Qualifiers
source                 1..471
                       mol_type = protein
                       organism = synthetic construct
SEQUENCE: 332
MEFGLSWIFL LAILKGVQCE VQLVESGGGL VQPGRSLRLS CAASGFNFDN YAMHWVRQVP    60
GKGLEWVSGI NWNSGYEAYA DSVKGRFIIS RDNAQNSLYL QMNSLRADDT AFYYCTKDTI   120
AAVGRGAFDI WGQGTGVSVS PASTKGPSVF PLAPCSRSTS GGTAALGCLV KDYFPEPVTV   180
SWNSGALTSG VHTFPAVLQS SGLYSLSSVV TVPSSSLGTQ TYICNVNHKP SNTKVDKRVE   240
PKSCDKTHTC PPCPAPELLG GPSVFLFPPK PKDTLMISRT PEVTCVVVDV SHEDPEVKFN   300
WYVDGVEVHN AKTKPREEQY NSTYRVVSVL TVLHQDWLNG KEYKCKVSNK ALPAPIEKTI   360
SKAKGQPREP QVYTLPPSRE EMTKNQVSLT CLVKGFYPSD IAVEWESNGQ PENNYKTTPP   420
VLDSDGSFFL YSKLTVDKSR WQQGNVFSCS VMHEALHNHY TQKSLSLSPG K            471

SEQ ID NO: 333         moltype = AA   length = 233
FEATURE                Location/Qualifiers
source                 1..233
                       mol_type = protein
                       organism = synthetic construct
SEQUENCE: 333
MAWIPLLLGL LSHCTGSVTS YLLTQPPSVS VAPGKTAMIT CGGSKIGGKS VHWYQQKPGQ    60
APVLVISYDS DRPSGIPKRF SGSNSGNTAT LTISGVEAGD EADYYCQVWD SSNVHRVFGG   120
GTKLTVLSQP KAAPSVTLFP PSSEELQANK ATLVCLISDF YPGAVTVAWK ADSSPVKAGV   180
ETTTPSKQSN NKYAASSYLS LTPEQWKSHR SYSCQVTHEG STVEKTVAPT ECS          233

SEQ ID NO: 334         moltype = AA   length = 476
FEATURE                Location/Qualifiers
source                 1..476
                       mol_type = protein
                       organism = synthetic construct
SEQUENCE: 334
MKHLWFFLLL VAAPRWVLSQ LQLQESGPGL VKPSETLSLT CSVSGDSISR SSDYWGWIRQ    60
PPGRGLEWIG SIYRTGSTYY NPSLSSRVTI SVDTSKSQFS LSLSSVTAAD TALYYCARVR   120
HDYVWGSIYY YGMDVWGQGT TVTVSSPSTK GPSVFPLAPC SRSTSGGTAA LGCLVKDYFP   180
EPVTVSWNSG ALTSGVHTFP AVLQSSGLYS LSSVVTVPSS SLGTQTYICN VNHKPSNTKV   240
DKRVEPKSCD KTHTCPPCPA PELLGGPSVF LFPPKPKDTL MISRTPEVTC VVVDVSHEDP   300
EVKFNWYVDG VEVHNAKTKP REEQYNSTYR VVSVLTVLHQ DWLNGKEYKC KVSNKALPAP   360
IEKTISKAKG QPREPQVYTL PPSREEMTKN QVSLTCLVKG FYPSDIAVEW ESNGQPENNY   420
KTTPPVLDSD GSFFLYSKLT VDKSRWQQGN VFSCSVMHEA LHNHYTQKSL SLSPGK       476

SEQ ID NO: 335         moltype = AA   length = 216
FEATURE                Location/Qualifiers
source                 1..216
                       mol_type = protein
                       organism = synthetic construct
SEQUENCE: 335
MAWIPLLLTQ GTGSWAQSAL TQPRSVSGSP GQSVTISCTG TGSDVGGYTY VSWYQQHPDK    60
APKLVIYDVT KRPSGVPDRF SGSKSGNTAS LTISGLRADD EADYYCCSYA GQPKAAPSVT   120
LFPPSSEELQ ANKATLVCLI SDFYPGAVTV AWKADSSPVK AGVETTTPSK QSNNKYAASS   180
YLSLTPEQWK SHRSYSCQVT HEGSTVEKTV APTECS                             216

SEQ ID NO: 336         moltype = AA   length = 473
FEATURE                Location/Qualifiers
source                 1..473
                       mol_type = protein
```

```
                             organism = synthetic construct
SEQUENCE: 336
MELGLCWVFL VAILEGVQCE VQLVESGGGL VQPGGSLRLS CSASGFTFRS YIINWVRQAP    60
GKGLEWVSYI SGSSGTKNYA DSVKGRFTIS RDNAKNSVYL QMNSLRAEDT AVYYCARDLD   120
CSGGGSCYDGM DVWGQGTTVT VSSASTKGPS VFPLAPCSRS TSGGTAALGC LVKDYFPEPV  180
TVSWNSGALT SGVHTFPAVL QSSGLYSLSS VVTVPSSSLG TQTYICNVNH KPSNTKVDKR   240
VEPKSCDKTH TCPPCPAPEL LGGPSVFLFP PKPKDTLMIS RTPEVTCVVV DVSHEDPEVK   300
FNWYVDGVEV HNAKTKPREE QYNSTYRVVS VLTVLHQDWL NGKEYKCKVS NKALPAPIEK   360
TISKAKGQPR EPQVYTLPPS REEMTKNQVS LTCLVKGFYP SDIAVEWESN GQPENNYKTT   420
PPVLDSDGSF FLYSKLTVDK SRWQQGNVFS CSVMHEALHN HYTQKSLSLS PGK          473

SEQ ID NO: 337              moltype = AA   length = 232
FEATURE                     Location/Qualifiers
source                      1..232
                            mol_type = protein
                            organism = synthetic construct
SEQUENCE: 337
MAWTPLFLGV LAYCTGSVAS FELTQPPSVS VSPGQTASIT CSGDKLGHHY AYWFQQRPGQ    60
SPVLVIYQHT KRPSGIPERF SGSKSGNTAT LTISGTQAMD EADYYCQAWD SSTYVVFGGG   120
TKLTVLGQPK AAPSVTLFPP SSEELQANKA TLVCLISDFY PGAVTVAWKA DSSPVKAGVE   180
TTTPSKQSNN KYAASSYLSL TPEQWKSHRS YSCQVTHEGS TVEKTVAPTE CS           232

SEQ ID NO: 338              moltype = AA   length = 473
FEATURE                     Location/Qualifiers
source                      1..473
                            mol_type = protein
                            organism = synthetic construct
SEQUENCE: 338
MELGLCWVFL VAILEGVQCE VQLVESGGGL VQPGGSLRLS CAASGFTFRS YMMNWVRQAP    60
GKGLEWVSYI SGSGGTKYYV DSVKGRFTIS RDNAKNSLYL QMHSLRAEDT AVYYCARDLD   120
CSGGTCYDGM DVWGQGTTVT VSSASTKGPS VFPLAPCSRS TSGGTAALGC LVKDYFPEPV   180
TVSWNSGALT SGVHTFPAVL QSSGLYSLSS VVTVPSSSLG TQTYICNVNH KPSNTKVDKR   240
VEPKSCDKTH TCPPCPAPEL LGGPSVFLFP PKPKDTLMIS RTPEVTCVVV DVSHEDPEVK   300
FNWYVDGVEV HNAKTKPREE QYNSTYRVVS VLTVLHQDWL NGKEYKCKVS NKALPAPIEK   360
TISKAKGQPR EPQVYTLPPS REEMTKNQVS LTCLVKGFYP SDIAVEWESN GQPENNYKTT   420
PPVLDSDGSF FLYSKLTVDK SRWQQGNVFS CSVMHEALHN HYTQKSLSLS PGK          473

SEQ ID NO: 339              moltype = AA   length = 231
FEATURE                     Location/Qualifiers
source                      1..231
                            mol_type = protein
                            organism = synthetic construct
SEQUENCE: 339
MAWIPLFLGV LAYCTGSVAS YELTQPPSVS VSPGQTASIT CSGDKLGHKY VYWFQHRPGQ    60
SPVLVIYQHT KRPSGIPERF SGSKSGNTAT LTISGTQALD EADYYCQAWD SSVVIFGGGT   120
KLTVLGQPKA APSVTLFPPS SEELQANKAT LVCLISDFYP GAVTVAWKAD SSPVKAGVET   180
TTPSKQSNNK YAASSYLSLT PEQWKSHRSY SCQVTHEGST VEKTVAPTEC S            231

SEQ ID NO: 340              moltype = AA   length = 473
FEATURE                     Location/Qualifiers
source                      1..473
                            mol_type = protein
                            organism = synthetic construct
SEQUENCE: 340
MDWTWRILFL VAAVTGAHSQ VQLVQSGPEV KRPGASVKVS CKASGYTLTT SSIHWVRQAP    60
GQRLEWMGWI NTGNDNTMYS QKFQGRVLIT TDTSASTAYL ELRSLRSEDT AVFYCARGPL   120
PYYYDSSGPL DYWGQGTLVT VSSASTKGPS VFPLAPSSKS TSGGTAALGC LVKDYFPEPV   180
TVSWNSGALT SGVHTFPAVL QSSGLYSLSS VVTVPSSSLG TQTYICNVNH KPSNTKVDKR   240
VEPKSCDKTH TCPPCPAPEL LGGPSVFLFP PKPKDTLMIS RTPEVTCVVV DVSHEDPEVK   300
FNWYVDGVEV HNAKTKPREE QYNSTYRVVS VLTVLHQDWL NGKEYKCKVS NKALPAPIEK   360
TISKAKGQPR EPQVYTLPPS REEMTKNQVS LTCLVKGFYP SDIAVEWESN GQPENNYKTT   420
PPVLDSDGSF FLYSKLTVDK SRWQQGNVFS CSVMHEALHN HYTQKSLSLS PGK          473

SEQ ID NO: 341              moltype = AA   length = 233
FEATURE                     Location/Qualifiers
source                      1..233
                            mol_type = protein
                            organism = synthetic construct
SEQUENCE: 341
MAWIPLLLGL LSHCTGSVTS YVLTQPPSVS VAPGKTATFT CGGDNIGTKS VHWYRQKPGQ    60
APVLVVYDDS DRPSGDPERF SGSNSGNTAT LTISRVEAGD EADYFCQVWI SSRDHPVFGE   120
GTRLTVLGQP KAAPSVTLFP PSSEELQANK ATLVCLISDF YPGAVTVAWK ADSSPVKAGV   180
ETTTPSKQSN NKYAASSYLS LTPEQWKSHR SYSCQVTHEG STVEKTVAPT ECS          233

SEQ ID NO: 342              moltype = AA   length = 474
FEATURE                     Location/Qualifiers
source                      1..474
                            mol_type = protein
                            organism = synthetic construct
```

```
SEQUENCE: 342
MDWTWRILFL VAAATGAHSQ VQLVQSGAEV KKPGASVKVS CKTSGYTFTA YHMHWVRQAP    60
GQGLEWMGWI NPNSGGTNYA QNFQGRVTVT RDTSISTVYM ELTRLRSDDT AVYYCARERE   120
PLMASYYYG MDVWGQGTTV TVSSASTKGP SVFPLAPCSR STSGGTAALG CLVKDYFPEP   180
VTVSWNSGAL TSGVHTFPAV LQSSGLYSLS SVVTVPSSSL GTQTYICNVN HKPSNTKVDK   240
RVEPKSCDKT HTCPPCPAPE LLGGPSVFLF PPKPKDTLMI SRTPEVTCVV VDVSHEDPEV   300
KFNWYVDGVE VHNAKTKPRE EQYNSTYRVV SVLTVLHQDW LNGKEYKCKV SNKALPAPIE   360
KTISKAKGQP REPQVYTLPP SREEMTKNQV SLTCLVKGFY PSDIAVEWES NGQPENNYKT   420
TPPVLDSDGS FFLYSKLTVD KSRWQQGNVF SCSVMHEALH NHYTQKSLSL SPGK         474

SEQ ID NO: 343         moltype = AA  length = 230
FEATURE                Location/Qualifiers
source                 1..230
                       mol_type = protein
                       organism = synthetic construct
SEQUENCE: 343
MAWATLLLTL CIGSVVSSEV TQDPAVSVAL GQTVRITCQG DSLRNYYTRW YQQKPGQAPI    60
LVIYRENNRP SGIPDRFSGS NSGNTASLTI TGAQAEDEAD YYCTSRASGS DHLVFGGGTK   120
LTVLGQPKAA PSVTLFPPSS EELQANKATL VCLISDFYPG AVTVAWKADS SPVKAGVETT   180
TPSKQSNNKY AASSYLSLTP EQWKSHRSYS CQVTHEGSTV EKTVAPTECS              230

SEQ ID NO: 344         moltype = AA  length = 474
FEATURE                Location/Qualifiers
source                 1..474
                       mol_type = protein
                       organism = synthetic construct
SEQUENCE: 344
MDWTWRILFL VAAATGAHSR VQLVQSGAEV KKPGASVKVS CKASGYTFTA YHMHWVRQAP    60
GQGLEWMGWI NPNSGGTNYA QRFQGRVTMT RDTSSSTAYM DLTRLRSDDT AVYYCARERE   120
PLMASFYHYG LGVWGQGTTV AVSSASTKGP SVFPLAPCSR STSGGTAALG CLVKDYFPEP   180
VTVSWNSGAL TSGVHTFPAV LQSSGLYSLS SVVTVPSSSL GTQTYICNVN HKPSNTKVDK   240
RVEPKSCDKT HTCPPCPAPE LLGGPSVFLF PPKPKDTLMI SRTPEVTCVV VDVSHEDPEV   300
KFNWYVDGVE VHNAKTKPRE EQYNSTYRVV SVLTVLHQDW LNGKEYKCKV SNKALPAPIE   360
KTISKAKGQP REPQVYTLPP SREEMTKNQV SLTCLVKGFY PSDIAVEWES NGQPENNYKT   420
TPPVLDSDGS FFLYSKLTVD KSRWQQGNVF SCSVMHEALH NHYTQKSLSL SPGK         474

SEQ ID NO: 345         moltype = AA  length = 229
FEATURE                Location/Qualifiers
source                 1..229
                       mol_type = protein
                       organism = synthetic construct
SEQUENCE: 345
MAWTPLLTLC IGSGGSSELT QDPAVSVALG QTVTITCQGD SLRIYYASWY QQKPGQAPIL    60
VIYDTNKRPS GIPDRFSGSS SGNTASLTIT GAQAEDEAEY YCDSRDSSGD HLLFGGGTRV   120
TVLGQPKAAP SVTLFPPSSE ELQANKATLV CLISDFYPGA VTVAWKADSS PVKAGVETTT   180
PSKQSNNKYA ASSYLSLTPE QWKSHRSYSC QVTHEGSTVE KTVAPTECS               229

SEQ ID NO: 346         moltype = AA  length = 476
FEATURE                Location/Qualifiers
source                 1..476
                       mol_type = protein
                       organism = synthetic construct
SEQUENCE: 346
MKHLWFFLLL VAAPRWVLSQ LQLQESGPGL VKPSETLSLT CSVSGDSISR SSDYWGWIRQ    60
PPGRGLEWIG SIYRTGSTYY NPSLSSRVTI SVDTSKSQFS LSLSSVTAAD TALYYCARVR   120
HDYVWGSIYY YGMDVWGQGT TVTVSSPSTK GPSVFPLAPC SRSTSGGTAA LGCLVKDYFP   180
EPVTVSWNSG ALTSGVHTFP AVLQSSGLYS LSSVVTVPSS SLGTQTYICN VNHKPSNTKV   240
DKRVEPKSCD KTHTCPPCPA PELLGGPSVF LFPPKPKDTL MISRTPEVTC VVVDVSHEDP   300
EVKFNWYVDG VEVHNAKTKP REEQYNSTYR VVSVLTVLHQ DWLNGKEYKC KVSNKALPAP   360
IEKTISKAKG QPREPQVYTL PPSREEMTKN QVSLTCLVKG FYPSDIAVEW ESNGQPENNY   420
KTTPPVLDSD GSFFLYSKLT VDKSRWQQGN VFSCSVMHEA LHNHYTQKSL SLSPGK       476

SEQ ID NO: 347         moltype = AA  length = 235
FEATURE                Location/Qualifiers
source                 1..235
                       mol_type = protein
                       organism = synthetic construct
SEQUENCE: 347
MAWTVLLLSL LTQGTGSWAQ SALTQPRSVS GSPGQSVTIS CTGTGSDVGG YTYVSWYQQH    60
PDKAPKLVIY DVTKRPSGVP DRFSGSKSGN TASLTISGLR ADDEADYYCC SYAGRYSWVF   120
GGGTKLTVLG QPKAAPSVTL FPPSSEELQA NKATLVCLIS DFYPGAVTVA WKADSSPVKA   180
GVETTTPSKQ SNNKYAASSY LSLTPEQWKS HRSYSCQVTH EGSTVEKTVA PTECS         235

SEQ ID NO: 348         moltype = AA  length = 474
FEATURE                Location/Qualifiers
source                 1..474
                       mol_type = protein
                       organism = synthetic construct
SEQUENCE: 348
```

```
MDWTWRILFL VAAATGAHSQ VQLVQSGAEV KKPGASVKVS CKTSGYTFTA YHMHWVRQAP  60
GQGLEWMGWI NPNSGGTNYA QKFQGRVTVT RDTSISTVYM ELTRLRSDDT AVYYCARERE  120
PLMASYYYG MDVWGQGTTV TVSSASTKGP SVFPLAPCSR STSGGTAALG CLVKDYFPEP  180
VTVSWNSGAL TSGVHTFPAV LQSSGLYSLS SVVTVPSSSL GTQTYICNVN HKPSNTKVDK  240
RVEPKSCDKT HTCPPCPAPE LLGGPSVFLF PPKPKDTLMI SRTPEVTCVV VDVSHEDPEV  300
KFNWYVDGVE VHNAKTKPRE EQYNSTYRVV SVLTVLHQDW LNGKEYKCKV SNKALPAPIE  360
KTISKAKGQP REPQVYTLPP SREEMTKNQV SLTCLVKGFY PSDIAVEWES NGQPENNYKT  420
TPPVLDSDGS FFLYSKLTVD KSRWQQGNVF SCSVMHEALH NHYTQKSLSL SPGK  474

SEQ ID NO: 349          moltype = AA  length = 233
FEATURE                 Location/Qualifiers
source                  1..233
                        mol_type = protein
                        organism = synthetic construct
SEQUENCE: 349
MAWIPLWLTL LTLCIGSVVS SEVTQDPAVS VALGQTVRIT CQGDSLRNYY TRWYQQKPGQ  60
APVLVIYREN NRPSGIPDRF SGSSSGNTAS LTITGAQAED EADYYCTSRA SSTDHLVFGG  120
GTKLTVLGQP KAAPSVTLFP PSSEELQANK ATLVCLISDF YPGAVTVAWK ADSSPVKAGV  180
ETTTPSKQSN NKYAASSYLS LTPEQWKSHR SYSCQVTHEG STVEKTVAPT ECS  233

SEQ ID NO: 350          moltype = AA  length = 472
FEATURE                 Location/Qualifiers
source                  1..472
                        mol_type = protein
                        organism = synthetic construct
SEQUENCE: 350
MELGLSWLFL VATLKGVQCE VQLLESGGGL MQPGGSLRLS CAASGFTFRS YAMNWVRQAP  60
GKGLEWVSTI SGNGGTTYYA DSVRGRFTIS RDNSKNTLFL QMNSLRAEDT AIYYCAQGEP  120
WSGYLEPLFA SWGQGTLVTV SSASTKGPSV FPLAPCSRST SGGTAALGCL VKDYFPEPVT  180
VSWNSGALTS GVHTFPAVLQ SSGLYSLSSV VTVPSSSLGT QTYICNVNHK PSNTKVDKRV  240
EPKSCDKTHT CPPCPAPELL GGPSVFLFPP KPKDTLMISR TPEVTCVVVD VSHEDPEVKF  300
NWYVDGVEVH NAKTKPREEQ YNSTYRVVSV LTVLHQDWLN GKEYKCKVSN KALPAPIEKT  360
ISKAKGQPRE PQVYTLPPSR EEMTKNQVSL TCLVKGFYPS DIAVEWESNG QPENNYKTTP  420
PVLDSDGSFF LYSKLTVDKS RWQQGNVFSC SVMHEALHNH YTQKSLSLSP GK  472

SEQ ID NO: 351          moltype = AA  length = 233
FEATURE                 Location/Qualifiers
source                  1..233
                        mol_type = protein
                        organism = synthetic construct
SEQUENCE: 351
MALTPLWLTL LTPCIGSVVS SELTQDPAVS VALGQTVRIT CQGDSLRNFY ASWYQQKPGQ  60
APVLVIYGKN NRPSGIPDRF SGSSSGNTVS LTITGAQAED DADYYCNSRD SSGNHVIFGG  120
GTKLTVLGQP KAAPSVTLFP PSSEELQANK ATLVCLISDF YPGAVTVAWK ADSSPVKAGV  180
ETTTPSKQSN NKYAASSYLS LTPEQWKSHR SYSCQVTHEG STVEKTVAPT ECS  233

SEQ ID NO: 352          moltype = AA  length = 475
FEATURE                 Location/Qualifiers
source                  1..475
                        mol_type = protein
                        organism = synthetic construct
SEQUENCE: 352
MELGLRWVFL VAILEGVHCE VQLVESGGGL VKPGGSLRLS CAASGFTFSS YSMNWVRQAP  60
GKGLEWVSSI STSKNYKKYA DSVKGRFTIS RDNAENSLYL QMNSLRAEDT AIYYCARVDY  120
DYIWGSYREK AMDVWGHGTT VTVSSASTKG PSVFPLAPCS RSTSGGTAAL GCLVKDYFPE  180
PVTVSWNSGA LTSGVHTFPA VLQSSGLYSL SSVVTVPSSS LGTQTYICNV NHKPSNTKVD  240
KRVEPKSCDK THTCPPCPAP ELLGGPSVFL FPPKPKDTLM ISRTPEVTCV VVDVSHEDPE  300
VKFNWYVDGV EVHNAKTKPR EEQYNSTYRV VSVLTVLHQD WLNGKEYKCK VSNKALPAPI  360
EKTISKAKGQ PREPQVYTLP PSREEMTKNQ VSLTCLVKGF YPSDIAVEWE SNGQPENNYK  420
TTPPVLDSDG SFFLYSKLTV DKSRWQQGNV FSCSVMHEAL HNHYTQKSLS LSPGK  475

SEQ ID NO: 353          moltype = AA  length = 232
FEATURE                 Location/Qualifiers
source                  1..232
                        mol_type = protein
                        organism = synthetic construct
SEQUENCE: 353
MAWSPLLLTQ GTGSWAQSAL TQPRSVSGSP GQSVTISCTG TGSDVGGYNY VSWYQQHPGK  60
APKVIIYDVS KRPSGVPDRF SGSKSGNTAS LTISGLQAED EADYHCCSYA GTYTWVFGGG  120
TKVTVLGQPK AAPSVTLFPP SSEELQANKA TLVCLISDFY PGAVTVAWKA DSSPVKAGVE  180
TTTPSKQSNN KYAASSYLSL TPEQWKSHRS YSCQVTHEGS TVEKTVAPTE CS  232

SEQ ID NO: 354          moltype = AA  length = 472
FEATURE                 Location/Qualifiers
source                  1..472
                        mol_type = protein
                        organism = synthetic construct
SEQUENCE: 354
MEFGLRWLFL VAILKGVQCE VQLLESGGGS VQPGGSLRLS CAASGFTFRN YAMNWVRQSP  60
```

```
GKGLEWVSTI SGTGGTTYYA DSVKGRFSIS RDNSRNTLYL NMNNLRVEDT AIYYCAKGEP  120
WSNYLEPLFD HWGQGTLVTV SSASTKGPSV FPLAPSSKST SGGTAALGCL VKDYFPEPVT  180
VSWNSGALTS GVHTFPAVLQ SSGLYSLSSV VTVPSSSLGT QTYICNVNHK PSNTKVDKRV  240
EPKSCDKTHT CPPCPAPELL GGPSVFLFPP KPKDTLMISR TPEVTCVVVD VSHEDPEVKF  300
NWYVDGVEVH NAKTKPREEQ YNSTYRVVSV LTVLHQDWLN GKEYKCKVSN KALPAPIEKT  360
ISKAKGQPRE PQVYTLPPSR EEMTKNQVSL TCLVKGFYPS DIAVEWESNG QPENNYKTTP  420
PVLDSDGSFF LYSKLTVDKS RWQQGNVFSC SVMHEALHNH YTQKSLSLSP GK          472
```

SEQ ID NO: 355                 moltype = AA   length = 230
FEATURE                        Location/Qualifiers
source                         1..230
                               mol_type = protein
                               organism = synthetic construct
SEQUENCE: 355

```
MALTPLLLTL CIGSVVSSEL TQDPAVSVAL GQTVRITCQG DSLRNFYATW YQQKPGQAPV  60
FVMYDKTNRP SGIPDRFSGS RSGNTAYLTI TGAQAEDEAD YYCNSRDSSG NYVIFGGGTK  120
LTVLGQPKAA PSVTLFPPSS EELQANKATL VCLISDFYPG AVTVAWKADS SPVKAGVETT  180
TPSKQSNNKY AASSYLSLTP EQWKSHRSYS CQVTHEGSTV EKTVAPTECS            230
```

SEQ ID NO: 356                 moltype = AA   length = 473
FEATURE                        Location/Qualifiers
source                         1..473
                               mol_type = protein
                               organism = synthetic construct
SEQUENCE: 356

```
MDWTWRILFL VAAATGAHSQ VQLVQSGAEV MRPGASLKVS CKASGYSFTM YSIHWVRQAP  60
GHRLEWMGWI NAANGNTIYS QNFQGRVTIS RDTSATTAHM ELGSLRSEDT AVYFCARGPI  120
PYYYDHSGPF DYWGQGTLVT VSSASTKGPS VFPLAPCSRS TSGGTAALGC LVKDYFPEPV  180
TVSWNSGALT SGVHTFPAVL QSSGLYSLSS VVTVPSSSLG TQTYICNVNH KPSNTKVDKR  240
VEPKSCDKTH TCPPCPAPEL LGGPSVFLFP PKPKDTLMIS RTPEVTCVVV DVSHEDPEVK  300
FNWYVDGVEV HNAKTKPREE QYNSTYRVVS VLTVLHQDWL NGKEYKCKVS NKALPAPIEK  360
TISKAKGQPR EPQVYTLPPS REEMTKNQVS LTCLVKGFYP SDIAVEWESN GQPENNYKTT  420
PPVLDSDGSF FLYSKLTVDK SRWQQGNVFS CSVMHEALHN HYTQKSLSLS PGK         473
```

SEQ ID NO: 357                 moltype = AA   length = 233
FEATURE                        Location/Qualifiers
source                         1..233
                               mol_type = protein
                               organism = synthetic construct
SEQUENCE: 357

```
MEAPAQLLFL LLLWLPDTTG EIVMTQSPPT LSVSPGERAI LSCRASQSVS SDLAWYQQQA  60
GQAPRLLIYG ASTRATGIPP RFSGSGSGTE FTLTISSLQS EDFAVYYCQQ YNKWVTFGGG  120
TKVEIKRTVA APSVFIFPPS DEQLKSGTAS VVCLLNNFYP REAKVQWKVD NALQSGNSQE  180
SVTEQDSKDS TYSLSSTLTL SKADYEKHKV YACEVTHQGL SSPVTKSFNR GEC         233
```

SEQ ID NO: 358                 moltype = AA   length = 474
FEATURE                        Location/Qualifiers
source                         1..474
                               mol_type = protein
                               organism = synthetic construct
SEQUENCE: 358

```
MDWTWRILFL VAAATGAHSQ VQLVQSGAEV KKPGASVKVS CRTSGYTFTA YHMHWVRQAP  60
GQGLEWMGWI NPNSGGTNYA QKFQGRVTVT RDTSLRTVYM EVTSLRSDDT AVYYCARERE  120
PLMASYYYG LDVWGQGTTV TVSSASTKGP SVFPLAPCSR STSGGTAALG CLVKDYFPEP  180
VTVSWNSGAL TSGVHTFPAV LQSSGLYSLS SVVTVPSSSL GTQTYICNVN HKPSNTKVDK  240
RVEPKSCDKT HTCPPCPAPE LLGGPSVFLF PPKPKDTLMI SRTPEVTCVV VDVSHEDPEV  300
KFNWYVDGVE VHNAKTKPRE EQYNSTYRVV SVLTVLHQDW LNGKEYKCKV SNKALPAPIE  360
KTISKAKGQP REPQVYTLPP SREEMTKNQV SLTCLVKGFY PSDIAVEWES NGQPENNYKT  420
TPPVLDSDGS FFLYSKLTVD KSRWQQGNVF SCSVMHEALH NHYTQKSLSL SPGK        474
```

SEQ ID NO: 359                 moltype = AA   length = 233
FEATURE                        Location/Qualifiers
source                         1..233
                               mol_type = protein
                               organism = synthetic construct
SEQUENCE: 359

```
MAWAPLWLTL LTLCIGSVVS SEVTQDPAVS VALGQTVRIT CQGDSLRNYY TRWYQQKPGQ  60
APILVIYREN NRPSGIPDRF SGTNSGNTAS LTITGAQAED EADYYCTSRA SGTDHLVFGR  120
GTKLTVLGQP KAAPSVTLFP PSSEELQANK ATLVCLISDF YPGAVTVAWK ADSSPVKAGV  180
ETTTPSKQSN NKYAASSYLS LTPEQWKSHR SYSCQVTHEG STVEKTVAPT ECS         233
```

SEQ ID NO: 360                 moltype = AA   length = 474
FEATURE                        Location/Qualifiers
source                         1..474
                               mol_type = protein
                               organism = synthetic construct
SEQUENCE: 360

```
MDWTWRILFL VAAATGAHSQ VQLVQSGAEV KKPGASVKVS CKTSGYAFTA FHLHWVRQAP  60
GQGLEWMGWI NPNSGDTNYA QKFQGRVTVT RDTSISTVYM ELTRLRSDDT AVYYCARERE  120
```

```
PLMASYYYYG MDVWGQGTTV TVSSASTKGP SVFPLAPCSR STSGGTAALG CLVKDYFPEP  180
VTVSWNSGAL TSGVHTFPAV LQSSGLYSLS SVVTVPSSSL GTQTYICNVN HKPSNTKVDK  240
RVEPKSCDKT HTCPPCPAPE LLGGPSVFLF PPKPKDTLMI SRTPEVTCVV VDVSHEDPEV  300
KFNWYVDGVE VHNAKTKPRE EQYNSTYRVV SVLTVLHQDW LNGKEYKCKV SNKALPAPIE  360
KTISKAKGQP REPQVYTLPP SREEMTKNQV SLTCLVKGFY PSDIAVEWES NGQPENNYKT  420
TPPVLDSDGS FFLYSKLTVD KSRWQQGNVF SCSVMHEALH NHYTQKSLSL SPGK        474

SEQ ID NO: 361            moltype = AA  length = 230
FEATURE                   Location/Qualifiers
source                    1..230
                          mol_type = protein
                          organism = synthetic construct
SEQUENCE: 361
MAWAPLLLTL CIGSVVSSEV TQDPAVSVAL GQTVRITCQG DSLRKYYTRW YQQKPGQAPV  60
LVIYRENNRP SGIPDRFSGS SSGNTASLTI TGAQAEDEAD YYCSSRASST DHLVFGGGTK  120
LTVLGQPKAA PSVTLFPPSS EELQANKATL VCLISDFYPG AVTVAWKADS SPVKAGVETT  180
TPSKQSNNKY AASSYLSLTP EQWKSHRSYS CQVTHEGSTV EKTVAPTECS            230

SEQ ID NO: 362            moltype = AA  length = 476
FEATURE                   Location/Qualifiers
source                    1..476
                          mol_type = protein
                          organism = synthetic construct
SEQUENCE: 362
MKHLWFFLLL VAAPRWVLSQ LQLQESGPGL VKPSETLSLT CSVSGDSISR SSDYWGWIRQ  60
PPGRGLEWIG SIYRTGSTYY NPSLSSRVTI SVDTSKSQFS LSLSSVTAAD TALYYCARVR  120
HDYVWGSIYY YGMDVWGQGT TVTVSSPSTK GPSVFPLAPC SRSTSGGTAA LGCLVKDYFP  180
EPVTVSWNSG ALTSGVHTFP AVLQSSGLYS LSSVVTVPSS SLGTQTYICN VNHKPSNTKV  240
DKRVEPKSCD KTHTCPPCPA PELLGGPSVF LFPPKPKDTL MISRTPEVTC VVVDVSHEDP  300
EVKFNWYVDG VEVHNAKTKP REEQYNSTYR VVSVLTVLHQ DWLNGKEYKC KVSNKALPAP  360
IEKTISKAKG QPREPQVYTL PPSREEMTKN QVSLTCLVKG FYPSDIAVEW ESNGQPENNY  420
KTTPPVLDSD GSFFLYSKLT VDKSRWQQGN VFSCSVMHEA LHNHYTQKSL SLSPGK      476

SEQ ID NO: 363            moltype = AA  length = 235
FEATURE                   Location/Qualifiers
VARIANT                   4..8
                          note = X can be any amino acid
VARIANT                   10
                          note = X can be any amino acid
VARIANT                   32
                          note = X can be any amino acid
source                    1..235
                          mol_type = protein
                          organism = synthetic construct
SEQUENCE: 363
MAWXXXXXSX LTQGTGSWAR SALTQPRSVS GXPGQSVTIS CTGTGSDVGG YTYVSWYQQH  60
PDKAPKLVIY DVTKRPSGVP DRFSGSKSGN TASLTISGLR ADDEADYYCC SYAGRYSWVF  120
GGGTKLTVLG QPKAAPSVTL FPPSSEELQA NKATLVCLIS DFYPGAVTVA WKADSSPVKA  180
GVETTTPSKQ SNNKYAASSY LSLTPEQWKS HRSYSCQVTH EGSTVEKTVA PTECS       235

SEQ ID NO: 364            moltype = AA  length = 472
FEATURE                   Location/Qualifiers
source                    1..472
                          mol_type = protein
                          organism = synthetic construct
SEQUENCE: 364
MKHLWFFLLL VAAPRWVLSQ VQLQESGPGL VKPSQTLSLT CTVSGGSISS GSHYWSWIRQ  60
PAGKGLEWIG RIYTSGRNSY NPSLKSRVTI SVDTFKNQFS LKVSSVTAAD TAVYYCARNN  120
RIYGGYELFD IWGQGTTVTV SSASTKGPSV FPLAPSSKST SGGTAALGCL VKDYFPEPVT  180
VSWNSGALTS GVHTFPAVLQ SSGLYSLSSV VTVPSSSLGT QTYICNVNHK PSNTKVDKRV  240
EPKSCDKTHT CPPCPAPELL GGPSVFLFPP KPKDTLMISR TPEVTCVVVD VSHEDPEVKF  300
NWYVDGVEVH NAKTKPREEQ YNSTYRVVSV LTVLHQDWLN GKEYKCKVSN KALPAPIEKT  360
ISKAKGQPRE PQVYTLPPSR EEMTKNQVSL TCLVKGFYPS DIAVEWESNG QPENNYKTTP  420
PVLDSDGSFF LYSKLTVDKS RWQQGNVFSC SVMHEALHNH YTQKSLSLSP GK          472

SEQ ID NO: 365            moltype = AA  length = 233
FEATURE                   Location/Qualifiers
source                    1..233
                          mol_type = protein
                          organism = synthetic construct
SEQUENCE: 365
MAWSPLLLGL LSHCTVSVTS FVLTQPPSVS VAPGKTARFS CGGDNIGSKP VHWYQQKPGQ  60
APALVIYYDS DRPSGIPERF SGSNSGNTAT LTISRVEAGD EADYYCQVWD TSGDHPVFGG  120
GTKLTVLGQP KAAPSVTLFP PSSEELQANK ATLVCLISDF YPGAVTVAWK ADSSPVKAGV  180
ETTTPSKQSN NKYAASSYLS LTPEQWKSHR SYSCQVTHEG STVEKTVAPT ECS         233

SEQ ID NO: 366            moltype = AA  length = 475
FEATURE                   Location/Qualifiers
source                    1..475
```

```
                              mol_type = protein
                              organism = synthetic construct
SEQUENCE: 366
MELGLCWVFL VAILEGVHCE VQLVESGGGL VKPGGSLRLS CAASGFTFSS YSMNWVRQAP    60
GKGLEWVSSI STSKNYKKYA DSVKGRFTIS RDNAENSLYL QMNSLRAEDT AIYYCARVDY   120
DYIWGSYREK AMDVWGHGTT VTVSSASTKG PSVFPLAPCS RSTSGGTAAL GCLVKDYFPE   180
PVTVSWNSGA LTSGVHTFPA VLQSSGLYSL SSVVTVPSSS LGTQTYICNV NHKPSNTKVD   240
KRVEPKSCDK THTCPPCPAP ELLGGPSVFL FPPKPKDTLM ISRTPEVTCV VVDVSHEDPE   300
VKFNWYVDGV EVHNAKTKPR EEQYNSTYRV VSVLTVLHQD WLNGKEYKCK VSNKALPAPI   360
EKTISKAKGQ PREPQVYTLP PSREEMTKNQ VSLTCLVKGF YPSDIAVEWE SNGQPENNYK   420
TTPPVLDSDG SFFLYSKLTV DKSRWQQGNV FSCSVMHEAL HNHYTQKSLS LSPGK        475

SEQ ID NO: 367           moltype = AA  length = 232
FEATURE                  Location/Qualifiers
source                   1..232
                         mol_type = protein
                         organism = synthetic construct
SEQUENCE: 367
MAWIPLLLTQ GTGSWAQSAL TQPRSVSGSP GQSVTISCTG TGSDVGGYNY VSWYQQHPGK    60
APKVIIYDVS KRPSGVPDRF SGSKSGNTAS LTISGLQAED EADYHCCSYA GTYTWVFGGG   120
TKVTVLGQPK AAPSVTLFPP SSEELQANKA TLVCLISDFY PGAVTVAWKA DSSPVKAGVE   180
TTTPSKQSNN KYAASSYLSL TPEQWKSHRS YSCQVTHEGS TVEKTVAPTE CS           232

SEQ ID NO: 368           moltype = AA  length = 481
FEATURE                  Location/Qualifiers
source                   1..481
                         mol_type = protein
                         organism = synthetic construct
SEQUENCE: 368
MDWTWRVFCL LAVAPGVHSQ VQLVQSGAEV KKPGASVRVS CKASGYTFTN YYMHWVRQAP    60
GQGLEWTGIV NPSGGSTNYA QKLQGRVTMT IDTSTSTVYM ELNSLTSEDT AVYYCARARK   120
HYFGSGTDYK GRYTAHALDL WGQGTMVIVS SASTKGPSVF PLAPSSKSTS GGTAALGCLV   180
KDYFPEPVTV SWNSGALTSG VHTFPAVLQS SGLYSLSSVV TVPSSSLGTQ TYICNVNHKP   240
SNTKVDKRVE PKSCDKTHTC PPCPAPELLG GPSVFLFPPK PKDTLMISRT PEVTCVVVDV   300
SHEDPEVKFN WYVDGVEVHN AKTKPREEQY NSTYRVVSVL TVLHQDWLNG KEYKCKVSNK   360
ALPAPIEKTI SKAKGQPREP QVYTLPPSRE EMTKNQVSLT CLVKGFYPSD IAVEWESNGQ   420
PENNYKTTPP VLDSDGSFFL YSKLTVDKSR WQQGNVFSCS VMHEALHNHY TQKSLSLSPG   480
K                                                                     481

SEQ ID NO: 369           moltype = AA  length = 240
FEATURE                  Location/Qualifiers
source                   1..240
                         mol_type = protein
                         organism = synthetic construct
SEQUENCE: 369
MVLQTQVFIS LLLWISGAYG DIVMTQSPDS LAVSLGERAT INCKSSQSLL YTSNNKNYLA    60
WYQQKAGQPP KLLIYWASTR ESGVPDRFSG SGSGTDFTLT ISSLQSEDVA VYYCQQYYST   120
PQTFGQGTKV EIKRTVAAPS VFIFPPSDEQ LKSGTASVVC LLNNFYPREA KVQWKVDNAL   180
QSGNSQESVT EQDSKDSTYS LSSTLTLSKA DYEKHKVYAC EVTHQGLSSP VTKSFNRGEC   240

SEQ ID NO: 370           moltype = AA  length = 476
FEATURE                  Location/Qualifiers
source                   1..476
                         mol_type = protein
                         organism = synthetic construct
SEQUENCE: 370
MKHLWFFLLL VAAPRWVLSQ VQLQESGPRL VKPSQTLSLT CSVSGGTVRT GDYYWSWIRQ    60
PPGKGLEWIG FIHYSGSTYY NPSLKSRVTI SLDTSRNQFS LKLSSVTAAD TAVYFCARIY   120
YDSSGYLHSL KIIDSWGQGT LVTVSSASTK GPSVFPLAPC SRSTSGGTAA LGCLVKDYFP   180
EPVTVSWNSG ALTSGVHTFP AVLQSSGLYS LSSVVTVPSS SLGTQTYICN VNHKPSNTKV   240
DKRVEPKSCD KTHTCPPCPA PELLGGPSVF LFPPKPKDTL MISRTPEVTC VVVDVSHEDP   300
EVKFNWYVDG VEVHNAKTKP REEQYNSTYR VVSVLTVLHQ DWLNGKEYKC KVSNKALPAP   360
IEKTISKAKG QPREPQVYTL PPSREEMTKN QVSLTCLVKG FYPSDIAVEW ESNGQPENNY   420
KTTPPVLDSD GSFFLYSKLT VDKSRWQQGN VFSCSVMHEA LHNHYTQKSL SLSPGK       476

SEQ ID NO: 371           moltype = AA  length = 234
FEATURE                  Location/Qualifiers
source                   1..234
                         mol_type = protein
                         organism = synthetic construct
SEQUENCE: 371
MRLPAQLLFL LLLWLPDTTG EIVLTQSPAT LSASPGERAT LSCRASQSVS SNLAWYRQKP    60
GQSPRLLIYG ASARATGIPA RFGGSGSGTE FTLTISSLQS EDFAVYYCQQ YNNWPLTFGG   120
GTKVEIKRTV AAPSVFIFPP SDEQLKSGTA SVVCLLNNFY PREAKVQWKV DNALQSGNSQ   180
ESVTEQDSKD STYSLSSTLT LSKADYEKHK VYACEVTHQG LSSPVTKSFN RGEC         234

SEQ ID NO: 372           moltype = AA  length = 477
FEATURE                  Location/Qualifiers
source                   1..477
```

```
                              mol_type = protein
                              organism = synthetic construct
SEQUENCE: 372
MDWTWRILFL VAAATGAHSQ VQLVQSGTEV KKPGASVKVS CKASGYTFNK YAMNWVRQAP    60
GQRLEWMGYI NADNGNTKYS QKFRDRVTIT RDTSASIVYM ELRSLRSEDT AMYYCARDGG   120
WSTTVNNQPY YYGMDVWGQG TTVTVSSAST KGPSVFPLAP SSKSTSGGTA ALGCLVKDYF   180
PEPVTVSWNS GALTSGVHTF PAVLQSSGLY SLSSVVTVPS SSLGTQTYIC NVNHKPSNTK   240
VDKRVEPKSC DKTHTCPPCP APELLGGPSV FLFPPKPKDT LMISRTPEVT CVVVDVSHED   300
PEVKFNWYVD GVEVHNAKTK PREEQYNSTY RVVSVLTVLH QDWLNGKEYK CKVSNKALPA   360
PIEKTISKAK GQPREPQVYT LPPSREEMTK NQVSLTCLVK GFYPSDIAVE WESNGQPENN   420
YKTTPPVLDS DGSFFLYSKL TVDKSRWQQG NVFSCSVMHE ALHNHYTQKS LSLSPGK     477

SEQ ID NO: 373              moltype = AA  length = 237
FEATURE                     Location/Qualifiers
source                      1..237
                            mol_type = protein
                            organism = synthetic construct
SEQUENCE: 373
MRLLAQLLFL LLLWLPDTTG EIVLTQSPGT LSLSPGERAT LSCRASQFVG SKYMAWYQQK    60
PGQAPRLLIY GASSRATGIP DRFSGSGSGT DFTLTISRLE PEDFAVYYCQ QFGSSPPMYA   120
FGQGTKLEIK RTVAAPSVFI FPPSDEQLKS GTASVVCLLN NFYPREAKVQ WKVDNALQSG   180
NSQESVTEQD SKDSTYSLSS TLTLSKADYE KHKVYACEVT HQGLSSPVTK SFNRGEC     237

SEQ ID NO: 374              moltype = AA  length = 475
FEATURE                     Location/Qualifiers
source                      1..475
                            mol_type = protein
                            organism = synthetic construct
SEQUENCE: 374
MKHLWFFLLL VAVPRWVLSQ VQLQESGPRL VKPSQTLSLT CTVSGGSISS GDYYWSWIRQ    60
APGTGLEWIG FIYNTETTYY SPSLRSRVSM SLDTSKNQFS LKLSSVTAAD TAVYYCARER   120
RPSHYDSGGY SLDYWGQGTL VTVSSASTKG PSVFPLAPSS KSTSGGTAAL GCLVKDYFPE   180
PVTVSWNSGA LTSGVHTFPA VLQSSGLYSL SSVVTVPSSS LGTQTYICNV NHKPSNTKVD   240
KRVEPKSCDK THTCPPCPAP ELLGGPSVFL FPPKPKDTLM ISRTPEVTCV VVDVSHEDPE   300
VKFNWYVDGV EVHNAKTKPR EEQYNSTYRV VSVLTVLHQD WLNGKEYCK VSNKALPAPI   360
EKTISKAKGQ PREPQVYTLP PSREEMTKNQ VSLTCLVKGF YPSDIAVEWE SNGQPENNYK   420
TTPPVLDSDG SFFLYSKLTV DKSRWQQGNV FSCSVMHEAL HNHYTQKSLS LSPGK       475

SEQ ID NO: 375              moltype = AA  length = 234
FEATURE                     Location/Qualifiers
source                      1..234
                            mol_type = protein
                            organism = synthetic construct
SEQUENCE: 375
MEAPAQLLFL LLLWLPDSTG EIVMTQSPAT LSVSPGERAT LSCRASQSVS SNLAWYQQKP    60
GQAPRLLIYG ASTRATGIPA RFSGSGSGTE FTLAISSLQS EDFALYYCQQ YNNWPRTFGQ   120
GTKVEIKRTV AAPSVIFPP SDEQLKSGTA SVVCLLNNFY PREAKVQKV DNALQSGNSQ   180
ESVTEQDSKD STYSLSSTLT LSKADYEKHK VYACEVTHQG LSSPVTKSFN RGEC        234

SEQ ID NO: 376              moltype = AA  length = 474
FEATURE                     Location/Qualifiers
source                      1..474
                            mol_type = protein
                            organism = synthetic construct
SEQUENCE: 376
MELGLCWVFL VAILEGVQCE VQLVESGGGL VKPGGSLRLS CAASGFTFST YSMNWVRQAP    60
GKGLEWVSSI SSSGTYTYYA DSVKGRFTIS RDNAKDSLYL QMNSLRADDT AVYYCARAPY   120
DYGDYRGGRY FDLWGRGSLV TVSSASTKGP SVFPLAPCSR STSGGTAALG CLVKDYFPEP   180
VTVSWNSGAL TSGVHTFPAV LQSSGLYSLS SVVTVPSSSL GTQTYICNVN HKPSNTKVDK   240
RVEPKSCDKT HTCPPCPAPE LLGGPSVFLF PPKPKDTLMI SRTPEVTCVV VDVSHEDPEV   300
KFNWYVDGVE VHNAKTKPRE EQYNSTYRVV SVLTVLHQDW LNGKEYKCKV SNKALPAPIE   360
KTISKAKGQP REPQVYTLPP SREEMTKNQV SLTCLVKGFY PSDIAVEWES NGQPENNYKT   420
TPPVLDSDGS FFLYSKLTVD KSRWQQGNVF SCSVMHEALH NHYTQKSLSL SPGK        474

SEQ ID NO: 377              moltype = AA  length = 234
FEATURE                     Location/Qualifiers
source                      1..234
                            mol_type = protein
                            organism = synthetic construct
SEQUENCE: 377
MRLPAQLLFL LLLWLPDTTG EIVMTQSPAT LSVSPGERAT LSCRASQSVS SKLAWYQQKP    60
GQAPRLLIFG ASTRATGIPA RFSGSGSGTE FTLTISSLQS EDFAVYYCQQ YNNWPRTFGQ   120
GTKVEIKRTV AAPSVIFPP SDEQLKSGTA SVVCLLNNFY PREAKVQKV DNALQSGNSQ   180
ESVTEQDSKD STYSLSSTLT LSKADYEKHK VYACEVTHQG LSSPVTKSFN RGEC        234

SEQ ID NO: 378              moltype = AA  length = 470
FEATURE                     Location/Qualifiers
source                      1..470
                            mol_type = protein
```

```
                        organism = synthetic construct
SEQUENCE: 378
MDTLCSTLLL LTIPSWVLSQ ITLKESGPTL VKPTQTLMLT CTFSGFSLST SGVGVGWIRQ   60
PPGKALEWLA FIYWNTDKRY NPSLKTRLTI TKDTSKTQVV LTMTNLDPVD TGTYYCVHHD  120
GYLAEYFNHW GQGTLVTSS ASTKGPSVFP LAPSSKSTSG GTAALGCLVK DYFPEPVTVS  180
WNSGALTSGV HTFPAVLQSS GLYSLSSVVT VPSSSLGTQT YICNVNHKPS NTKVDKRVEP  240
KSCDKTHTCP PCPAPELLGG PSVFLFPPKP KDTLMISRTP EVTCVVVDVS HEDPEVKFNW  300
YVDGVEVHNA KTKPREEQYN STYRVVSVLT VLHQDWLNGK EYKCKVSNKA LPAPIEKTIS  360
KAKGQPREPQ VYTLPPSREE MTKNQVSLTC LVKGFYPSDI AVEWESNGQP ENNYKTTPPV  420
LDSDGSFFLY SKLTVDKSRW QQGNVFSCSV MHEALHNHYT QKSLSLSPGK             470

SEQ ID NO: 379          moltype = AA  length = 235
FEATURE                 Location/Qualifiers
source                  1..235
                        mol_type = protein
                        organism = synthetic construct
SEQUENCE: 379
MALTPLLLTL LIHCTGSWAQ SVLTQPPSVS AAPGQRVTIS CSGTTSNIGN YYVSWYQEVP   60
GTAPKLLIYD NVKRPSGIPD RFSASKSGTS ATLGISGLQT GDEADYYCGT WDGRLSAWVF  120
GGGTKLTVLG QPKAAPSVTL FPPSSEELQA NKATLVCLIS DFYPGAVTVA WKADSSPVKA  180
GVETTTPSKQ SNNKYAASSY LSLTPEQWKS HRSYSCQVTH EGSTVEKTVA PTECS       235

SEQ ID NO: 380          moltype = AA  length = 471
FEATURE                 Location/Qualifiers
source                  1..471
                        mol_type = protein
                        organism = synthetic construct
SEQUENCE: 380
MKHLWFFLLL VAAPRWVLSQ VQLQQWGAGL LRPSETLSLT CGVSGGALSG YIWSWIRQPP   60
GKGLEWIGEI NHSGTTNYSP SLKSRVTISV DTSKNHFSLR LSSVTAADSA MYYCARGGVR  120
NWQLGPALDF WGQGTLVTVS SASTKGPSVF PLAPSSKSTS GGTAALGCLV KDYFPEPVTV  180
SWNSGALTSG VHTFPAVLQS SGLYSLSSVV TVPSSSLGTQ TYICNVNHKP SNTKVDKRVE  240
PKSCDKTHTC PPCPAPELLG GPSVFLFPPK PKDTLMISRT PEVTCVVVDV SHEDPEVKFN  300
WYVDGVEVHN AKTKPREEQY NSTYRVVSVL TVLHQDWLNG KEYKCKVSNK ALPAPIEKTI  360
SKAKGQPREP QVYTLPPSRE EMTKNQVSLT CLVKGFYPSD IAVEWESNGQ PENNYKTTPP  420
VLDSDGSFFL YSKLTVDKSR WQQGNVFSCS VMHEALHNHY TQKSLSLSPG K           471

SEQ ID NO: 381          moltype = AA  length = 236
FEATURE                 Location/Qualifiers
source                  1..236
                        mol_type = protein
                        organism = synthetic construct
SEQUENCE: 381
MRLPAQLLGL LLLWLPGARC AIQLTQSPSS LSASVGDRVT ITCRASQDIS SFLAWFQQKP   60
GRAPKLLLYA ASTLQSGVPS RFSGSGSGTD FSLTIGSLQP EDFATYYCQS LNNYPRSFTF  120
GPGTKVDIKR TVAAPSVFIF PPSDEQLKSG TASVVCLLNN FYPREAKVQW KVDNALQSGN  180
SQESVTEQDS KDSTYSLSST LTLSKADYEK HKVYACEVTH QGLSSPVTKS FNRGEC      236

SEQ ID NO: 382          moltype = AA  length = 474
FEATURE                 Location/Qualifiers
source                  1..474
                        mol_type = protein
                        organism = synthetic construct
SEQUENCE: 382
MKHLWFFLLL VAAPRWVLSQ VQLQESGPGL VKPSETLSLT CSVSGDSMAS DYWSWIRQPP   60
GKGLEWIGYV SYSGTTYYIP SLKSRVTISL DRSRTQFSLK VTSVTSADTA VYYCARGRRG  120
HSSGGWGIEF FHQWGQGTLV TVSPASTKGP SVFPLAPSSK STSGGTAALG CLVKDYFPEP  180
VTVSWNSGAL TSGVHTFPAV LQSSGLYSLR SVVTVPSSSL GTQTYICNVN HKPSNTKVDK  240
RVEPKSCDKT HTCPPCPAPE LLGGPSVFLF PPKPKDTLMI SRTPEVTCVV VDVSHEDPEV  300
KFNWYVDGVE VHNAKTKPRE EQYNSTYRVV SVLTVLHQDW LNGKEYKCKV SNKALPAPIE  360
KTISKAKGQP REPQVYTLPP SREEMTKNQV SLTCLVKGFY PSDIAVEWES NGQPENNYKT  420
TPPVLDSDGS FFLYSKLTVD KSRWQQGNVF SCSVMHEALH NHYTQKSLSL SPGK        474

SEQ ID NO: 383          moltype = AA  length = 233
FEATURE                 Location/Qualifiers
source                  1..233
                        mol_type = protein
                        organism = synthetic construct
SEQUENCE: 383
MEAPAQLLFL LLLWLPDTTG EIVMTQSPPT LSVSPGERAT LSCRASQSVS SDLAWYQQQA   60
GQAPRLLIYD ASTRATGIPP RFSGSGSGTE FTLTISSLQS EDFAVYYCQQ YNKWVTFGGG  120
TKVEIKRTVA APSVFIFPPS DEQLKSGTAS VVCLLNNFYP REAKVQWKVD NALQSGNSQE  180
SVTEQDSKDS TYSLSSTLTL SKADYEKHKV YACEVTHQGL SSPVTKSFNR GEC         233

SEQ ID NO: 384          moltype = AA  length = 473
FEATURE                 Location/Qualifiers
source                  1..473
                        mol_type = protein
                        organism = synthetic construct
```

```
SEQUENCE: 384
MDWTWRILFL VAAATGAHSQ VQLVQSGAEV MRPGASLKVS CKASGYSFTM YSIHWVRQAP    60
GHRLEWMGWI NAANGNTIYS QNFQGRVTIS RDTSATTAHM ELGSLRSEDT AVYFCARGPI   120
PYYYDHSGPF DYWGQGTLVT VSSASTKGPS VFPLAPCSRS TSGGTAALGC LVKDYFPEPV   180
TVSWNSGALT SGVHTFPAVL QSSGLYSLSS VVTVPSSSLG TQTYICNVNH KPSNTKVDKR   240
VEPKSCDKTH TCPPCPAPEL LGGPSVFLFP PKPKDTLMIS RTPEVTCVVV DVSHEDPEVK   300
FNWYVDGVEV HNAKTKPREE QYNSTYRVVS VLTVLHQDWL NGKEYKCKVS NKALPAPIEK   360
TISKAKGQPR EPQVYTLPPS REEMTKNQVS LTCLVKGFYP SDIAVEWESN GQPENNYKTT   420
PPVLDSDGSF FLYSKLTVDK SRWQQGNVFS CSVMHEALHN HYTQKSLSLS PGK          473

SEQ ID NO: 385             moltype = AA   length = 233
FEATURE                    Location/Qualifiers
source                     1..233
                           mol_type = protein
                           organism = synthetic construct
SEQUENCE: 385
MEAPAQLLFL LLLWLPDTTG EIVMTQSPPT LSVSPGERAI LSCRASQSVS SDLAWYQQQA    60
GQAPRLLIYG ASTRATGIPP RFSGSGSGTE FTLTISSLQS EDFAVYYCQQ YNKWVTFGGG   120
TKVEIKRTVA APSVFIFPPS DEQLKSGTAS VVCLLNNFYP REAKVQWKVD NALQSGNSQE   180
SVTEQDSKDS TYSLSSTLTL SKADYEKHKV YACEVTHQGL SSPVTKSFNR GEC          233

SEQ ID NO: 386             moltype = AA   length = 15
FEATURE                    Location/Qualifiers
source                     1..15
                           mol_type = protein
                           organism = Human polyomavirus BKV
SEQUENCE: 386
RVDGQPMYGM ESQVE                                                     15

SEQ ID NO: 387             moltype = AA   length = 15
FEATURE                    Location/Qualifiers
source                     1..15
                           mol_type = protein
                           organism = Human polyomavirus BKV
SEQUENCE: 387
KVDGQPMYGM ESQVE                                                     15

SEQ ID NO: 388             moltype = AA   length = 15
FEATURE                    Location/Qualifiers
source                     1..15
                           mol_type = protein
                           organism = Human polyomavirus BKV
SEQUENCE: 388
KVDGQPMYGM ESQVE                                                     15

SEQ ID NO: 389             moltype = AA   length = 15
FEATURE                    Location/Qualifiers
source                     1..15
                           mol_type = protein
                           organism = Human polyomavirus BKV
SEQUENCE: 389
RVDGQPMYGM ESQVE                                                     15

SEQ ID NO: 390             moltype = AA   length = 15
FEATURE                    Location/Qualifiers
source                     1..15
                           mol_type = protein
                           organism = Human polyomavirus JCV
SEQUENCE: 390
RVDGQPMYGM DAQVE                                                     15

SEQ ID NO: 391             moltype = AA   length = 15
FEATURE                    Location/Qualifiers
source                     1..15
                           mol_type = protein
                           organism = Merkel cell polyomavirus
SEQUENCE: 391
KVSGQPMEGK DNQVE                                                     15

SEQ ID NO: 392             moltype = AA   length = 12
FEATURE                    Location/Qualifiers
source                     1..12
                           mol_type = protein
                           organism = Human polyomavirus BKV
SEQUENCE: 392
NPTAQSQVMN TD                                                        12

SEQ ID NO: 393             moltype = AA   length = 12
FEATURE                    Location/Qualifiers
```

-continued

```
source                    1..12
                          mol_type = protein
                          organism = Human polyomavirus BKV
SEQUENCE: 393
NPTAQSQVMN TD                                                          12

SEQ ID NO: 394            moltype = AA  length = 12
FEATURE                   Location/Qualifiers
source                    1..12
                          mol_type = protein
                          organism = Human polyomavirus BKV
SEQUENCE: 394
NPTAQSQVMN TD                                                          12

SEQ ID NO: 395            moltype = AA  length = 12
FEATURE                   Location/Qualifiers
source                    1..12
                          mol_type = protein
                          organism = Human polyomavirus BKV
SEQUENCE: 395
NPTAQSQVMN TD                                                          12

SEQ ID NO: 396            moltype = AA  length = 12
FEATURE                   Location/Qualifiers
source                    1..12
                          mol_type = protein
                          organism = Human polyomavirus JCV
SEQUENCE: 396
NATVQSQVMN TE                                                          12

SEQ ID NO: 397            moltype = AA  length = 12
FEATURE                   Location/Qualifiers
source                    1..12
                          mol_type = protein
                          organism = Merkel cell polyomavirus
SEQUENCE: 397
KMTPKNQGLD PQ                                                          12

SEQ ID NO: 398            moltype = AA  length = 6
FEATURE                   Location/Qualifiers
source                    1..6
                          mol_type = protein
                          organism = Human polyomavirus BKV
SEQUENCE: 398
PDENLR                                                                 6

SEQ ID NO: 399            moltype = AA  length = 6
FEATURE                   Location/Qualifiers
source                    1..6
                          mol_type = protein
                          organism = Human polyomavirus BKV
SEQUENCE: 399
PDDNLR                                                                 6

SEQ ID NO: 400            moltype = AA  length = 6
FEATURE                   Location/Qualifiers
source                    1..6
                          mol_type = protein
                          organism = Human polyomavirus BKV
SEQUENCE: 400
PDDNLR                                                                 6

SEQ ID NO: 401            moltype = AA  length = 6
FEATURE                   Location/Qualifiers
source                    1..6
                          mol_type = protein
                          organism = Human polyomavirus BKV
SEQUENCE: 401
PDNNLR                                                                 6

SEQ ID NO: 402            moltype = AA  length = 6
FEATURE                   Location/Qualifiers
source                    1..6
                          mol_type = protein
                          organism = Human polyomavirus JCV
SEQUENCE: 402
PDEHLR                                                                 6

SEQ ID NO: 403            moltype = AA  length = 6
```

-continued

```
FEATURE            Location/Qualifiers
source             1..6
                   mol_type = protein
                   organism = Merkel cell polyomavirus
SEQUENCE: 403
NSPDLP                                                              6

SEQ ID NO: 404     moltype = AA  length = 7
FEATURE            Location/Qualifiers
source             1..7
                   mol_type = protein
                   organism = Human polyomavirus BKV
SEQUENCE: 404
PERKMLP                                                             7

SEQ ID NO: 405     moltype = AA  length = 7
FEATURE            Location/Qualifiers
source             1..7
                   mol_type = protein
                   organism = Human polyomavirus BKV
SEQUENCE: 405
PDKKMLP                                                            7

SEQ ID NO: 406     moltype = AA  length = 7
FEATURE            Location/Qualifiers
source             1..7
                   mol_type = protein
                   organism = Human polyomavirus BKV
SEQUENCE: 406
PDRKMLP                                                            7

SEQ ID NO: 407     moltype = AA  length = 7
FEATURE            Location/Qualifiers
source             1..7
                   mol_type = protein
                   organism = Human polyomavirus BKV
SEQUENCE: 407
PDRKMLP                                                            7

SEQ ID NO: 408     moltype = AA  length = 7
FEATURE            Location/Qualifiers
source             1..7
                   mol_type = protein
                   organism = Human polyomavirus JCV
SEQUENCE: 408
PSKDMLP                                                            7

SEQ ID NO: 409     moltype = AA  length = 7
FEATURE            Location/Qualifiers
source             1..7
                   mol_type = protein
                   organism = Merkel cell polyomavirus
SEQUENCE: 409
PIKENLP                                                            7

SEQ ID NO: 410     moltype = AA  length = 5
FEATURE            Location/Qualifiers
source             1..5
                   mol_type = protein
                   organism = Human polyomavirus BKV
SEQUENCE: 410
KYPDG                                                              5

SEQ ID NO: 411     moltype = AA  length = 5
FEATURE            Location/Qualifiers
source             1..5
                   mol_type = protein
                   organism = Human polyomavirus BKV
SEQUENCE: 411
KYPQG                                                              5

SEQ ID NO: 412     moltype = AA  length = 5
FEATURE            Location/Qualifiers
source             1..5
                   mol_type = protein
                   organism = Human polyomavirus BKV
SEQUENCE: 412
KYPQG                                                              5
```

```
SEQ ID NO: 413            moltype = AA   length = 5
FEATURE                   Location/Qualifiers
source                    1..5
                          mol_type = protein
                          organism = Human polyomavirus BKV
SEQUENCE: 413
KYPEG                                                                    5

SEQ ID NO: 414            moltype = AA   length = 5
FEATURE                   Location/Qualifiers
source                    1..5
                          mol_type = protein
                          organism = Human polyomavirus JCV
SEQUENCE: 414
KYPDG                                                                    5

SEQ ID NO: 415            moltype = AA   length = 5
FEATURE                   Location/Qualifiers
source                    1..5
                          mol_type = protein
                          organism = Merkel cell polyomavirus
SEQUENCE: 415
EYPKT                                                                    5

SEQ ID NO: 416            moltype = AA   length = 4
FEATURE                   Location/Qualifiers
source                    1..4
                          mol_type = protein
                          organism = Human polyomavirus BKV
SEQUENCE: 416
LDKN                                                                     4

SEQ ID NO: 417            moltype = AA   length = 4
FEATURE                   Location/Qualifiers
source                    1..4
                          mol_type = protein
                          organism = Human polyomavirus BKV
SEQUENCE: 417
LDKN                                                                     4

SEQ ID NO: 418            moltype = AA   length = 4
FEATURE                   Location/Qualifiers
source                    1..4
                          mol_type = protein
                          organism = Human polyomavirus BKV
SEQUENCE: 418
LDKN                                                                     4

SEQ ID NO: 419            moltype = AA   length = 4
FEATURE                   Location/Qualifiers
source                    1..4
                          mol_type = protein
                          organism = Human polyomavirus BKV
SEQUENCE: 419
LDKN                                                                     4

SEQ ID NO: 420            moltype = AA   length = 4
FEATURE                   Location/Qualifiers
source                    1..4
                          mol_type = protein
                          organism = Human polyomavirus JCV
SEQUENCE: 420
LDKN                                                                     4

SEQ ID NO: 421            moltype = AA   length = 4
FEATURE                   Location/Qualifiers
source                    1..4
                          mol_type = protein
                          organism = Merkel cell polyomavirus
SEQUENCE: 421
LDKD                                                                     4

SEQ ID NO: 422            moltype = AA   length = 12
FEATURE                   Location/Qualifiers
VARIANT                   6
                          note = G or S
SITE                      1..12
                          note = Variant residues given in the sequence have no
                           preference with respect to those in the annotations for
```

-continued

```
                              variant positions
source                        1..12
                              mol_type = protein
                              organism = synthetic construct
SEQUENCE: 422
GGSISXGGYY WS                                            12

SEQ ID NO: 423                moltype = AA  length = 8
FEATURE                       Location/Qualifiers
VARIANT                       5
                              note = N or S
VARIANT                       6
                              note = R or G
VARIANT                       7
                              note = G or S
SITE                          1..8
                              note = Variant residues given in the sequence have no
                               preference with respect to those in the annotations for
                               variant positions
source                        1..8
                              mol_type = protein
                              organism = synthetic construct
SEQUENCE: 423
YIYYXXXT                                                  8

SEQ ID NO: 424                moltype = AA  length = 15
FEATURE                       Location/Qualifiers
VARIANT                       15
                              note = R or I
SITE                          1..15
                              note = Variant residues given in the sequence have no
                               preference with respect to those in the annotations for
                               variant positions
source                        1..15
                              mol_type = protein
                              organism = synthetic construct
SEQUENCE: 424
ARCVLGGYGS DAFDX                                          15

SEQ ID NO: 425                moltype = AA  length = 11
FEATURE                       Location/Qualifiers
VARIANT                       9
                              note = H or Y
SITE                          1..11
                              note = Variant residues given in the sequence have no
                               preference with respect to those in the annotations for
                               variant positions
source                        1..11
                              mol_type = protein
                              organism = synthetic construct
SEQUENCE: 425
RASQSVSSXL A                                              11

SEQ ID NO: 426                moltype = AA  length = 8
FEATURE                       Location/Qualifiers
VARIANT                       5
                              note = S or N
VARIANT                       8
                              note = N or T
SITE                          1..8
                              note = Variant residues given in the sequence have no
                               preference with respect to those in the annotations for
                               variant positions
source                        1..8
                              mol_type = protein
                              organism = synthetic construct
SEQUENCE: 426
YDASXRAX                                                  8
```

-continued

```
SEQ ID NO: 427        moltype = AA   length = 11
FEATURE               Location/Qualifiers
VARIANT               5
                      note = S or N
SITE                  1..11
                      note = Variant residues given in the sequence have no
                       preference with respect to those in the annotations for
                       variant positions
source                1..11
                      mol_type = protein
                      organism = synthetic construct
SEQUENCE: 427
QQRSXWPPSL T                                                          11
```